United States Patent
Ren et al.

(10) Patent No.: US 9,359,349 B2
(45) Date of Patent: Jun. 7, 2016

(54) SUBSTITUTED QUINAZOLINES AS KINASE INHIBITORS

(71) Applicant: Intellikine LLC, La Jolla, CA (US)

(72) Inventors: Pingda Ren, San Diego, CA (US); Yi Liu, San Diego, CA (US); Troy Edward Wilson, Rolling Hills Estates, CA (US)

(73) Assignee: INTELLIKINE LLC, La Jolla, CA (US)

(*) Notice: Subject to any disclaimer, the term of this patent is extended or adjusted under 35 U.S.C. 154(b) by 0 days.

(21) Appl. No.: 14/491,929

(22) Filed: Sep. 19, 2014

(65) Prior Publication Data

US 2015/0141442 A1  May 21, 2015

Related U.S. Application Data

(63) Continuation of application No. 14/139,723, filed on Dec. 23, 2013, now abandoned, which is a continuation of application No. 12/677,098, filed as application No. PCT/US2008/078990 on Oct. 6, 2008, now abandoned.

(60) Provisional application No. 60/997,922, filed on Oct. 4, 2007.

(51) Int. Cl.
| | |
|---|---|
| A61K 31/517 | (2006.01) |
| C07D 239/84 | (2006.01) |
| C07D 471/04 | (2006.01) |
| C07D 239/94 | (2006.01) |
| C07D 401/12 | (2006.01) |
| C07D 401/14 | (2006.01) |
| C07D 403/04 | (2006.01) |
| C07D 239/42 | (2006.01) |

(52) U.S. Cl.
CPC ............ *C07D 471/04* (2013.01); *A61K 31/517* (2013.01); *C07D 239/42* (2013.01); *C07D 239/84* (2013.01); *C07D 239/94* (2013.01); *C07D 401/12* (2013.01); *C07D 401/14* (2013.01); *C07D 403/04* (2013.01)

(58) Field of Classification Search
CPC ........................... A61K 31/517; C07D 239/84
USPC ................. 514/266.4; 544/292; 546/113, 304
See application file for complete search history.

(56) References Cited

U.S. PATENT DOCUMENTS

| | | | |
|---|---|---|---|
| 4,704,381 A | 11/1987 | Schaumann et al. |
| 5,240,941 A | 8/1993 | Bruneau |
| 5,310,731 A | 5/1994 | Olsson et al. |
| 5,364,862 A | 11/1994 | Spada et al. |
| 5,420,419 A | 5/1995 | Wood |
| 5,428,125 A | 6/1995 | Hefner, Jr. et al. |
| 5,442,039 A | 8/1995 | Hefner, Jr. et al. |
| 5,506,347 A | 4/1996 | Erion et al. |
| 5,561,134 A | 10/1996 | Spada et al. |
| 5,563,257 A | 10/1996 | Zilch et al. |
| 5,593,997 A | 1/1997 | Dow et al. |
| 5,646,128 A | 7/1997 | Firestein et al. |
| 5,652,366 A | 7/1997 | Spada et al. |
| 5,654,307 A | 8/1997 | Bridges et al. |
| 5,665,721 A | 9/1997 | Bhagwat et al. |
| 5,674,998 A | 10/1997 | Boyer et al. |
| 5,686,455 A | 11/1997 | Adams et al. |
| 5,736,554 A | 4/1998 | Spada et al. |
| 5,747,235 A | 5/1998 | Farid et al. |
| 5,756,711 A | 5/1998 | Zilch et al. |
| 5,763,596 A | 6/1998 | Boyer et al. |
| 5,763,597 A | 6/1998 | Ugarkar et al. |
| 5,763,885 A | 6/1998 | Murphy et al. |
| 5,795,977 A | 8/1998 | Ugarkar et al. |
| 5,824,492 A | 10/1998 | Hiles et al. |
| 5,858,753 A | 1/1999 | Chantry et al. |
| 5,914,488 A | 6/1999 | Sone |
| 5,919,808 A | 7/1999 | Petrie et al. |
| 5,922,753 A | 7/1999 | Petrie et al. |
| 5,948,776 A | 9/1999 | Petrie et al. |
| 5,965,573 A | 10/1999 | Petrie et al. |

(Continued)

FOREIGN PATENT DOCUMENTS

| | | |
|---|---|---|
| CA | 1338379 | 6/1996 |
| CN | 101602768 | 12/2009 |
| DE | 2004713 A1 | 8/1971 |
| EP | 0773023 A1 | 5/1997 |
| EP | 1020445 B1 | 8/2008 |

(Continued)

OTHER PUBLICATIONS

U.S. Appl. No. 14/106,479, filed Dec. 13, 2013, Knight et al.
U.S. Appl. No. 14/186,486, filed Feb. 21, 2014, Tanaka et al.
Abdel-Mohsen. Synthesis, Reactions and Antimicrobial Activity of 2-Amino-4-(8-quinolinol-5-yI)-1-(p-tolyl)-pyrrole-3-carbonitrile. Bull. Korean Chem. Soc. 2005;26(5):719-728.

(Continued)

*Primary Examiner* — Douglas M Willis
(74) *Attorney, Agent, or Firm* — Honigman Miller Schwartz and Cohn LLP; Lucy X. Yang; Jonathan P. O'Brien

(57) ABSTRACT

The present invention provides compounds of Formula I

Formula I

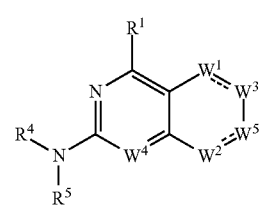

that modulate PI3 kinase activity and methods of treatment of diseases and conditions associated with PI3 kinase activity.

9 Claims, No Drawings

(56) References Cited

U.S. PATENT DOCUMENTS

| | | |
|---|---|---|
| 5,977,061 A | 11/1999 | Holy et al. |
| 5,981,533 A | 11/1999 | Traxler et al. |
| 5,985,589 A | 11/1999 | Chantry et al. |
| 5,990,169 A | 11/1999 | Petrie et al. |
| 5,994,358 A | 11/1999 | Petrie et al. |
| 6,001,839 A | 12/1999 | Calderwood et al. |
| 6,057,305 A | 5/2000 | Holy et al. |
| 6,084,095 A | 7/2000 | Bridges et al. |
| 6,093,737 A | 7/2000 | Anthony et al. |
| 6,127,121 A | 10/2000 | Meyer, Jr. et al. |
| 6,153,631 A | 11/2000 | Petrie et al. |
| 6,191,170 B1 | 2/2001 | Medina |
| 6,214,834 B1 | 4/2001 | Jadhav et al. |
| 6,251,901 B1 | 6/2001 | Petrie et al. |
| 6,265,410 B1 | 7/2001 | Bridges et al. |
| 6,268,370 B1 | 7/2001 | Adams et al. |
| 6,312,894 B1 | 11/2001 | Hedgpeth et al. |
| 6,319,660 B1 | 11/2001 | Allway et al. |
| 6,323,201 B1 | 11/2001 | Carson et al. |
| 6,342,514 B1 | 1/2002 | Petrie et al. |
| 6,350,741 B1 | 2/2002 | Golec et al. |
| 6,383,790 B1 | 5/2002 | Shokat |
| 6,384,039 B1 | 5/2002 | Fossa |
| 6,387,894 B1 | 5/2002 | Fossa |
| 6,390,821 B1 | 5/2002 | Shokat |
| 6,417,194 B1 | 7/2002 | Fox et al. |
| 6,455,534 B2 | 9/2002 | Bridges et al. |
| 6,472,153 B1 | 10/2002 | Dempcy et al. |
| 6,482,623 B1 | 11/2002 | Vanhaesebroeck et al. |
| 6,485,906 B2 | 11/2002 | Meyer, Jr. et al. |
| 6,492,346 B1 | 12/2002 | Hedgpeth et al. |
| 6,506,769 B2 | 1/2003 | Snow et al. |
| 6,518,277 B1 | 2/2003 | Sadhu et al. |
| 6,521,417 B1 | 2/2003 | Shokat |
| 6,521,620 B1 | 2/2003 | Bridges et al. |
| 6,531,491 B1 | 3/2003 | Kania et al. |
| 6,534,524 B1 | 3/2003 | Kania et al. |
| 6,545,005 B1 | 4/2003 | Price et al. |
| 6,552,192 B1 | 4/2003 | Hanus et al. |
| 6,562,819 B2 | 5/2003 | Carson et al. |
| 6,583,161 B1 | 6/2003 | Medina |
| 6,613,798 B1 | 9/2003 | Porter et al. |
| 6,624,119 B1 | 9/2003 | Reinhard et al. |
| 6,630,495 B1 | 10/2003 | Cooke et al. |
| 6,632,789 B1 | 10/2003 | June |
| 6,645,989 B2 | 11/2003 | Adams et al. |
| 6,649,631 B1 | 11/2003 | Orme et al. |
| 6,653,296 B1 | 11/2003 | Holy et al. |
| 6,653,306 B1 | 11/2003 | Alexander et al. |
| 6,660,744 B1 | 12/2003 | Hirst et al. |
| 6,660,845 B1 | 12/2003 | Gall et al. |
| 6,664,269 B2 | 12/2003 | Martin et al. |
| 6,667,300 B2 | 12/2003 | Sadhu et al. |
| 6,690,583 B1 | 2/2004 | Bergstedt et al. |
| 6,713,474 B2 | 3/2004 | Hirst et al. |
| 6,713,484 B2 | 3/2004 | Bridges et al. |
| 6,720,344 B2 | 4/2004 | Kerwin et al. |
| 6,734,187 B1 | 5/2004 | Ono et al. |
| 6,770,639 B2 | 8/2004 | Snow et al. |
| 6,777,425 B2 | 8/2004 | Burli et al. |
| 6,777,439 B2 | 8/2004 | Durden |
| 6,790,844 B2 | 9/2004 | Ueno et al. |
| 6,800,620 B2 | 10/2004 | Sadhu et al. |
| 6,800,633 B2 | 10/2004 | Castelhano et al. |
| 6,849,420 B2 | 2/2005 | Vanhaesebroeck et al. |
| 6,849,713 B2 | 2/2005 | Zhang et al. |
| 6,852,727 B2 | 2/2005 | Goulet et al. |
| 6,906,103 B2 | 6/2005 | Zhang et al. |
| 6,919,332 B2 | 7/2005 | Noe et al. |
| 6,921,763 B2 | 7/2005 | Hirst et al. |
| 6,949,535 B2 | 9/2005 | Sadhu et al. |
| 7,026,461 B1 | 4/2006 | Shokat |
| 7,041,676 B2 | 5/2006 | McDonald et al. |
| 7,049,116 B2 | 5/2006 | Shokat |
| 7,049,312 B1 | 5/2006 | Rafferty et al. |
| 7,064,218 B2 | 6/2006 | Dyatkina et al. |
| 7,071,355 B2 | 7/2006 | Leban et al. |
| 7,115,627 B2 | 10/2006 | Pinto et al. |
| 7,115,653 B2 | 10/2006 | Baxter et al. |
| 7,144,903 B2 | 12/2006 | Collins et al. |
| 7,148,228 B2 | 12/2006 | Kasibhatla et al. |
| 7,157,487 B2 | 1/2007 | Nakayama et al. |
| 7,166,293 B2 | 1/2007 | Teng et al. |
| 7,208,601 B2 | 4/2007 | Mjalli et al. |
| 7,217,794 B2 | 5/2007 | Abdel-Meguid et al. |
| 7,241,890 B2 | 7/2007 | Kasibhatla et al. |
| 7,244,741 B2 | 7/2007 | Simon et al. |
| 7,247,736 B2 | 7/2007 | Leban et al. |
| 7,262,204 B2 | 8/2007 | Collins et al. |
| 7,265,111 B2 | 9/2007 | Bigot et al. |
| 7,265,131 B2 | 9/2007 | Johnson et al. |
| 7,271,262 B2 | 9/2007 | La Greca et al. |
| 7,329,765 B2 | 2/2008 | Burli et al. |
| 7,332,497 B2 | 2/2008 | Hirst et al. |
| 7,348,427 B2 | 3/2008 | Burli et al. |
| 7,365,094 B2 | 4/2008 | Leban et al. |
| 7,384,967 B2 | 6/2008 | Polisetti et al. |
| 7,396,836 B2 | 7/2008 | Harada et al. |
| 7,414,036 B2 | 8/2008 | Sevillano et al. |
| 7,429,596 B2 | 9/2008 | Tanaka et al. |
| 7,439,254 B2 | 10/2008 | Bergnes |
| 7,459,462 B2 | 12/2008 | Simon et al. |
| 7,459,472 B2 | 12/2008 | Mjalli et al. |
| 7,470,721 B2 | 12/2008 | Durden |
| 7,501,538 B2 | 3/2009 | Mjalli et al. |
| 7,534,797 B2 | 5/2009 | Arnold et al. |
| 7,541,373 B2 | 6/2009 | Polisetti et al. |
| 7,569,571 B2 | 8/2009 | Dong et al. |
| 7,572,913 B2 | 8/2009 | McKerracher et al. |
| 7,579,348 B2 | 8/2009 | Wang et al. |
| 7,585,868 B2 | 9/2009 | Knight et al. |
| 7,608,594 B2 | 10/2009 | Blagg et al. |
| 7,615,552 B2 | 11/2009 | Ono et al. |
| 7,622,451 B2 | 11/2009 | Blagg et al. |
| 7,678,803 B2 | 3/2010 | Huang et al. |
| 7,700,607 B2 | 4/2010 | Hu et al. |
| 7,745,485 B2 | 6/2010 | Durden |
| 7,772,231 B2 | 8/2010 | Sheppard et al. |
| 7,932,260 B2 | 4/2011 | Fowler et al. |
| 8,476,282 B2 | 7/2013 | Ren et al. |
| 8,476,431 B2 | 7/2013 | Ren et al. |
| 2001/0024833 A1 | 9/2001 | Laborde et al. |
| 2001/0027197 A1 | 10/2001 | Bridges et al. |
| 2002/0016460 A1 | 2/2002 | Snow et al. |
| 2002/0016976 A1 | 2/2002 | Shokat |
| 2002/0037856 A1 | 3/2002 | Zhang et al. |
| 2002/0102590 A1 | 8/2002 | Taing et al. |
| 2002/0146690 A1 | 10/2002 | Meyer et al. |
| 2002/0147160 A1 | 10/2002 | Bhat et al. |
| 2002/0156081 A1 | 10/2002 | Hirst et al. |
| 2002/0161014 A1 | 10/2002 | Sadhu et al. |
| 2002/0173524 A1 | 11/2002 | Collins et al. |
| 2003/0001141 A1 | 1/2003 | Sun et al. |
| 2003/0008896 A1 | 1/2003 | Martin et al. |
| 2003/0018022 A1 | 1/2003 | Collins et al. |
| 2003/0022344 A1 | 1/2003 | Williams et al. |
| 2003/0064997 A1 | 4/2003 | Adams et al. |
| 2003/0073218 A1 | 4/2003 | Shokat et al. |
| 2003/0083268 A1 | 5/2003 | Burli et al. |
| 2003/0109248 A1 | 6/2003 | Lewis |
| 2003/0113765 A1 | 6/2003 | Dempcy et al. |
| 2003/0119479 A1 | 6/2003 | Arima et al. |
| 2003/0119791 A1 | 6/2003 | Kerwin et al. |
| 2003/0139427 A1 | 7/2003 | Castelhano et al. |
| 2003/0143602 A1 | 7/2003 | Meyer, Jr. et al. |
| 2003/0166929 A1 | 9/2003 | Snow et al. |
| 2003/0180924 A1 | 9/2003 | Desimone |
| 2003/0186987 A1 | 10/2003 | Bridges et al. |
| 2003/0187001 A1 | 10/2003 | Calderwood et al. |
| 2003/0195211 A1 | 10/2003 | Sadhu et al. |
| 2003/0199516 A1 | 10/2003 | Moser et al. |
| 2003/0212113 A1 | 11/2003 | Dyatkina et al. |
| 2003/0225098 A1 | 12/2003 | Hirst et al. |
| 2003/0232849 A1 | 12/2003 | Noe et al. |

(56) References Cited

U.S. PATENT DOCUMENTS

| | | |
|---|---|---|
| 2003/0235822 A1 | 12/2003 | Lokhov et al. |
| 2004/0039035 A1 | 2/2004 | Collins et al. |
| 2004/0043983 A1 | 3/2004 | Li |
| 2004/0067901 A1 | 4/2004 | Bhat et al. |
| 2004/0067915 A1 | 4/2004 | McMahon et al. |
| 2004/0072766 A1 | 4/2004 | June |
| 2004/0072788 A1 | 4/2004 | Bhat et al. |
| 2004/0102423 A1 | 5/2004 | MacLaughlan et al. |
| 2004/0102437 A1 | 5/2004 | Takami et al. |
| 2004/0110717 A1 | 6/2004 | Carroll et al. |
| 2004/0110945 A1 | 6/2004 | Nakayama et al. |
| 2004/0116689 A1 | 6/2004 | Gall et al. |
| 2004/0122235 A1 | 6/2004 | Polisetti et al. |
| 2004/0127434 A1 | 7/2004 | Bigot et al. |
| 2004/0176458 A1 | 9/2004 | Leban et al. |
| 2004/0176601 A1 | 9/2004 | Goulet et al. |
| 2004/0192758 A1 | 9/2004 | Leban et al. |
| 2004/0266780 A1 | 12/2004 | Sadhu et al. |
| 2005/0004149 A1 | 1/2005 | Harada et al. |
| 2005/0043239 A1 | 2/2005 | Douangpanya et al. |
| 2005/0049310 A1 | 3/2005 | Mjalli et al. |
| 2005/0054614 A1 | 3/2005 | Diacovo et al. |
| 2005/0059713 A1 | 3/2005 | Mjalli et al. |
| 2005/0085472 A1 | 4/2005 | Tanaka et al. |
| 2005/0101551 A1 | 5/2005 | Sevillano et al. |
| 2005/0124637 A1 | 6/2005 | Cheng et al. |
| 2005/0143317 A1 | 6/2005 | Abdel-Meguid et al. |
| 2005/0153997 A1 | 7/2005 | Simon et al. |
| 2005/0171148 A1 | 8/2005 | Mjalli et al. |
| 2005/0182045 A1 | 8/2005 | Nagase et al. |
| 2005/0187230 A1 | 8/2005 | Ding et al. |
| 2005/0187418 A1 | 8/2005 | Small et al. |
| 2005/0197340 A1 | 9/2005 | Arora et al. |
| 2005/0215579 A1 | 9/2005 | Simon et al. |
| 2005/0222177 A1 | 10/2005 | Sim et al. |
| 2005/0239809 A1 | 10/2005 | Watts et al. |
| 2005/0250770 A1 | 11/2005 | Ono et al. |
| 2005/0256066 A1 | 11/2005 | Abel et al. |
| 2005/0261317 A1 | 11/2005 | Sadhu et al. |
| 2005/0272751 A1 | 12/2005 | McKerracher et al. |
| 2006/0019988 A1 | 1/2006 | McDonald et al. |
| 2006/0069034 A1 | 3/2006 | Burli et al. |
| 2006/0079538 A1 | 4/2006 | Hallahan et al. |
| 2006/0106038 A1 | 5/2006 | Bouscary et al. |
| 2006/0116326 A1 | 6/2006 | Burli et al. |
| 2006/0135790 A1 | 6/2006 | Hyett et al. |
| 2006/0156485 A1 | 7/2006 | Lim |
| 2006/0166997 A1 | 7/2006 | Zhang et al. |
| 2006/0183783 A1 | 8/2006 | Polisetti et al. |
| 2006/0199776 A1 | 9/2006 | Blagg et al. |
| 2006/0235031 A1 | 10/2006 | Arnold et al. |
| 2006/0246551 A1 | 11/2006 | Stack et al. |
| 2006/0276470 A1 | 12/2006 | Jackson et al. |
| 2006/0287295 A1 | 12/2006 | Barlaam et al. |
| 2007/0015773 A1 | 1/2007 | Bergeron et al. |
| 2007/0027193 A1 | 2/2007 | Leban et al. |
| 2007/0032640 A1 | 2/2007 | Varghese et al. |
| 2007/0054915 A1 | 3/2007 | Arora et al. |
| 2007/0072897 A1 | 3/2007 | Mahaney et al. |
| 2007/0099871 A1 | 5/2007 | Davis et al. |
| 2007/0112005 A1 | 5/2007 | Chen et al. |
| 2007/0142405 A1 | 6/2007 | Dong et al. |
| 2007/0149521 A1 | 6/2007 | Crew et al. |
| 2007/0203143 A1 | 8/2007 | Sheppard et al. |
| 2007/0213355 A1 | 9/2007 | Capraro et al. |
| 2007/0224672 A1 | 9/2007 | Leban et al. |
| 2007/0249598 A1 | 10/2007 | Wang et al. |
| 2007/0254883 A1 | 11/2007 | Crew et al. |
| 2007/0270452 A1 | 11/2007 | Blagg et al. |
| 2007/0293489 A1 | 12/2007 | Adams et al. |
| 2007/0293516 A1 | 12/2007 | Knight et al. |
| 2008/0003254 A1 | 1/2008 | Mack et al. |
| 2008/0032960 A1 | 2/2008 | Knight et al. |
| 2008/0039491 A1 | 2/2008 | Ronan et al. |
| 2008/0058521 A1 | 3/2008 | Krishnan et al. |
| 2008/0070935 A1 | 3/2008 | Huang et al. |
| 2008/0119454 A1 | 5/2008 | Polisetti et al. |
| 2008/0119455 A1 | 5/2008 | Polisetti et al. |
| 2008/0119461 A1 | 5/2008 | Sin et al. |
| 2008/0200465 A1 | 8/2008 | Burli et al. |
| 2008/0249090 A1 | 10/2008 | Hu et al. |
| 2008/0261956 A1 | 10/2008 | Choi et al. |
| 2008/0287469 A1 | 11/2008 | Diacovo et al. |
| 2008/0292626 A1 | 11/2008 | Wang et al. |
| 2008/0293674 A1 | 11/2008 | Schwarz et al. |
| 2008/0306053 A1 | 12/2008 | Tachdjian et al. |
| 2008/0306093 A1 | 12/2008 | Servant et al. |
| 2008/0312180 A1 | 12/2008 | Liang et al. |
| 2008/0318942 A1 | 12/2008 | Simon et al. |
| 2009/0030023 A1 | 1/2009 | Harada et al. |
| 2009/0053192 A1 | 2/2009 | Millan et al. |
| 2009/0088452 A1 | 4/2009 | Coleman et al. |
| 2009/0099214 A1 | 4/2009 | Fairhurst et al. |
| 2009/0105233 A1 | 4/2009 | Chua et al. |
| 2009/0118283 A1 | 5/2009 | Defert et al. |
| 2009/0124638 A1 | 5/2009 | Shokat et al. |
| 2009/0124654 A1 | 5/2009 | Mjalli et al. |
| 2009/0163481 A1 | 6/2009 | Murphy et al. |
| 2009/0163709 A1 | 6/2009 | Blagg |
| 2009/0170879 A1 | 7/2009 | Szucova et al. |
| 2009/0181920 A1 | 7/2009 | Watkins et al. |
| 2009/0181988 A1 | 7/2009 | Tanaka et al. |
| 2009/0187014 A1 | 7/2009 | Blagg |
| 2009/0203689 A1 | 8/2009 | Dhalla et al. |
| 2009/0232768 A1 | 9/2009 | Birkus et al. |
| 2009/0247513 A1 | 10/2009 | Burli et al. |
| 2009/0253694 A1 | 10/2009 | Ono et al. |
| 2009/0264409 A1 | 10/2009 | Dong et al. |
| 2009/0264423 A2 | 10/2009 | Chua et al. |
| 2009/0270567 A1 | 10/2009 | Small et al. |
| 2009/0312319 A1 | 12/2009 | Ren et al. |
| 2009/0312406 A1 | 12/2009 | Hsieh et al. |
| 2009/0325967 A1 | 12/2009 | Fairhurst et al. |
| 2010/0009963 A1 | 1/2010 | Knight et al. |
| 2010/0022585 A1 | 1/2010 | deLong et al. |
| 2010/0029658 A1 | 2/2010 | Gavish et al. |
| 2010/0029693 A1 | 2/2010 | Douangpanya et al. |
| 2010/0048540 A1 | 2/2010 | Boyle et al. |
| 2010/0048882 A1 | 2/2010 | Blagg et al. |
| 2010/0056494 A1 | 3/2010 | Winzeler et al. |
| 2010/0105630 A1 | 4/2010 | Blagg |
| 2010/0184760 A1 | 7/2010 | Ren et al. |
| 2010/0190749 A1 | 7/2010 | Ren et al. |
| 2010/0273776 A1 | 10/2010 | Lindquist et al. |
| 2011/0046165 A1 | 2/2011 | Ren et al. |
| 2011/0077268 A1 | 3/2011 | Liu et al. |
| 2011/0124641 A1 | 5/2011 | Ren et al. |
| 2011/0144134 A1 | 6/2011 | Shokat et al. |
| 2011/0160232 A1 | 6/2011 | Ren et al. |
| 2011/0172228 A1 | 7/2011 | Ren et al. |
| 2011/0224223 A1 | 9/2011 | Shokat et al. |
| 2011/0269779 A1 | 11/2011 | Wilson et al. |
| 2011/0281866 A1 | 11/2011 | Ren et al. |
| 2011/0301144 A1 | 12/2011 | Knight et al. |
| 2012/0059000 A1 | 3/2012 | Ren et al. |
| 2012/0065154 A1 | 3/2012 | Tanaka et al. |
| 2012/0294930 A1 | 11/2012 | Ren et al. |
| 2012/0329776 A1 | 12/2012 | Ren et al. |
| 2014/0030256 A1 | 1/2014 | Ren et al. |
| 2014/0128599 A1 | 5/2014 | Ren et al. |

FOREIGN PATENT DOCUMENTS

| | | |
|---|---|---|
| GB | 812366 | 4/1959 |
| GB | 937725 | 9/1963 |
| GB | 1291417 A | 10/1972 |
| JP | 61109797 | 5/1986 |
| JP | 5256693 A | 10/1993 |
| JP | 8295667 A | 11/1996 |
| JP | 9143163 A | 6/1997 |
| JP | 10206995 A | 8/1998 |
| JP | 2000072773 A | 3/2000 |
| JP | 2002-037787 | 2/2002 |
| JP | 2002131859 A | 5/2002 |

(56) References Cited

FOREIGN PATENT DOCUMENTS

| | | |
|---|---|---|
| JP | 2003073357 A | 3/2003 |
| JP | 2004161716 A | 6/2004 |
| WO | WO 83/01446 A1 | 4/1983 |
| WO | WO 91/17161 A1 | 11/1991 |
| WO | WO 92/14733 A1 | 9/1992 |
| WO | WO 93/16091 A1 | 8/1993 |
| WO | WO 93/16092 A1 | 8/1993 |
| WO | WO 93/18035 A1 | 9/1993 |
| WO | WO 93/22443 A1 | 11/1993 |
| WO | WO 94/13677 A1 | 6/1994 |
| WO | WO 94/17803 A1 | 8/1994 |
| WO | WO 95/12588 A1 | 5/1995 |
| WO | WO 95/29673 A1 | 11/1995 |
| WO | WO 95/32984 A1 | 12/1995 |
| WO | WO 96/31510 A1 | 10/1996 |
| WO | WO 96/40706 A1 | 12/1996 |
| WO | WO 97/28133 A1 | 8/1997 |
| WO | WO 97/28161 A1 | 8/1997 |
| WO | WO 98/14450 A1 | 4/1998 |
| WO | WO 98/41525 A1 | 9/1998 |
| WO | WO 98/52611 A1 | 11/1998 |
| WO | WO 98/57952 A1 | 12/1998 |
| WO | WO 00/17202 A1 | 3/2000 |
| WO | WO 00/42042 A2 | 7/2000 |
| WO | WO 00/42042 A3 | 11/2000 |
| WO | WO 01/02369 A2 | 1/2001 |
| WO | WO 01/16114 A2 | 3/2001 |
| WO | WO 01/19829 A2 | 3/2001 |
| WO | WO 01/25238 A2 | 4/2001 |
| WO | WO 01/31063 A1 | 5/2001 |
| WO | WO 01/38584 A2 | 5/2001 |
| WO | WO 01/16114 A3 | 8/2001 |
| WO | WO 01/55140 A1 | 8/2001 |
| WO | WO 01/56988 A1 | 8/2001 |
| WO | WO 01/19829 A3 | 9/2001 |
| WO | WO 01/25238 A3 | 10/2001 |
| WO | WO 01/38584 A3 | 10/2001 |
| WO | WO 01/81346 A2 | 11/2001 |
| WO | WO 02/06192 A1 | 1/2002 |
| WO | WO 01/81346 A3 | 3/2002 |
| WO | WO 01/02369 A3 | 4/2002 |
| WO | WO 02/30944 A2 | 4/2002 |
| WO | WO 02/057425 A2 | 7/2002 |
| WO | WO 02/076986 A1 | 10/2002 |
| WO | WO 02/080926 A1 | 10/2002 |
| WO | WO 02/083143 A1 | 10/2002 |
| WO | WO 02/088025 A1 | 11/2002 |
| WO | WO 02/090334 A1 | 11/2002 |
| WO | WO 02/30944 A3 | 1/2003 |
| WO | WO 03/000187 A2 | 1/2003 |
| WO | WO 03/000688 A1 | 1/2003 |
| WO | WO 03/016275 A1 | 2/2003 |
| WO | WO 03/020880 A2 | 3/2003 |
| WO | WO 03/024969 A1 | 3/2003 |
| WO | WO 03/035075 A1 | 5/2003 |
| WO | WO 03/059884 A1 | 7/2003 |
| WO | WO 03/020880 A3 | 10/2003 |
| WO | WO 03/082341 A1 | 10/2003 |
| WO | WO 03/106426 A1 | 12/2003 |
| WO | WO 2004/006906 A2 | 1/2004 |
| WO | WO 2004/006906 A3 | 3/2004 |
| WO | WO 2004/018058 A2 | 3/2004 |
| WO | WO 2004/031177 A1 | 4/2004 |
| WO | WO 2004/039774 A2 | 5/2004 |
| WO | WO 2004/018058 A3 | 7/2004 |
| WO | WO 2004/039774 A3 | 7/2004 |
| WO | WO 03/000187 A3 | 8/2004 |
| WO | WO 2004/087053 A2 | 10/2004 |
| WO | WO 2004/111014 A1 | 12/2004 |
| WO | WO 2005/002585 A1 | 1/2005 |
| WO | WO 2005/007085 A2 | 1/2005 |
| WO | WO 2005/012323 A2 | 2/2005 |
| WO | WO 2005/016348 A1 | 2/2005 |
| WO | WO 2005/016349 A1 | 2/2005 |
| WO | WO 2005/016528 A2 | 2/2005 |
| WO | WO 2005/021533 A1 | 3/2005 |
| WO | WO 02/057425 A3 | 4/2005 |
| WO | WO 2005/012323 A3 | 5/2005 |
| WO | WO 2005/016528 A3 | 5/2005 |
| WO | WO 2005/044181 A2 | 5/2005 |
| WO | WO 2005/047289 A1 | 5/2005 |
| WO | WO 2005/061460 A1 | 7/2005 |
| WO | WO 2005/063258 A1 | 7/2005 |
| WO | WO 2005/067901 A2 | 7/2005 |
| WO | WO 2005/074603 A2 | 8/2005 |
| WO | WO 2005/007085 A3 | 9/2005 |
| WO | WO 2005/085248 A1 | 9/2005 |
| WO | WO 2005/097800 A1 | 10/2005 |
| WO | WO 2005/105760 A1 | 11/2005 |
| WO | WO 2005/067901 A3 | 12/2005 |
| WO | WO 2005/112935 A1 | 12/2005 |
| WO | WO 2005/113556 A1 | 12/2005 |
| WO | WO 2005/117889 A1 | 12/2005 |
| WO | WO 2005/120511 A1 | 12/2005 |
| WO | WO 2005/044181 A3 | 3/2006 |
| WO | WO 2006/030032 A1 | 3/2006 |
| WO | WO 2006/038865 A1 | 4/2006 |
| WO | WO 2006/050501 A2 | 5/2006 |
| WO | WO 2006/050946 A1 | 5/2006 |
| WO | WO 2006/068760 A2 | 6/2006 |
| WO | WO 2004/087053 A3 | 8/2006 |
| WO | WO 2006/089106 A2 | 8/2006 |
| WO | WO 2006/108107 A1 | 10/2006 |
| WO | WO 2006/112666 A1 | 10/2006 |
| WO | WO 2005/074603 A3 | 11/2006 |
| WO | WO 2006/114064 A2 | 11/2006 |
| WO | WO 2006/114065 A2 | 11/2006 |
| WO | WO 2006/114180 A1 | 11/2006 |
| WO | WO 2006/068760 A3 | 12/2006 |
| WO | WO 2006/089106 A3 | 12/2006 |
| WO | WO 2007/002293 A2 | 1/2007 |
| WO | WO 2007/006547 A1 | 1/2007 |
| WO | WO 2007/020046 A1 | 2/2007 |
| WO | WO 2007/002293 A3 | 3/2007 |
| WO | WO 2007/023115 A2 | 3/2007 |
| WO | WO 2007/025090 A2 | 3/2007 |
| WO | WO 2007/023115 A3 | 4/2007 |
| WO | WO 2006/050501 A3 | 5/2007 |
| WO | WO 2007/061737 A2 | 5/2007 |
| WO | WO 2006/114064 A3 | 6/2007 |
| WO | WO 2006/114065 A3 | 6/2007 |
| WO | WO 2007/025090 A3 | 6/2007 |
| WO | WO 2007/075554 A2 | 7/2007 |
| WO | WO 2007/079164 A2 | 7/2007 |
| WO | WO 2007/095223 A2 | 8/2007 |
| WO | WO 2007/075554 A3 | 9/2007 |
| WO | WO 2007/103308 A2 | 9/2007 |
| WO | WO 2007/106503 A2 | 9/2007 |
| WO | WO 2007/112005 A2 | 10/2007 |
| WO | WO 2007/114926 A2 | 10/2007 |
| WO | WO 2007/121453 A2 | 10/2007 |
| WO | WO 2007/121920 A2 | 11/2007 |
| WO | WO 2007/121924 A2 | 11/2007 |
| WO | WO 2007/124405 A2 | 11/2007 |
| WO | WO 2007/124854 A1 | 11/2007 |
| WO | WO 2007/125310 A2 | 11/2007 |
| WO | WO 2007/125315 A2 | 11/2007 |
| WO | WO 2007/126841 A2 | 11/2007 |
| WO | WO 2007/134828 A1 | 11/2007 |
| WO | WO 2007/135380 A2 | 11/2007 |
| WO | WO 2007/135398 A1 | 11/2007 |
| WO | WO 2007/061737 A3 | 12/2007 |
| WO | WO 2007/125315 A3 | 12/2007 |
| WO | WO 2007/121920 A3 | 1/2008 |
| WO | WO 2008/012326 A1 | 1/2008 |
| WO | WO 2007/103308 A3 | 2/2008 |
| WO | WO 2007/112005 A3 | 2/2008 |
| WO | WO 2007/125310 A3 | 3/2008 |
| WO | WO 2008/025755 A1 | 3/2008 |
| WO | WO 2008/031594 A1 | 3/2008 |
| WO | WO 2008/037477 A1 | 4/2008 |
| WO | WO 2008/047821 A1 | 4/2008 |
| WO | WO 2007/106503 A3 | 5/2008 |
| WO | WO 2008/063625 A2 | 5/2008 |

(56) References Cited

FOREIGN PATENT DOCUMENTS

| | | |
|---|---|---|
| WO | WO 2008/064018 A1 | 5/2008 |
| WO | WO 2007/121453 A3 | 7/2008 |
| WO | WO 2007/135380 A3 | 7/2008 |
| WO | WO 2008/063625 A3 | 7/2008 |
| WO | WO 2008/079028 A1 | 7/2008 |
| WO | WO 2008/082487 A2 | 7/2008 |
| WO | WO 2008/083070 A1 | 7/2008 |
| WO | WO 2008/094737 A2 | 8/2008 |
| WO | WO 2007/121924 A3 | 9/2008 |
| WO | WO 2008/112715 A2 | 9/2008 |
| WO | WO 2007/114926 A3 | 10/2008 |
| WO | WO 2008/118454 A2 | 10/2008 |
| WO | WO 2008/118455 A1 | 10/2008 |
| WO | WO 2008/118468 A1 | 10/2008 |
| WO | WO 2008/125014 A1 | 10/2008 |
| WO | WO 2008/125207 A1 | 10/2008 |
| WO | WO 2008/127226 A2 | 10/2008 |
| WO | WO 2007/126841 A3 | 11/2008 |
| WO | WO 2008/112715 A3 | 11/2008 |
| WO | WO 2008/118454 A3 | 11/2008 |
| WO | WO 2008/136457 A1 | 11/2008 |
| WO | WO 2007/124405 A2 | 12/2008 |
| WO | WO 2008/082487 A3 | 12/2008 |
| WO | WO 2008/127226 A3 | 12/2008 |
| WO | WO 2009/000412 A1 | 12/2008 |
| WO | WO 2009/004621 A1 | 1/2009 |
| WO | WO 2009/010925 A2 | 1/2009 |
| WO | WO 2009/021990 A1 | 2/2009 |
| WO | WO 2009/023718 A2 | 2/2009 |
| WO | WO 2008/094737 A3 | 3/2009 |
| WO | WO 2009/023718 A3 | 4/2009 |
| WO | WO 2009/044707 A1 | 4/2009 |
| WO | WO 2009/050506 A2 | 4/2009 |
| WO | WO 2009/059304 A2 | 5/2009 |
| WO | WO 2009/064802 A2 | 5/2009 |
| WO | WO 2009/010925 A3 | 7/2009 |
| WO | WO 2009/064802 A3 | 7/2009 |
| WO | WO 2009/088986 A1 | 7/2009 |
| WO | WO 2009/088990 A1 | 7/2009 |
| WO | WO 2009/059304 A3 | 8/2009 |
| WO | WO 2009/100406 A2 | 8/2009 |
| WO | WO 2007/079164 A3 | 9/2009 |
| WO | WO 2009/114874 A2 | 9/2009 |
| WO | WO 2009/117157 A1 | 9/2009 |
| WO | WO 2009/050506 A3 | 11/2009 |
| WO | WO 2009/100406 A3 | 11/2009 |
| WO | WO 2009/114874 A3 | 12/2009 |
| WO | WO 2010/009207 A1 | 1/2010 |
| WO | WO 2010/019210 A2 | 2/2010 |
| WO | WO 2010/036380 A1 | 4/2010 |
| WO | WO 2010/039534 A2 | 4/2010 |
| WO | WO 2010/019210 A3 | 5/2010 |
| WO | WO 2010/051043 A1 | 5/2010 |
| WO | WO 2010/039534 A3 | 8/2010 |
| WO | WO 2010/088050 A2 | 8/2010 |
| WO | WO 2010/099139 A2 | 9/2010 |
| WO | WO 2010/099139 A3 | 10/2010 |
| WO | WO 2010/118367 A2 | 10/2010 |
| WO | WO 2010/088050 A3 | 11/2010 |
| WO | WO 2010/129816 A2 | 11/2010 |
| WO | WO 2010/118367 A3 | 3/2011 |

OTHER PUBLICATIONS

Ames et al., "Heterocyclic Synthesis from o-Halogen-acids. Part II. Thienopyridinones and Thienopyranones from 3- bromothiophene -2- and 4-Bromothiophene-3-Carboxylic Acids", Journal of the Chemical Society, Perkin Transactions 1, Jan., 14:1390-1395 (1975).

Andrews, R.C., et al. "Effects of the 11β-Hydroxysteroid Dehydrogenase Inhibitor Carbenoxolone on Insulin Sensitivity in Men with Type 2 Diabetes", J. Clin. Endocrinol. Metab. (2003) 88(1):285-291.

Apsel, et al. Targeted polypharmacology: discovery of dual inhibitors of tyrosine and phosphoinositide kinases. Nat Chem Biol. Nov. 2008;4(11):691-9.

Arnold, et al. "Pyrrolo[2,3-d]pyrimidines containing an extended 5-substituent as potent and selective inhibitors of lck I", Bioorg. & Med. Chem. Lett (2000) 10:2167-70.

Banker, G.S., et al. Modem Pharmaceutics, 3ed, Marcel Dekker, New York, 1996, pp. 451-596.

Barf, T. et al. "Arylsulfonamidothiazoles as a New Class of Potential Antidiabetic Drugs. Discovery of Potent and Selective Inhibitors of the 11β-Hydroxysteroid Dehydrogenase Type 1", J. Med. Chem. (2002) 45(18):3813-3815.

Barnes, P.J., et al. "Efficacy and Safety of Inhaled Corticosteroids in Asthma", Am. Rev. Respir. Dis. (1993) 148:S1-26.

Basotest®, "Test Kit for the Quantitative Determination of the Degranulation of Basophilic Granulocytes in Heparinized Human Whole Blood", [www.biocarta.com/TDS/10-0500.pdf], Retrieved from the Internet Nov. 29, 2011.

Beeram, et al. Akt-induced endocrine therapy resistance is reversed by inhibition of mTOR signaling. Ann Oncol. Aug. 2007;18(8):1323-8.

Bell, G., et al. "Glucokinase Mutations Insulin Secretion, and Diabetes Mellitus", Annu. Rev. Physiol., (1996) 58:171-186.

Bhat, et al. Pyrazotopyrimidine nucleosides. 12. Synthesis and biological activity of certain pyrazolo[3,4-d]pyrimidine nucleosides related to adenosine. J Med Chem. Oct. 1981;24(10):1165-72.

Bishop, A.C. et al. "Generation of monospecific nanomolar tyrosine kinase inhibitors via a chemical genetic approach", Journal of the American Chemical Society, American Chemical Society, Washington, DC, US, vol. 121, No. 4, 1999, pp. 627-631.

Bogert, et al. "Researches on quinazolines (Fifteenth paper), on a 3-aminoquinazoline, and the corresponding 3.3'-diquinazolyl, from 6-nitroacetanthranil and hydrazine hydrate" Journal of the American Chemical Society, (1906), 28(7), 884-893.

Bohren, K.M., et al. "Expression, Crystallization and Preliminary Crystallographic Analysis of Human Carbonyl Reductase", J. Mol. Biol. (1994) 224:659-664.

Cámpora, et al. Binuclear complexes of nickel bridged by hydrocarbon ligands. Isocyanide insertion chemistry and amide formation by intramolecular coupling of acyl and imidoyl functionalities. Organometallics. Jan. 1992;11(1):11-13.

Cámpora, et al. Isocyanide insertion chemistry. Synthesis and structural characterization of bridging imidoyl complexes of nickel and amide formation by intramolecular coupling of acyl and imidoyl functionalities. Organometallics. Oct. 1993;12(10):4025-31.

Chaisuparat, et al. Dual Inhibition of PI3K(alpha) and mTOR as an Alternative Treatment for Kaposi's Sarcoma. Cancer Research. 2008;68:8361.

Chappelow, et al. Neovascular Age-Related Macular Degeneration: Potential Therapies. Drugs. 2008;68(8):1029-1036.

Cox, B., et al. "Human Colorectal Cancer Cells Efficiently Conjugate the Cyclopentenone Prostaglandin, Prostaglandin J2 to Glutathione", Biochim. Biophys. Acta (2002) 1584:37-45.

Davis, et al. The Preparation of Substituted 1(2H)-Isoquinolinones from Dilithiated 2-Methyl-N-arylbenzamides, 2-Methyl-N-(arylmethyl)-benzamides, or 2-Methylbenzoic Acid, 2,2-Dimethylhydrazide. Synthetic Communications. Sep. 1997;27(17):2961-9.

Diederich, S., et al. "In the Search for Specific Inhibitors of Human 11β-Hydroxysteroid-Dehydrogenases (11β-HSDs): Chenodeoxycholic Acid Selectively Inhibits 11β-HSD-I", Eur. J. Endocrinol. (2000) 142:200-207.

Dijksman, et al. 271. 1 : 2-Dihydro-2-thianaphthalene derivatives. Part I. Preparation and reactions of 1 : 2-dihydro-1-keto-2-thianaphthalenes. J. Chem. Soc. 1951:1213-18.

Ding, S., et al. "A Combinatorial Scaffold Approach Toward Kinase-Directed Heterocycle Libraries", J. Am. Chem. Soc. (2002) 124(8):1594-1596.

Ding, S., et al. "A Concise and Traceless Linker Strategy Toward Combinatorial Libraries of 2,6,9-Substituted Purines", J. Org. Chem. (2001) 66:8273-8276.

(56) References Cited

OTHER PUBLICATIONS

Ding, S., et al. "Resin-Capture and Release Strategy Toward Combinatorial Libraries of 2,6,9-Substituted Purines", J. Comb. Chem.(2002) 4:183-186.
Donati. Emerging Therapies for Neovascular Age-Related Macular Degeneration: State of the Art. Ophthalmologica. 2007;221:366-377.
Elslager, et al. "Synthetic schistosomicides. VII. 6-Alkoxy-8-(aminoalkyl)amino-5-azoquinolines" Journal of Medicinal Chemisty (1964), 7(5) 663-4.
European Examination Report dated Sep. 14, 2011 for EP Application No. 07873406.8, 4 pages.
European extended search report and search opinion dated Jan. 31, 2012 for EP Application No. 09795147.9.
European search report and search opinion dated Oct. 26, 2011 for Application No. 9700424.6.
European search report dated Jan. 4, 2013 for EP Application No. 12175019.4.
European search report dated Feb. 4, 2011 for EP Application No. 05857011.0.
European search report dated Feb. 24, 2010 for EP Application No. 07754845.1.
European Search Report dated Mar. 1, 2010 for EP Application No. 07873406.8.
Examination report dated Oct. 27, 2010 for GB Application No. GB0819947.3.
Extended European Search Report from corresponding European Application No. 09700784.3 dated Oct. 28, 2011.
Fajans, S., et al."Maturity Onset Diabetes of the Young (MODY)", Diabet. Med. (1996) 13:S90-S95.
Fan, et al. A dual phosphoinositide-3-kinase alpha/mTOR inhibitor cooperates with blockade of epidermal growth factor receptor in PTEN-mutant glioma. Cancer Res. Sep. 1, 2007;67(17):7960-5.
Farag, et al. Synthesis and reactivity of 2-(benzothiazol-2-yl)-1-bromo-1,2- ethanedione-1-arylhydrazones. Heteroatom Chemistry. 1997; 8(1):45-50.
Feinstein, M.B., et al. "Regulation of the Action of Hydrocotisone in Airway Epithelial Cells by 11β-Hydroxysteroid Dehydrogenase", Am. J. Respir. Cell. Mol. Biol. (1999) 21:403-408.
Feldman, et al. Active-site inhibitors of mTOR target rapamycin-resistant outputs of mTORC I and mTORC2. PLoS Biol. Feb. 10, 2009;7(2):371-383.
Fingl, E., et al. "General Principles", The Pharmacological Basis of Therapeutics, Fifth Edition (1975), Ch. 1, 1-46.
Forrest, G.L., et al. "Carbonyl Reductase", Chem. Biol. Interact. (2000) 129:21-40.
Forrest, G.L., et al. "Induction of a Human Carbonyl Reductase Gene Located on Chromosome 21", Biochim. Biophys. Acta. (1990) 1048:149-155.
Franzen, R. "The Suzuki, the Heck, and the Stine reaction—three versative methods for the introduction of new C—C bonds on solid support", Can J. Chem. (2000) 78:957-962.
Funder, J.W., et al. "Mineralocorticoid Action: Target Tissue Specificity Is Enzyme, Not Receptor, Mediated", Science (1998) 242:583-585.
Garber, M.E., et al. "Diversity of Gene Expression in Adenocarcinoma of the Lung", Proc. Nat. Acad. Sci. USA (2001) 98(24):13784-13789.
Gonzalez, B., et al. "Protection against Daunorubicin Cytotoxicity by Expression of a Cloned Human Carbonyl Reductase cDNA in K562 Leukemia Cells", Cancer Res. (1995) 55:4646-4650.
Graupera, et al. Angiogenesis selectively requires the p110 isoform of PI3K to control endothelial cell migration. Nature. 2008;453:662-666.
Haase, A.,et al. "Detection of Viral Nucleic Acids by in Situ Hybridization", Methods in Virology (1984) VII:189-226.
Hanefeld, U., et al. "One-pot Synthesis of Tetrasubstituted Pyrazoles Proof of Regiochemistry", J. Chem. Soc. Perkin Trans. (1996) 1:1545-1552.
Hansch, et al. "Quantitative structure-activity relation of antimalarial and dihydrofolate reductase inhibition by quinazolines and 5-substituted benzyl-2,4-diaminopyrirnidines" Journal of Medicinal Chemistry (1977), 20(1), 96-102.
Hellwinkel, et al. Heterocyclensynthesen mit MF/Al2O3-Basensystemen: 2-Arylbenzofurane and 2,3-Diarylisochinolin-1(2H)-one. Synthesis. 1995;1995(9):1135-41.
International Preliminary Report on Patentability and Written Opinion dated Apr. 19, 2011 for International Application No. PCT/US2009/060985, 6 pages.
International Preliminary Report on Patentability and Written Opinion dated Jan. 1, 2011 for International Application No. PCT/US2009/049969, 7 pages.
International Preliminary Report on Patentability and Written Opinion dated May 22, 2007 for International Application No. PCT/US2005/042524, 12 pages.
International Preliminary Report on Patentability and Written Opinion dated Nov. 4, 2008 for International Application No. PCT/US2007/008355, 7 pages.
International Preliminary Report on Patentability and Written Opinion dated Oct. 8, 2008 for International Application No. PCT/US2007/008395, 6 pages.
International Preliminary Report on Patentability from International Application No. PCT/US2009/000042 issued Jul. 6, 2010.
International search report and written opinion dated Jan. 15, 2010 for PCT/US2009/064717.
International search report and written opinion dated Jul. 22, 2005 for PCT/US2004/019782.
International search report and written opinion dated Aug. 22, 2011 for PCT/US2011/037412.
International search report and written opinion dated Nov. 20, 2009 for PCT/US2009/005380.
International search report and written opinion dated Dec. 11, 2008 for PCT Application No. US08/78990.
International search report and written opinion dated Mar. 15, 2010 for PCT Application No. US2009/049969.
International search report dated Feb. 17, 2010 for PCT Application No. US2009/049983.
International search report dated Apr. 5, 2006 for PCT/FR2005/051073.
International search report dated Aug. 27, 2008 for PCT/US2007/008395.
International search report dated Sep. 25, 2008 for PCT/US2007/008355.
International search report dated Jan. 11, 2010 for PCT Application No. US2009/05959.
International search report dated Jan. 12, 2010 for PCT Application No. US2009/05958.
International search report dated Oct. 2, 2006 for PCT/US2005/042524.
International search report dated Nov. 2, 2010 for PCT Application No. US10/02020.
International search report dated Dec. 24, 2009 for PCT Application No. IJS09/37313.
International search report dated Mar. 11, 2009 for PCT Application No. US2009/00038.
International search report dated Mar. 23, 2009 for PCT Application No. US2009/00042.
International search report dated Aug. 13, 2010 for PCT Applilcation No. US09/37324.
International Search Report dated Jun. 28, 2010 for International Application No. PCT/US2009/060985, 5 pages.
Ishiyama, T., et al. "A Stoichiometric Aromatic C—H Borylation Catalyzed by Iridium(I)/2,2'-Bipyridine Complexes at Room Temperature", Angew. Chem. Int. Ed. (2002) 41(16)3056-3058.
Ishiyama, T., et al. "Mild Iridium-Catalyzed Borylation of Arenes. High Turnover Numbers, Room Temperature Reactions, and Isolation of a Potential Intermediate", J. Am. Chem. Soc. (2002) 124(3):390-391.
Kajita, et al. Nickel-catalyzed decarbonylative addition of phthalimides to alkynes. J Am Chem Soc. May 14, 2008;130(19):6058-9.

(56) References Cited

OTHER PUBLICATIONS

Kallberg, et al. Short-Chain Dehydrogenase/Reductase (SDR) Relationships: a Large Family with Eight Clusters Common to Human, Animal, and Plant Genomes. Protein Sci. (2002) 11:636-641.
Kallberg, et al. Short-Chain Dehydrogenases/Reductases (SDRs). Eur. J. Biochem. (2002) 269:4409-4417.
Kim, et al. Activation and function of the mTORC1 pathway in mast cells. J Immunol. Apr. 1, 2008;180(7):4586-95.
Knight, et al. "A Pharmacological Map of the P13-K Family Defines a Role for p110α in Insulin Signaling", Cell (2006) 125:733-747.
Kost et al., "Recyclization of 3-Alkyl- and 1,3-Dialkylisoquinolinium Salts to Naphthylamines", Chemistry of Heterocyclic Compounds, Jan., 16(9):965-970 (1981).
Kraybill, B.C. et al. "Inhibitor scaffolds as new allele specific kinase substrates", Journal of the American Chemical Society, American Chemical Society, Washington, DC, US, vol. 124, No. 41, Oct. 16, 2002, pp. 12118-12128.
Kreutzberger, et al. 5-Substituierte 4-Aminopyrimidine dumb Aminomethinylierung von Acetonitrilen. Liebigs Ann. Chem. 1977:537-544.
Kumar et al., "Keten Dithioacetals. Part II. Reaction of 3-Cyano-4-Methylthio-2(1H)-pyridones with Hydazine and Guanidine: Synthesis of Novel Substituted and Fused Pyrazolo[4,3-c]pyridone and Pyrido[4,3-d]pyrimidine Derivatives", Journal of the Chemical Society, Perkin Transactions 1, Chemical Society, Letchworth, Jan., 8:857-862 (1978).
Kundu, et al. Palladium-Catalysed Heteroannulation with Terminal Alkynes: a Highly Regio- and Stereoselective Synthesis of (Z)-3-Aryl(alkyl)idene Isoindolin-1-ones1. Tetrahedron. Jun. 30, 2000;56(27):4777-92.
Kwok, B.H., et al. "The Anti-Inflammatory Natural Product Parthenolide from the Medicinal Herb Feverfew Directly Binds to and Inhibits IkB Kinase", Chem. Biol. (2001) 8:759-766.
Lee, et al. All roads lead to mTOR: integrating inflammation and tumor angiogenesis.. Cell Cycle. 2007;6(24):3011-3014.
Majumder, et al. mTOR inhibition reverses Akt-dependent prostate intraepithelial neoplasia through regulation of apoptotic and HIF-1-dependent pathways. Nature Medicine. 2004;10:594-601.
Mayer, T.U., et al. "Small Molecule Inhibitor of Mitotic Spindle Bipolarity Identified in a Pheontype-Based Screen", Science (1999) 286:971-974.
McMahon, et al. VEGF receptor signaling in tumor angiogenesis. The Oncologist. 2000; 5(suppl 1):3-10.
Mellinghoff, et al. TORward AKTually useful mouse models. Nature Medicine. 2004;10:579-580.
Miyaura, N., et al., "Palladium-Catalyzed Cross-Coupling Reactions of Organoboron Compounds," Chem. Rev. (1995) 95(7):2457-2483.
Modi, et at. Isoquinolones: Part IV—Synthesis of 3-Methyl, 3-Formyl & Other 3-Substituted N-Arylisoquinolones, Indian J. Chem. 1979; 18B:304-306.
Moon, H.S., et al. "A Novel Microtubule Destabilizing Entity from Orthogonal Synthesis of Triazine Library and Zebrafish Embryo Screening", J. Am. Chem. Soc. (2002) 124:11608-11609.
Nakanishi, M., et al. "Cloning and Sequence Analysis of a cDNA Encoding Tetrameric Carbonyl Reductase of Pig Lung", Biochem. Biophys. Acta (1993) 194(3):1311-1316.
Nemazanyi, et al. 3-Amino-4-aryl-1(2H)-isoquinolones. Chemistry of Heterocyclic Compounds. Mar. 1991;27(3):307-8.
Niswender, C.M., et al. "Protein Engineering of Protein Kinase A Catalytic Subunits Results in the Acquisition of Novel Inhibitor Sensitivity", The Journal of Biological Chemistry (2002) 277(32):28916-28922.
Nobel, C.S.I., et al. "Purification of Full-Length Recombinant Human and Rat Type 1 11β-hydroxysteroid Dehydrogenases with Retained Oxidoreductase Activities", Protein Expr. Purif. (2002) 26:349-356.
Oda, et al. PIK3CA Cooperates with Other Phosphatidylinositol 3'-Kinase Pathway Mutations to Effect Oncogenic Transformation. Cancer Research. 2008;68:8127.
Office action dated Feb. 8, 2013 for U.S. Appl. No. 12/509,281.

Office action dated Feb. 11, 2013 for U.S. Appl. No. 13/003,562.
Office action dated Feb. 27, 2013 for U.S. Appl. No. 12/920,970.
Office action dated Mar. 14, 2007 for U.S. Appl. No. 10/871,732.
Office action dated Mar. 23, 2006 for U.S. Appl. No. 10/871,732.
Office action dated May 10, 2012 for U.S. Appl. No. 12/586,241.
Office action dated May 10, 2012 for U.S. Appl. No. 12/586,309.
Office action dated May 29, 2012 for U.S. Appl. No. 12/509,281.
Office action dated Jun. 3, 2009 for U.S. Appl. No. 11/732,856.
Office action dated Jun. 20, 2012 for U.S. Appl. No. 11/719,722.
Office action dated Jul. 8, 2013 for U.S. Appl. No. 12/677,098.
Office action dated Oct. 11, 2011 for U.S. Appl. No. 11/719,722.
Office action dated Oct. 25, 2012 for U.S. Appl. No. 12/586,241.
Office action dated Oct. 25, 2012 for U.S. Appl. No. 12/586,309.
Office action dated Oct. 30, 2006 for U.S. Appl. No. 10/871,732.
Office action dated Nov. 20, 2007 for U.S. Appl. No. 10/871,732.
Office action dated Dec. 24, 2008 for U.S. Appl. No. 11/732,856.
Oppermann, U.C., et al. "Forms and Functions of Human SDR Enzymes", Chem. Biol. Interact. (2001) 130-132(1-3):699-705.
Ozaki, et al. Studies on 4 (1H)-Quinazolinones. IV. Convenient Syntheses of 12-Methyl-6H-isoquino [2,1-a] quinazolin-6-one and 6-Methyl-13H-quinazolino [3,4-a] quinazolin-13-one. Chem. Pharm. Bull. Jun. 25, 1984;32(6):2160-4.
Ozol, et al. Autoxidative transformations of 2-substituted 3-alkyl-4-hydroxy-1-oxo-1, 2-dihydroisoquinolines. Chemistry of Heterocyclic Compounds. Jun. 1978;14(6):644-8.
Patel, et al. Immunopathological aspects of age-related macular degeneration. Seminars in Immunopathology. 2008;30(2);97-110.
Persson, C.G. "Glucocorticoids for Asthma—Early Contributions", Pulm. Pharmacol. (1989) 2:163-166.
Petrie, et al. A novel biotinylated adenylate analogue derived from pyrazolo[3,4-d]pyrimidine for labeling DNA probes. Bioconjug Chem. Nov.-Dec. 1991;2(6):441-6.
Pinedo, et al. Translational research: the role of VEGF in tumor angiogenesis. The Oncologist. 2000; 5(suppl 1):1-2.
Pudlo, J.S., et al. "Synthesis, Antiproliferative, and Antiviral Activity of Certain 4-Substituted and 4,5 Disubstituted 7-[1,3-Dihydroxy-2-propoxy)methyl]pyrrolo[2,3-d]pyrimidines", J. Med. Chem. (1990) 33:1984-1992.
Report of the Expert Committee on the Diagnosis and Classification of Diabetes Mellitus. Diabetes Care (1992) 2(Suppl 1):S5-S19.
Richter, et al. "Inhibition of mammalian dihydrofolate reductase by selected 2,4-diaminoquinazolines and related compounds" Journal of Medicinal Chemistry (1974), 17(9), 943-7.
Robertson, R.P. "Eicosanoids and Human Disease", Harrison's Principles of Internal. Medicine, Isselbacher K.J., et al. (eds.), McGraw-Hill, New York City (1994) 1:431-435.
Romero, D.G., et al. "Cloning and Expression of the Bovine 11β—hydroxysteroid Dehydrogenase Type-2", J. Steroid Biochm. Mol. Biol. (2000) 72:231-237.
Singer, R.H., et al. "Optimization of in situ Hybridization Using Isotopic and Non-Isotopic Detection Methods", Biotechniques (1986) 4(3):230-250.
Soldan, M., et al. "Induction of Daunorubicin Carbonyl Reducing Enzymes by Daunorubicin in Sensitive and Resistant Pancreas Carcinoma Cells", Biochem. Pharmacol. (1996) 51:117-123.
Stanoeva et al. Homophthalic anhydrides and their application to the synthesis of heterocyclic compounds (review). Chemistry of Heterocyclic Compounds. Dec. 1984;20(12);1305-15.
Supplementary European Examination Report dated Sep. 20, 2011 for EP Application No. 07754845.1, 4 pages.
Takeuchi, et al. Synergistic augmentation of rapamycin-induced autophagy in malignant glioma cells by phosphatidylinositol 3-kinase/protein kinase B inhibitors. Cancer Res. Apr. 15, 2005;65(8):3336-46.
Tanaka, M., et al. "An Unbiased Cell Morphology-Based Screen for New, Biologically Active Small Molecules", PLoS Biology (2005) 3(5):0764-0776.
Tseng, et al. Synergistic interactions between imatinib mesylate and the novel phosphoinositide-dependent kinase-1 inhibitor OSU-03012 in overcoming imatinib mesylate resistance. Blood. May 15, 2005;105(10):4021-7. Epub Jan. 21, 2005.

(56) References Cited

OTHER PUBLICATIONS

Ugarkar, B.G., et al. "Adenosine Kinase Inhibitors. 2. Synthesis, Enzyme Inhibition, and Antiseizure Activity of Diaryltubercidin Analogues", J. Med. Chem. (2000) 43:2894-2905.

Vasilevsky et al., "Study of the Heterocyclization of vic-Substituted Hydrazides of Acetylenylpyrazolecarboxylic Acids into N-Amino Pyrazolopyridinones", Journal of Heterocyclic Chemistry, Nov., 39(6):1229-1233 (2002).

Vasilevsky et al., "Unexpected results in the heterocyclization of 5-acetylenylpyrazole-4-carboxylic acid hydrazides under the influence of CuCI: formatin of a diazepinone and dehydrodimerization into the corresponding bis(pyrazolo [4,3-d] [1,2] diazepinone)", Tetrahedron Letters, Jan., 46(26): 4457-4459 (2005).

Vopicka, et al. "Quinazolines. III. Interaction of aniline with 2-chloro-4-alkoxyquinazolines and 2-chloro-4-ketodihydroquinazoline" Journal of the American Chemical Society (1932), 54, 1068-1070.

White, P.C., et al. "11β—Hydroxysteroid Dehydrogenase and the Syndrome of Apparent Mineralocorticoid Excess", Endocr. Rev. (1997) 18(1):135-156.

Widler, L., et al. "7-Alkyl- and 7-Cycloalkyl-5-aryl-pyrrolo[2,3-d]pyrimidines-Potent Inhibitors of the Tyrosine Kinase c-Src," Bioorganic & Medicinal Chemistry Letters (2001) 11(6):849-852.

Wolff, M. E. Burger's Medicinal Chemistry, 5ed, Part 1, John Wiley & Sons, 1995, pp. 975-977.

Wu, et al. One-pot two-step microwave-assisted reaction in constructing 4,5-disubstituted pyrazolopyrimidines. Org Lett. Oct. 2, 2003;5(20):3587-90.

Yaguchi, et al. Antitumor activity of ZSTK474, a new phosphatidylinositol 3-kinase inhibitor. J. Natl. Cancer. Inst. 2006; 98(8): 545-556. Abstract only.

Office action dated Mar. 26, 2014 for U.S. Appl. No. 11/719,722.

Office action dated May 6, 2014 for U.S. Appl. No. 13/003,562.

Office action dated Oct. 4, 2013 for U.S. Appl. No. 13/002,438.

Office action dated Dec. 2, 2013 for U.S. Appl. No. 12/920,966.

Sam, et al. Benzoxazoles: Potent skeletal muscle relaxants. Pharm Sci. May 1964; 53:538-44.

West, et al. Activation of the PI3K/Akt pathway and chemotherapeutic resistance. Drug Resist Updat. Dec. 2002;5(6):234-48.

SUBSTITUTED QUINAZOLINES AS KINASE INHIBITORS

CROSS-REFERENCE TO RELATED APPLICATIONS

This application is a continuation of U.S. application Ser. No. 14/139,723 filed Dec. 23, 2013, which is a continuation of U.S. application Ser. No. 12/677,098 filed Feb. 7, 2013, which is a national phase of PCT/US2008/78990, filed Oct. 6, 2008, published as W02009/046448, which claims the benefit under 35 USC §119(e) of U.S. Provisional Application No. 60/997,922, filed on Oct. 4, 2007, each incorporated herein by reference in its entirety.

BACKGROUND OF THE INVENTION

The activity of cells can be regulated by external signals that stimulate or inhibit intracellular events. The process by which stimulatory or inhibitory signals are transmitted into and within a cell to elicit an intracellular response is referred to as signal transduction. Over the past decades, cascades of signal transduction events have been elucidated and found to play a central role in a variety of biological responses. Defects in various components of signal transduction pathways have been found to account for a vast number of diseases, including numerous forms of cancer, inflammatory disorders, metabolic disorders, vascular and neuronal diseases (Gaestel et al. *Current Medicinal Chemistry* (2007) 14:2214-2234).

Kinases represent a class of important signaling molecules. Kinases can generally be classified into protein kinases and lipid kinases, and certain kinases exhibit dual specificities. Protein kinases are enzymes that phosphorylate other proteins and/or themselves (i.e., autophosphorylation). Protein kinases can be generally classified into three major groups based upon their substrate utilization: tyrosine kinases which predominantly phosphorylate substrates on tyrosine residues (e.g., erb2, PDGF receptor, EGF receptor, VEGF receptor, src, abl), serine/threonine kinases which predominantly phosphorylate substrates on serine and/or threonine residues (e.g., mTor C1, mTor C2, ATM, ATR, DNA-PK, Akt), and dual-specificity kinases which phosphorylate substrates on tyrosine, serine and/or threonine residues.

Lipid kinases are enzymes that catalyze the phosphorylation of lipids within cells. These enzymes, and the resulting phosphorylated lipids and lipid derived biologically active organic molecules, play a role in many different physiological processes, including cell proliferation, migration, adhesion, and differentiation. A particular group of lipid kinases comprises membrane lipid kinases, i.e., kinases that catalyze the phosphorylation of lipids contained in or associated with cell membranes. Examples of such enzymes include phosphinositide(s) kinases (such as PI3-kinases, PI4-Kinases), diacylglycerol kinases, and sphingosine kinases.

The phosphoinositide 3-kinases (PI3Ks) signaling pathway is one of the most highly mutated systems in human cancers. PI3Ks are members of a unique and conserved family of intracellular lipid kinases that phosphorylate the 3'—OH group on phosphatidylinositols or phosphoinositides. The PI3K family comprises 15 kinases with distinct substrate specificities, expression patterns, and modes of regulation (Katso et al., 2001). The class I PI3Ks (p110α, p110β, p110δ, and p110γ) are typically activated by tyrosine kinases or G-protein coupled receptors to generate PIP3, which engages downstream effectors such as the Akt/PDK1 pathway, mTOR, the Tec family kinases, and the Rho family GTPases. The class II and III PI3-Ks play a key role in intracellular trafficking through the synthesis of PI(3)P and Pi(3,4)P2. The PIKKs are protein kinases that control cell growth (mTORC1) or monitor genomic integrity (ATM, ATR, DNA-PK, and hSmg-1).

Downstream mediators of the PI3K signal transduction pathway include Akt and mammalian target of rapamycin (mTOR). Akt possesses a plckstrin homology (PH) domain that binds PIP3, leading to Akt kinase activation. Akt phosphorylates many substrates and is a central downstream effector of PI3K for diverse cellular responses. Full activation of Akt typically requires phosphorylation of T308 in the activation loop and S473 in a hydrophobic motif. One important function of Akt is to augment the activity of mTOR, through phosphorylation of TSC2 and other mechanisms. mTOR is a serine-threonine kinase related to the lipid kinases of the PI3K family. mTOR has been implicated in a wide range of biological processes including cell growth, cell proliferation, cell motility and survival. Disregulation of the mTOR pathway has been reported in various types of cancer. mTOR is a multifunctional kinase that integrates growth factor and nutrient signals to regulate protein translation, nutrient uptake, autophagy, and mitochondrial function.

Dysregulation of signaling pathways mediated by many kinases is a key factor in the development of human diseases. Aberrant or excessive protein kinase activity or expression has been observed in many disease states including benign and malignant proliferative diseases, disorders such as allergic contact dermatitis, rheumatoid arthritis, osteoarthritis, inflammatory bowel diseases, chronic obstructive pulmonary disorder, psoriasis, multiple sclerosis, asthma, disorders related to diabetic complications, and inflammatory complications of the cardiovascular system such as acute coronary syndrome.

As such, kinases, particularly protein kinases and PI3Ks are prime targets for drug development. The present invention addresses a need in the art by providing a new class of kinase inhibitors.

SUMMARY OF THE INVENTION

In a first aspect, the invention provides a compound of Formula I and its pharmaceutically acceptable salts thereof:

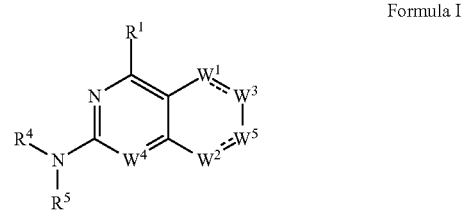

Formula I wherein $W^1$ is $CR^6$, $CHR^6$, $NR^6$ or N; $W^2$ is $CR^7$, N, or $NR^7$; $W^3$ is $CR^2$, $CHR^2$, N, or $NR^2$; $W^4$ is $CR^{11}$ or N; $W^5$ is $C(O)$, $CHR^3$, or $CR^3$; and no more than two adjacent ring atoms are N or $NR^7$. $R^1$ is hydrogen, amino, alkyl, alkoxy, aryl, heteroaryl, or cyano. $R^2$ is hydrogen, halo, amino, alkyl, cycloalkyl, heterocycloalkyl, aryl, or heteroaryl or X. $R^3$ is hydrogen, amino, alkyl, cycloalkyl, heterocycloalkyl, aryl, heteroaryl, or X. $R^4$ is hydrogen and $R^5$ is hydrogen, alkyl, cycloalkyl, heterocycloalkyl, aryl, heteroaryl, amino, alkoxycarbonyl, or acyl; or $R^4$ and $R^5$, taken together with any intervening atoms, form a heteroaryl ring. $R^6$ is hydrogen, halo, amino, alkoxy, lower alkyl, cyano, or X when $W^1$ is $CR^6$ or $CHR^6$; or $R^6$ is hydrogen or lower alkyl when $W^1$ is $NR^6$.

$R^7$ is hydrogen, halo, lower alkyl, or aryl; or $R^7$ and $R^3$, taken together with any intervening atoms, form a cycloalkyl, heterocycloalkyl, or heteroaryl ring. $R^8$ and $R^9$ are independently hydrogen, alkyl, cycloalkyl, heterocycloalkyl, aryl, and heteroaryl, or $R^8$ and $R^9$ taken together with any intervening atoms, form a heterocycloalkyl ring. $R^{19}$ is hydrogen, alkyl, cycloalkyl, heterocycloalkyl, aryl, or heteroaryl. $R^{11}$ is hydrogen, alkyl, cycloalkyl, heterocycloalkyl, aryl, heteroaryl, or X; or $R^{11}$ and $R^5$ taken together with any intervening atoms, form a heterocycloalkyl or heteroaryl ring. X is —C(O)NR$^8$R$^9$, —SO$_2$NR$^8$R$^9$, —NHC(O)NR$^8$R$^9$, or —NR$^8$C(O)R$^{10}$.

In a second aspect, the invention provides a compound of Formula I, and pharmaceutically acceptable salts thereof:

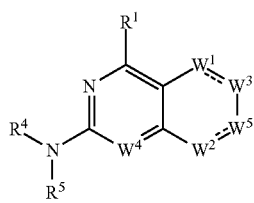

Formula I wherein W$^1$ is CR$^6$ or N; W$^2$ is CR$^7$, N, or NR$^7$; W$^3$ is CR$^2$, N, or NR$^2$; W$^4$ is CR$^{11}$ or N; W$^5$ is C(O), CHR$^3$, CR$^3$ or NR$^3$; and no more than two adjacent ring atoms are N or NR$^7$. $R^1$ is amino or methyl. $R^2$ is hydrogen, halo, alkyl, cycloalkyl, heterocycloalkyl, aryl, or heteroaryl. $R^3$ is hydrogen, alkyl, cycloalkyl, heterocycloalkyl, or X. $R^4$ is hydrogen and $R^5$ is hydrogen, alkyl, cycloalkyl, heterocycloalkyl, aryl, heteroaryl, amino, alkoxycarbonyl, or acyl; or $R^4$ and $R^5$, taken together with any intervening atoms, form a heteroaryl ring. $R^6$ is hydrogen, halo, or lower alkyl when W$^1$ is CR$^6$; or $R^6$ is hydrogen or lower alkyl when W$^1$ is N. $R^7$ is hydrogen, halo, lower alkyl, or aryl when W$^2$ is CR$^7$; or $R^7$ is hydrogen, lower alkyl, or aryl when W$^2$ is CR$^7$; or $R^7$ and $R^3$, taken together with any intervening atoms, form a cycloalkyl, heterocycloalkyl, or heteroaryl ring. $R^8$ and $R^9$ are independently hydrogen, alkyl, cycloalkyl, heterocycloalkyl, aryl, and heteroaryl, or $R^8$ and $R^9$ taken together with any intervening atoms, form a heterocycloalkyl ring. $R^{10}$ is hydrogen, alkyl, cycloalkyl, heterocycloalkyl, aryl, or heteroaryl. $R^{11}$ is hydrogen, alkyl, cycloalkyl, heterocycloalkyl, aryl, or heteroaryl; or $R^{11}$ and $R^5$ taken together with any intervening atoms, form a heterocycloalkyl or heteroaryl ring. X is —C(O)NR$^8$R$^9$, —SO$_2$NR$^8$R$^9$, —NHC(O)NR$^8$R$^9$, or —NR$^8$C(O)R$^{10}$.

In some embodiments the compound of Formula I is the compound wherein W$^2$ is NR$^7$. In other embodiments the compound of Formula I is the compound wherein W$^2$ is N. In further embodiments the compound of Formula I is the compound wherein W$^2$ is CR$^7$. In yet other embodiments the compound of Formula I is the compound wherein $R^7$ is hydrogen, halo, or lower alkyl. In some embodiments the compound of Formula I is the compound wherein $R^7$ is hydrogen.

In some embodiments the compound of Formula I is the compound wherein W$^5$ is CR$^3$. In some embodiments the compound of Formula I is the compound wherein $R^3$ is hydrogen, lower alkyl, cycloalkyl, heterocycloalkyl, or X. In some embodiments the compound of Formula I is the compound wherein $R^3$ is hydrogen, lower alkyl, cycloalkyl or X. In some embodiments the compound of Formula I is the compound wherein $R^3$ is hydrogen, lower alkyl, cyclopentyl, cyclohexyl or X. In some embodiments the compound of Formula I is the compound wherein $R^7$ and $R^3$, taken together with any intervening atoms, form a heteroaryl ring. In some embodiments the heteroaryl ring is substituted with an alkyl, cycloalkyl, or heterocycloalkyl group. In some embodiments the heteroaryl ring is a furanyl, imidazolyl, or pyrrolyl ring.

In some embodiments the compound of Formula I is the compound wherein X is —SO$_2$—NR$^8$R$^9$. In other embodiments the compound of Formula I is the compound wherein X is —NHC(O)—NR$^8$R$^9$. In yet other embodiments, the compound of Formula I is the compound wherein $R^8$ is alkyl, cycloalkyl, heterocycloalkyl, aryl, or heteroaryl and $R^9$ is hydrogen or alkyl. In some other embodiments, $R^9$ is hydrogen or lower alkyl. In some embodiments, $R^9$ is hydrogen. In other embodiments, $R^8$ is alkyl. In some embodiments, $R^5$ is lower alkyl. In some embodiments, $R^1$ is t-butyl or 2-hydroxyethyl.

In some embodiments the compound of Formula I is the compound wherein $R^1$ is methyl. In some embodiments the compound of Formula I is the compound wherein $R^1$ is methyl substituted by one or more halo. In other embodiments, $R^1$ is methyl substituted with one or more fluoro.

In some embodiments the compound of Formula I is the compound wherein $R^4$ is hydrogen and $R^5$ is hydrogen, amino, alkyl, aryl, amino, acyl, aminocarbonyl, alkoxycarbonyl, or heteroaryl. In other embodiments $R^5$ is hydrogen, lower alkyl, phenyl, or heteroaryl. In yet other embodiments, $R^5$ is hydrogen, methyl, ethyl, phenyl, pyridinyl, or pyrimidinyl. In some embodiments, $R^5$ is amino, acyl, aminocarbonyl, or alkoxycarbonyl. In some other embodiments the compound of Formula I is the compound wherein $R^4$ and $R^5$, taken together with any intervening atoms, form an imidazole ring. In yet other embodiments, $R^4$ and $R^5$, taken together with any intervening atoms, form a pyrazole ring.

In some embodiments the compound of Formula I is the compound wherein $R^{11}$ is hydrogen or alkyl. In other embodiments, $R^{11}$ is hydrogen or lower alkyl. In some embodiments, $R^{11}$ is hydrogen. In yet other embodiments the compound of Formula I is the compound wherein $R^{11}$ and $R^5$ taken together with any intervening atoms, form a heteroaryl ring.

In some embodiments the compound of Formula I is the compound wherein $R^2$ is heteroaryl. In some embodiments, $R^2$ is a 5- to 9-membered heteroaryl having at least one nitrogen ring atom. In other embodiments, the heteroaryl comprises up to two additional heteroatom ring atoms.

In some embodiments the compound of Formula I is the compound wherein W$^1$ is CR$^6$. In some embodiments, $R^6$ is hydrogen.

In some embodiments the compound of Formula I is the compound wherein W$^1$ is CR$^6$; W$^2$ is CR$^7$; W$^3$ is CR$^2$; and W$^4$ is CR$^{11}$. In some embodiments the compound of Formula I is the compound wherein W$^4$ is N.

In a third aspect, the invention provides a compound of Formula II and pharmaceutically acceptable salts thereof:

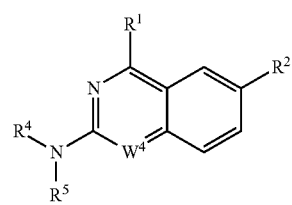

Formula II wherein W$^4$ is CR$^{11}$ or N. $R^1$ is hydrogen, amino, alkyl, alkoxy, aryl, heteroaryl, or cyano. $R^2$ is hydrogen, halo, alkyl, cycloalkyl, heterocycloalkyl, aryl, or heteroaryl. $R^4$ is hydrogen and $R^5$ is hydrogen, alkyl, cycloalkyl, heterocycloalkyl, aryl, heteroaryl, amino, alkoxycarbonyl, or acyl; or $R^4$ and $R^5$, taken together with any intervening atoms, form a heteroaryl ring. $R^{11}$ is hydrogen, alkyl, cycloalkyl, heterocycloalkyl, aryl, heteroaryl, or X.

In some embodiments the compound of Formula II is the compound wherein $W^4$ is N. In some embodiments the compound of Formula II is the compound wherein $R^1$ is amino or alkyl. In other embodiments, $R^1$ is methyl or methyl substituted by one or more halo. In yet other embodiments, $R^1$ is methyl substituted by one or more fluoro. In some embodiments the compound of Formula II is the compound wherein $R^2$ is aryl, or heteroaryl. In some embodiments, when $R^2$ is aryl, it is substituted at the meta position or at both meta positions. In some embodiments, $R^2$ is bicyclic. In some embodiments the compound of Formula II is the compound wherein $R^5$ is alkyl, aryl, or heteroaryl.

In some embodiments the compound of Formula I or Formula II inhibits a protein kinase. In some embodiments the compound of Formula I or Formula II inhibits a lipid kinase.

In a fourth aspect, the invention provides a pharmaceutical composition comprising a pharmaceutically acceptable carrier and a compound of Formula I or Formula II. In some embodiments, the pharmaceutical composition is formulated as a solid, semi-solid, liquid, or aerosol dosage form.

In a fifth aspect, the invention provides a method of modulating the catalytic activity of a PI3 kinase comprising contacting said PI3 kinase with an effective amount of a compound of Formula I or Formula II.

In a sixth aspect, the invention provides a method of treating a condition or disorder mediated by PI3 kinase activity in a subject in need of such treatment comprising administering to a mammal in need thereof a therapeutically effective amount of a compound of Formula I or Formula II. In some embodiments, the PI3 kinase related disorder is a cancer, bone disorder, inflammatory disease, immune disease, nervous system disease, metabolic disease, respiratory disease, or cardiac disease.

In some embodiments of the methods of the invention, the compound binds the p110α-affinity pocket of PI3 kinase.

In some embodiments of the methods of the invention, the method further comprises the step of administering a second therapeutic agent.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Provided are certain chemical entities that inhibit p110α kinase, pharmaceutical compositions and methods for treatment of diseases and conditions associated with p110α kinase.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this invention.

The compounds of the present invention may also contain unnatural proportions of atomic isotopes at one or more of atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are encompassed within the scope of the present invention.

When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

The following abbreviations and terms have the indicated meanings throughout
PI3-K=Phosphoinositide 3-kinase
PI=phosphatidylinositol
PDK=Phosphoinisitide Dependent Kinase
ATP=Adenosine Triphosphate
GTP=Guanosine Triphosphate
ATM=Ataxia Telangiectasia Mutated
DNA-PK=Deoxyribose Nucleic Acid Dependent Protein Kinase
PTEN=Phosphatase and Tensin homolog deleted on chromosome Ten
PIKK=Phoshoinositide Kinase Like Kinase
MMP=Matrix Metalloproteinase
PPAR=Peroxisome Proliferator Activated Receptor
PPar=Peroxisome Proliferator Activated Receptor
5-$HT_D$=5-HydroxyTryptamine
IGF=Insulin-like Growth Factor
TRH=Thyrotropin-releasing hormone
AIDS=Acquired Immuno Deficiency Syndrome
HIV=Human Immunodeficiency Virus
MeI=Methyl Iodide
$POCl_3$=Phosphorous Oxychloride
KCNS=Potasssium IsoThiocyanate
TLC=Thin Layer Chromatography
MeOH=Methanol
$CHCl_3$=Chloroform
cc=cubic centimeter
mL=milli Liter Abbreviations used herein have their conventional meaning within the chemical and biological arts.

By "optional" or "optionally" is meant that the subsequently described event or circumstance may or may not occur, and that the description includes instances where the event or circumstance occurs and instances in which it does not. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible, and/or inherently unstable.

"Alkyl" encompasses straight chain and branched chain having the indicated number of carbon atoms, usually from 1 to 20 carbon atoms, for example 1 to 8 carbon atoms, such as 1 to 6 carbon atoms. For example $C_1$-$C_6$ alkyl encompasses both straight and branched chain alkyl of from 1 to 6 carbon atoms. Another example is $C_1$-$C_4$ alkyl, which encompasses both straight and branched chain alkyls of from 1 to 4 carbon atoms. When an alkyl residue having a specific number of carbons is named, all branched and straight chain versions having that number of carbons are intended to be encompassed; thus, for example, "butyl" is meant to include n-butyl, sec-butyl, isobutyl and t-butyl; "propyl" includes n-propyl and isopropyl. "Lower alkyl" refers to alkyl groups having one to six carbons. In some embodiments, "lower alkyl" refers to alkyl groups comprising one to four carbons. Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, and the like. Alkylene is a subset of alkyl, referring to the same residues as alkyl, but having two points of attachment. Alkylene groups will usually have from 2 to 20 carbon atoms, for example 2 to 8 carbon atoms, such as from 2 to 6 carbon atoms. For example, $C_0$ alkylene indicates a covalent bond and $C_1$ alkylene is a methylene group.

"Alkenyl" refers to an unsaturated branched or straight-chain alkyl group having at least one carbon-carbon double bond derived by the removal of one molecule of hydrogen from adjacent carbon atoms of the parent alkyl. The group may be in either the cis or trans configuration about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl; butenyls such as but-1-en-1-yl, but-1-en-2-yl, but-2-en-1-yl, but-2-en-1-yl, but-2-en-2-yl, buta-1,3-dien-1-yl, buta-1,3-dien-2-yl; and the like. In certain embodiments, an alkenyl group has from 2 to 20 carbon atoms and in other embodiments, from 2 to 6 carbon atoms. "Lower alkenyl" refers to alkenyl groups having two to six carbons. In some embodiments, "lower alkenyl" refers to alkenyl groups having two to five carbons. In some embodiments, $C_2$-$C_5$ alkenyl refers to an alkenyl group, straight or branched, of from 2 to 5 carbon atoms.

"Alkynyl" refers to an unsaturated branched or straight-chain alkyl group having at least one carbon-carbon triple bond derived by the removal of two molecules of hydrogen from adjacent carbon atoms of the parent alkyl. Typical alkynyl groups include, but are not limited to, ethynyl; propynyls such as prop-1-yn-1-yl, prop-2-yn-1-yl; butynyls such as but-1-yn-1-yl, but-1-yn-3-yl, but-3-yn-1-yl; and the like. In certain embodiments, an alkynyl group has from 2 to 20 carbon atoms and in other embodiments, from 3 to 6 carbon atoms. "Lower alkynyl" refers to alkynyl groups having two to six carbons. In some embodiments, lower alkynyl can be alkynyl groups having two to five carbons. In some embodiments, $C_2$-$C_5$ alkynyl refers to an alkynyl group, straight or branched, of from 2 to 5 carbon atoms.

"Cycloalkyl" indicates a non-aromatic carbocyclic ring, usually having from 3 to 7 ring carbon atoms. The ring may be saturated or have one or more carbon-carbon double bonds. Examples of cycloalkyl groups include cyclopropyl, cyclobutyl, cyclopentyl, cyclopentenyl, cyclohexyl, and cyclohexenyl, as well as bridged and caged ring groups such as norbornane. In some embodiments, lower cycloalkyl can be a cycloalkyl group having from 3 to 5 ring carbon atoms.

"Alkoxy" refers to the group —O-alkyl, including from 1 to 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. "Lower alkoxy" refers to alkoxy groups containing one to six carbons. In some embodiments, lower alkoxy can be an alkoxy group containing one to four carbons. In some embodiments, $C_1$-$C_4$ alkyl, is an alkyl group which encompasses both straight and branched chain alkyls of from 1 to 4 carbon atoms.

"Substituted alkoxy" refers to alkoxy wherein the alkyl constituent is substituted (i.e., —O-(substituted alkyl)) wherein "substituted alkyl" refers to alkyl wherein one or more (such as up to 5, for example, up to 3) hydrogen atoms are replaced by a substituent independently chosen from:

—$R^a$, —$OR^b$, optionally substituted amino (including —$NR^cCOR^b$, —$NR^cCO_2R^a$, —$NR^cCONR^bR^c$, —$NR^bC(NR^c)NR^bR^c$, —$NR^bC(NCN)NR^bR^c$, and —$NR^cSO_2R^a$), halo, cyano, nitro, oxo (as a substituent for cycloalkyl, heterocycloalkyl, and heteroaryl), optionally substituted acyl (such as —$COR^b$), optionally substituted alkoxycarbonyl (such as —$CO_2R^b$), aminocarbonyl (such as —$CONR^bR^c$), —$OCOR^b$, —$OCO_2R^a$, —$OCONR^bR^c$, sulfanyl (such as $SR^b$), sulfanyl (such as —$SOR^a$), and sulfonyl (such as —$SO_2R^a$ and —$SO_2NR^bR^c$), where $R^a$ is chosen from optionally substituted $C_1$-$C_6$ alkyl, optionally substituted alkenyl, optionally substituted alkynyl, optionally substituted aryl, and optionally substituted heteroaryl;

$R^b$ is chosen from H, optionally substituted $C_1$-$C_6$ alkyl, optionally substituted cycloalkyl, optionally substituted heterocycloalkyl, optionally substituted aryl, and optionally substituted heteroaryl; and $R^c$ is independently chosen from hydrogen and optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —$OC_1$-$C_4$ alkyl, —$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —$N(C_1$-$C_4$ alkyl)($C_1$-$C_4$ alkyl), —$NH(C_1$-$C_4$ alkyl), —$N(C_1$-$C_4$ alkyl)($C_1$-$C_4$ alkylphenyl), —$NH(C_1$-$C_4$ alkylphenyl), cyano, nitro, oxo (as a substituent for cycloalkyl, heterocycloalkyl, or heteroaryl), —$CO_2H$, —$C(O)OC_1$-$C_4$ alkyl, —$CON(C_1$-$C_4$ alkyl)($C_1$-$C_4$ alkyl), —$CONH(C_1$-$C_4$ alkyl), —$CONH_2$, —$NHC(O)$ ($C_1$-$C_4$ alkyl), —$NHC(O)$(phenyl), —$N(C_1$-$C_4$ alkyl)C (O)($C_1$-$C_4$ alkyl), —$N(C_1$-$C_4$ alkyl)C(O)(phenyl), —$C(O)C_1$-$C_4$ alkyl, —$C(O)C_1$-$C_4$ alkylphenyl, —$C(O)$ $C_1$-$C_4$ haloalkyl, —$OC(O)C_1$-$C_4$ alkyl, —$SO_2(C_1$-$C_4$ alkyl), —$SO_2$(phenyl), —$SO_2(C_1$-$C_4$ haloalkyl), —$SO_2NH_2$, —$SO_2NH(C_1$-$C_4$ alkyl), —$SO_2NH$(phenyl), —$NHSO_2(C_1$-$C_4$ alkyl), —$NHSO_2$(phenyl), and —$NHSO_2(C_1$-$C_4$ haloalkyl).

In some embodiments, a substituted alkoxy group is "polyalkoxy" or —O-(optionally substituted alkylene)-(optionally substituted alkoxy), and includes groups such as —$OCH_2CH_2OCH_3$, and residues of glycol ethers such as polyethyleneglycol, and —$O(CH_2CH_2O)_xCH_3$, where x is an integer of 2-20, such as 2-10, and for example, 2-5. Another substituted alkoxy group is hydroxyalkoxy or —$OCH_2$ $(CH_2)_yOH$, where y is an integer of 1-10, such as 1-4.

"Alkoxycarbonyl" refers to a group of the formula (alkoxy) (C═O)— attached through the carbonyl carbon wherein the alkoxy group has the indicated number of carbon atoms. Thus a $C_1$-$C_6$ alkoxycarbonyl group is an alkoxy group having from 1 to 6 carbon atoms attached through its oxygen to a carbonyl linker. "Lower alkoxycarbonyl" refers to an alkoxycarbonyl group wherein the alkoxy group is a lower alkoxy group. In some embodiments, $C_1$-$C_4$ alkoxy, is an alkoxy group which encompasses both straight and branched chain alkoxy groups of from 1 to 4 carbon atoms.

"Substituted alkoxycarbonyl" refers to the group (substituted alkyl)-O—C(O)— wherein the group is attached to the parent structure through the carbonyl functionality and wherein substituted refers to alkyl wherein one or more (such as up to 5, for example, up to 3) hydrogen atoms are replaced by a substituent independently chosen from:

$R^a$, —$OR^b$, optionally substituted amino (including —$NR^cCOR^b$, —$NR^cCO_2R^a$, —$NR^cCONR^bR^c$, —$NR^bC(NRc)NR^bR^c$, —$NR^bC(NCN)NR^bR^c$, and —$NR^cSO_2R^a$), halo, cyano, nitro, oxo (as a substituent for cycloalkyl, heterocycloalkyl, and heteroaryl), optionally substituted acyl (such as —$COR^b$), optionally substituted alkoxycarbonyl (such as —$CO_2R^b$), aminocarbonyl (such as —$CONR^bR^c$), —$OCOR^b$, —$OCO_2R^a$, —$OCONR^bR^c$, sulfanyl (such as $SR^b$), sulfinyl (such as —$SOR^a$), and sulfonyl (such as —$SO_2R^a$ and —$SO_2NR^bR^c$), where $R^a$ is chosen from optionally substituted $C_1$-$C_6$ alkyl, optionally substituted alkenyl, optionally substituted alkynyl, optionally substituted aryl, and optionally substituted heteroaryl;

$R^b$ is chosen from H, optionally substituted $C_1$-$C_6$ alkyl, optionally substituted cycloalkyl, optionally substituted heterocycloalkyl, optionally substituted aryl, and optionally substituted heteroaryl; and $R^c$ is independently chosen from hydrogen and optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —$OC_1$-$C_4$ alkyl, —$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —$N(C_1$-$C_4$ alkyl)($C_1$-$C_4$ alkyl), —$NH(C_1$-$C_4$ alkyl), —$N(C_1$-$C_4$ alkyl)($C_1$-$C_4$ alkylphenyl), —$NH(C_1$-$C_4$ alkylphenyl), cyano, nitro, oxo (as a substituent for cycloalkyl, heterocycloalkyl, or heteroaryl), —$CO_2H$, —$C(O)OC_1$-$C_4$ alkyl, —$CON(C_1$-$C_4$ alkyl)($C_1$-$C_4$ alkyl), —$CONH(C_1$-$C_4$ alkyl), —$CONH_2$, —$NHC(O)(C_1$-$C_4$ alkyl), —$NHC(O)(phenyl)$, —$N(C_1$-$C_4$ alkyl)C(O)(C_1$-$C_4$ alkyl), —$N(C_1$-$C_4$ alkyl)C(O)(phenyl), —$C(O)C_1$-$C_4$ alkyl, —$C(O)C_1$-$C_4$ alkylphenyl, —$C(O)C_1$-$C_4$ haloalkyl, —$OC(O)C_1$-$C_4$ alkyl, —$SO_2(C_1$-$C_4$ alkyl), —$SO_2(phenyl)$, —$SO_2(C_1$-$C_4$ haloalkyl), —$SO_2NH_2$, —$SO_2NH(C_1$-$C_4$ alkyl), —$SO_2NH(phenyl)$, —$NHSO_2(C_1$-$C_4$ alkyl), —$NHSO_2(phenyl$, and —$NHSO_2(C_1$-$C_4$ haloalkyl).

"Acyl" refers to the groups (alkyl)-C(O)—, (aryl)-C(O)—, (heteroaryl)-C(O)—, and (heterocycloalkyl)-C(O)—, wherein the group is attached to the parent structure through the carbonyl functionality, and wherein alkyl, aryl, heteroaryl, and heterocycloalkyl are optionally substituted as described herein. Examples include acetyl, benzoyl, propionyl, isobutyryl, t-butoxycarbonyl, benzyloxycarbonyl and the like. "Lower-acyl" refers to groups containing one to six carbons and "acyloxy" refers to the group O-acyl. In some embodiments, "lower-acyl" refers to groups containing one to four carbons.

"Unsubstituted Amino" refers to the group —$NH_2$.

"Substituted amino" refers to the group —$NHR^d$ or —$NR^dR^e$ wherein $R^d$ is chosen from hydroxy, optionally substituted alkoxy, optionally substituted alkyl, optionally substituted cycloalkyl, optionally substituted acyl, optionally substituted carbamimidoyl, aminocarbonyl, optionally substituted aryl, optionally substituted heteroaryl, optionally substituted heterocycloalkyl, optionally substituted alkoxycarbonyl, sulfinyl and sulfonyl, and $R^e$ is chosen from optionally substituted alkyl, optionally substituted cycloalkyl, optionally substituted aryl, optionally substituted heteroaryl, and optionally substituted heterocycloalkyl, or $R^d$ and $R^e$ may optionally be taken together with the nitrogen to which they are bound, to form an optionally substituted 5- to 7-membered nitrogen-containing heterocycloalkyl which optionally includes or 2 additional heteroatoms selected from O, N, and S in the heterocycloalkyl ring;

and wherein substituted alkyl, cycloalkyl, aryl, heterocycloalkyl, and heteroaryl refer respectively to alkyl, cycloalkyl, aryl, heterocycloalkyl, and heteroaryl wherein one or more (such as up to 5, for example, up to 3) hydrogen atoms are replaced by a substituent independently chosen from:

—$R^a$, —$OR^b$, optionally substituted amino (including —$NR^cCOR^b$, —$NR^cCO_2R^a$, —$NR^cCONR^bR^c$, $NR^b$-$C(NR^c)NR^bR^c$, —$NR^bC(NCN)NR^bR^c$, and —$NR^cSO_2R^a$), halo, cyano, nitro, oxo (as a substituent for cycloalkyl, heterocycloalkyl, and heteroaryl), optionally substituted acyl (such as —$COR^b$), optionally substituted alkoxycarbonyl (such as —$CO_2R^b$), aminocarbonyl (such as —$CONR^bR^c$), —$OCOR^b$, —$OCO_2R^a$, —$OCONR^bR^c$, sulfanyl (such as $SR^b$), sulfinyl (such as —SOW), and sulfonyl (such as —$SO_2R^a$ and —$SO_2NR^bR^c$), where $R^a$ is chosen from optionally substituted $C_1$-$C_6$ alkyl, optionally substituted alkenyl, optionally substituted alkynyl, optionally substituted aryl, and optionally substituted heteroaryl;

$R^b$ is chosen from H, optionally substituted $C_1$-$C_6$ alkyl, optionally substituted cycloalkyl, optionally substituted heterocycloalkyl, optionally substituted aryl, and optionally substituted heteroaryl; and $R^c$ is independently chosen from hydrogen and optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —$OC_1$-$C_4$ alkyl, —$OC_1$-$C_4$ alkylphenyl, alkyl-OH, —$OC_1$-$C_4$ haloalkyl, halo, —OH, —$NH_2$, —$C_1$-$C_4$ alkyl-$NH_2$, —$N(C_1$-$C_4$ alkyl)($C_1$-$C_4$—$NH(C_1$-$C_4$ alkyl), —$N(C_1$-$C_4$ alkyl)($C_1$-$C_4$ alkylphenyl), —NH ($C_1$-$C_4$ alkylphenyl), cyano, nitro, oxo (as a substituent for cycloalkyl, heterocycloalkyl, or heteroaryl), —$CO_2H$, —$C(O)OC_1$-$C_4$ alkyl, —$CON(C_1$-$C_4$ alkyl) ($C_1$-$C_4$ alkyl), —$CONH(C_1$-$C_4$ alkyl), —$CONH_2$, —$NHC(O)(C_1$-$C_4$ alkyl), —$NHC(O)(phenyl)$, —$N(C_1$-$C_4$ alkyl)C(O)(C_1$-$C_4$ alkyl), —$N(C_1$-$C_4$ alkyl)C(O)(phenyl), —$C(O)C_1$-$C_4$ alkyl, —$C(O)C_1$-$C_4$ alkylphenyl, —$C(O)C_1$-$C_4$ haloalkyl, —OC(O)

C₁-C₄ alkyl, —SO₂(C₁-C₄ alkyl), —SO₂(phenyl), —SO₂(C₁-C₄ haloalkyl), —SO₂NH₂, —SO₂NH(C₁-C₄ alkyl), —SO₂NH(phenyl), —NHSO₂(C₁-C₄ alkyl), —NHSO₂(phenyl), and —NHSO₂(C₁-C₄ haloalkyl); and wherein optionally substituted acyl, optionally substituted alkoxycarbonyl, sulfinyl and sulfonyl are as defined herein.

"Substituted amino" also refers to N-oxides of the groups —NHR$^d$, and NR$^d$R$^d$ each as described above. N-oxides can be prepared by treatment of the corresponding amino group with, for example, hydrogen peroxide or m-chloroperoxybenzoic acid. The person skilled in the art is familiar with reaction conditions for carrying out the N-oxidation.

The term "aminocarbonyl", "amide", or "amido" refers to the group —CONR$^b$R$^c$ where R$^b$ is chosen from H, optionally substituted C₁-C₆ alkyl, optionally substituted cycloalkyl, optionally substituted heterocycloalkyl, optionally substituted aryl, and optionally substituted heteroaryl; and R$^c$ is independently chosen from hydrogen and optionally substituted C₁-C₄ alkyl; or R$^b$ and R$^c$ taken together with the nitrogen to which they are bound, form an optionally substituted 5- to 7-membered nitrogen-containing heterocycloalkyl which optionally includes 1 or 2 additional heteroatoms selected from O, N, and S in the heterocycloalkyl ring;

where each substituted group is independently substituted with one or more substituents independently selected from C₁-C₄ alkyl, aryl, heteroaryl, aryl-C₁-C₄ alkyl-, heteroaryl-C₁-C₄ alkyl-, C₁-C₄ haloalkyl, —OC₁-C₄ alkyl, —OC₁-C₄ alkylphenyl, alkyl-OH, —OC₁-C₄ haloalkyl, halo, —OH, —NH₂, —C₁-C₄ alkyl-NH₂, —N(C₁-C₄ alkyl)(C₁-C₄ alkyl), —NH(C₁-C₄—N(C₁-C₄ alkyl)(C₄-C₄ alkylphenyl), —NH(C₁-C₄ alkylphenyl), cyano, nitro, oxo (as a substituent for cycloalkyl, heterocycloalkyl, or heteroaryl), —CO₂H, —C(O)OC₄-C₄ alkyl, —CON(C₁-C₄ alkyl)(C₄-C₄ alkyl), —CONH (C₁-C₄ alkyl), —CONH₂, —NHC(O)(C₁-C₄ alkyl), —NHC(O)(phenyl), —N(C₁-C₄ alkyl)C(O)(C₁-C₄ alkyl), —N(C₁-C₄ alkyl)C(O)(phenyl), —C(O)C₄-C₄ alkyl, —C(O)C₄-C₄ alkylphenyl, —C(O)C₁-C₄ haloalkyl, —OC(O)C₁-C₄ alkyl, —SO₂(C₄-C₄ alkyl), —SO₂(phenyl), —SO₂(C₁-C₄ haloalkyl), —SO₂NH₂, —SO₂NH(C₄-C₄ alkyl), —SO₂NH(phenyl), —NHSO₂ (C₁-C₄ alkyl), —NHSO₂(phenyl), and —NHSO₂ (C₁-C₄ haloalkyl).

"Aryl" encompasses:

6-membered carbocyclic aromatic rings, for example, benzene;

bicyclic ring systems wherein at least one ring is carbocyclic and aromatic, for example, naphthalene, indane, and tetralin; and tricyclic ring systems wherein at least one ring is carbocyclic and aromatic, for example, fluorene.

For example, aryl includes 6-membered carbocyclic aromatic rings fused to a 5- to 7-membered heterocycloalkyl ring containing 1 or more heteroatoms chosen from N, O, and S. For such fused, bicyclic ring systems wherein only one of the rings is a carbocyclic aromatic ring, the point of attachment may be at the carbocyclic aromatic ring or the heterocycloalkyl ring. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene.

"Arylalkyl" refers to a moiety having an aryl moiety, as described herein, connected to an alkylene moiety, as described herein, wherein the connection to the remainder of the molecule is through the alkylene group.

"Halogen" or "halo" refers to fluorine, chlorine, bromine or iodine. Dihaloaryl, dihaloalkyl, trihaloaryl etc. refer to aryl and alkyl substituted with a plurality of halogens, but not necessarily a plurality of the same halogen; thus 4-chloro-3-fluorophenyl is within the scope of dihaloaryl.

"Heteroalkyl" refers to optionally substituted stright or branched alkyl moieties which have one or more skeletal chain atoms selected from an atom other than carbon, e.g., oxygen, nitrogen, sulfur, phosphorus or combinations thereof. A numerical range may be given, e.g. C₁-C₄ heteroalkyl which refers to the chain length in total, which in this example is 4 atoms long. For example, a —CH₂OCH₂CH₃ radical is referred to as a "C₄" heteroalkyl, which includes the heteroatom center in the atom chain length description. Connection to the rest of the molecule may be through either a heteroatom or a carbon in the heteroalkyl chain. In some embodiments, lower heteroalkyl can be a heteroalkyl group having 1 to 4 carbons.

"Heteroaryl" encompasses:

5- to 7-membered aromatic, monocyclic rings containing one or more, for example, from 1 to 4, or in certain embodiments, from 1 to 3, heteroatoms chosen from N, O, and S, with the remaining ring atoms being carbon;

bicyclic heterocycloalkyl rings containing one or more, for example, from 1 to 4, or in certain embodiments, from 1 to 3, heteroatoms chosen from N, O, and S, with the remaining ring atoms being carbon and wherein at least one heteroatom is present in an aromatic ring; and tricyclic heterocycloalkyl rings containing one or more, for example, from 1 to 5, or in certain embodiments, from 1 to 4, heteroatoms chosen from N, O, and S, with the remaining ring atoms being carbon and wherein at least one heteroatom is present in an aromatic ring.

For example, heteroaryl includes a 5- to 7-membered heterocycloalkyl, aromatic ring fused to a 5- to 7-membered cycloalkyl or heterocycloalkyl ring. For such fused, bicyclic heteroaryl ring systems wherein only one of the rings contains one or more heteroatoms, the point of attachment may be at either ring. When the total number of S and O atoms in the heteroaryl group exceeds 1, those heteroatoms are not adjacent to one another. In certain embodiments, the total number of S and O atoms in the heteroaryl group is not more than 2. In certain embodiments, the total number of S and O atoms in the aromatic heterocycle is not more than 1. Examples of heteroaryl groups include, but are not limited to azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzofuranonyl, benzofurazanyl, benzothiazolyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl,isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene. Heteroaryl does not encompass or overlap with aryl, cycloalkyl, or heterocycloalkyl, as defined herein Substituted heteroaryl also includes ring systems substituted with one or more oxide (—O⁻) substituents, such as pyridinyl N-oxides.

"Heteroarylalkyl" refers to a moiety having a heteroaryl moiety, as described herein, connected to an alkylene moiety, as described herein, wherein the connection to the remainder of the molecule is through the alkylene group.

"Heterocycloalkyl" or "Heterocyclyl" refers to a stable 3- to 18-membered non-aromatic ring (e.g., $C_3$-$C_{18}$ heterocyclyl) radical that comprises two to twelve carbon atoms and from one to six heteroatoms selected from nitrogen, oxygen and sulfur. Whenever it appears herein, a numerical range such as "3 to 18" refers to each integer in the given range; e.g., "3 to 18 ring atoms" means that the heteroaryl group may consist of 3 ring atoms, 4 ring atoms, etc., up to and including 18 ring atoms. In some embodiments, it is a $C_5$-$C_{10}$ heterocyclyl. In some embodiments, it is a $C_4$-$C_{10}$ heterocyclyl. In some embodiments, it is a $C_3$-$C_{10}$ heterocyclyl. Unless stated otherwise specifically in the specification, the heterocyclyl radical is a monocyclic, bicyclic, tricyclic or tetracyclic ring system, which may include fused or bridged ring systems. The heteroatoms in the heterocyclyl radical may be optionally oxidized. One or more nitrogen atoms, if present, are optionally quaternized. The heterocyclyl may be attached to the rest of the molecule through any atom of the ring(s). Examples of such heterocyclyl groups include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Substituted heterocycloalkyl also includes ring systems substituted with one or more oxo (=O) or oxide (—O) substituents, such as piperidinyl N-oxide, morpholinyl-N-oxide, 1-oxo-1-thiomorpholinyl and 1,1-dioxo-1-thiomorpholinyl.

"Heterocycloalkyl" also includes bicyclic ring systems wherein one non-aromatic ring, usually with 3 to 7 ring atoms, contains at least 2 carbon atoms in addition to 1-3 heteroatoms independently selected from oxygen, sulfur, and nitrogen, as well as combinations comprising at least one of the foregoing heteroatoms; and the other ring, usually with 3 to 7 ring atoms, optionally contains 1-3 heteroatoms independently selected from oxygen, sulfur, and nitrogen and is not aromatic.

"Urea" refers to the moiety —NHC(=O)NHR$^d$ or —NHC(=O)NR$^d$R$^e$ wherein R$^d$ and R$^e$ are as described for amino above and wherein R$^d$ and R$^e$ are optionally substituted by the same moieties as described for amino above.

"Isomers" are different compounds that have the same molecular formula. "Stereoisomers" are isomers that differ only in the way the atoms are arranged in space. "Enantiomers" are a pair of stereoisomers that are non-superimposable mirror images of each other. A 1:1 mixture of a pair of enantiomers is a "racemic" mixture. The term "(.±.)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R—S system. When a compound is a pure enantiomer the stereochemistry at each chiral carbon can be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry, as (R)- or (S)-. The present chemical entities, pharmaceutical compositions and methods are meant to include all such possible isomers, including racemic mixtures, optically pure forms and intermediate mixtures. Optically active (R)- and (S)- isomers can be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers.

"Tautomers" are structurally distinct isomers that interconvert by tautomerization. "Tautomerization" is a form of isomerization and includes prototropic or proton-shift tautomerization, which is considered a subset of acid-base chemistry. "Prototropic tautomerization" or "proton-shift tautomerization" involves the migration of a proton accompanied by changes in bond order, often the interchange of a single bond with an adjacent double bond. Where tautomerization is possible (e.g. in solution), a chemical equilibrium of tautomers can be reached. An example of tautomerization is keto-enol tautomerization. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are encompassed within the scope of the present invention.

A leaving group or atom is any group or atom that will, under the reaction conditions, cleave from the starting material, thus promoting reaction at a specified site. Suitable examples of such groups unless otherwise specified are halogen atoms, mesyloxy, p-nitrobenzensulphonyloxy and tosyloxy groups.

"Pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

Protecting group has the meaning conventionally associated with it in organic synthesis, i.e. a group that selectively blocks one or more reactive sites in a multifunctional compound such that a chemical reaction can be carried out selectively on another unprotected reactive site and such that the group can readily be removed after the selective reaction is complete. A variety of protecting groups are disclosed, for example, in T. H. Greene and P. G. M. Wuts, Protective Groups in Organic Synthesis, Third Edition, John Wiley & Sons, New York (1999). For example, a hydroxy protected form is where at least one of the hydroxy groups present in a compound is protected with a hydroxy protecting group. Likewise, amines and other reactive groups may similarly be protected.

"Pharmaceutically acceptable salt" refers to salts that retain the biological effectiveness and properties of the compounds described herein and, which are not biologically or otherwise undesirable. In many cases, the compounds described herein are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

"Solvate" refers to a compound (e.g., a compound selected from Formula I or a pharmaceutically acceptable salt thereof) in physical association with one or more molecules of a pharmaceutically acceptable solvent. It will be understood that "a compound of Formula I" encompass the compound of Formula I and solvates of the compound, as well as mixtures thereof.

"Substituted" alkyl, alkenyl, alkynyl, cycloalkyl, aryl, heteroalkyl, heterocycloalkyl, and heteroaryl, unless otherwise expressly defined, refer respectively to alkyl, alkenyl, alkynyl, cycloalkyl, aryl, heteroalkyl, heterocycloalkyl, and heteroaryl wherein one or more (such as up to 5, for example, up to 3) hydrogen atoms are replaced by a substituent independently chosen from:

$R^a$, —$OR^b$, optionally substituted amino (including —$NR^cCOR^b$, —$NR^cCO_2R^a$, —$NR^cCONR^bR^c$, —$NR^bC(NR^c)NR^bR^c$, —$NR^bC(NCN)NR^bR^c$, and —$NR^cSO_2R^a$), halo, cyano, nitro, oxo (as a substituent for cycloalkyl, heterocycloalkyl, and heteroaryl), optionally substituted acyl (such as —$COR^b$), optionally substituted alkoxycarbonyl (such as —$CO_2R^b$), aminocarbonyl (such as —$CONR^bR^c$), —$OCOR^b$, —$OCO_2R^a$, —$OCONR^bR^c$, sulfanyl (such as $SR^b$), sulfinyl (such as —$SOR^a$), and sulfonyl (such as —$SO_2R^a$ and —$SO_2NR^bR^c$), where $R^a$ is chosen from optionally substituted $C_1$-$C_6$ alkyl, optionally substituted cycloalkyl, optionally substituted heterocycloalkyl, optionally substituted alkenyl, optionally substituted alkynyl, optionally substituted aryl, and optionally substituted heteroaryl;

$R^b$ is chosen from hydrogen, optionally substituted $C_1$-$C_6$ alkyl, optionally substituted cycloalkyl, optionally substituted heterocycloalkyl, optionally substituted aryl, and optionally substituted heteroaryl; and $R^c$ is independently chosen from hydrogen and optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —$OC_1$-$C_4$ alkyl, —$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —$N(C_1$-$C_4$ alkyl)($C_1$-$C_4$ alkyl), —$NH(C_1$-$C_4$ alkyl), —$N(C_1$-$C_4$ alkyl)($C_1$-$C_4$ alkylphenyl), —$NH(C_1$-$C_4$ alkylphenyl), cyano, nitro, oxo (as a substituent for cycloalkyl or heterocycloalkyl), —$CO_2H$, —$C(O)C_1$-$C_4$ alkyl, —$CON(C_1$-$C_4$ alkyl)($C_1$-$C_4$—$CONH(C_1$-$C_4$ alkyl), —$CONH_2$, —$NHC(O)(C_1$-$C_4$ alkyl), —$NHC(O)$ (phenyl), —$N(C_1$-$C_4$ alkyl)$C(O)(C_1$-$C_4$ alkyl), —$N(C_1$-$C_4$ alkyl)$C(O)$(phenyl), —$C(O)C_1$-$C_4$ alkyl, —$C(O)C_1$-$C_4$ alkylphenyl, —$C(O)C_1$-$C_4$ haloalkyl, —$OC(O)C_1$-$C_4$ alkyl, —$SO_2(C_1$-$C_4$ alkyl), —$SO_2$(phenyl), —$SO_2$($C_1$-$C_4$ haloalkyl), —$SO_2NH_2$, —$SO_2NH(C_1$-$C_4$ alkyl), —$SO_2NH$(phenyl), —$NHSO_2(C_1$-$C_4$ alkyl), —$NHSO_2$ (phenyl), and —$NHSO_2(C_1$-$C_4$ haloalkyl).

"Sulfanyl" refers to the groups: —S-(optionally substituted alkyl), —S-(optionally substituted aryl), —S-(optionally substituted heteroaryl), and —S-(optionally substituted heterocycloalkyl).

"Sulfinyl" refers to the groups: —S(O)—H, —S(O)-(optionally substituted alkyl), —S(O)-(optionally substituted amino), —S(O)-(optionally substituted aryl), —S(O)-(optionally substituted heteroaryl), and —S(O)-(optionally substituted heterocycloalkyl).

"Sulfonyl" refers to the groups: —S(O$_2$)—H, —S(O$_2$)-(optionally substituted alkyl), —S(O$_2$)-(optionally substituted amino), —S(O$_2$)-(optionally substituted aryl), —S(O$_2$)-(optionally substituted heteroaryl), and —S(O$_2$)-(optionally substituted heterocycloalkyl).

"Sulfonamidyl" or "sulfonamido" refers to a —S(=O)$_2$—NRR radical, where each R is selected independently from the group consisting of hydrogen, alkyl, cycloalkyl, aryl, heteroaryl (bonded through a ring carbon) and heteroalicyclic (bonded through a ring carbon). In some embodiments, it is a $C_1$-$C_4$ sulfonamido, wherein each R in sulfonamido contains 1 carbon, 2 carbons, 3 carbons, or 4 carbons total. A sulfonamido group is optionally substituted by one or more of the substituents described for alkyl, cycloalkyl, aryl, heteroaryl respectively.

A "therapeutic effect," as that term is used herein, encompasses a therapeutic benefit and/or a prophylactic benefit. A prophylactic effect includes delaying or eliminating the appearance of a disease or condition, delaying or eliminating the onset of symptoms of a disease or condition, slowing, halting, or reversing the progression of a disease or condition, or any combination thereof.

"Therapeutically effective amount" or "effective amount" refers to that amount of a compound selected from Formula I that is sufficient to effect a certain action, such as treatment, as defined below, when administered to a mammal in need of such treatment; modulating the catalytic activity of PI3 kinase, such as when administered to an environment where modulation of the catalytic activity of a PI3 kinase, such as p110δ kinase, is desired; or disrupting the function of a leukocyte or osteoclast, such as when administered to an environment where disrupting the function of a leukocyte or osteoclast is desired. The therapeutically effective amount will vary depending upon the subject and disease condition being treated, the weight and age of the subject, the severity of the disease condition, the particular compound selected from Formula I, the dosing regimen to be followed, timing of administration, the manner of administration and the like, all of which can readily be determined by one of ordinary skill in the art.

Where substituent groups are specified by their conventional chemical formulae, written from left to right, they equally encompass the chemically identical substituents that would result from writing the structure from right to left, e.g., —CH$_2$O— is equivalent to —OCH$_2$—.

Compounds of Formula I also include crystalline and amorphous forms of those compounds, including, for example, polymorphs, pseudopolymorphs, solvates, hydrates, unsolvated polymorphs (including anhydrates), conformational polymorphs, and amorphous forms of the compounds, as well as mixtures thereof. "Crystalline form," "polymorph," and "novel form" may be used interchangeably herein, and are meant to include all crystalline and amorphous forms of the compound, including, for example, polymorphs, pseudopolymorphs, solvates, hydrates, unsolvated polymorphs (including anhydrates), conformational polymorphs, and amorphous forms, as well as mixtures thereof, unless a particular crystalline or amorphous form is referred to.

Chemical entities include, but are not limited to, compounds of Formula I, and all pharmaceutically acceptable forms thereof. Pharmaceutically acceptable forms of the compounds recited herein include pharmaceutically acceptable salts, chelates, non-covalent complexes, prodrugs, and mixtures thereof. In certain embodiments, the compounds described herein are in the form of pharmaceutically acceptable salts. Hence, the terms "chemical entity" and "chemical entities" also encompass pharmaceutically acceptable salts, chelates, non-covalent complexes, prodrugs, and mixtures.

"Pharmaceutically acceptable salts" include, but are not limited to salts with inorganic acids, such as hydrochlorate, phosphate, diphosphate, hydrobromate, sulfate, sulfinate, nitrate, and like salts; as well as salts with an organic acid, such as malate, maleate, fumarate, tartrate, succinate, citrate, acetate, lactate, methanesulfonate, p-toluenesulfonate, 2-hydroxyethylsulfonate, benzoate, salicylate, stearate, and alkanoate such as acetate, HOOC—(CH$_2$)$_n$—COOH where n ranges from 0 to 4, and like salts. Similarly, pharmaceutically acceptable cations include, but are not limited to sodium, potassium, calcium, aluminum, lithium, and ammonium.

In addition, if the compound of Formula I or Formula II is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

As noted above, prodrugs also fall within the scope of chemical entities, for example, ester or amide derivatives of the compounds selected from Formula I or Formula II. The term "prodrug" includes any compound that becomes a compound of Formula I or Formula II when administered to a patient, e.g., upon metabolic processing of the prodrug. Examples of prodrugs include, but are not limited to, acetate, formate, benzoate, and like derivatives of functional groups (such as alcohol or amine groups) in the compounds selected from Formula I or Formula II.

The term "chelate" refers to the chemical entity formed by the coordination of a compound to a metal ion at two (or more) points.

The term "non-covalent complex" refers to the chemical entity formed by the interaction of a compound and another molecule wherein a covalent bond is not formed between the compound and the molecule. For example, complexation can occur through van der Waals interactions, hydrogen bonding, and electrostatic interactions (also called ionic bonding).

The term "active agent" is used to indicate a chemical entity which has biological activity. In certain embodiments, an "active agent" is a compound having pharmaceutical utility.

By "significant" is meant any detectable change that is statistically significant in a standard parametric test of statistical significance such as Student's T-test, where $p<0.05$.

"Patient" refers to an animal, such as a mammal, for example a human, that has been or will be the object of treatment, observation or experiment. The methods described herein can be useful in both human therapy and veterinary applications. In some embodiments, the patient is a mammal, and in some embodiments, the patient is human.

"Treatment" or "treating" means any treatment of a disease in a patient, including: preventing the disease, that is, causing the clinical symptoms of the disease not to develop; inhibiting the disease; slowing or arresting the development of clinical symptoms; and/or relieving the disease, that is, causing the regression of clinical symptoms.

The term "selective inhibition" or "selectively inhibit" as referred to a biologically active agent refers to the agent's ability to preferentially reduce the target signaling activity as compared to off-target signaling activity, via direct or interact interaction with the target.

Compounds of the Invention

A compound of Formula I and its pharmaceutically acceptable salts is provided, wherein:

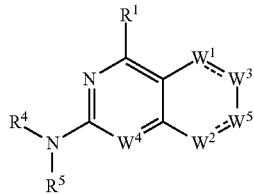

Formula I $W^1$ is $CR^6$, $CHR^6$, $NR^6$ or N;
$W^2$ is $CR^7$, N, or $NR^7$;
$W^3$ is $CR^2$, $CHR^2$, N, or $NR^2$;
$W^4$ is $CR^{11}$ or N;
$W^5$ is C(O), $CHR^3$, $CR^3$ or $NR^3$; and no more than two adjacent ring atoms are N or $NR^7$;
$R^1$ is hydrogen, amino, alkyl, alkoxy, aryl, heteroaryl, or cyano;
$R^2$ is hydrogen, halo, amino, alkyl, cycloalkyl, heterocycloalkyl, aryl, or heteroaryl or X;
$R^3$ is hydrogen, halo, amino, alkyl, cycloalkyl, heterocycloalkyl, aryl, heteroaryl, or X;
$R^4$ is hydrogen and $R^5$ is hydrogen, alkyl, cycloalkyl, heterocycloalkyl, aryl, heteroaryl, amino, alkoxycarbonyl, or acyl; or $R^4$ and $R^3$, taken together with any intervening atoms, form a heteroaryl ring;
$R^6$ is hydrogen, halo, amino, alkoxy, lower alkyl, cyano, or X when $W^1$ is $CR^6$ or $CHR^6$; or $R^6$ is hydrogen or lower alkyl when $W^1$ is $NR^6$;
$R^7$ is hydrogen, halo, lower alkyl, or aryl when $W^2$ is $CR^7$; or $R^7$ is hydrogen, lower alkyl, or aryl when $W^2$ is $NR^7$; or $R^7$ and $R^3$, taken together with any intervening atoms, form a cycloalkyl, heterocycloalkyl, or heteroaryl ring;
$R^8$ and $R^9$ are independently hydrogen, alkyl, cycloalkyl, heterocycloalkyl, aryl, and heteroaryl, or $R^8$ and $R^9$ takentogether with any intervening atoms, form a heterocycloalkyl ring;
$R^{10}$ is hydrogen, alkyl, cycloalkyl, heterocycloalkyl, aryl, or heteroaryl;
$R^{11}$ is hydrogen, alkyl, cycloalkyl, heterocycloalkyl, aryl, heteroaryl, or X; or $R^{11}$ and $R^5$ taken together with any intervening atoms, form a heterocycloalkyl or heteroaryl ring; and
X is $-C(O)NR^8R^9$, $-SO_2NR^8R^9$, $-NHC(O)NR^6R^9$, or $-NR^8C(O)R^{19}$.

In some embodiments, $W^1$ is $CR^6$.
In some embodiments, $W^1$ is $CHR^6$.
In some embodiments, $W^1$ is N.
In some embodiments, $W^1$ is $NR^6$.
In some embodiments, $W^2$ is $CR^7$.
In some embodiments, $W^2$ is N.
In some embodiments, $W^2$ is $NR^7$.
In some embodiments, $W^3$ is $CR^2$,
In some embodiments, $W^3$ is $CHR^2$.
In some embodiments, $W^3$ is N.
In some embodiments, $W^3$ is $NR^2$.
In some embodiments, $W^4$ is $CR^{11}$.
In some embodiments, $W^4$ is N.
In some embodiments, $W^5$ is C(O).
In some embodiments, $W^5$ is $CHR^3$.
In some embodiments, $W^5$ is $CR^3$.
In some embodiments, $W^5$ is $NR^3$.
In some embodiments, $W^1$ is $CR^6$, $W^3$ is $CR^2$, $W^5$ is $CR^3$, $W^2$ is $CR^7$, and $W^4$ is N.
In some embodiments, $W^1$ is $CR^6$, $W^3$ is $CR^2$, $W^5$ is $CR^3$, $W^2$ is $CR^7$, and $W^4$ is $CR^{11}$.
In some embodiments, $W^1$ is $CR^6$, $W^3$ is $CR^2$, $W^5$ is $CR^3$, $W^2$ is $NR^7$, and $W^4$ is N.
In some embodiments, $W^1$ is $CR^6$, $W^3$ is $CR^2$, $W^5$ is $CR^3$, $W^2$ is $NR^7$, and $W^4$ is $CR^{11}$.
In some embodiments, $W^1$ is $CR^6$, $W^3$ is $CR^2$, $W^5$ is $NR^3$, $W^2$ is $CR^7$, and $W^4$ is N.
In some embodiments, $W^1$ is $CR^6$, $W^3$ is $CR^2$, $W^5$ is $NR^3$, $W^2$ is $CR^7$, and $W^4$ is $CR^{11}$.
In some embodiments, $W^1$ is $CR^6$, $W^3$ is $CR^2$, $W^5$ is C(O), $W^2$ is $NR^7$, and $W^4$ is N.
In some embodiments, $W^1$ is $CR^6$, $W^3$ is $CR^2$, $W^5$ is C(O), $W^2$ is $NR^7$, and $W^4$ is $CR^{11}$.
In some embodiments, $W^1$ is $CHR^6$, $W^3$ is $CHR^2$, $W^5$ is C(O), $W^2$ is $NR^7$, and $W^4$ is N.
In some embodiments, $W^1$ is $CHR^6$, $W^3$ is $CHR^2$, $W^5$ is C(O), $W^2$ is $NR^7$, and $W^4$ is $CR^{11}$.
In some embodiments, $W^1$ is $CHR^6$, $W^3$ is $NR^2$, $W^5$ is C(O), $W^2$ is $NR^7$, and $W^4$ is N.
In some embodiments, $W^1$ is $CHR^6$, $W^3$ is $NR^2$, $W^5$ is C(O), $W^2$ is $NR^7$, and $W^4$ is $CR^{11}$.
In some embodiments, $W^1$ is $CHR^6$, $W^3$ is $NR^2$$W^5$ is $CR^3$, $W^2$ is $NR^7$, and $W^4$ is N.
In some embodiments, $W^1$ is $CHR^6$, $W^3$ is $NR^2$, $W^5$ is $CR^3$, $W^2$ is $NR^7$, and $W^4$ is $CR^{11}$.
In some embodiments, $W^1$ is $NR^6$, $W^3$ is $CHR^2$, $W^5$ is C(O), $W^2$ is $NR^7$, and $W^4$ is N.
In some embodiments, $W^1$ is $NR^6$, $W^3$ is $CHR^2$, $W^5$ is C(O), $W^2$ is $NR^7$, and $W^4$ is $CR^{11}$.
In some embodiments, $W^1$ is N, $W^3$ is $CR^2$, $W^5$ is $CR^3$, $W^2$ is $CR^7$, and $W^4$ is N.
In some embodiments, $W^1$ is N, $W^3$ is $CR^2$, $W^5$ is $CR^3$, $W^2$ is $CR^7$, and $W^4$ is $CR^{11}$.
In some embodiments, $W^1$ is N, $W^3$ is $CR^2$, $W^5$ is N, $W^2$ is $CR^7$, and $W^4$ is N.
In some embodiments, $W^1$ is N, $W^3$ is $CR^2$, $W^5$ is N, $W^2$ is $CR^7$, and $W^4$ is $CR^{11}$.

In some embodiments, $R^1$ is hydrogen. In some embodiments, $R^1$ is unsubstituted amino. In some embodiments, $R^1$ is substituted amino. In some embodiments, $R^1$ is unsubstituted alkyl. In some embodiments, $R^1$ is substituted alkyl. In some embodiments, $R^1$ is unsubstituted methyl. In some embodiments, $R^1$ is substituted methyl. In some embodiments, when $R^1$ is substituted methyl, it is substituted by one or more halo. In some embodiments, when $R^1$ is substituted methyl, it is substituted by one or more fluoro. In some embodiments, $R^1$ is unsubstituted alkoxy. In some embodiments, $R^1$ is substituted alkoxy. In some embodiments, $R^1$ is unsubstituted aryl. In some embodiments, $R^1$ is substituted aryl. In some embodiments, $R^1$ is unsubstituted heteroaryl. In some embodiments, $R^1$ is substituted heteroaryl. In some embodiments, $R^1$ is cyano.

In some embodiments, $R^2$ is hydrogen. In some embodiments, $R^2$ is halo. In some embodiments, $R^2$ is unsubstituted amino. In some embodiments, $R^2$ is substituted amino. In some embodiments, $R^2$ is unsubstituted alkyl. In some embodiments, $R^2$ is substituted alkyl. In some embodiments, $R^2$ is unsubstituted lower alkyl. In some embodiments, $R^2$ is substituted lower alkyl. In some embodiments, $R^2$ is unsubstituted cycloalkyl. In some embodiments, $R^2$ is substituted cycloalkyl. In some embodiments, $R^2$ is unsubstituted heterocycloalkyl. In some embodiments, $R^2$ is substituted heterocycloalkyl. In some embodiments, $R^2$ is unsubstituted aryl. In some embodiments, $R^2$ is substituted aryl. In some embodiments, $R^2$ is unsubstituted heteroaryl. In some embodiments, $R^2$ is substituted heteroaryl. In some embodiments, $R^2$ is X, wherein X is —C(O)NR$^8$R$^9$. In some embodiments, $R^2$ is X, wherein X is —C(O)NR$^8$R$^9$, and any of $R^8$ or $R^9$ are substituted. In some embodiments, $R^2$ is X, wherein X is —SO$_2$NR$^8$R$^9$. In some embodiments, $R^2$ is X, wherein X is —SO$_2$NR$^8$R$^9$, and any of $R^8$ or $R^9$ are substituted. In some embodiments, $R^2$ is X, wherein X is —NR$^8$C(O)R$^{10}$. In some embodiments, $R^2$ is X, wherein X is —NR$^8$C(O)R$^{10}$, and any of $R^8$ or $R^{10}$ are substituted.

In some embodiments, $R^2$ is a 5- to 9-membered heteroaryl having at least one nitrogen ring atom. In some embodiments, wherein $R^2$ is a 5- to 9-membered heteroaryl having at least one nitrogen ring atom, the heteroaryl ring comprises up to two additional heteroatom ring atoms. In some embodiments, $R^2$ is monocyclic. In some embodiments, $R^2$ is bicyclic.

In some embodiments, $R^2$ is one of the following moieties:

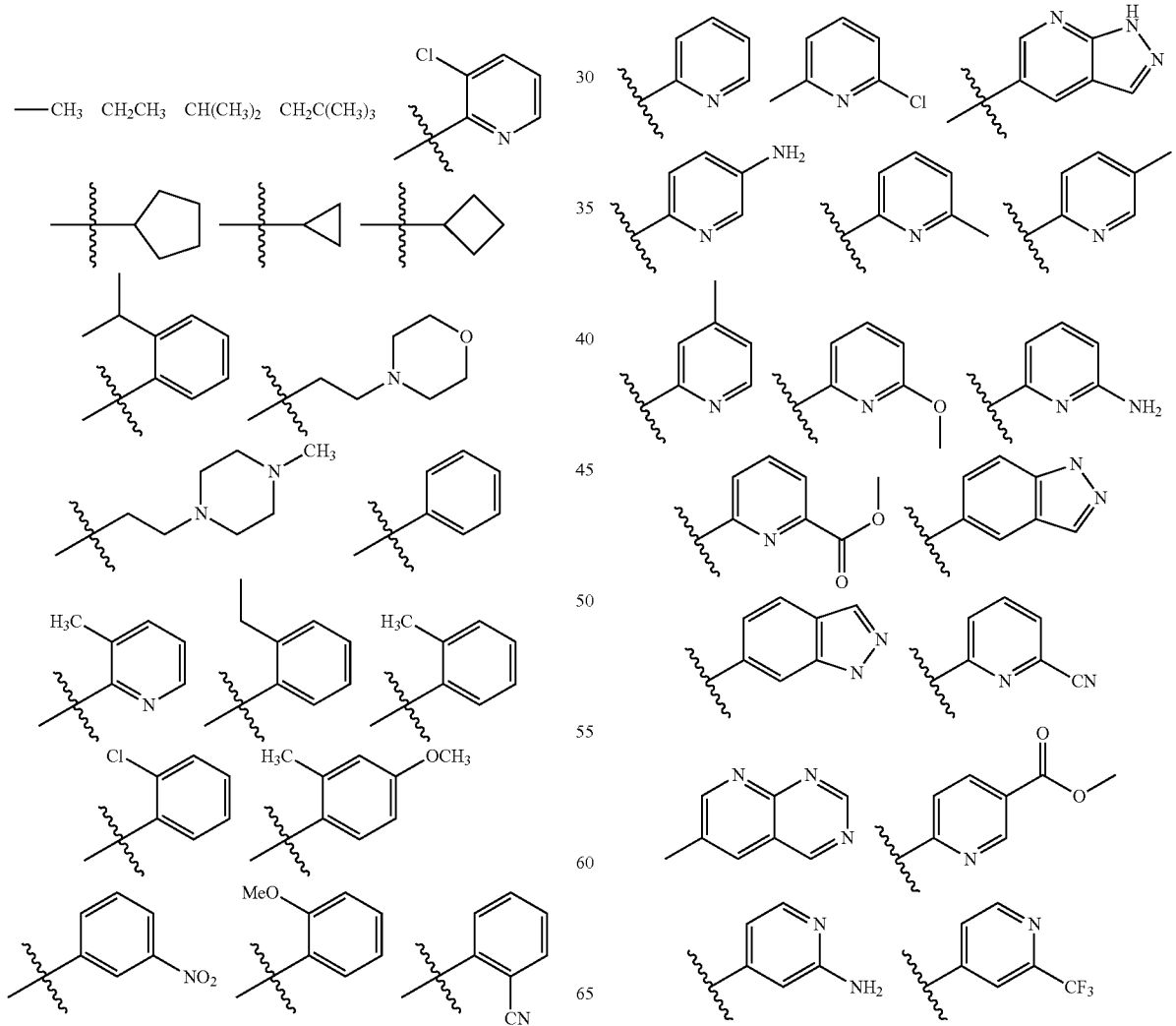

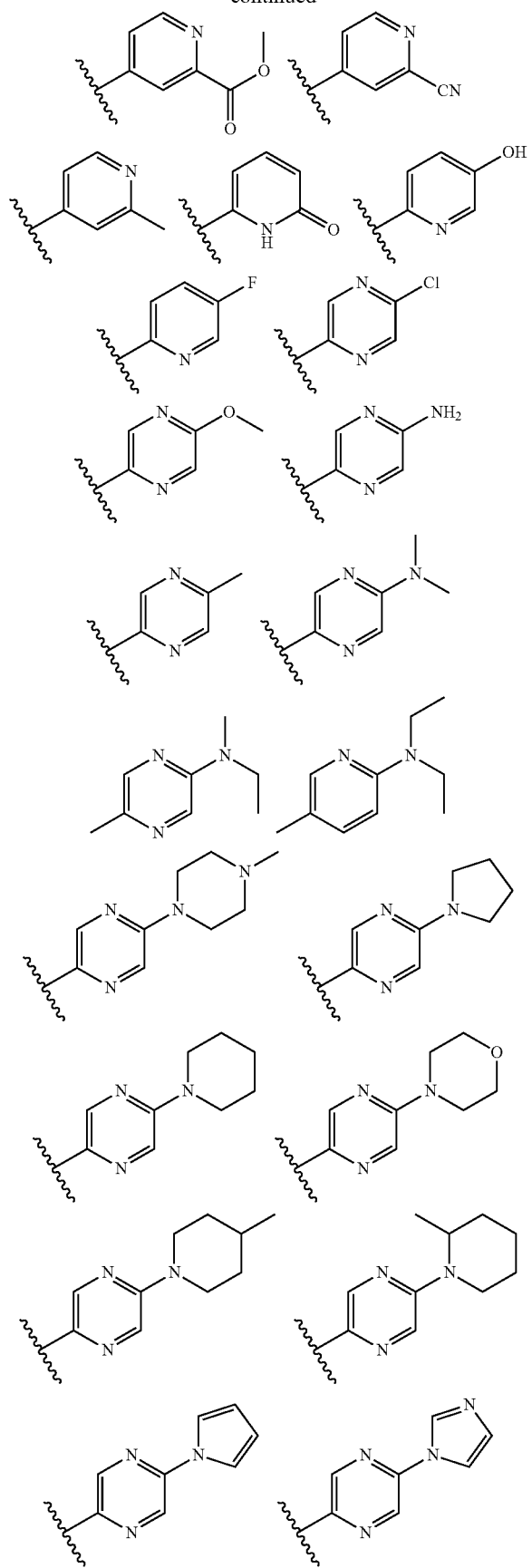
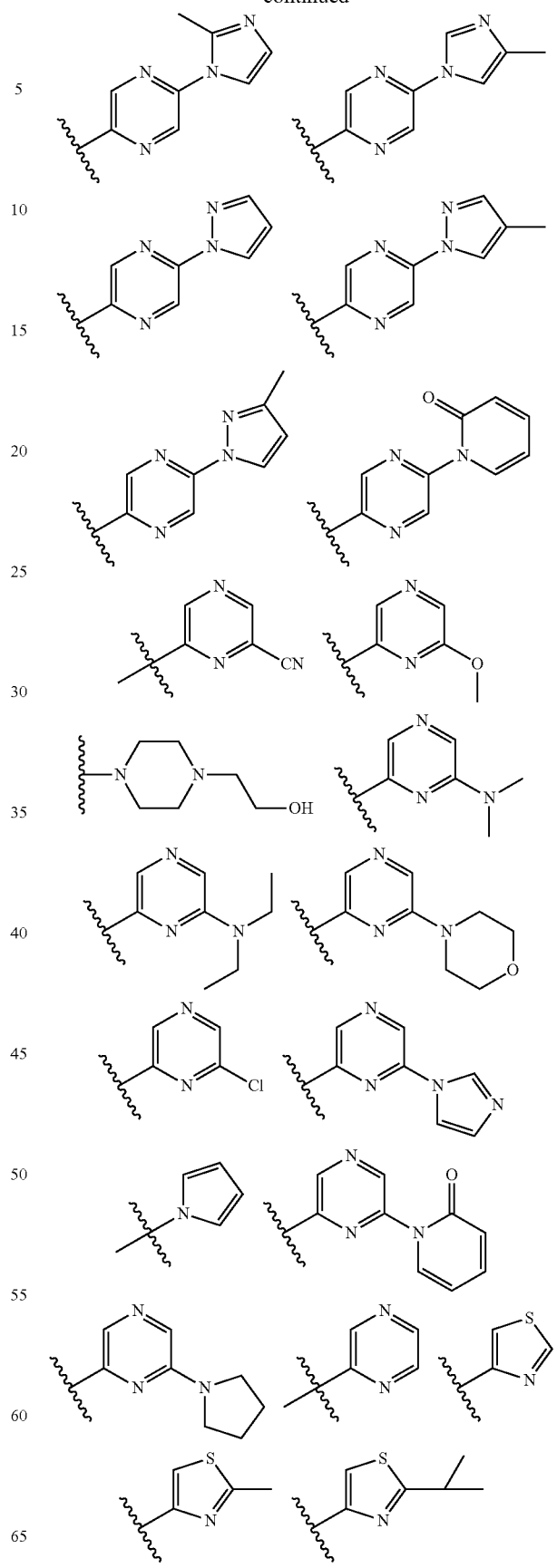

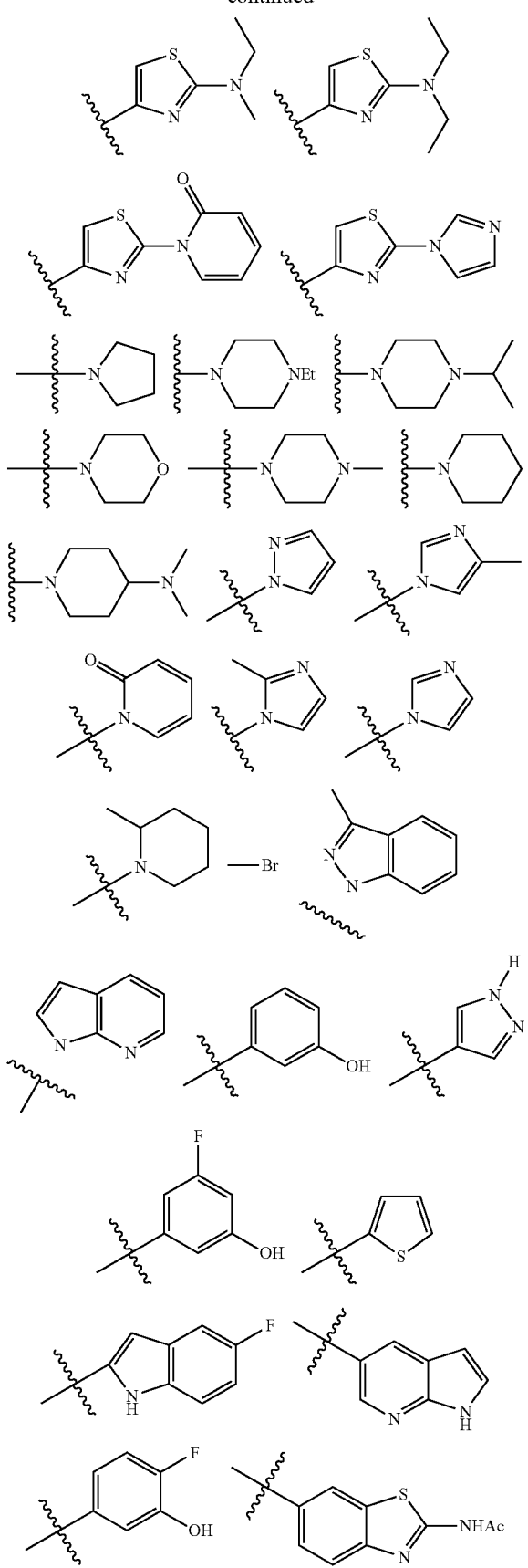
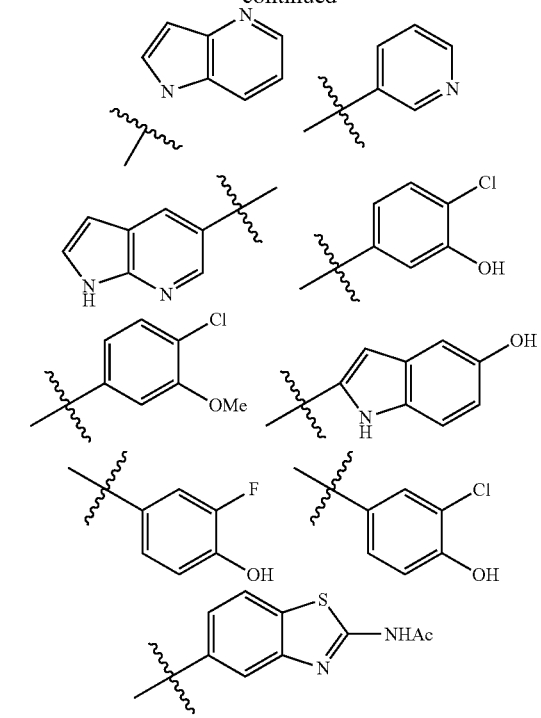

In some embodiments, $R^3$ is hydrogen. In some embodiments, $R^3$ is halo. In some embodiments, $R^3$ is unsubstituted amino. In some embodiments, $R^3$ is substituted amino. In some embodiments, $R^3$ is unsubstituted alkyl. In some embodiments, $R^3$ is unsubstituted lower alkyl. In some embodiments, $R^3$ is substituted lower alkyl. In some embodiments, $R^3$ is substituted alkyl. In some embodiments, $R^3$ is unsubstituted cycloalkyl. In some embodiments, $R^3$ is substituted cycloalkyl. In some embodiments, $R^3$ is unsubstituted heterocycloalkyl. In some embodiments, $R^3$ is substituted heterocycloalkyl. In some embodiments, $R^3$ is unsubstituted aryl. In some embodiments, $R^3$ is substituted aryl. In some embodiments, $R^3$ is unsubstituted heteroaryl. In some embodiments, $R^3$ is substituted heteroaryl. In some embodiments, $R^3$ is X, wherein X is —C(O)NR$^8$R$^9$. In some embodiments, $R^3$ is X, wherein X is —C(O)NR$^8$R$^9$, and any of $R^8$ or $R^9$ are substituted. In some embodiments, $R^3$ is X, wherein X is —SO$_2$NR$^8$R$^9$. In some embodiments, $R^3$ is X, wherein X is —SO$_2$NR$^8$R$^9$, and any of $R^8$ or $R^9$ are substituted. In some embodiments, $R^3$ is X, wherein X is —NR$^8$C(O)R$^{10}$. In some embodiments, $R^3$ is X, wherein X is —NR$^8$C(O)R$^{10}$, and any of $R^8$ or $R^{10}$ are substituted.

In some embodiments, $R^4$ is hydrogen and $R^5$ is hydrogen. In some embodiments, $R^4$ is hydrogen and $R^5$ is unsubstituted alkyl. In some embodiments, $R^4$ is hydrogen and $R^5$ is substituted alkyl. In some embodiments, $R^4$ is hydrogen and $R^5$ is unsubstituted lower alkyl. In some embodiments, $R^4$ is hydrogen and $R^5$ is substituted lower alkyl. In some embodiments, $R^4$ is hydrogen and $R^5$ is unsubstituted cycloalkyl. In some embodiments, $R^4$ is hydrogen and $R^5$ is substituted cycloalkyl. In some embodiments, $R^4$ is hydrogen and $R^5$ is unsubstituted heterocycloalkyl. In some embodiments, $R^4$ is hydrogen and $R^5$ is substituted heterocycloalkyl. In some embodiments, $R^4$ is hydrogen and $R^5$ is unsubstituted aryl. In some embodiments, $R^4$ is hydrogen and $R^5$ is substituted aryl. In some embodiments, $R^4$ is hydrogen and $R^5$ is unsubstituted heteroaryl. In some embodiments, $R^4$ is hydrogen and $R^5$ is substituted heteroaryl. In some embodiments, $R^4$ is hydrogen and $R^5$ is unsubstituted amino. In some embodiments, $R^4$ is hydrogen and $R^5$ is substituted amino. In some embodiments, $R^4$ is hydrogen and $R^5$ is unsubstituted alkoxycarbonyl. In some embodiments, $R^4$ is hydrogen and $R^5$ is substituted alkoxycarbonyl. In some embodiments, $R^4$ is hydrogen and $R^5$ is unsubstituted acyl. In some embodiments, $R^4$ is hydrogen and $R^5$ is substituted acyl.

In some embodiments $R^5$ is one of the following moieties:

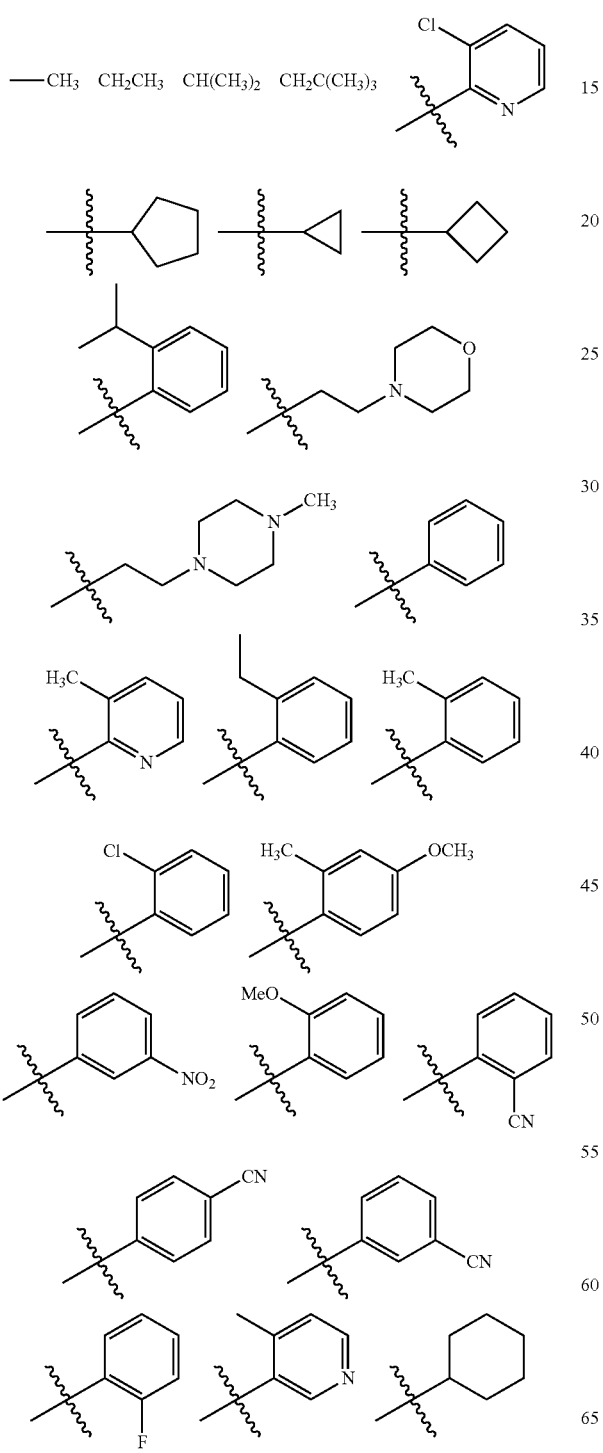

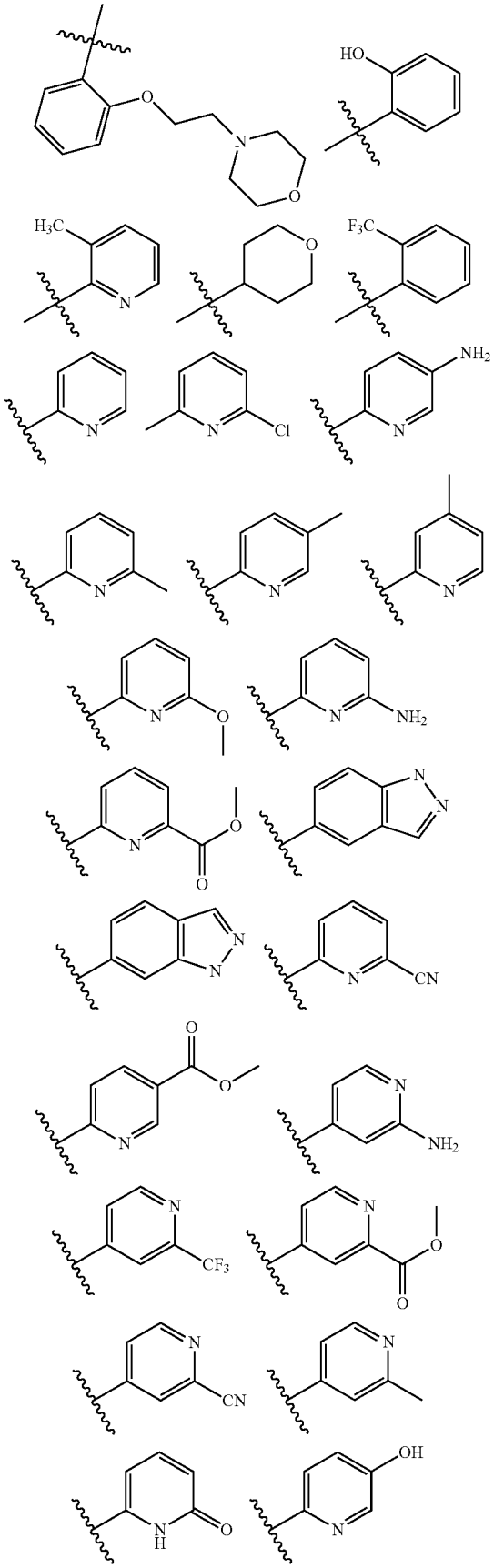

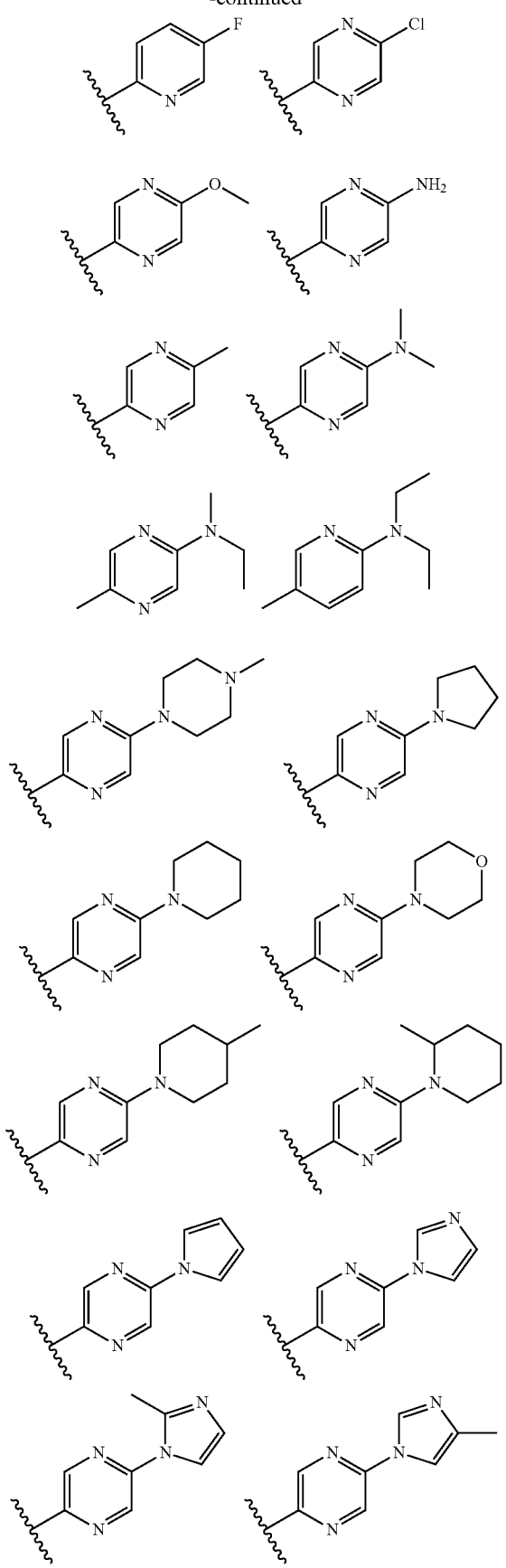
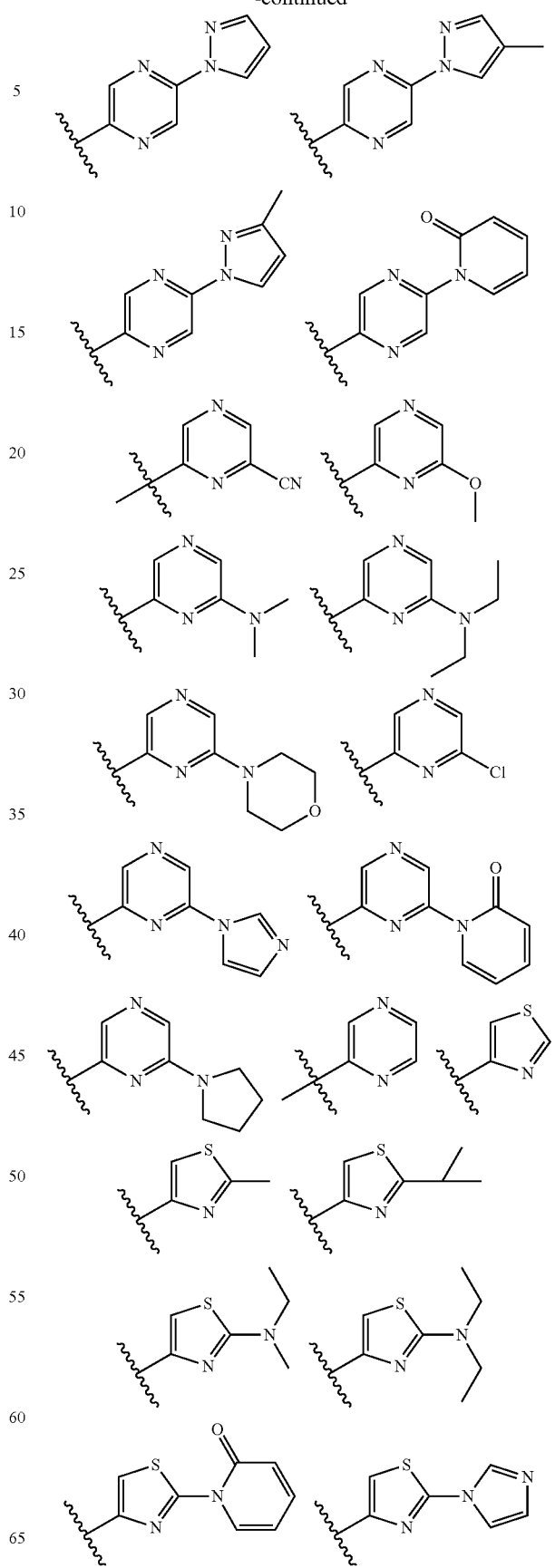

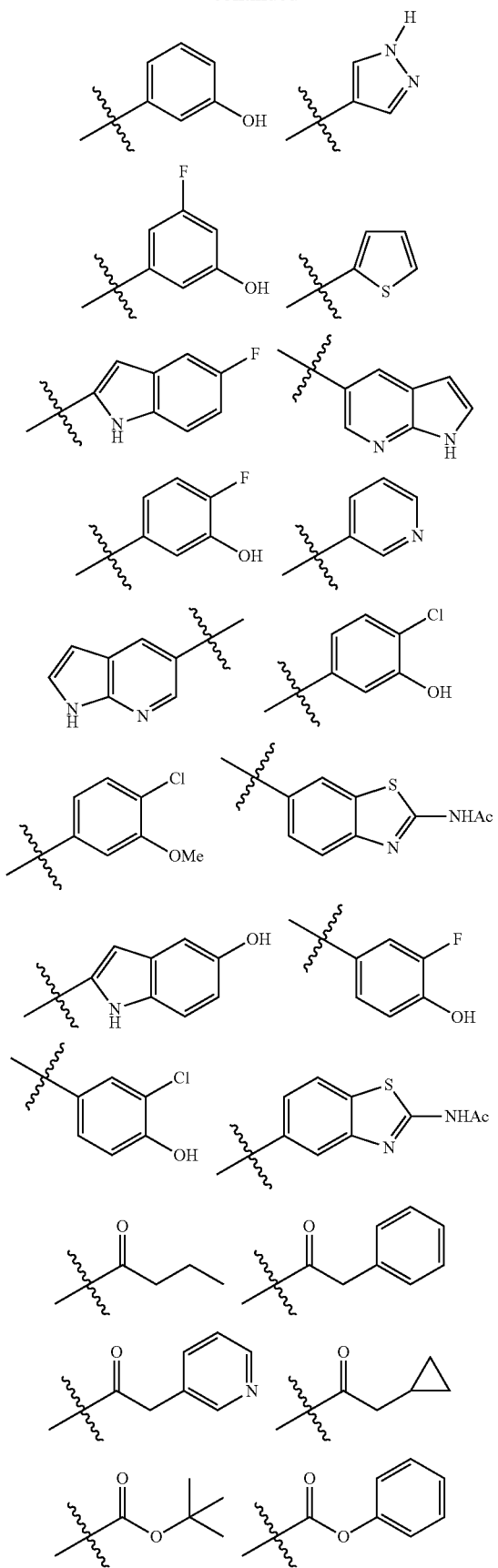
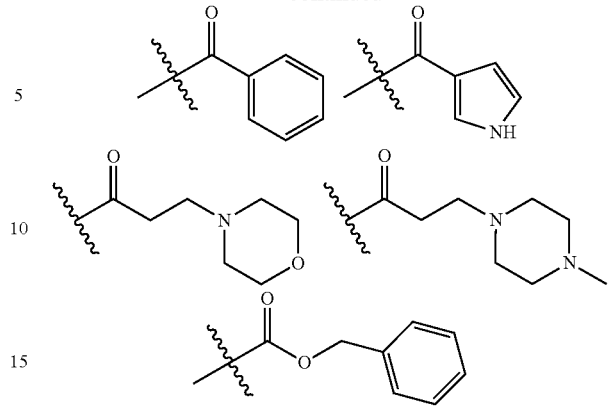

In some embodiments, R⁴ and R⁵, taken together with any intervening atoms, form an unsubstituted heteroaryl ring. In some embodiments, R⁴ and R⁵, taken together with any intervening atoms, form a substituted heteroaryl ring. In some embodiments, R⁴ and R⁵, taken together with any intervening atoms, form an imidazole ring. In some embodiments, R⁴ and R⁵, taken together with any intervening atoms, form a pyrazole ring.

In some embodiments, R⁶ is hydrogen. In some embodiments, R⁶ is halo. In some embodiments, R⁶ is unsubstituted lower alkyl. In some embodiments, R⁶ is substituted lower alkyl. In some embodiments, R⁶ is unsubstituted amino. In some embodiments, R⁶ is substituted amino. In some embodiments, R⁶ is unsubstituted alkoxy. In some embodiments, R⁶ is substituted alkoxy. In some embodiments, R⁶ is cyano In some embodiments, R⁶ is X. In some embodiments, when R⁶ is X, X is —C(O)NR⁸R⁹. In some embodiments, when R⁶ is X, X is —SO₂NR$^P$R⁹. In some embodiments, when R⁶ is X, X is —NHC(O)NR⁸R⁹. In some embodiments, when R⁶ is X, X is —NR⁸C(O)R¹⁶.

In some embodiments, R⁷ is hydrogen. In some embodiments, R⁷ is halo. In some embodiments, R⁷ is unsubstituted lower alkyl. In some embodiments, R⁷ is substituted lower alkyl. In some embodiments, R⁷ is unsubstituted aryl. In some embodiments, R⁷ is substituted aryl. In some embodiments, R⁷ and R³, taken together with any intervening atoms, form an unsubstituted cycloalkyl ring. In some embodiments, R⁷ and R³, taken together with any intervening atoms, form a substituted cycloalkyl ring. In some embodiments, R⁷ and R³, taken together with any intervening atoms, form an unsubstituted heterocycloalkyl ring. In some embodiments, R⁷ and R³, taken together with any intervening atoms, form an substituted heterocycloalkyl ring. In some embodiments, R⁷ and R³, taken together with any intervening atoms, form an unsubstituted heteroaryl ring. In some embodiments, R⁷ and R³, taken together with any intervening atoms, form an substituted heteroaryl ring.

In some embodiments, R⁸ is hydrogen. In some embodiments, R⁸ is unsubstituted alkyl. In some embodiments, R⁸ is substituted alkyl. In some embodiments, R⁸ is unsubstituted lower alkyl. In some embodiments, R⁸ is substituted lower alkyl. In some embodiments, R⁸ is unsubstituted cycloalkyl. In some embodiments, R⁸ is substituted cycloalkyl. In some embodiments, R⁸ is unsubstituted heterocycloalkyl. In some embodiments, R⁸ is substituted heterocycloalkyl. In some embodiments, R⁸ is unsubstituted aryl. In some embodiments, R⁸ is substituted aryl. In some embodiments, R⁸ is unsubstituted heteroaryl. In some embodiments, R⁸ is substituted heteroaryl.

In some embodiments, $R^9$ is hydrogen. In some embodiments, $R^9$ is unsubstituted alkyl. In some embodiments, $R^9$ is substituted alkyl. In some embodiments, $R^9$ is unsubstituted lower alkyl. In some embodiments, $R^9$ is substituted lower alkyl. In some embodiments, $R^9$ is unsubstituted cycloalkyl. In some embodiments, $R^9$ is substituted cycloalkyl. In some embodiments, $R^9$ is unsubstituted heterocycloalkyl. In some embodiments, $R^9$ is substituted heterocycloalkyl. In some embodiments, $R^9$ is unsubstituted aryl. In some embodiments, $R^9$ is substituted aryl. In some embodiments, $R^9$ is unsubstituted heteroaryl. In some embodiments, $R^9$ is substituted heteroaryl.

In some embodiments, $R^8$ and $R^9$ taken together with any intervening atoms, form an unsubstituted heterocycloalkyl ring. In some embodiments, $R^8$ and $R^9$ taken together with any intervening atoms, form a substituted heterocycloalkyl ring.

In some embodiments, $R^8$ is t-butyl or 2-hydroxyethyl.

In some embodiments, $R^{10}$ is hydrogen. In some embodiments, $R^{19}$ is unsubstituted alkyl. In some embodiments, $R^{19}$ is substituted alkyl. In some embodiments, $R^{10}$ is unsubstituted lower alkyl. In some embodiments, $R^{10}$ is substituted lower alkyl. In some embodiments, $R^{19}$ is unsubstituted cycloalkyl. In some embodiments, $R^{19}$ is substituted cycloalkyl. In some embodiments, $R^{19}$ is unsubstituted heterocycloalkyl. In some embodiments, $R^{19}$ is substituted heterocycloalkyl. In some embodiments, $R^{19}$ is unsubstituted aryl. In some embodiments, $R^{10}$ is substituted aryl. In some embodiments, $R^{10}$ is unsubstituted heteroaryl. In some embodiments, $R^{10}$ is substituted heteroaryl.

In some embodiments, $R^{11}$ is hydrogen. In some embodiments, $R^{11}$ is unsubstituted alkyl. In some embodiments, $R^{11}$ is substituted alkyl. In some embodiments, $R^{11}$ is unsubstituted lower alkyl. In some embodiments, $R^{11}$ is substituted lower alkyl. In some embodiments, $R^{11}$ is unsubstituted cycloalkyl. In some embodiments, $R^{11}$ is substituted cycloalkyl. In some embodiments, $R^{11}$ is unsubstituted heterocycloalkyl. In some embodiments, $R^{11}$ is substituted heterocycloalkyl. In some embodiments, $R^{11}$ is unsubstituted aryl. In some embodiments, $R^{11}$ is substituted aryl. In some embodiments, $R^{11}$ is unsubstituted heteroaryl. In some embodiments, $R^{11}$ is substituted heteroaryl. In some embodiments, $R^{11}$ is X. In some embodiments, when $R^{11}$ is X, X is —C(O)NR$^8$R$^9$. In some embodiments, when $R^{11}$ is X, X is —SO$_2$NR$^8$R$^9$. In some embodiments, when $R^{11}$ is X, X is —NHC(O)NR$^8$R$^9$. In some embodiments, when $R^{11}$ is X, X is —NR$^8$C(O)R$^{10}$.

In some embodiments, $R^{11}$ and $R^5$ taken together with any intervening atoms, form a heterocycloalkyl or heteroaryl ring;

In other embodiments, a compound of Formula I and its pharmaceutically acceptable salts is provided, wherein,
$W^1$ is CR$^6$ or N;
$W^2$ is CR$^7$, N, or NR$^7$;
$W^3$ is CR$^2$, N, or NR$^2$;
$W^4$ is CR$^{11}$ or N;
$W^5$ is C(O), CHR$^3$, CR$^3$ or NR$^3$; and no more than two adjacent ring atoms are N or NR$^7$;
$R^1$ is amino or methyl;
$R^2$ is hydrogen, halo, alkyl, cycloalkyl, heterocycloalkyl, aryl, or heteroaryl;
$R^3$ is hydrogen, alkyl, cycloalkyl, heterocycloalkyl, or X;
$R^4$ is hydrogen and $R^5$ is hydrogen, alkyl, cycloalkyl, heterocycloalkyl, aryl, heteroaryl, amino, alkoxycarbonyl, or acyl; or $R^4$ and $R^5$, taken together with any intervening atoms, form a heteroaryl ring;

$R^6$ is hydrogen, halo, or lower alkyl when $W^1$ is CR$^6$;
$R^6$ is hydrogen or lower alkyl when $W^1$ is N;
$R^7$ is hydrogen, halo, lower alkyl, or aryl when $W^2$ is CR$^7$; or $R^7$ is hydrogen, lower alkyl, or aryl when $W^2$ is N; or $R^7$ and $R^3$, taken together with any intervening atoms, form a cycloalkyl, heterocycloalkyl, or heteroaryl ring;
$R^8$ and $R^9$ are independently hydrogen, alkyl, cycloalkyl, heterocycloalkyl, aryl, and heteroaryl, or $R^8$ and $R^9$ taken together with any intervening atoms, form a heterocycloalkyl ring;
$R^{10}$ is hydrogen, alkyl, cycloalkyl, heterocycloalkyl, aryl, or heteroaryl;
$R^{11}$ is hydrogen, alkyl, cycloalkyl, heterocycloalkyl, aryl, or heteroaryl; or $R^{11}$ and $R^5$ taken together with any intervening atoms, form a heterocycloalkyl or heteroaryl ring; and
X is —C(O)NR$^8$R$^9$, —SO$_2$NR$^8$R$^9$, —NHC(O)NR$^8$R$^9$, or —NR$^8$C(O)R$^{10}$.

In some embodiments, $W^1$ is CR$^6$, $W^3$ is CR$^2$, $W^5$ is CR$^3$, $W^2$ is CR$^7$, and $W^4$ is N.

In some embodiments, $W^1$ is CR$^6$, $W^3$ is CR$^2$, $W^5$ is CR$^3$, $W^2$ is CR$^7$, and $W^4$ is CR$^{11}$.

In some embodiments, $W^1$ is CR$^6$, $W^3$ is CR$^2$, $W^5$ is CR$^3$, $W^2$ is NR$^7$, and $W^4$ is N.

In some embodiments, $W^1$ is CR$^6$, $W^3$ is CR$^2$, $W^5$ is CR$^3$, $W^2$ is NR$^7$, and $W^4$ is CR$^{11}$.

In some embodiments, when $R^1$ is methyl, it is substituted by one or more fluoro.

In another aspect of the invention, a compound of Formula II and its pharmaceutically acceptable salts are provided, wherein:

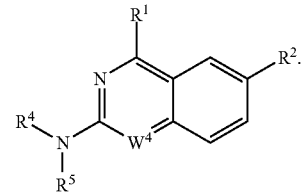

Formula II $W^4$ is CR$^{11}$ or N;
$R^1$ is hydrogen, amino, alkyl, alkoxy, aryl, heteroaryl, or cyano;
$R^2$ is hydrogen, halo, amino, alkyl, cycloalkyl, heterocycloalkyl, aryl, or heteroaryl or X; and
$R^4$ is hydrogen and $R^5$ is hydrogen, alkyl, cycloalkyl, heterocycloalkyl, aryl, heteroaryl, amino, alkoxycarbonyl, or acyl; or $R^4$ and $R^5$, taken together with any intervening atoms, form a heteroaryl ring;
$R^8$ and $R^9$ are independently hydrogen, alkyl, cycloalkyl, heterocycloalkyl, aryl, and heteroaryl, or $R^5$ and $R^9$ taken together with any intervening atoms, form a heterocycloalkyl ring;
$R^{10}$ is hydrogen, alkyl, cycloalkyl, heterocycloalkyl, aryl, or heteroaryl;
$R^{11}$ is hydrogen, alkyl, cycloalkyl, heterocycloalkyl, aryl, heteroaryl, or X; or $R^{11}$ and $R^5$ taken together with any intervening atoms, form a heterocycloalkyl or heteroaryl ring; and
X is —C(O)NR$^8$R$^9$, —SO$_2$NR$^8$R$^9$, —NHC(O)NR$^8$R$^9$, or —NR$^8$C(O)R$^{10}$.

In some embodiments, $W^4$ is CR$^{11}$.

In some embodiments, $W^4$ is N.

In some embodiments, $R^1$ is hydrogen. In some embodiments, $R^1$ is unsubstituted amino. In some embodiments, $R^1$ is substituted amino. In some embodiments, $R^1$ is unsubstituted alkyl. In some embodiments, $R^1$ is substituted alkyl. In some embodiments, $R^1$ is unsubstituted methyl. In some embodiments, $R^1$ is substituted methyl. In some embodiments, when $R^1$ is substituted methyl, it is substituted by one or more halo. In some embodiments, when $R^1$ is substituted methyl, it is substituted by one or more fluoro. In some embodiments, $R^1$ is unsubstituted alkoxy. In some embodiments, $R^1$ is substituted alkoxy. In some embodiments, $R^1$ is unsubstituted aryl. In some embodiments, $R^1$ is substituted aryl. In some embodiments, $R^1$ is unsubstituted heteroaryl. In some embodiments, $R^1$ is substituted heteroaryl. In some embodiments, $R^1$ is cyano.

In some embodiments, $R^2$ is hydrogen. In some embodiments, $R^2$ is halo. In some embodiments, $R^2$ is unsubstituted amino. In some embodiments, $R^2$ is substituted amino. In some embodiments, $R^2$ is unsubstituted alkyl. In some embodiments, $R^2$ is substituted alkyl. In some embodiments, $R^2$ is unsubstituted lower alkyl. In some embodiments, $R^2$ is substituted lower alkyl. In some embodiments, $R^2$ is unsubstituted cycloalkyl. In some embodiments, $R^2$ is substituted cycloalkyl. In some embodiments, $R^2$ is unsubstituted heterocycloalkyl. In some embodiments, $R^2$ is substituted heterocycloalkyl. In some embodiments, $R^2$ is unsubstituted aryl. In some embodiments, $R^2$ is substituted aryl. In some embodiments, $R^2$ is unsubstituted heteroaryl. In some embodiments, $R^2$ is substituted heteroaryl. In some embodiments, $R^2$ is X, wherein X is —C(O)NR$^8$R$^9$. In some embodiments, $R^2$ is X, wherein X is —C(O)NR$^8$R$^9$, and any of $R^8$ or $R^9$ are substituted. In some embodiments, $R^2$ is X, wherein X is —SO$_2$NR$^8$R$^9$. In some embodiments, $R^2$ is X, wherein X is —SO$_2$NR$^8$R$^9$, and any of $R^8$ or $R^9$ are substituted. In some embodiments, $R^2$ is X, wherein X is —NR$^8$C(O)R$^{10}$. In some embodiments, $R^2$ is X, wherein X is —NR$^8$C(O)R$^{10}$, and any of $R^8$ or $R^{10}$ are substituted.

In some embodiments, $R^2$ is a 5- to 9-membered heteroaryl having at least one nitrogen ring atom. In some embodiments, wherein $R^2$ is a 5- to 9-membered heteroaryl having at least one nitrogen ring atom, the heteroaryl ring comprises up to two additional heteroatom ring atoms. In some embodiments, $R^2$ is monocyclic. In some embodiments, $R^2$ is bicyclic.

In some embodiments, $R^2$ is one of the following moieties:

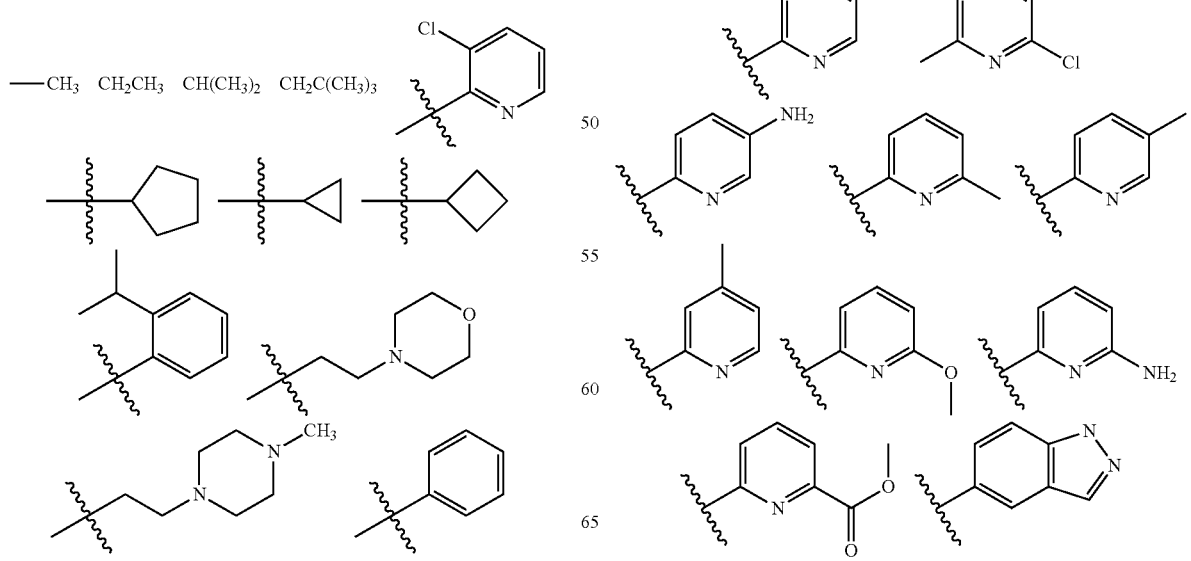

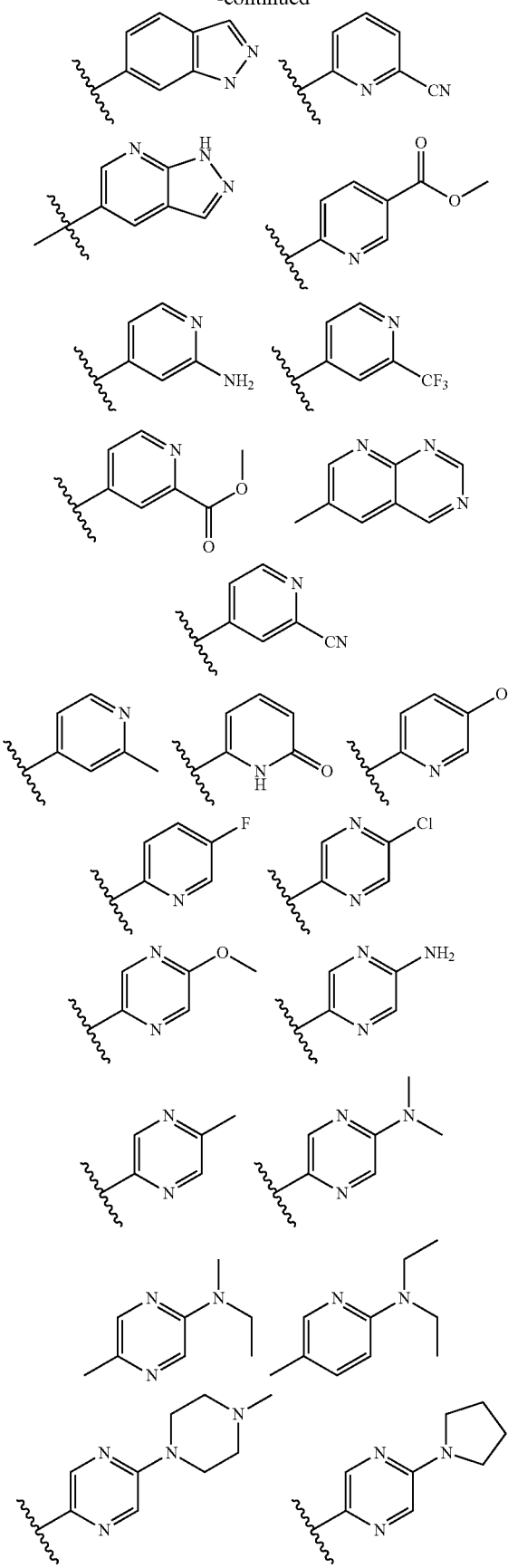
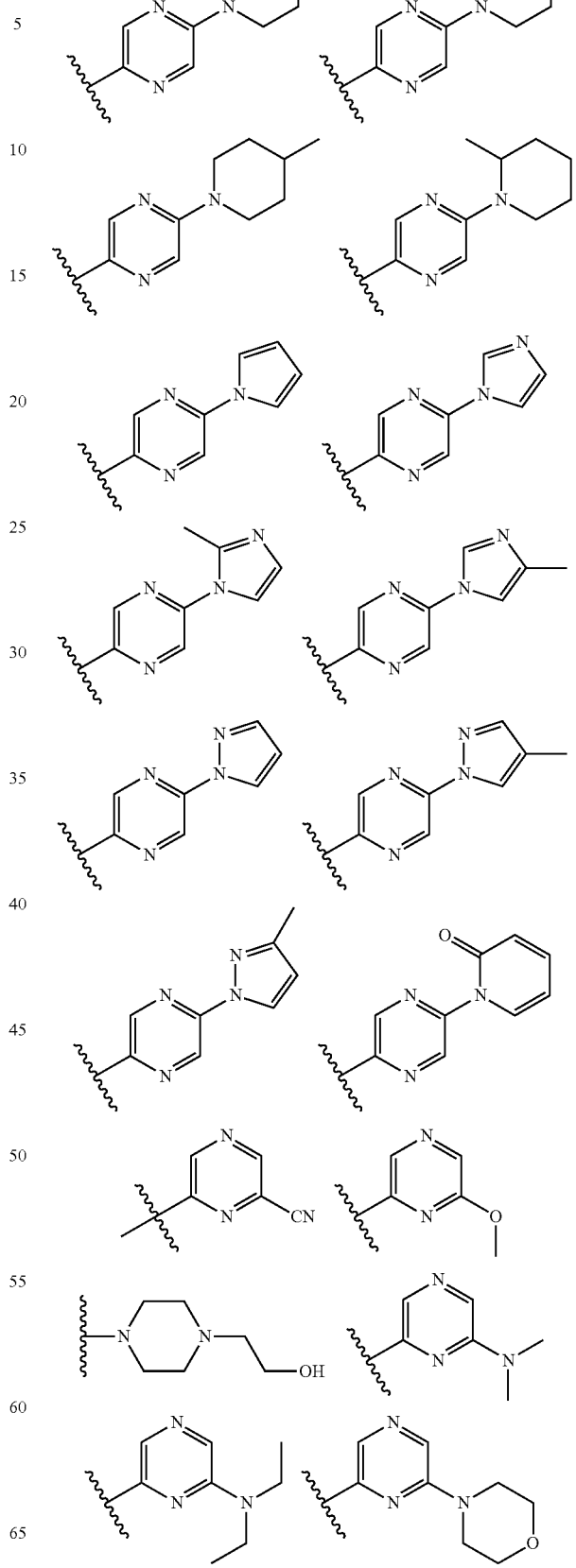

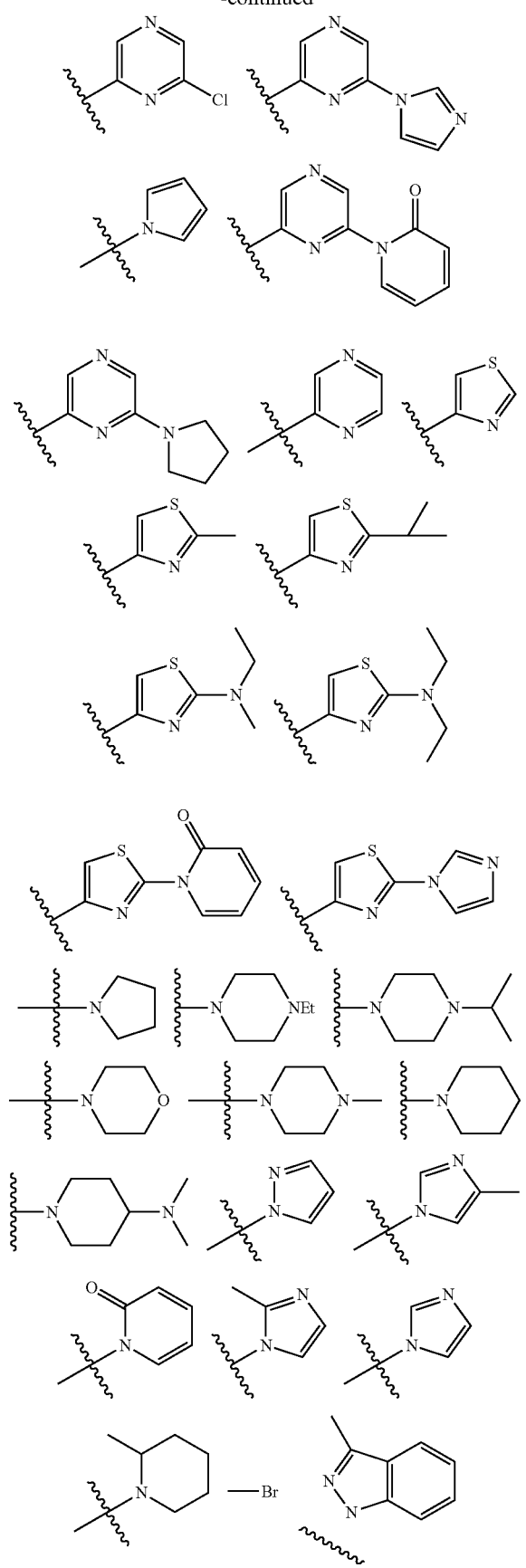
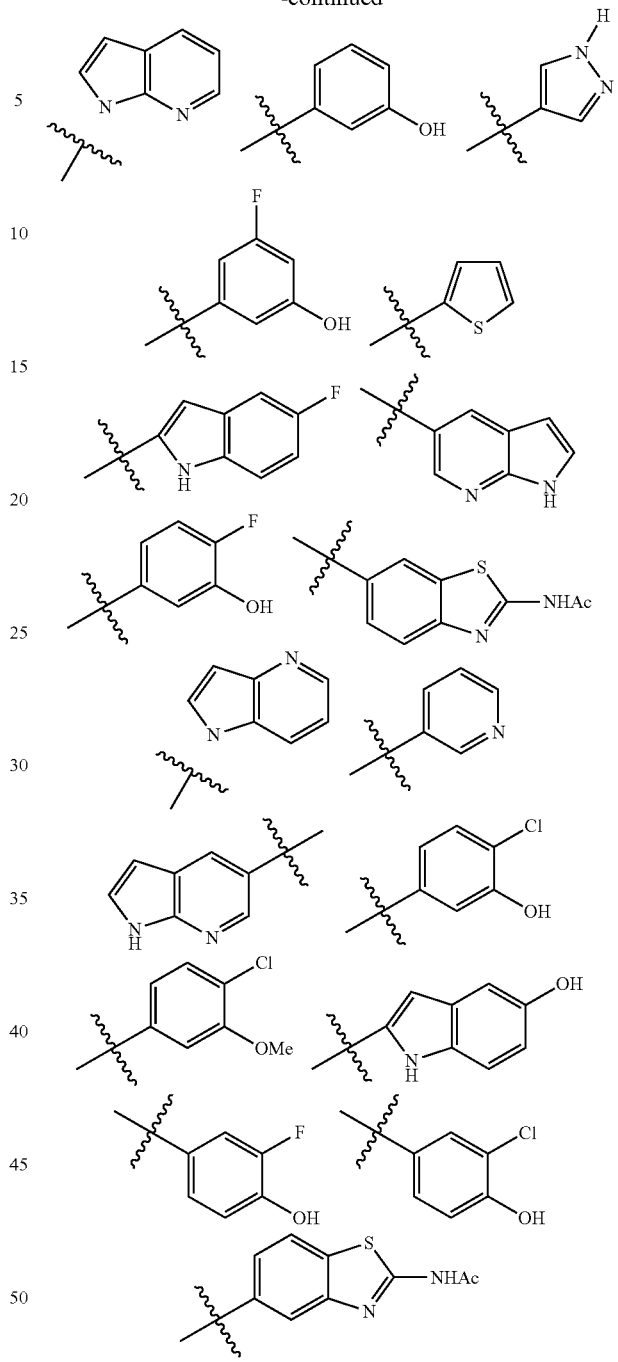

In some embodiments, $R^4$ is hydrogen and $R^5$ is hydrogen. In some embodiments, $R^4$ is hydrogen and $R^5$ is unsubstituted alkyl. In some embodiments, $R^4$ is hydrogen and $R^5$ is substituted alkyl. In some embodiments, $R^4$ is hydrogen and $R^5$ is unsubstituted lower alkyl. In some embodiments, $R^4$ is hydrogen and $R^5$ is substituted lower alkyl. In some embodiments, $R^4$ is hydrogen and $R^5$ is unsubstituted cycloalkyl. In some embodiments, $R^4$ is hydrogen and $R^5$ is substituted cycloalkyl. In some embodiments, $R^4$ is hydrogen and $R^5$ is unsubstituted heterocycloalkyl. In some embodiments, $R^4$ is hydrogen and $R^5$ is substituted heterocycloalkyl. In some embodiments, $R^4$ is hydrogen and $R^5$ is unsubstituted aryl. In some embodiments, $R^4$ is hydrogen and $R^5$ is substituted aryl.

In some embodiments, $R^4$ is hydrogen and $R^5$ is unsubstituted heteroaryl. In some embodiments, $R^4$ is hydrogen and $R^5$ is substituted heteroaryl. In some embodiments, $R^4$ is hydrogen and $R^5$ is unsubstituted amino. In some embodiments, $R^4$ is hydrogen and $R^5$ is substituted amino. In some embodiments, $R^4$ is hydrogen and $R^5$ is unsubstituted alkoxycarbonyl. In some embodiments, $R^4$ is hydrogen and $R^5$ is substituted alkoxycarbonyl. In some embodiments, $R^4$ is hydrogen and $R^5$ is unsubstituted acyl. In some embodiments, $R^4$ is hydrogen and $R^5$ is substituted acyl.

In some embodiments $R^5$ is one of the following moieties:

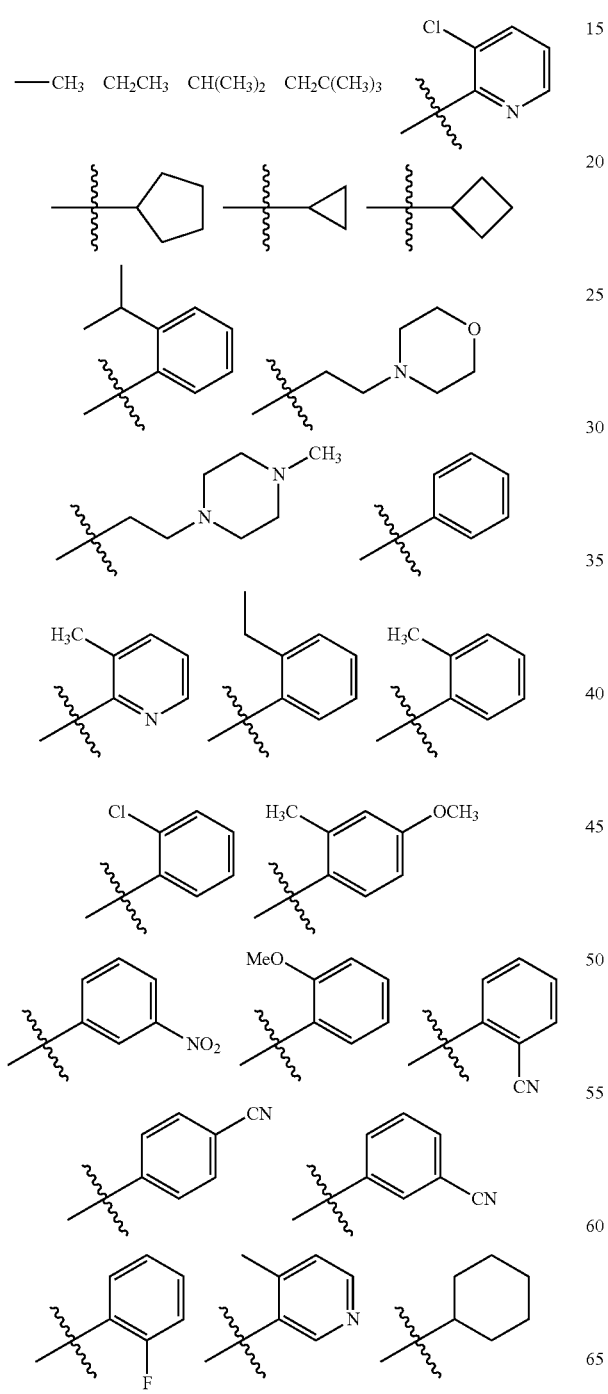

-continued

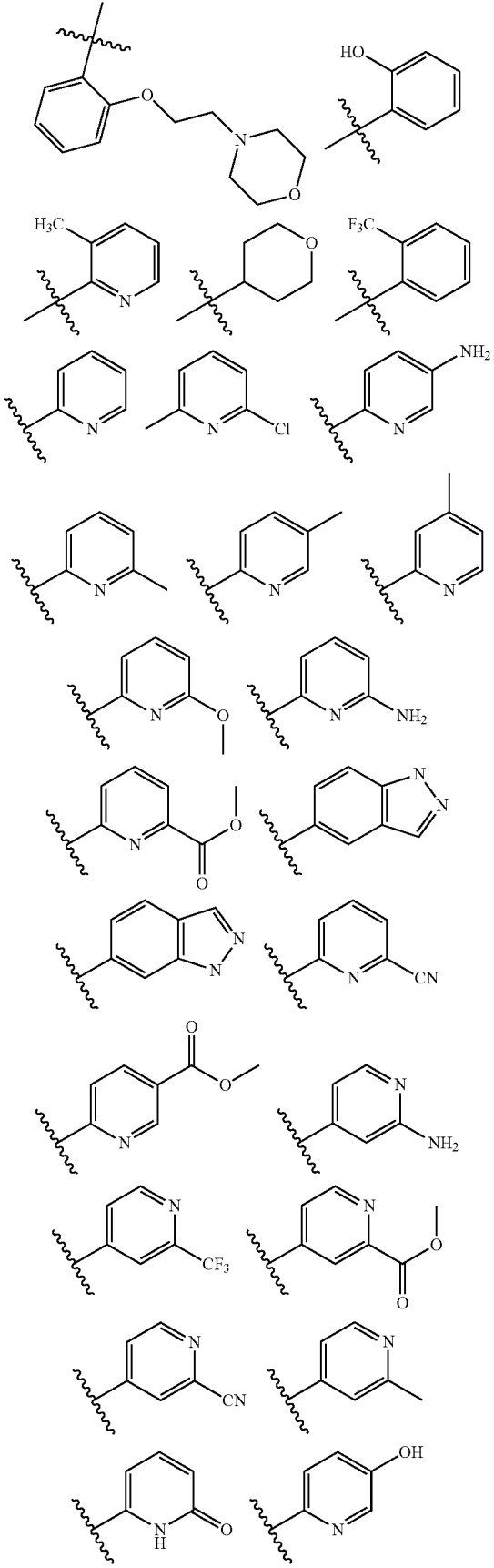

-continued
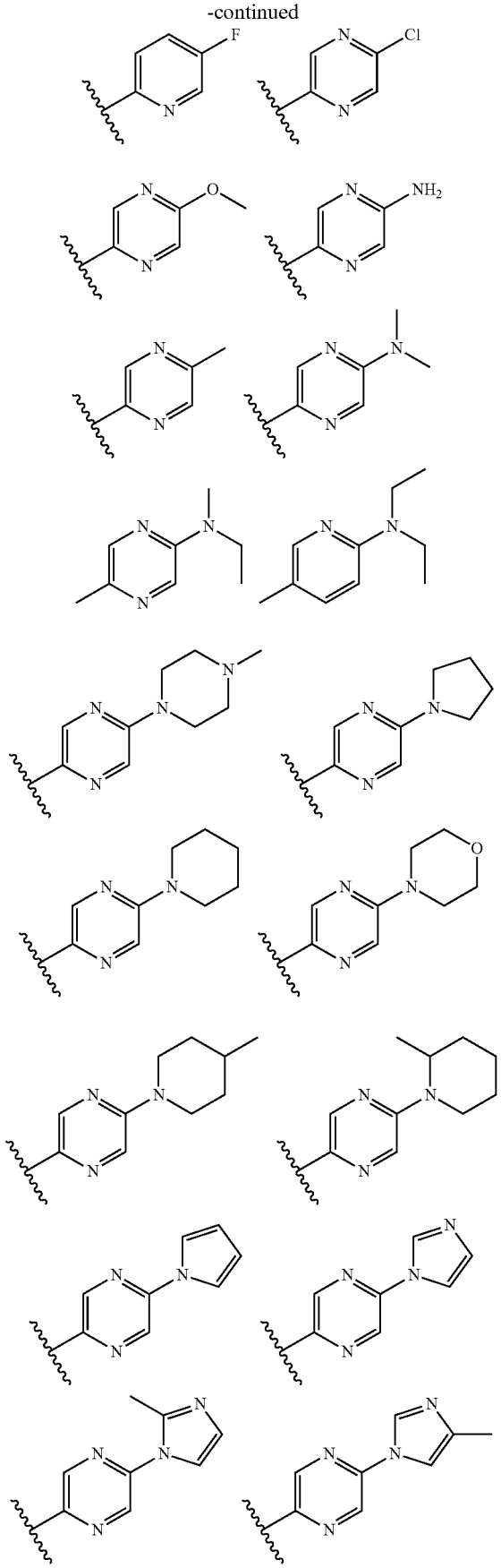
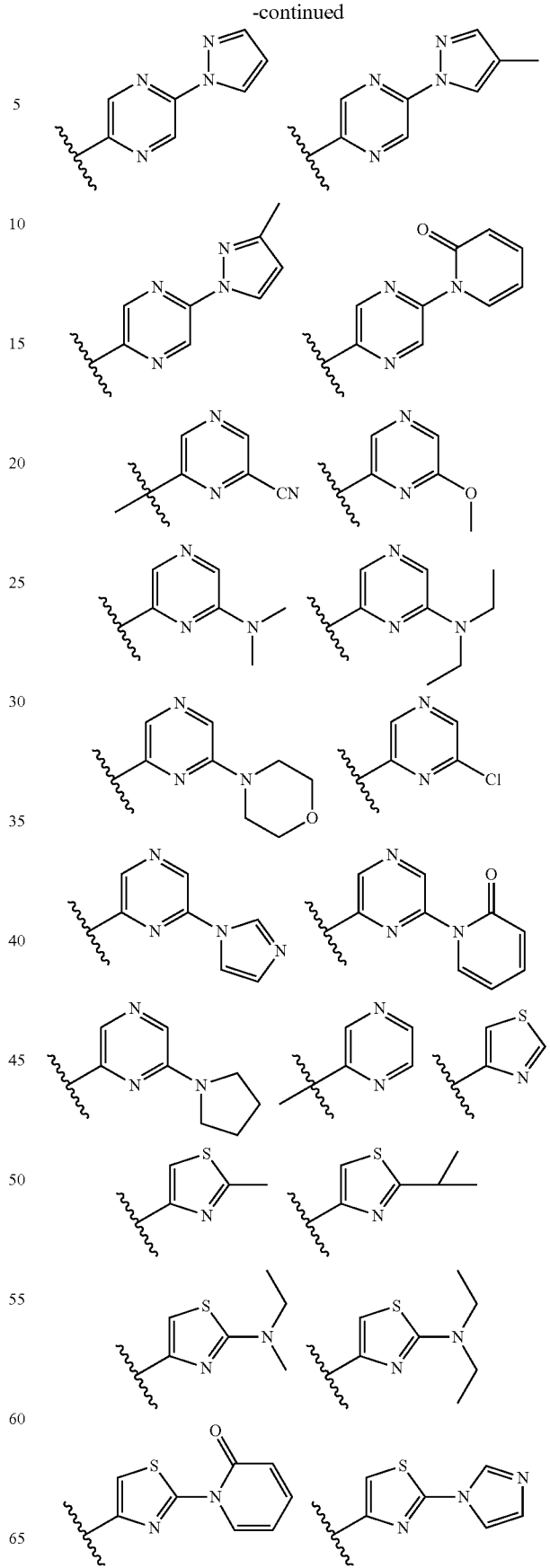

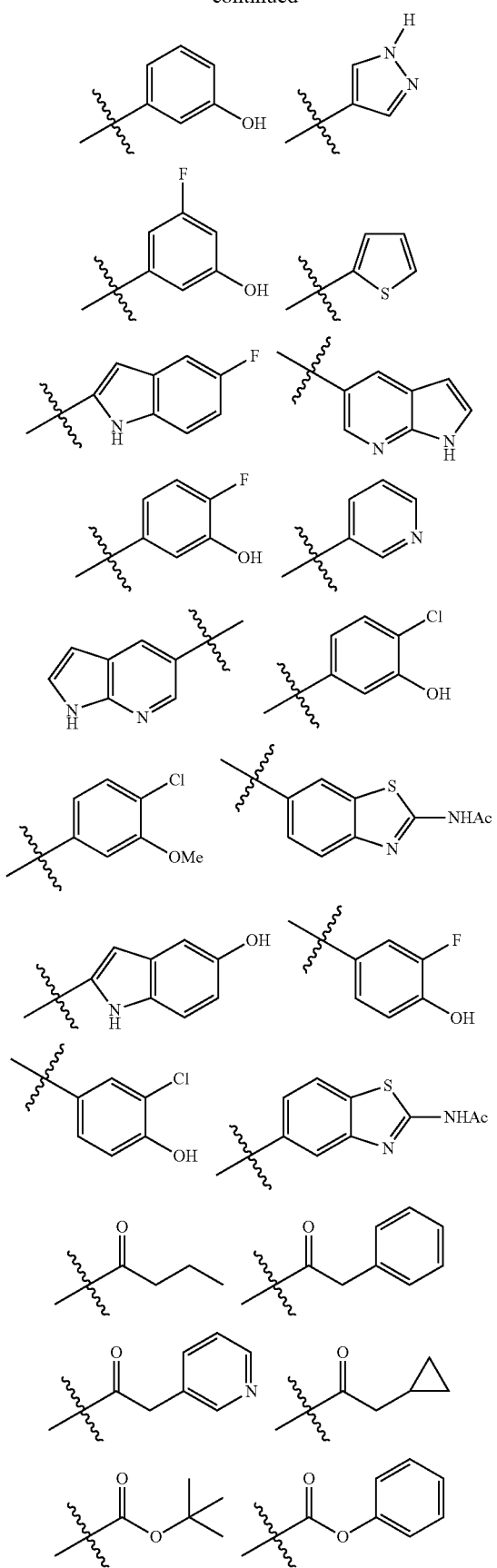
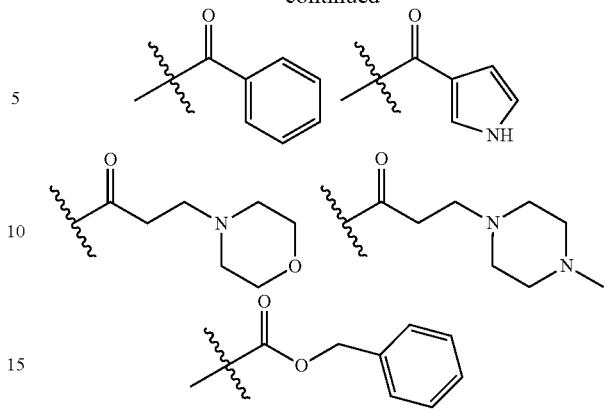

In some embodiments, $R^4$ and $R^5$, taken together with any intervening atoms, form an unsubstituted heteroaryl ring. In some embodiments, $R^4$ and $R^5$, taken together with any intervening atoms, form a substituted heteroaryl ring. In some embodiments, $R^4$ and $R^5$, taken together with any intervening atoms, form an imidazole ring. In some embodiments, $R^4$ and $R^5$, taken together with any intervening atoms, form a pyrazole ring.

In some embodiments, $R^8$ is hydrogen. In some embodiments, $R^8$ is unsubstituted alkyl. In some embodiments, $R^8$ is substituted alkyl. In some embodiments, $R^8$ is unsubstituted lower alkyl. In some embodiments, $R^8$ is substituted lower alkyl. In some embodiments, $R^8$ is unsubstituted cycloalkyl. In some embodiments, $R^8$ is substituted cycloalkyl. In some embodiments, $R^8$ is unsubstituted heterocycloalkyl. In some embodiments, $R^8$ is substituted heterocycloalkyl. In some embodiments, $R^8$ is unsubstituted aryl. In some embodiments, $R^8$ is substituted aryl. In some embodiments, $R^8$ is unsubstituted heteroaryl. In some embodiments, $R^8$ is substituted heteroaryl.

In some embodiments, $R^9$ is hydrogen. In some embodiments, $R^9$ is unsubstituted alkyl. In some embodiments, $R^9$ is substituted alkyl. In some embodiments, $R^9$ is unsubstituted lower alkyl. In some embodiments, $R^9$ is substituted lower alkyl. In some embodiments, $R^9$ is unsubstituted cycloalkyl. In some embodiments, $R^9$ is substituted cycloalkyl. In some embodiments, $R^9$ is unsubstituted heterocycloalkyl. In some embodiments, $R^9$ is substituted heterocycloalkyl. In some embodiments, $R^9$ is unsubstituted aryl. In some embodiments, $R^9$ is substituted aryl. In some embodiments, $R^9$ is unsubstituted heteroaryl. In some embodiments, $R^9$ is substituted heteroaryl.

In some embodiments, $R^8$ and $R^9$ taken together with any intervening atoms, form an unsubstituted heterocycloalkyl ring. In some embodiments, $R^8$ and $R^9$ taken together with any intervening atoms, form a substituted heterocycloalkyl ring.

In some embodiments, $R^8$ is t-butyl or 2-hydroxyethyl.

In some embodiments, $R^{10}$ is hydrogen. In some embodiments, $R^{10}$ is unsubstituted alkyl. In some embodiments, $R^{10}$ is substituted alkyl. In some embodiments, $R^{10}$ is unsubstituted lower alkyl. In some embodiments, $R^{10}$ is substituted lower alkyl. In some embodiments, $R^{10}$ is unsubstituted cycloalkyl. In some embodiments, $R^{10}$ is substituted cycloalkyl. In some embodiments, $R^{10}$ is unsubstituted heterocycloalkyl. In some embodiments, $R^{10}$ is substituted heterocycloalkyl. In some embodiments, $R^{10}$ is unsubstituted aryl. In some embodiments, $R^{10}$ is substituted aryl. In some embodiments, $R^{10}$ is unsubstituted heteroaryl. In some embodiments, $R^{10}$ is substituted heteroaryl.

In some embodiments, $R^{11}$ is hydrogen. In some embodiments, $R^{11}$ is unsubstituted alkyl. In some embodiments, $R^{11}$ is substituted alkyl. In some embodiments, $R^{11}$ is unsubstituted lower alkyl. In some embodiments, $R^{11}$ is substituted lower alkyl. In some embodiments, $R^{11}$ is unsubstituted cycloalkyl. In some embodiments, $R^{11}$ is substituted cycloalkyl. In some embodiments, $R^{11}$ is unsubstituted heterocycloalkyl. In some embodiments, $R^{11}$ is substituted heterocycloalkyl. In some embodiments, $R^{11}$ is unsubstituted aryl. In some embodiments, $R^{11}$ is substituted aryl. In some embodiments, $R^{11}$ is unsubstituted heteroaryl. In some embodiments, $R^{11}$ is substituted heteroaryl. In some embodiments, $R^{11}$ is X. In some embodiments, when $R^{11}$ is X, X is —C(O)NR$^8$R$^9$. In some embodiments, when $R^{11}$ is X, X is —SO$_2$NR$^8$R$^9$. In some embodiments, when $R^{11}$ is X, X is —NHC(O)NR$^8$R$^9$. In some embodiments, when $R^{11}$ is X, X is —NR$^8$C(O)R$^{10}$.

In some embodiments, $R^{11}$ and $R^5$ taken together with any intervening atoms, form a heterocycloalkyl or heteroaryl ring;

In some embodiments, wherein $R^2$ is aryl, the aryl group is substituted at the meta position or at both meta positions.

In some embodiments, wherein $R^2$ is aryl or heteroaryl, $R^2$ is bicyclic.

Illustrative Compounds of the Invention

A number of alternative core skeletons are encompassed by the compounds of Formula I. Illustrative examples are described in Table 1.

TABLE 1

Illustrative Alternate core skeletons of the compounds of the invention.

| Core # | |
|---|---|
| 1 | 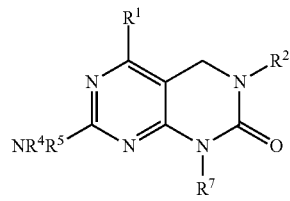 |
| 2 | 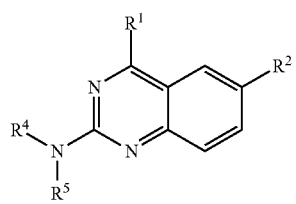 |
| 3 | 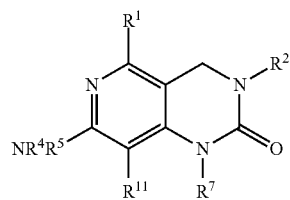 |

TABLE 1-continued

Illustrative Alternate core skeletons of the compounds of the invention.

| Core # | |
|---|---|
| 4 | |
| 5 | |
| 6 | |
| 7 | |
| 8 | |
| 9 | |
| 10 | |

TABLE 1-continued
Illustrative Alternate core skeletons of the compounds of the invention.
Core #
| 11 | 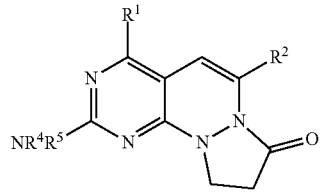 |
| 12 | 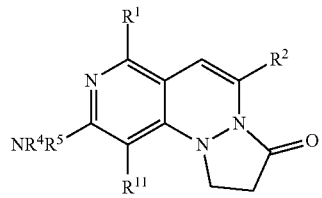 |
| 13 | 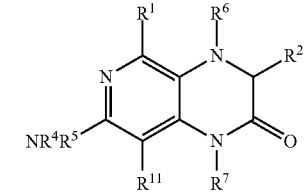 |
| 14 | 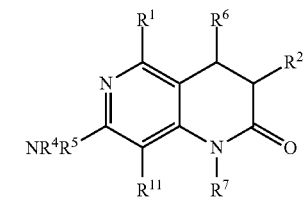 |
| 15 | 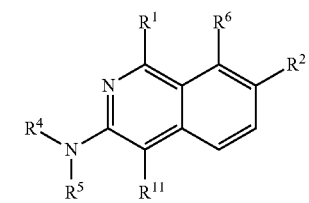 |
| 16 | 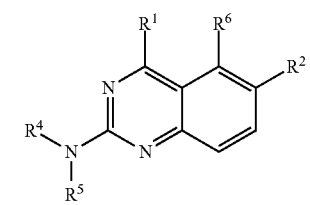 |
TABLE 1-continued
Illustrative Alternate core skeletons of the compounds of the invention.
Core #
| 17 | 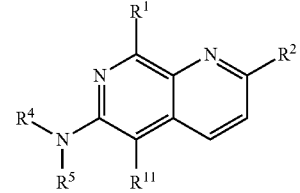 |
| 18 | 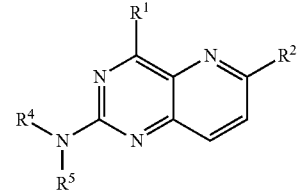 |
| 19 | 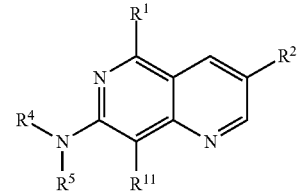 |
| 20 | 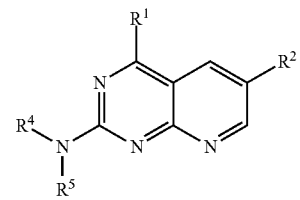 |
| 21 | 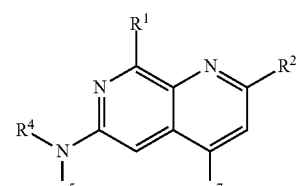 |
| 22 | 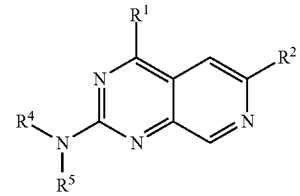 |
| 23 | 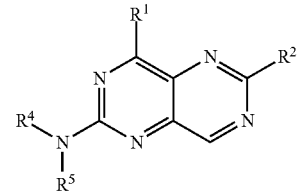 |

TABLE 1-continued

Illustrative Alternate core skeletons of the compounds of the invention.

| Core # | |
|---|---|
| 24 | 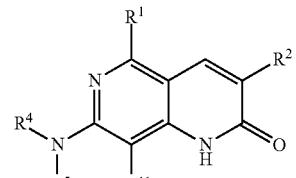 |
| 25 | |
| 26 | |
| 27 | |

Formula II

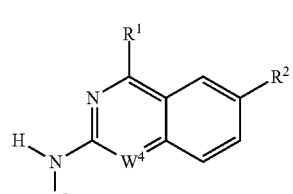

In some embodiments of the invention, compounds of Formula II are provided as illustrated for $R^1$, $W^4$ and $R^5$ in Table 2a, and in combination with any $R^2$ as illustrated in Table 2b.

TABLE 2a

Exemplary $R^1$, $W^4$ and $R^5$ for compounds of Formula II, in combination with the $R^2$ of Table 2b.

| Sub class # | W⁴ | | | | | R¹ | | R⁵ | | | | |
|---|---|---|---|---|---|---|---|---|---|---|---|---|
| | C-i-Pr | CH | CMe | N | NH₂ | Me | CF₃ | H | i-Pr | Me | cyclopentyl | N-Me-piperidyl |
| 1 | | x | | | | | x | x | | | | |
| 2 | | x | | | | | x | | x | x | | |
| 3 | | x | | | | | x | | | | x | |
| 4 | | x | | | | | x | | | | | x |
| 5 | | x | | | | | x | | | | | |
| 6 | | x | | | | | x | | | | | |
| 7 | | x | | | | | x | | | | | |
| 8 | | x | | | | | x | | | | | |
| 9 | | x | | | | | x | | | | | |
| 10 | | x | | | | x | | x | | | | |
| 11 | | x | | | | x | | | x | | | |
| 12 | | x | | | | x | | | | x | | |
| 13 | | x | | | | x | | | | | x | |
| 14 | | x | | | | x | | | | | | x |
| 15 | | x | | | | x | | | | | | |
| 16 | | x | | | | x | | | | | | |
| 17 | | x | | | | x | | | | | | |
| 18 | | x | | | | x | | | | | | |
| 19 | | x | | | | x | | | | | | |
| 20 | | x | | x | | | | x | | | | |
| 21 | | x | | x | | | | | x | | | |
| 22 | | x | | x | | | | | | x | | |
| 23 | | x | | x | | | | | | | x | |
| 24 | | x | | x | | | | | | | | x |
| 25 | | x | | x | | | | | | | | |
| 26 | | x | | x | | | | | | | | |
| 27 | | x | | x | | | | | | | | |
| 28 | | x | | x | | | | | | | | |

TABLE 2a-continued

Exemplary R¹, W⁴ and R⁵ for compounds of Formula II, in combination with the R² of Table 2b.

| # | | | | | | | | | |
|---|---|---|---|---|---|---|---|---|---|
| 29 | | | x | x | | | | | |
| 30 | | x | | | x | x | | | |
| 31 | | x | | | x | | x | | |
| 32 | | x | | | x | | | x | |
| 33 | | x | | | x | | | | x |
| 34 | | x | | | x | | | | | x |
| 35 | | x | | | x | | | | |
| 36 | | x | | | x | | | | |
| 37 | | x | | | x | | | | |
| 38 | | x | | | x | | | | |
| 39 | | x | | | x | | | | |
| 40 | | x | | x | | x | | | |
| 41 | | x | | x | | | x | | |
| 42 | | x | | x | | | | x | |
| 43 | | x | | x | | | | | x |
| 44 | | x | | x | | | | | | x |
| 45 | | x | | x | | | | | |
| 46 | | x | | x | | | | | |
| 47 | | x | | x | | | | | |
| 48 | | x | | x | | | | | |
| 49 | | x | | x | | | | | |
| 50 | | x | x | | | x | | | |
| 51 | | x | x | | | | x | | |
| 52 | | x | x | | | | | x | |
| 53 | | x | x | | | | | | x |
| 54 | | x | x | | | | | | | x |
| 55 | | x | x | | | | | | |
| 56 | | x | x | | | | | | |
| 57 | | x | x | | | | | | |
| 58 | | x | x | | | | | | |
| 59 | | x | x | | | | | | |
| 60 | x | | | | x | x | | | |
| 61 | x | | | | x | | x | | |
| 62 | x | | | | x | | | x | |
| 63 | x | | | | x | | | | x |
| 64 | x | | | | x | | | | | x |
| 65 | x | | | | x | | | | |
| 66 | x | | | | x | | | | |
| 67 | x | | | | x | | | | |
| 68 | x | | | | x | | | | |
| 69 | x | | | | x | | | | |
| 70 | x | | | x | | x | | | |
| 71 | x | | | x | | | x | | |
| 72 | x | | | x | | | | x | |
| 73 | x | | | x | | | | | x |
| 74 | x | | | x | | | | | | x |
| 75 | x | | | x | | | | | |
| 76 | x | | | x | | | | | |
| 77 | x | | | x | | | | | |
| 78 | x | | | x | | | | | |
| 79 | x | | | x | | | | | |
| 80 | x | | x | | | x | | | |
| 81 | x | | x | | | | x | | |
| 82 | x | | x | | | | | x | |
| 83 | x | | x | | | | | | x |
| 84 | x | | x | | | | | | | x |
| 85 | x | | x | | | | | | |
| 86 | x | | x | | | | | | |
| 87 | x | | x | | | | | | |
| 88 | x | | x | | | | | | |
| 89 | x | | x | | | | | | |
| 90 | x | | | | x | x | | | |
| 91 | x | | | | x | | x | | |
| 92 | x | | | | x | | | x | |
| 93 | x | | | | x | | | | x |
| 94 | x | | | | x | | | | | x |
| 95 | x | | | | x | | | | |
| 96 | x | | | | x | | | | |
| 97 | x | | | | x | | | | |
| 98 | x | | | | x | | | | |
| 99 | x | | | | x | | | | |
| 100 | x | | | x | | x | | | |
| 101 | x | | | x | | | x | | |
| 102 | x | | | x | | | | x | |
| 103 | x | | | x | | | | | x |
| 104 | x | | | x | | | | | | x |
| 105 | x | | | x | | | | | |
| 106 | x | | | x | | | | | |

TABLE 2a-continued

Exemplary R¹, W⁴ and R⁵ for compounds of Formula II, in combination with the R² of Table 2b.

| | | | | |
|---|---|---|---|---|
| 107 | x | | x | |
| 108 | x | | x | |
| 109 | x | | x | |
| 110 | x | x | | x |
| 111 | x | x | | | x |
| 112 | x | x | | | | x |
| 113 | x | x | | | | | x |
| 114 | x | x | | | | | | x |
| 115 | x | x | | | | | | |
| 116 | x | x | | | | | | |
| 117 | x | x | | | | | | |
| 118 | x | x | | | | | | |
| 119 | x | x | | | | | | |

| Sub class # | R⁵ 3-hydroxyphenyl | 3-pyridyl | isobutyryl | methoxycarbonyl | 5-methylisoxazol-3-yl |
|---|---|---|---|---|---|
| 1 | | | | | |
| 2 | | | | | |
| 3 | | | | | |
| 4 | | | | | |
| 5 | x | | | | |
| 6 | | x | | | |
| 7 | | | x | | |
| 8 | | | | x | |
| 9 | | | | | x |
| 10 | | | | | |
| 11 | | | | | |
| 12 | | | | | |
| 13 | | | | | |
| 14 | | | | | |
| 15 | x | | | | |
| 16 | | x | | | |
| 17 | | | x | | |
| 18 | | | | x | |
| 19 | | | | | x |
| 20 | | | | | |
| 21 | | | | | |
| 22 | | | | | |
| 23 | | | | | |
| 24 | | | | | |
| 25 | x | | | | |
| 26 | | x | | | |
| 27 | | | x | | |
| 28 | | | | x | |
| 29 | | | | | x |
| 30 | | | | | |
| 31 | | | | | |
| 32 | | | | | |
| 33 | | | | | |
| 34 | | | | | |
| 35 | x | | | | |
| 36 | | x | | | |
| 37 | | | x | | |
| 38 | | | | x | |
| 39 | | | | | x |
| 40 | | | | | |
| 41 | | | | | |
| 42 | | | | | |
| 43 | | | | | |
| 44 | | | | | |
| 45 | x | | | | |
| 46 | | x | | | |
| 47 | | | x | | |
| 48 | | | | x | |
| 49 | | | | | x |
| 50 | | | | | |

TABLE 2a-continued

Exemplary $R^1$, $W^4$ and $R^5$ for compounds of Formula II, in combination with the $R^2$ of Table 2b.

| | | | | | |
|---|---|---|---|---|---|
| 51 | | | | | |
| 52 | | | | | |
| 53 | | | | | |
| 54 | | | | | |
| 55 | x | | | | |
| 56 | | x | | | |
| 57 | | | x | | |
| 58 | | | | x | |
| 59 | | | | | x |
| 60 | | | | | |
| 61 | | | | | |
| 62 | | | | | |
| 63 | | | | | |
| 64 | | | | | |
| 65 | x | | | | |
| 66 | | x | | | |
| 67 | | | x | | |
| 68 | | | | x | |
| 69 | | | | | x |
| 70 | | | | | |
| 71 | | | | | |
| 72 | | | | | |
| 73 | | | | | |
| 74 | | | | | |
| 75 | x | | | | |
| 76 | | x | | | |
| 77 | | | x | | |
| 78 | | | | x | |
| 79 | | | | | x |
| 80 | | | | | |
| 81 | | | | | |
| 82 | | | | | |
| 83 | | | | | |
| 84 | | | | | |
| 85 | x | | | | |
| 86 | | x | | | |
| 87 | | | x | | |
| 88 | | | | x | |
| 89 | | | | | x |
| 90 | | | | | |
| 91 | | | | | |
| 92 | | | | | |
| 93 | | | | | |
| 94 | | | | | |
| 95 | x | | | | |
| 96 | | x | | | |
| 97 | | | x | | |
| 98 | | | | x | |
| 99 | | | | | x |
| 100 | | | | | |
| 101 | | | | | |
| 102 | | | | | |
| 103 | | | | | |
| 104 | | | | | |
| 105 | x | | | | |
| 106 | | x | | | |
| 107 | | | x | | |
| 108 | | | | x | |
| 109 | | | | | x |
| 110 | | | | | |
| 111 | | | | | |
| 112 | | | | | |
| 113 | | | | | |
| 114 | | | | | |
| 115 | x | | | | |
| 116 | | x | | | |
| 117 | | | x | | |
| 118 | | | | x | |
| 119 | | | | | x |

TABLE 2b
Exemplary R² for compounds of Formula II, in combination with the R¹, W⁴ and R⁵ of Table 2a.
| Sub-class # | R² |
|---|---|
| 1 | —CH₃ |
| 2 | —CH₂CH₃ |
| 3 | —CH(CH₃)2 |
| 4 | 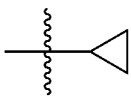 [SMILES: *C1CC1] |
| 5 | 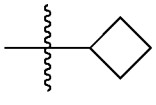 [SMILES: *C1CCC1] |
| 6 | 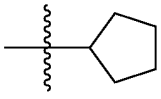 |
| 7 | 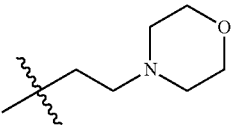 |
| 8 | 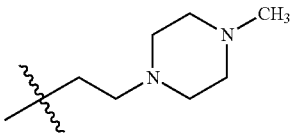 [SMILES: *CCN1CCN(C)CC1] |
| 9 | 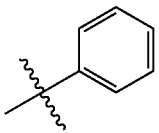 [SMILES: *c1ccccc1] |
| 10 | 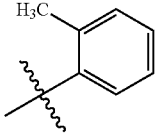 [SMILES: *c1ccccc1C] |
| 11 | 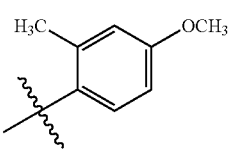 [SMILES: *c1ccc(OC)cc1C] |
| 12 | 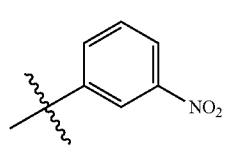 [SMILES: *c1cccc([N+](=O)[O-])c1] |
| 13 | 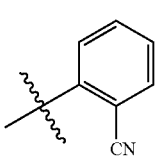 [SMILES: *c1ccccc1C#N] |
TABLE 2b-continued
Exemplary R² for compounds of Formula II, in combination with the R¹, W⁴ and R⁵ of Table 2a.
| Sub-class # | R² |
|---|---|
| 14 | 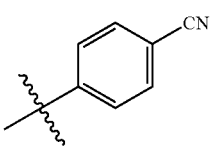 [SMILES: *c1ccc(C#N)cc1] |
| 15 | 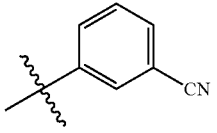 [SMILES: *c1cccc(C#N)c1] |
| 16 | 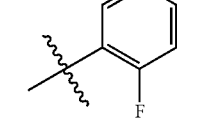 |
| 17 | 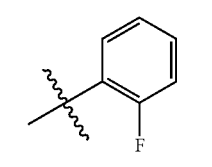 [SMILES: *c1ccccc1F] |
| 18 | 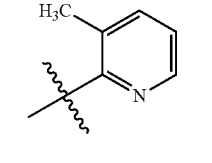 [SMILES: *c1ncccc1C] |
| 19 | 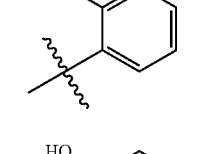 |
| 20 | 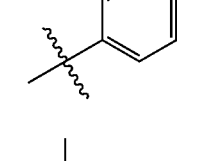 |
| 21 | 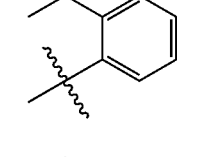 |
| 22 | 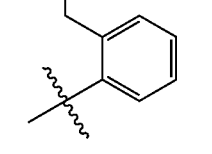 |

TABLE 2b-continued
Exemplary R² for compounds of Formula II, in combination with the R¹, W⁴ and R⁵ of Table 2a.
| Sub-class # | R² |
|---|---|
| 23 | 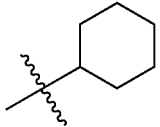 [SMILES: *C1CCCCC1] |
| 24 | 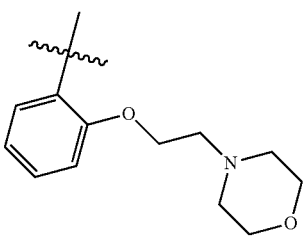 [SMILES: *c1ccccc1OCCN1CCOCC1] |
| 25 | 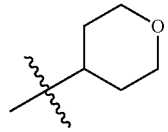 [SMILES: *C1CCOCC1] |
| 26 | 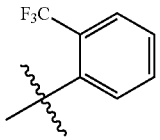 |
| 27 | 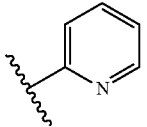 [SMILES: *c1ccccn1] |
| 28 | 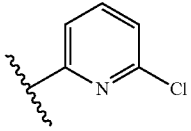 [SMILES: *c1cccc(Cl)n1] |
| 29 | 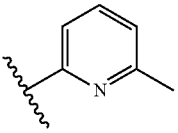 [SMILES: *c1cccc(C)n1] |
| 30 | 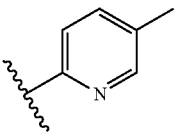 [SMILES: *c1ccc(C)cn1] |
| 31 | 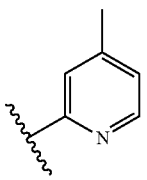 [SMILES: *c1cc(C)ccn1] |
TABLE 2b-continued
Exemplary R² for compounds of Formula II, in combination with the R¹, W⁴ and R⁵ of Table 2a.
| Sub-class # | R² |
|---|---|
| 32 | 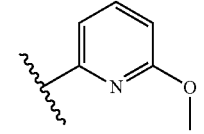 [SMILES: *c1cccc(OC)n1] |
| 33 | 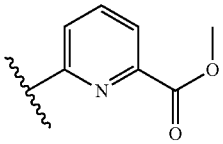 [SMILES: *c1cccc(C(=O)OC)n1] |
| 34 | 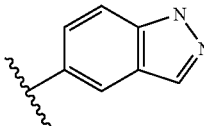 |
| 35 | 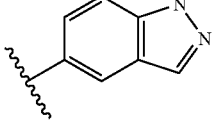 |
| 36 | 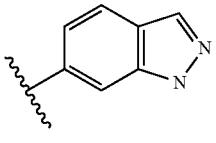 [SMILES: *c1ccc2cn[nH]c2c1] |
| 37 | 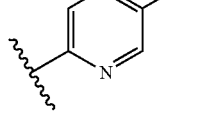 |
| 38 | 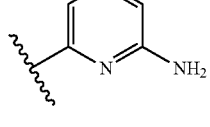 |
| 39 | 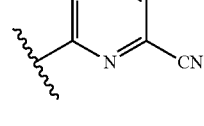 |
| 40 | 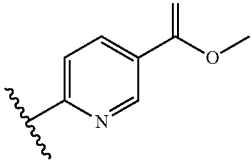 |
| 41 | 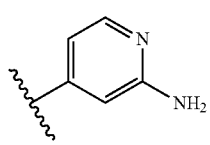 [SMILES: *c1ccnc(N)c1] |

TABLE 2b-continued

Exemplary R² for compounds of Formula II, in combination with the R¹, W⁴ and R⁵ of Table 2a.

| Sub-class # | R² |
|---|---|
| 42 | 4-pyridyl with 2-C(O)OCH₃ |
| 43 | 4-pyridyl with 2-CN |
| 44 | 4-pyridyl with 2-CH₃ |
| 45 | 6-(2-oxo-1H-pyridyl) |
| 46 | 5-hydroxy-2-pyridyl |
| 47 | 5-fluoro-2-pyridyl |
| 48 | 5-chloro-2-pyrazinyl |
| 49 | 5-methoxy-2-pyrazinyl |
| 50 | 5-amino-2-pyrazinyl |
| 51 | 5-methyl-2-pyrazinyl |
| 52 | 5-(dimethylamino)-2-pyrazinyl |
| 53 | 5-(N-methyl-N-ethylamino)-2-pyrazinyl |
| 54 | 5-(diethylamino)-2-pyrazinyl |
| 55 | 5-(4-methylpiperazin-1-yl)-2-pyrazinyl |
| 56 | 5-(pyrrolidin-1-yl)-2-pyrazinyl |
| 57 | 5-(piperidin-1-yl)-2-pyrazinyl |
| 58 | 5-(morpholin-4-yl)-2-pyrazinyl |

TABLE 2b-continued

Exemplary R² for compounds of Formula II, in combination with the R¹, W⁴ and R⁵ of Table 2a.

| Sub-class # | R² |
|---|---|
| 59 | [pyrazine substituted with 4-methylpiperidin-1-yl] |
| 60 | [pyrazine substituted with 2-methylpiperidin-1-yl] |
| 61 | [pyrazine substituted with pyrrol-1-yl] |
| 62 | [pyrazine substituted with imidazol-1-yl] |
| 63 | [pyrazine substituted with 2-methylimidazol-1-yl] |
| 64 | [pyrazine substituted with 4-methylimidazol-1-yl] |
| 65 | [pyrazine substituted with pyrazol-1-yl] |
| 66 | [pyrazine substituted with 4-methylpyrazol-1-yl] |
| 67 | [pyrazine substituted with 3-methylpyrazol-1-yl] |
| 68 | [pyrazine substituted with 2-oxopyridin-1-yl] |
| 69 | [pyrazine substituted with CN] |
| 70 | [pyrazine substituted with OMe] |
| 71 | [pyrazine substituted with N(Me)₂] |
| 72 | [pyrazine substituted with N(Et)₂] |
| 73 | [pyrazine substituted with morpholin-4-yl] |

TABLE 2b-continued

Exemplary R² for compounds of Formula II, in combination with the R¹, W⁴ and R⁵ of Table 2a.

| Sub-class # | R² |
|---|---|
| 74 | pyrazine with Cl |
| 75 | pyrazine with imidazole |
| 76 | pyrazine with pyridinone |
| 77 | pyrazine with pyrrolidine |
| 78 | pyrazine |
| 79 | thiazole |
| 80 | 2-methylthiazole |
| 81 | 2-isopropylthiazole |
| 82 | 2-(N-ethyl-N-methylamino)thiazole |
| 83 | 2-(N,N-diethylamino)thiazole |
| 84 | 2-(pyridinon-1-yl)thiazole |

In some other embodiments of the invention, additional exemplary compounds of Formula II are provided wherein R¹ and W⁴ are provided as described in Table 2a and R² is provided as described in Table 2b and R⁵ is provided as described in Table 2c.

TABLE 2c

Additional exemplary embodiments of R⁵ of Formula II.

| Sub-class # | R⁵ |
|---|---|
| 1 | —CH₃ |
| 2 | —CH₂CH₃ |
| 3 | —CH(CH₃)₂ |
| 4 | cyclopropyl |
| 5 | cyclobutyl |
| 6 | cyclopentyl |
| 7 | propyl-morpholine |
| 8 | propyl-(4-methylpiperazine) |

TABLE 2c-continued
Additional exemplary embodiments of $R^5$ of Formula II.
| Sub-class # | $R^5$ |
|---|---|
| 9 | 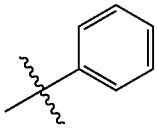 [SMILES: *c1ccccc1] |
| 10 | 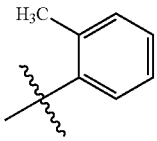 |
| 11 | 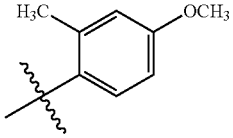 [SMILES: *c1ccc(OC)cc1C] |
| 12 | 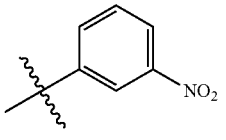 [SMILES: *c1cccc([N+](=O)[O-])c1] |
| 13 | 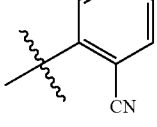 |
| 14 | 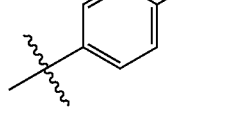 |
| 15 | 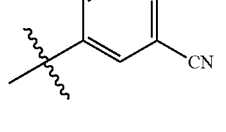 |
| 16 | 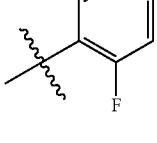 |
| 17 | 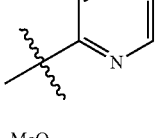 |
| 18 | 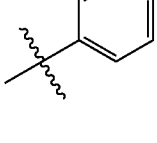 |
| 19 | 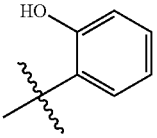 [SMILES: *c1ccccc1O] |
| 20 | 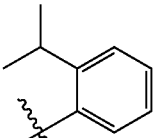 |
| 21 | 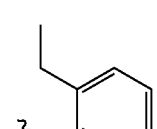 |
| 22 | 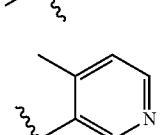 |
| 23 | 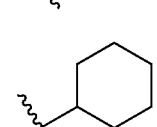 |
| 24 |  |
| 25 | 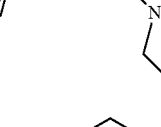 |
| 26 | 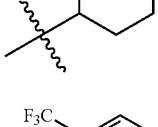 |
| 27 | 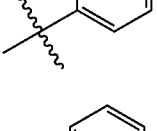 |

TABLE 2c-continued

Additional exemplary embodiments of R⁵ of Formula II.

| Sub-class # | R⁵ |
|---|---|
| 28 | 6-chloropyridin-2-yl |
| 29 | 6-methylpyridin-2-yl |
| 30 | 5-methylpyridin-2-yl |
| 31 | 4-methylpyridin-2-yl |
| 32 | 6-methoxypyridin-2-yl |
| 33 | methyl pyridine-2-carboxylate-6-yl |
| 34 | 1H-indazol-5-yl |
| 35 | 1H-indazol-6-yl |
| 36 | 5-aminopyridin-2-yl |
| 37 | 6-aminopyridin-2-yl |
| 38 | 6-cyanopyridin-2-yl |
| 39 | methyl pyridine-3-carboxylate-6-yl |
| 40 | 2-aminopyridin-4-yl |
| 41 | 2-(trifluoromethyl)pyridin-4-yl |
| 42 | methyl pyridine-2-carboxylate-4-yl |
| 43 | 2-cyanopyridin-4-yl |
| 44 | 2-methylpyridin-4-yl |
| 45 | 6-oxo-1,6-dihydropyridin-2-yl |
| 46 | 5-hydroxypyridin-2-yl |
| 47 | 5-fluoropyridin-2-yl |

TABLE 2c-continued
Additional exemplary embodiments of R⁵ of Formula II.
| Sub-class # | R⁵ |
|---|---|
| 48 | 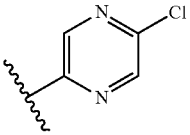 [SMILES: *c1cnc(Cl)cn1] |
| 49 | 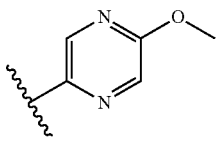 [SMILES: *c1cnc(OC)cn1] |
| 50 | 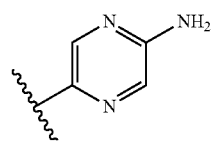 [SMILES: *c1cnc(N)cn1] |
| 51 | 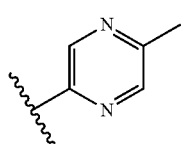 [SMILES: *c1cnc(C)cn1] |
| 52 | 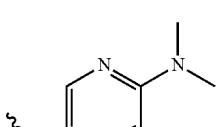 |
| 53 | 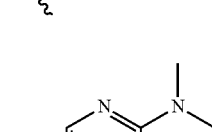 |
| 54 | 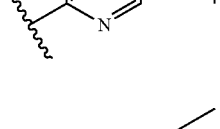 |
| 55 | 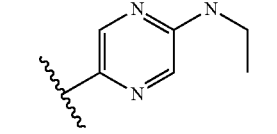 |
| 56 | 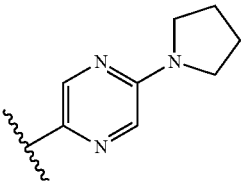 [SMILES: *c1cnc(N2CCCC2)cn1] |
| 57 | 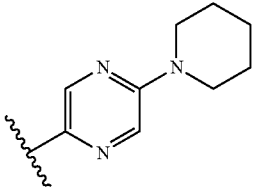 [SMILES: *c1cnc(N2CCCCC2)cn1] |
| 58 | 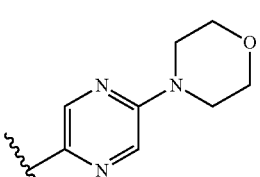 |
| 59 | 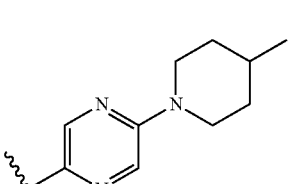 |
| 60 | 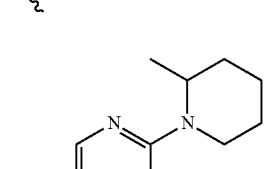 |
| 61 | 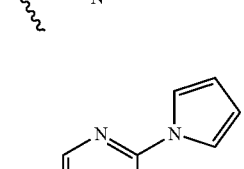 |
| 62 | 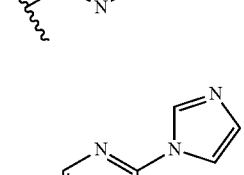 |

TABLE 2c-continued
Additional exemplary embodiments of R⁵ of Formula II.
| Sub-class # | R⁵ |
|---|---|
| 63 | 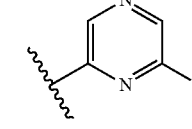 |
| 64 | 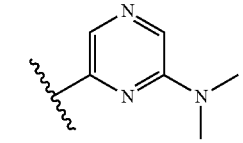 [SMILES: *c1cncc(N(C)C)n1] |
| 65 | 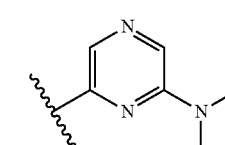 |
| 66 | 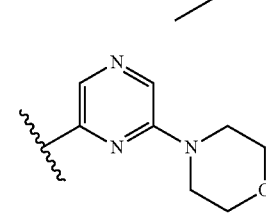 |
| 67 | 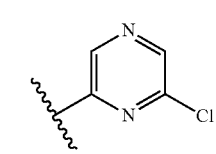 |
| 68 | 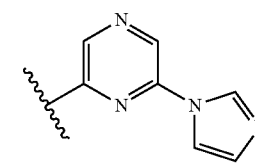 |
| 69 | 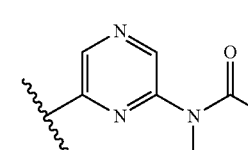 |
| 70 | 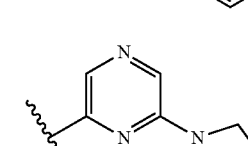 |
| 71 | 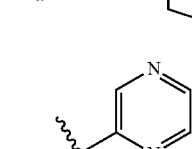 |
| 72 | |
| 73 | |
| 74 | |
| 75 | |
| 76 | |
| 77 | |
| 78 | |

TABLE 2c-continued

Additional exemplary embodiments of R⁵ of Formula II.

| Sub-class # | R⁵ |
|---|---|
| 79 | thiazol-4-yl |
| 80 | 2-methylthiazol-4-yl |
| 81 | 2-isopropylthiazol-4-yl |
| 82 | 2-(N-methyl-N-methylamino)thiazol-4-yl |
| 83 | 2-(diethylamino)thiazol-4-yl |
| 84 | 2-(2-oxopyridin-1-yl)thiazol-4-yl |
| 85 | 2-(imidazol-1-yl)thiazol-4-yl |
| 86 | 3-hydroxyphenyl |
| 87 | 1H-pyrazol-4-yl |
| 88 | thiophen-2-yl |
| 89 | 5-fluoro-1H-indol-2-yl |
| 90 | 1H-pyrrolo[2,3-b]pyridin-5-yl |
| 91 | 2-(NHAc)benzothiazol-5-yl |
| 92 | pyridin-3-yl |
| 93 | 1H-pyrrolo[2,3-b]pyridin-5-yl |
| 94 | 3-fluoro-5-hydroxyphenyl |
| 95 | 4-fluoro-3-hydroxyphenyl |
| 96 | 4-chloro-3-hydroxyphenyl |
| 97 | 4-chloro-3-methoxyphenyl |

TABLE 2c-continued
Additional exemplary embodiments of R⁵ of Formula II.
| Sub-class # | R⁵ |
|---|---|
| 98 | 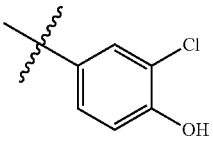 [SMILES: *c1ccc(O)c(Cl)c1] |
| 99 | 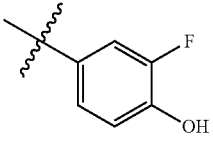 [SMILES: *c1ccc(O)c(F)c1] |
| 100 | 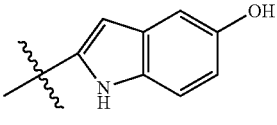 [SMILES: *c1cc2cc(O)ccc2[nH]1] |
| 101 | 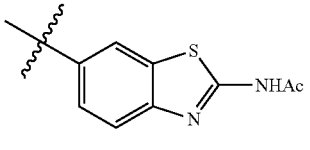 [SMILES: *c1ccc2nc(NC(C)=O)sc2c1] |
| 102 | 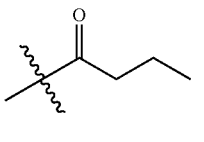 [SMILES: *C(=O)CCC] |
| | 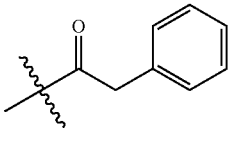 [SMILES: *C(=O)Cc1ccccc1] |
| | 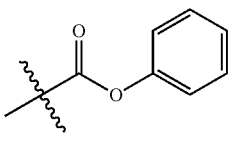 |
| | 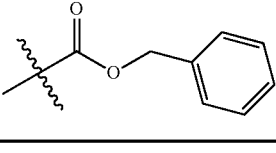 |
| | 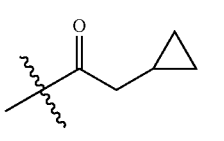 [SMILES: *C(=O)CC1CC1] |
| | 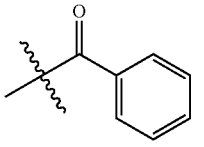 [SMILES: *C(=O)c1ccccc1] |
| | 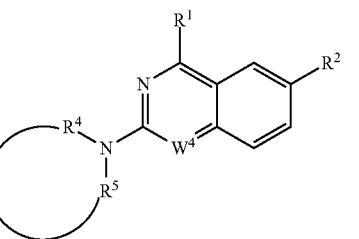 |
| | 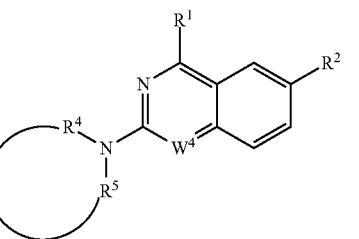 |
| | 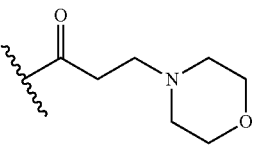 [SMILES: *C(=O)CCN1CCOCC1] |
| | 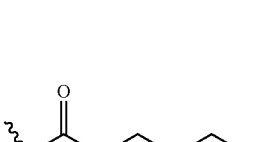 |
| | 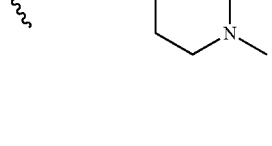 |
| | 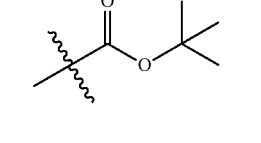 |
In other embodiments of the invention, compounds of Formula III are provided with $R^1$, $R^2$, $W^4$ and ($R^4$ plus $R^5$) as illustrated in Tables 3a and 3b.
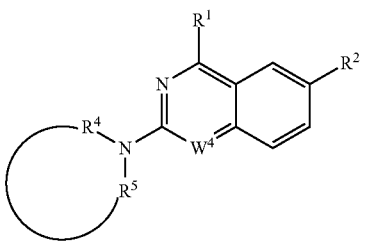
Formula III TABLE 3a Exemplary R$^1$, W$^4$ and (R$^4$ plus R$^5$) for compounds of Formula III, in combination with the R$^2$ of Table 3b.

| Sub class # | R$^1$ C-i-Pr | R$^1$ CH | R$^1$ CMe | R$^1$ N | W$^4$ NH$_2$ | W$^4$ Me | W$^4$ CF$_3$ | (R$^4$ plus R$^5$) 7-azaindolyl | (R$^4$ plus R$^5$) pyrazolyl | (R$^4$ plus R$^5$) 2-methylimidazolyl |
|---|---|---|---|---|---|---|---|---|---|---|
| 1 |  |  |  | x |  |  | x | x |  |  |
| 2 |  |  |  | x |  |  | x |  | x |  |
| 3 |  |  |  | x |  |  | x |  |  | x |
| 4 |  |  |  | x |  |  | x |  |  |  |
| 5 |  |  |  | x |  |  | x |  |  |  |
| 6 |  |  |  | x |  |  | x |  |  |  |
| 7 |  |  |  | x |  | x |  | x |  |  |
| 8 |  |  |  | x |  | x |  |  | x |  |
| 9 |  |  |  | x |  | x |  |  |  | x |
| 10 |  |  |  | x |  | x |  |  |  |  |
| 11 |  |  |  | x |  | x |  |  |  |  |
| 12 |  |  |  | x |  | x |  |  |  |  |
| 13 |  |  |  | x | x |  |  | x |  |  |
| 14 |  |  |  | x | x |  |  |  | x |  |
| 15 |  |  |  | x | x |  |  |  |  | x |
| 16 |  |  |  | x | x |  |  |  |  |  |
| 17 |  |  |  | x | x |  |  |  |  |  |
| 18 |  |  |  | x | x |  |  |  |  |  |
| 19 |  |  | x |  |  |  | x | x |  |  |
| 20 |  |  | x |  |  |  | x |  | x |  |
| 21 |  |  | x |  |  |  | x |  |  | x |
| 22 |  |  |  |  |  |  | x |  |  |  |
| 23 |  |  |  |  |  |  | x |  |  |  |
| 24 |  |  |  |  |  |  | x |  |  |  |
| 25 |  |  |  |  |  | x |  | x |  |  |
| 26 |  |  |  |  |  | x |  |  | x |  |
| 27 |  |  |  |  |  | x |  |  |  | x |
| 28 |  |  |  |  |  | x |  |  |  |  |
| 29 |  |  |  |  |  | x |  |  |  |  |
| 30 |  |  |  |  |  | x |  |  |  |  |
| 31 |  |  |  |  | x |  |  | x |  |  |
| 32 |  |  |  |  | x |  |  |  | x |  |
| 33 |  |  |  |  | x |  |  |  |  | x |
| 34 |  | x |  |  | x |  |  |  |  |  |
| 35 |  | x |  |  | x |  |  |  |  |  |
| 36 |  | x |  |  | x |  |  |  |  |  |
| 37 |  | x |  |  |  |  | x | x |  |  |
| 38 |  | x |  |  |  |  | x |  | x |  |
| 39 |  | x |  |  |  |  | x |  |  | x |
| 40 |  | x |  |  |  |  | x |  |  |  |
| 41 |  | x |  |  |  |  | x |  |  |  |
| 42 |  | x |  |  |  |  | x |  |  |  |
| 43 |  | x |  |  |  | x |  | x |  |  |
| 44 |  | x |  |  |  | x |  |  | x |  |
| 45 |  | x |  |  |  | x |  |  |  | x |
| 46 |  | x |  |  |  | x |  |  |  |  |
| 47 |  | x |  |  |  | x |  |  |  |  |
| 48 |  | x |  |  |  | x |  |  |  |  |
| 49 |  | x |  |  | x |  |  | x |  |  |
| 50 |  | x |  |  | x |  |  |  | x |  |
| 51 |  | x |  |  | x |  |  |  |  | x |
| 52 |  | x |  |  | x |  |  |  |  |  |
| 53 |  | x |  |  | x |  |  |  |  |  |
| 54 |  | x |  |  | x |  |  |  |  |  |
| 55 | x |  |  |  |  |  | x | x |  |  |
| 56 | x |  |  |  |  |  | x |  | x |  |
| 57 | x |  |  |  |  |  | x |  |  | x |
| 58 | x |  |  |  |  |  | x |  |  |  |
| 59 | x |  |  |  |  |  | x |  |  |  |
| 60 | x |  |  |  |  |  | x |  |  |  |
| 61 | x |  |  |  |  | x |  | x |  |  |
| 62 | x |  |  |  |  | x |  |  | x |  |
| 63 | x |  |  |  |  | x |  |  |  | x |
| 64 | x |  |  |  |  | x |  |  |  |  |
| 65 | x |  |  |  |  | x |  |  |  |  |
| 66 | x |  |  |  |  | x |  |  |  |  |
| 67 | x |  |  |  | x |  |  | x |  |  |
| 68 | x |  |  |  | x |  |  |  | x |  |
| 69 | x |  |  |  | x |  |  |  |  | x |

TABLE 3a-continued

Exemplary $R^1$, $W^4$ and ($R^4$ plus $R^5$) for compounds of Formula III, in combination with the $R^2$ of Table 3b.

| | | |
|---|---|---|
| 70 | x | x |
| 71 | x | x |
| 72 | x | x |

| Sub class # | ($R^4$ plus $R^5$) pyrrole | ($R^4$ plus $R^5$) pyrrolo-pyridine | ($R^4$ plus $R^5$) 5-hydroxyindole |
|---|---|---|---|
| 1 | | | |
| 2 | | | |
| 3 | | | |
| 4 | x | | |
| 5 | | x | |
| 6 | | | x |
| 7 | | | |
| 8 | | | |
| 9 | | | |
| 10 | x | | |
| 11 | | x | |
| 12 | | | x |
| 13 | | | |
| 14 | | | |
| 15 | | | |
| 16 | x | | |
| 17 | | x | |
| 18 | | | x |
| 19 | | | |
| 20 | | | |
| 21 | | | |
| 22 | x | | |
| 23 | | x | |
| 24 | | | x |
| 25 | | | |
| 26 | | | |
| 27 | | | |
| 28 | x | | |
| 29 | | x | |
| 30 | | | x |
| 31 | | | |
| 32 | | | |
| 33 | | | |
| 34 | x | | |
| 35 | | x | |
| 36 | | | x |
| 37 | | | |
| 38 | | | |
| 39 | | | |
| 40 | x | | |
| 41 | | x | |
| 42 | | | x |
| 43 | | | |
| 44 | | | |
| 45 | | | |
| 46 | x | | |
| 47 | | x | |
| 48 | | | x |
| 49 | | | |
| 50 | | | |
| 51 | | | |
| 52 | x | | |
| 53 | | x | |
| 54 | | | x |
| 55 | | | |
| 56 | | | |
| 57 | | | |
| 58 | x | | |
| 59 | | x | |
| 60 | | | x |
| 61 | | | |
| 62 | | | |
| 63 | | | |
| 64 | x | | |
| 65 | | x | |

TABLE 3a-continued

Exemplary R¹, W⁴ and (R⁴ plus R⁵) for compounds of Formula III, in combination with the R² of Table 3b.

| | | | | |
|---|---|---|---|---|
| 66 | | | | x |
| 67 | | | | |
| 68 | | | | |
| 69 | | | | |
| 70 | x | | | |
| 71 | | | x | |
| 72 | | | | x |

TABLE 3b

Exemplary R² for compounds of Formula II, in combination with the R¹, W⁴, and (R⁴ plus R⁵) of Table 3a.

| Sub-class # | R² |
|---|---|
| 1 | —CH₃ |
| 2 | —CH₂CH₃ |
| 3 | —CH(CH₃)2 |
| 4 | 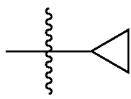 |
| 5 | 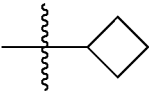 [SMILES: *C1CCC1] |
| 6 | 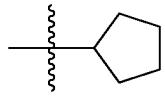 |
| 7 | 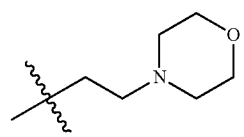 [SMILES: *CCN1CCOCC1] |
| 8 | 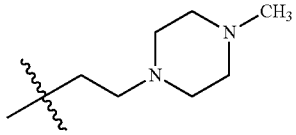 [SMILES: *CCN1CCN(C)CC1] |
| 9 | 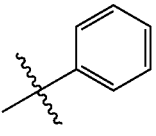 |
| 10 | 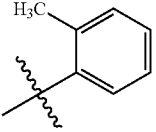 [SMILES: *c1ccccc1C] |
| 11 | 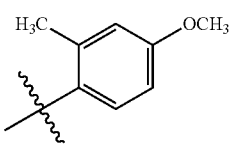 [SMILES: *c1ccc(OC)cc1C] |

TABLE 3b-continued

Exemplary R² for compounds of Formula II, in combination with the R¹, W⁴, and (R⁴ plus R⁵) of Table 3a.

| Sub-class # | R² |
|---|---|
| 12 | 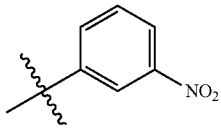 [SMILES: *c1cccc([N+](=O)[O-])c1] |
| 13 | 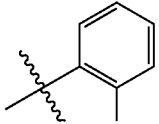 |
| 14 | 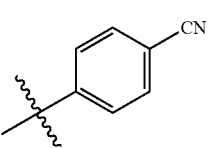 [SMILES: *c1ccc(C#N)cc1] |
| 15 | 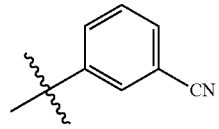 [SMILES: *c1cccc(C#N)c1] |
| 16 | 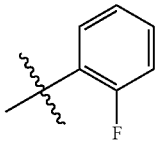 [SMILES: *c1ccccc1F] |
| 17 | 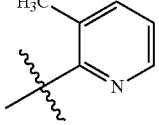 |
| 18 | 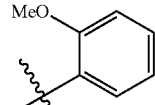 |
| 19 | 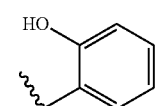 |

TABLE 3b-continued

Exemplary R² for compounds of Formula II, in combination with the R¹, W⁴, and (R⁴ plus R⁵) of Table 3a.

| Subclass # | R² |
|---|---|
| 20 | 2-isopropylphenyl |
| 21 | 2-ethylphenyl |
| 22 | 4-methylpyridin-3-yl |
| 23 | cyclohexyl |
| 24 | 2-(2-morpholinoethoxy)phenyl |
| 25 | tetrahydro-2H-pyran-4-yl |
| 26 | 2-(trifluoromethyl)phenyl |
| 27 | pyridin-2-yl |
| 28 | 6-chloropyridin-2-yl |
| 29 | 6-methylpyridin-2-yl |
| 30 | 5-methylpyridin-2-yl |
| 31 | 4-methylpyridin-2-yl |
| 32 | 6-methoxypyridin-2-yl |
| 33 | methyl 6-(pyridin-2-yl)carboxylate |
| 34 | 1H-indazol-5-yl |
| 35 | 1H-indazol-6-yl |
| 36 | 5-aminopyridin-2-yl |
| 37 | 6-aminopyridin-2-yl |

TABLE 3b-continued

Exemplary R² for compounds of Formula II, in combination with the R¹, W⁴, and (R⁴ plus R⁵) of Table 3a.

| Subclass # | R² |
|---|---|
| 38 | 6-cyanopyridin-2-yl |
| 39 | 5-(methoxycarbonyl)pyridin-2-yl |
| 40 | 2-aminopyridin-4-yl |
| 41 | 2-(trifluoromethyl)pyridin-4-yl |
| 42 | 2-(methoxycarbonyl)pyridin-4-yl |
| 43 | 2-cyanopyridin-4-yl |
| 44 | 2-methylpyridin-4-yl |
| 45 | 2-oxo-1,2-dihydropyridin-6-yl |
| 46 | 5-hydroxypyridin-2-yl |
| 47 | 5-fluoropyridin-2-yl |
| 48 | 5-chloropyrazin-2-yl |
| 49 | 5-methoxypyrazin-2-yl |
| 50 | 5-aminopyrazin-2-yl |
| 51 | 5-methylpyrazin-2-yl |
| 52 | 5-(dimethylamino)pyrazin-2-yl |
| 53 | 5-(N-methyl-N-ethylamino)pyrazin-2-yl |
| 54 | 5-(diethylamino)pyrazin-2-yl |

TABLE 3b-continued
Exemplary R² for compounds of Formula II, in combination with the R¹, W⁴, and (R⁴ plus R⁵) of Table 3a.
| Sub-class # | R² |
|---|---|
| 55 | 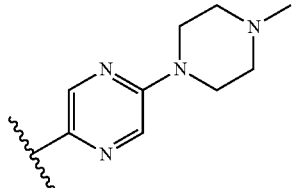 |
| 56 | 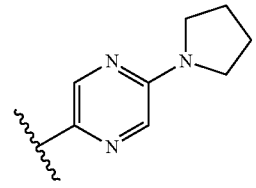 [SMILES: *c1cnc(N2CCCC2)cn1] |
| 57 | 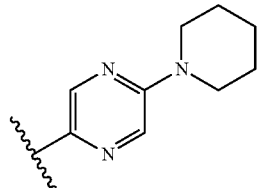 [SMILES: *c1cnc(N2CCCCC2)cn1] |
| 58 | 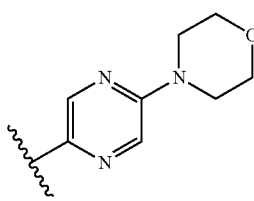 |
| 59 | 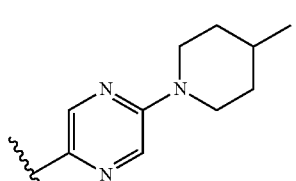 |
| 60 | 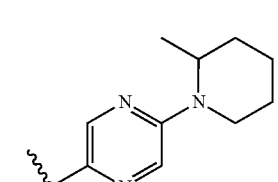 |
| 61 | 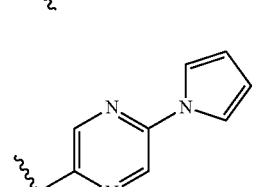 |
| 62 | 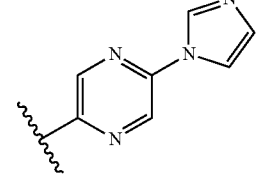 |
| 63 | 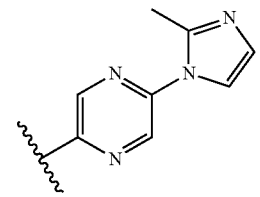 [SMILES: *c1cnc(-n2ccnc2C)cn1] |
| 64 | 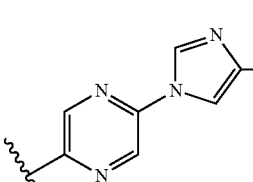 |
| 65 | 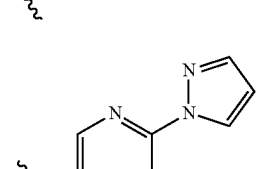 |
| 66 | 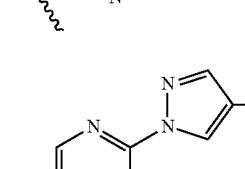 |
| 67 | 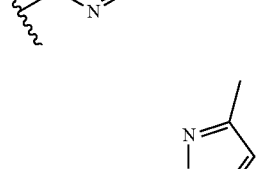 |
| 68 | 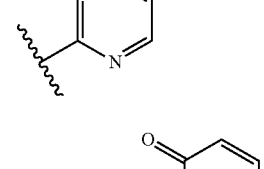 |

TABLE 3b-continued
Exemplary R² for compounds of Formula II, in combination with the R¹, W⁴, and (R⁴ plus R⁵) of Table 3a.
| Sub-class # | R² |
|---|---|
| 69 | 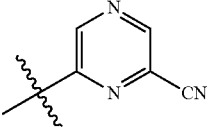 [SMILES: *c1cncc(C#N)n1] |
| 70 | 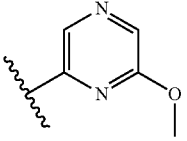 [SMILES: *c1cncc(OC)n1] |
| 71 | 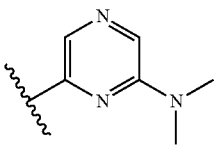 |
| 72 | 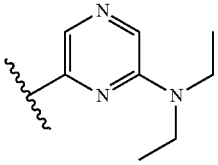 [SMILES: *c1cncc(N(CC)CC)n1] |
| 73 | 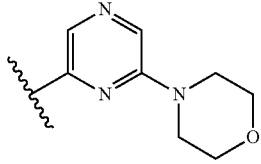 [SMILES: *c1cncc(N2CCOCC2)n1] |
| 74 | 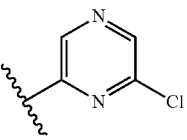 [SMILES: *c1cncc(Cl)n1] |
| 75 | 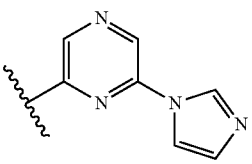 [SMILES: *c1cncc(-n2ccnc2)n1] |
| 76 | 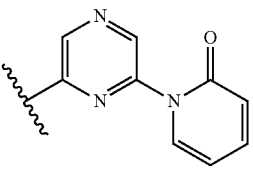 [SMILES: *c1cncc(-n2ccccc2=O)n1] |
| 77 | 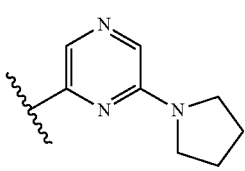 [SMILES: *c1cncc(N2CCCC2)n1] |
| 78 | 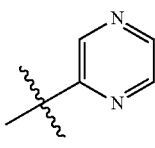 [SMILES: *c1cnccn1] |
| 79 | 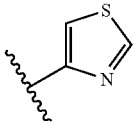 [SMILES: *c1cscn1] |
| 80 | 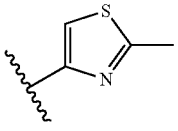 [SMILES: *c1csc(C)n1] |
| 81 | 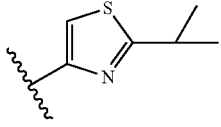 |
| 82 | 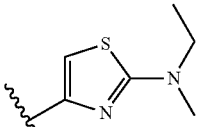 |
| 83 | 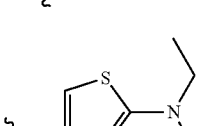 |
| 84 | 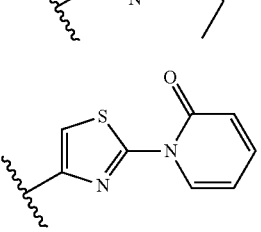 |
| 85 | 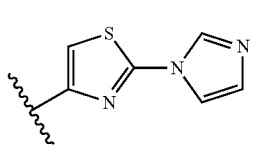 [SMILES: *c1csc(-n2ccnc2)n1] |
| 86 | 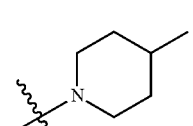 |
| 87 | 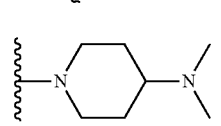 |

TABLE 3b-continued
Exemplary R² for compounds of Formula II, in combination with the R¹, W⁴, and (R⁴ plus R⁵) of Table 3a.
| Sub-class # | R² |
|---|---|
| 88 | 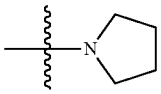 |
| 89 | 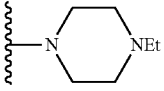 |
| 90 | 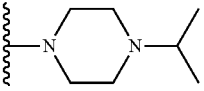 [SMILES: *N1CCN(C(C)C)CC1] |
| 91 | 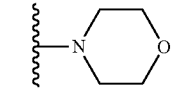 |
| 92 | 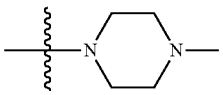 |
| 92 | 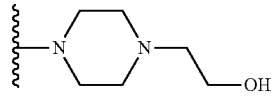 |
| 94 | 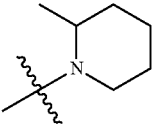 [SMILES: *N1CCCCC1C] |
| 95 | 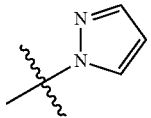 [SMILES: *n1cccn1] |
| 96 | 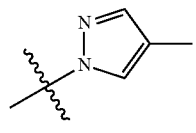 [SMILES: *n1cc(C)cn1] |
| 97 | 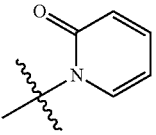 [SMILES: *n1ccccc1=O] |
| 98 | 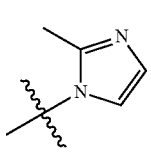 [SMILES: *n1ccnc1C] |
| 99 | 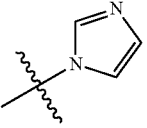 [SMILES: *n1ccnc1] |
| 100 | 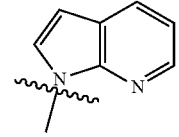 |
| 101 | —Br |
| 102 | 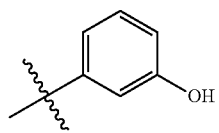 [SMILES: *c1cccc(O)c1] |
| 103 | 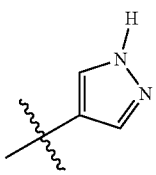 [SMILES: *c1cn[nH]c1] |
| 104 | 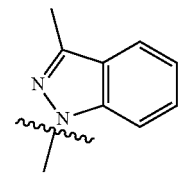 |
| 105 | 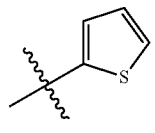 [SMILES: *c1cccs1] |
| 106 | 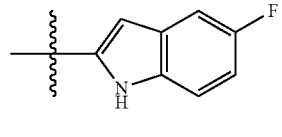 [SMILES: *c1cc2cc(F)ccc2[nH]1] |
| 107 | 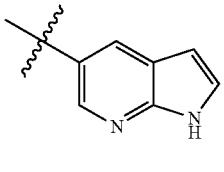 [SMILES: *c1cnc2[nH]ccc2c1] |
| 108 | 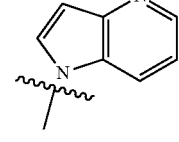 |
| 109 | |

TABLE 3b-continued

Exemplary R² for compounds of Formula II, in combination with the R¹, W⁴, and (R⁴ plus R⁵) of Table 3a.

| Subclass # | R² |
|---|---|
| 110 | (3-pyridyl) |
| 111 | (7-azaindol-5-yl) |
| 112 | (3-fluoro-5-hydroxyphenyl) |
| 113 | (4-fluoro-3-hydroxyphenyl) |
| 114 | (4-chloro-3-hydroxyphenyl) |
| 115 | (4-chloro-3-methoxyphenyl) |
| 116 | (3-chloro-4-hydroxyphenyl) |
| 117 | (3-fluoro-4-hydroxyphenyl) |
| 118 | (5-hydroxy-1H-indol-2-yl) |
| 119 | (2-acetamidobenzothiazol-6-yl) |
| 120 | (2-acetamidobenzothiazol-5-yl) |
| 121 | (1H-pyrazolo[3,4-b]pyridin-5-yl) |
| 122 | (6-methylpyrido[2,3-d]pyrimidin-?-yl) |

In other embodiments of the invention, compounds of Formula IV are provided with $R^1$, $R^2$, $R^5$, $W^1$, $W^2$, $W^4$ and $W^5$ as illustrated in Tables 4a, 4b, and 4c.

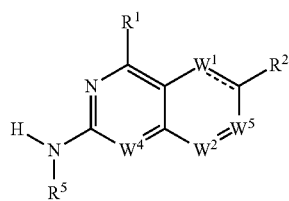

TABLE 4a

Exemplary $R^1$, $W^1$, $W^2$, $W^4$ and $W^5$ for Compounds of Formula IV in combination with $R^2$ and $R^5$ as illustrated in Tables 4b and 4c.

| Subclass # | $R^1$ | | | $W^1$ | | $W^2$ | | $W^4$ | | $W^5$ | | | |
|---|---|---|---|---|---|---|---|---|---|---|---|---|---|
| 1 | NH₂ | CMe | CF₃ | NEt | N | CMe | CH | CMe | CH | N | N | CH | C(O) | CMe |
| 2 | | x | | | x | | x | | x | x | x | | | |
| 3 | | x | | | x | | x | | x | | | x | | |

TABLE 4a-continued

Exemplary R¹, W¹, W², W⁴ and W⁵ for Compounds of Formula IV in combination with R² and R⁵ as illustrated in Tables 4b and 4c.

| Sub class # | R¹ | | | W¹ | | | | W² | | | W⁴ | | | W⁵ | | | |
|---|---|---|---|---|---|---|---|---|---|---|---|---|---|---|---|---|---|
| 1 | NH₂ | CMe | CF₃ | NEt | N | CMe | CH | CMe | CH | N | CMe | CH | N | N | CH | C(O) | CMe |
| 4 | | | x | | | x | | x | | | x | | | | x | | |
| 5 | | | x | | | x | | x | | | x | | | | | | x |
| 6 | | | x | | | x | | x | | | | x | | x | | | |
| 7 | | | x | | | x | | x | | | | x | | | x | | |
| 8 | | | x | | | x | | x | | | | x | | | | x | |
| 9 | | | x | | | x | | x | | | | x | | | | | x |
| 10 | | | x | | | x | | x | | | | | x | | x | | |
| 11 | | | x | | | x | | x | | | | | x | | | x | |
| 12 | | | x | | | x | | x | | | | | x | | | | x |
| 13 | | | x | | | x | | x | | | | | x | x | | | |
| 14 | | | x | | | x | | | x | | x | | | | x | | |
| 15 | | | x | | | x | | | x | | x | | | | | x | |
| 16 | | | x | | | x | | | x | | x | | | | | | x |
| 17 | | | x | | | x | | | x | | x | | | x | | | |
| 18 | | | x | | | x | | | x | | | x | | | x | | |
| 19 | | | x | | | x | | | x | | | x | | | | x | |
| 20 | | | x | | | x | | | x | | | x | | | | | x |
| 21 | | | x | | | x | | | x | | | x | | x | | | |
| 22 | | | x | | | x | | | x | x | | | | | x | | |
| 23 | | | x | | | x | | | x | x | | | | | | x | |
| 24 | | | x | | | x | | | x | x | | | | | | | x |
| 25 | | | x | | | x | | | x | x | | | | x | | | |
| 26 | | | x | | | | x | x | | | x | | | | x | | |
| 27 | | | x | | | | x | x | | | x | | | | | x | |
| 28 | | | x | | | | x | x | | | x | | | | | | x |
| 29 | | | x | | | | x | x | | | x | | | x | | | |
| 30 | | | x | | | | x | x | | | | x | | | x | | |
| 31 | | | x | | | | x | x | | | | x | | | | x | |
| 32 | | | x | | | | x | x | | | | x | | | | | x |
| 33 | | | x | | | | x | x | | | | x | | x | | | |
| 34 | | | x | | | | x | x | | | | | x | | x | | |
| 35 | | | x | | | | x | x | | | | | x | | | x | |
| 36 | | | x | | | | x | x | | | | | x | | | | x |
| 37 | | | x | | | | x | x | | | | | x | x | | | |
| 38 | | | x | | x | | | | x | | x | | | | x | | |
| 39 | | | x | | x | | | | x | | x | | | | | x | |
| 40 | | | x | | x | | | | x | | x | | | | | | x |
| 41 | | | x | | x | | | | x | | x | | | x | | | |
| 42 | | | x | | x | | | | x | | | x | | | x | | |
| 43 | | | x | | x | | | | x | | | x | | | | x | |
| 44 | | | x | | x | | | | x | | | x | | | | | x |
| 45 | | | x | | x | | | | x | | | x | | x | | | |
| 46 | | | x | | x | | | | x | x | | | | | x | | |
| 47 | | | x | | x | | | | x | x | | | | | | x | |
| 48 | | | x | | x | | | | x | x | | | | | | | x |
| 49 | | | x | | x | | | | x | x | | | | x | | | |
| 50 | | | x | | x | | | x | | | x | | | | x | | |
| 51 | | | x | | x | | | x | | | x | | | | | x | |
| 52 | | | x | | x | | | x | | | x | | | | | | x |
| 53 | | | x | | x | | | x | | | x | | | x | | | |
| 54 | | | x | | x | | | x | | | | x | | | x | | |
| 55 | | | x | | x | | | x | | | | x | | | | x | |
| 56 | | | x | | x | | | x | | | | x | | | | | x |
| 57 | | | x | | x | | | x | | | | x | | x | | | |
| 58 | | | x | | x | | | x | | | | | x | | x | | |
| 59 | | | x | | x | | | x | | | | | x | | | x | |
| 60 | | | x | | x | | | x | | | | | x | | | | x |
| 61 | | | x | | x | | | x | | | | | x | x | | | |
| 62 | | | x | | x | | | | | x | x | | | | x | | |
| 63 | | | x | | x | | | | | x | x | | | | | x | |
| 64 | | | x | | x | | | | | x | x | | | | | | x |
| 65 | | | x | | x | | | | | x | x | | | x | | | |
| 66 | | | x | | x | | | | | x | | x | | | x | | |
| 67 | | | x | | x | | | | | x | | x | | | | x | |
| 68 | | | x | | x | | | | | x | | x | | | | | x |
| 69 | | | x | | x | | | | | x | | x | | x | | | |
| 70 | | | x | | x | | | | | x | | | x | | x | | |
| 71 | | | x | | x | | | | | x | | | x | | | x | |
| 72 | | | x | | x | | | | | x | | | x | | | | x |
| 73 | | | x | | x | | | | | x | | | x | x | | | |
| 74 | | | x | x | | | | | x | | x | | | | x | | |
| 75 | | | x | x | | | | | x | | x | | | | | x | |

TABLE 4a-continued

Exemplary R¹, W¹, W², W⁴ and W⁵ for Compounds of Formula IV in combination with R² and R⁵ as illustrated in Tables 4b and 4c.

| Sub class # | R¹ | | | W¹ | | | | W² | | | W⁴ | | | W⁵ | | | |
|---|---|---|---|---|---|---|---|---|---|---|---|---|---|---|---|---|---|
| 1 | NH₂ | CMe | CF₃ | NEt | N | CMe | CH | CMe | CH | N | CMe | CH | N | N | CH | C(O) | CMe |
| 76 | | | x | | x | | | | | x | | | x | | | x | |
| 77 | | | x | | x | | | | | x | | | x | | | | x |
| 78 | | | x | | x | | | | | x | | x | | | x | | |
| 79 | | | x | | x | | | | | x | | x | | | | x | |
| 80 | | | x | | x | | | | | x | | x | | | | | x |
| 81 | | | x | | x | | | | | x | | x | | | | | x |
| 82 | | | x | | x | | | | | x | x | | | | x | | |
| 83 | | | x | | x | | | | | x | x | | | | | x | |
| 84 | | | x | | x | | | | | x | x | | | | | x | |
| 85 | | | x | | x | | | | | x | x | | | | | | x |
| 86 | | | x | | x | | | | x | | | | | x | x | | |
| 87 | | | x | | x | | | | x | | | | | x | | x | |
| 88 | | | x | | x | | | | x | | | | | x | | x | |
| 89 | | | x | | x | | | | x | | | | | x | | | x |
| 90 | | | x | | x | | | | x | | | x | | | x | | |
| 91 | | | x | | x | | | | x | | | x | | | | x | |
| 92 | | | x | | x | | | | x | | | x | | | | x | |
| 93 | | | x | | x | | | | x | | | x | | | | | x |
| 94 | | | x | | x | | | | x | | x | | | | x | | |
| 95 | | | x | | x | | | | x | | x | | | | | x | |
| 96 | | | x | | x | | | | x | | x | | | | | x | |
| 97 | | | x | | x | | | | x | | x | | | | | | x |
| 98 | | | x | | x | | | x | | | | | | x | x | | |
| 99 | | | x | | x | | | x | | | | | | x | | x | |
| 100 | | | x | | x | | | x | | | | | | x | | x | |
| 101 | | | x | | x | | | x | | | | | | x | | | x |
| 102 | | | x | | x | | | x | | | | x | | | x | | |
| 103 | | | x | | x | | | x | | | | x | | | | x | |
| 104 | | | x | | x | | | x | | | | x | | | | x | |
| 105 | | | x | | x | | | x | | | | x | | | | | x |
| 106 | | | x | | x | | | x | | | x | | | | x | | |
| 107 | | | x | | x | | | x | | | x | | | | | x | |
| 108 | | | x | | x | | | x | | | x | | | | | x | |
| 109 | | | x | | x | | | x | | | x | | | | | | x |
| 110 | | x | | x | | | | | | x | | | | x | x | | |
| 111 | | x | | x | | | | | | x | | | | x | | x | |
| 112 | | x | | x | | | | | | x | | | | x | | x | |
| 113 | | x | | x | | | | | | x | | | | x | | | x |
| 114 | | x | | x | | | | | | x | | x | | | x | | |
| 115 | | x | | x | | | | | | x | | x | | | | x | |
| 116 | | x | | x | | | | | | x | | x | | | | x | |
| 117 | | x | | x | | | | | | x | | x | | | | | x |
| 118 | | x | | x | | | | | | x | x | | | | x | | |
| 119 | | x | | x | | | | | | x | x | | | | | x | |
| 120 | | x | | x | | | | | | x | x | | | | | x | |
| 121 | | x | | x | | | | | | x | x | | | | | | x |
| 122 | | x | | x | | | | x | | | | | | x | x | | |
| 123 | | x | | x | | | | x | | | | | | x | | x | |
| 124 | | x | | x | | | | x | | | | | | x | | x | |
| 125 | | x | | x | | | | x | | | | | | x | | | x |
| 126 | | x | | x | | | | x | | | | x | | | x | | |
| 127 | | x | | x | | | | x | | | | x | | | | x | |
| 128 | | x | | x | | | | x | | | | x | | | | x | |
| 129 | | x | | x | | | | x | | | | x | | | | | x |
| 130 | | x | | x | | | | x | | | x | | | | x | | |
| 131 | | x | | x | | | | x | | | x | | | | | x | |
| 132 | | x | | x | | | | x | | | x | | | | | x | |
| 133 | | x | | x | | | | x | | | x | | | | | | x |
| 134 | | x | | x | | | x | | | | | | | x | x | | |
| 135 | | x | | x | | | x | | | | | | | x | | x | |
| 136 | | x | | x | | | x | | | | | | | x | | x | |
| 137 | | x | | x | | | x | | | | | | | x | | | x |
| 138 | | x | | x | | | x | | | | | x | | | x | | |
| 139 | | x | | x | | | x | | | | | x | | | | x | |
| 140 | | x | | x | | | x | | | | | x | | | | x | |
| 141 | | x | | x | | | x | | | | | x | | | | | x |
| 142 | | x | | x | | | x | | | | x | | | | x | | |
| 143 | | x | | x | | | x | | | | x | | | | | x | |
| 144 | | x | | x | | | x | | | | x | | | | | x | |
| 145 | | x | | x | | | x | | | | x | | | | | | x |
| 146 | x | | | | | x | | | | x | | | | x | x | | |
| 147 | x | | | | | x | | | | x | | | | x | | x | |

TABLE 4a-continued

Exemplary R¹, W¹, W², W⁴ and W⁵ for Compounds of Formula IV in combination with R² and R⁵ as illustrated in Tables 4b and 4c.

| Sub class # | R¹ | | | W¹ | | | | W² | | | W⁴ | | | W⁵ | | | |
|---|---|---|---|---|---|---|---|---|---|---|---|---|---|---|---|---|---|
| 1 | NH₂ | CMe | CF₃ | NEt | N | CMe | CH | CMe | CH | N | CMe | CH | N | N | CH | C(O) | CMe |
| 148 | | x | | | | | x | | | x | | x | | | | x | |
| 149 | | x | | | | | x | | | x | | x | | | | | x |
| 150 | | x | | | | | x | | | x | x | | | x | | | |
| 151 | | x | | | | | x | | | x | x | | | | x | | |
| 152 | | x | | | | | x | | | x | x | | | | | x | |
| 153 | | x | | | | | x | | | x | x | | | | | | x |
| 154 | | x | | | | | x | | | x | x | | | x | | | |
| 155 | | x | | | | | x | | | x | x | | | | x | | |
| 156 | | x | | | | | x | | | x | x | | | | | x | |
| 157 | | x | | | | | x | | | x | x | | | | | | x |
| 158 | | x | | | | | x | | x | | | x | | x | | | |
| 159 | | x | | | | | x | | x | | | x | | | x | | |
| 160 | | x | | | | | x | | x | | | x | | | | x | |
| 161 | | x | | | | | x | | x | | | x | | | | | x |
| 162 | | x | | | | | x | | x | | x | | | x | | | |
| 163 | | x | | | | | x | | x | | x | | | | x | | |
| 164 | | x | | | | | x | | x | | x | | | | | x | |
| 165 | | x | | | | | x | | x | | x | | | | | | x |
| 166 | | x | | | | | x | | x | | x | | x | | | | |
| 167 | | x | | | | | x | | x | | x | | | x | | | |
| 168 | | x | | | | | x | | x | | x | | | | x | | |
| 169 | | x | | | | | x | | x | | x | | | | | | x |
| 170 | | x | | | | | x | x | | | | x | | x | | | |
| 171 | | x | | | | | x | x | | | | x | | | x | | |
| 172 | | x | | | | | x | x | | | | x | | | | x | |
| 173 | | x | | | | | x | x | | | | x | | | | | x |
| 174 | | x | | | | | x | x | | | x | | | x | | | |
| 175 | | x | | | | | x | x | | | x | | | | x | | |
| 176 | | x | | | | | x | x | | | x | | | | | x | |
| 177 | | x | | | | | x | x | | | x | | | | | | x |
| 178 | | x | | | | | x | x | | | x | | x | | | | |
| 179 | | x | | | | | x | x | | | x | | | x | | | |
| 180 | | x | | | | | x | x | | | x | | | | x | | |
| 181 | | x | | | | | x | x | | | x | | | | | | x |
| 182 | | x | | | | x | | | x | | | x | | x | | | |
| 183 | | x | | | | x | | | x | | | x | | | x | | |
| 184 | | x | | | | x | | | x | | | x | | | | x | |
| 185 | | x | | | | x | | | x | | | x | | | | | x |
| 186 | | x | | | | x | | | x | | x | | | x | | | |
| 187 | | x | | | | x | | | x | | x | | | | x | | |
| 188 | | x | | | | x | | | x | | x | | | | | x | |
| 189 | | x | | | | x | | | x | | x | | | | | | x |
| 190 | | x | | | | x | | | x | x | | | | x | | | |
| 191 | | x | | | | x | | | x | x | | | | | x | | |
| 192 | | x | | | | x | | | x | x | | | | | | x | |
| 193 | | x | | | | x | | | x | x | | | | | | | x |
| 194 | | x | | | | x | | x | | | | x | | x | | | |
| 195 | | x | | | | x | | x | | | | x | | | x | | |
| 196 | | x | | | | x | | x | | | | x | | | | x | |
| 197 | | x | | | | x | | x | | | | x | | | | | x |
| 198 | | x | | | | x | | x | | | x | | | x | | | |
| 199 | | x | | | | x | | x | | | x | | | | x | | |
| 200 | | x | | | | x | | x | | | x | | | | | x | |
| 201 | | x | | | | x | | x | | | x | | | | | | x |
| 202 | | x | | | | x | | x | | x | | | | x | | | |
| 203 | | x | | | | x | | x | | x | | | | | x | | |
| 204 | | x | | | | x | | x | | x | | | | | | x | |
| 205 | | x | | | | x | | x | | x | | | | | | | x |
| 206 | | x | | | | x | | | x | | | x | | x | | | |
| 207 | | x | | | | x | | | x | | | x | | | x | | |
| 208 | | x | | | | x | | | x | | | x | | | | x | |
| 209 | | x | | | | x | | | x | | | x | | | | | x |
| 210 | | x | | | | x | | | x | | x | | | x | | | |
| 211 | | x | | | | x | | | x | | x | | | | x | | |
| 212 | | x | | | | x | | | x | | x | | | | | x | |
| 213 | | x | | | | x | | | x | | x | | | | | | x |
| 214 | | x | | | | x | | | x | x | | | | x | | | |
| 215 | | x | | | | x | | | x | x | | | | | x | | |
| 216 | | x | | | | x | | | x | x | | | | | | x | |
| 217 | | x | | | | x | | | x | x | | | | | | | x |
| 218 | | x | | | x | | | | x | | | x | | x | | | |
| 219 | | x | | | x | | | | x | | | x | | | x | | |

TABLE 4a-continued

Exemplary R¹, W¹, W², W⁴ and W⁵ for Compounds of Formula IV in combination with R² and R⁵ as illustrated in Tables 4b and 4c.

| Sub class # | R¹ | | | W¹ | | | | W² | | | W⁴ | | | W⁵ | | | |
|---|---|---|---|---|---|---|---|---|---|---|---|---|---|---|---|---|---|
| 1 | $NH_2$ | CMe | $CF_3$ | NEt | N | CMe | CH | CMe | CH | N | CMe | CH | N | N | CH | C(O) | CMe |
| 220 | | x | | | x | | | x | | | x | | | | x | | |
| 221 | | x | | | x | | | x | | | x | | | | | | x |
| 222 | | x | | | x | | | x | | | | x | | x | | | |
| 223 | | x | | | x | | | x | | | | x | | | x | | |
| 224 | | x | | | x | | | x | | | | x | | | | x | |
| 225 | | x | | | x | | | x | | | | x | | | | | x |
| 226 | | x | | | x | | | x | | | | | x | x | | | |
| 227 | | x | | | x | | | x | | | | | x | | x | | |
| 228 | | x | | | x | | | x | | | | | x | | | x | |
| 229 | | x | | | x | | | x | | | | | x | | | | x |
| 230 | | x | | | x | | | | x | | x | | | x | | | |
| 231 | | x | | | x | | | | x | | x | | | | x | | |
| 232 | | x | | | x | | | | x | | x | | | | | x | |
| 233 | | x | | | x | | | | x | | x | | | | | | x |
| 234 | | x | | | x | | | | x | | | x | | x | | | |
| 235 | | x | | | x | | | | x | | | x | | | x | | |
| 236 | | x | | | x | | | | x | | | x | | | | x | |
| 237 | | x | | | x | | | | x | | | x | | | | | x |
| 238 | | x | | | x | | | | x | | | | x | x | | | |
| 239 | | x | | | x | | | | x | | | | x | | x | | |
| 240 | | x | | | x | | | | x | | | | x | | | x | |
| 241 | | x | | | x | | | | x | | | | x | | | | x |
| 242 | | x | | | x | | | | | x | x | | | x | | | |
| 243 | | x | | | x | | | | | x | x | | | | x | | |
| 244 | | x | | | x | | | | | x | x | | | | | x | |
| 245 | | x | | | x | | | | | x | x | | | | | | x |
| 246 | | x | | | x | | | | | x | | x | | x | | | |
| 247 | | x | | | x | | | | | x | | x | | | x | | |
| 248 | | x | | | x | | | | | x | | x | | | | x | |
| 249 | | x | | | x | | | | | x | | x | | | | | x |
| 250 | | x | | | x | | | | | x | | | x | x | | | |
| 251 | | x | | | x | | | | | x | | | x | | x | | |
| 252 | | x | | | x | | | | | x | | | x | | | x | |
| 253 | | x | | | x | | | | | x | | | x | | | | x |
| 254 | | x | | x | | | | x | | | x | | | x | | | |
| 255 | | x | | x | | | | x | | | x | | | | x | | |
| 256 | | x | | x | | | | x | | | x | | | | | x | |
| 257 | | x | | x | | | | x | | | x | | | | | | x |
| 258 | | x | | x | | | | x | | | | x | | x | | | |
| 259 | | x | | x | | | | x | | | | x | | | x | | |
| 260 | | x | | x | | | | x | | | | x | | | | x | |
| 261 | | x | | x | | | | x | | | | x | | | | | x |
| 262 | | x | | x | | | | x | | | | | x | x | | | |
| 263 | | x | | x | | | | x | | | | | x | | x | | |
| 264 | | x | | x | | | | x | | | | | x | | | x | |
| 265 | | x | | x | | | | x | | | | | x | | | | x |
| 266 | | x | | x | | | | | x | | x | | | x | | | |
| 267 | | x | | x | | | | | x | | x | | | | x | | |
| 268 | | x | | x | | | | | x | | x | | | | | x | |
| 269 | | x | | x | | | | | x | | x | | | | | | x |
| 270 | | x | | x | | | | | x | | | x | | x | | | |
| 271 | | x | | x | | | | | x | | | x | | | x | | |
| 272 | | x | | x | | | | | x | | | x | | | | x | |
| 273 | | x | | x | | | | | x | | | x | | | | | x |
| 274 | | x | | x | | | | | x | | | | x | x | | | |
| 275 | | x | | x | | | | | x | | | | x | | x | | |
| 276 | | x | | x | | | | | x | | | | x | | | x | |
| 277 | | x | | x | | | | | x | | | | x | | | | x |
| 278 | | x | | x | | | | | | x | x | | | x | | | |
| 279 | | x | | x | | | | | | x | x | | | | x | | |
| 280 | | x | | x | | | | | | x | x | | | | | x | |
| 281 | | x | | x | | | | | | x | x | | | | | | x |
| 282 | | x | | x | | | | | | x | | x | | x | | | |
| 283 | | x | | x | | | | | | x | | x | | | x | | |
| 284 | | x | | x | | | | | | x | | x | | | | x | |
| 285 | | x | | x | | | | | | x | | x | | | | | x |
| 286 | x | | | | | | | x | | | x | | | x | | | |
| 287 | x | | | | | | | x | | | x | | | | x | | |
| 288 | x | | | | | | | x | | | x | | | | | x | |
| 289 | x | | | | | | | x | | | x | | | | | | x |
| 290 | x | | | | | | | x | | | | x | | x | | | |
| 291 | x | | | | | | | x | | | | x | | | x | | |

TABLE 4a-continued

Exemplary R¹, W¹, W², W⁴ and W⁵ for Compounds of Formula IV in combination with R² and R⁵ as illustrated in Tables 4b and 4c.

| Sub class # | R¹ | | | W¹ | | | | W² | | | W⁴ | | | W⁵ | | | |
|---|---|---|---|---|---|---|---|---|---|---|---|---|---|---|---|---|---|
| 1 | NH₂ | CMe | CF₃ | NEt | N | CMe | CH | CMe | CH | N | CMe | CH | N | N | CH | C(O) | CMe |
| 292 | x | | | | | x | | x | | | x | | | | x | | |
| 293 | x | | | | | x | | x | | | x | | | | | | x |
| 294 | x | | | | | x | | x | | | x | | | x | | | |
| 295 | x | | | | | x | | x | | | x | | | | x | | |
| 296 | x | | | | | x | | x | | | x | | | | | x | |
| 297 | x | | | | | x | | x | | | x | | | | | | x |
| 298 | x | | | | | x | | | x | | | x | | x | | | |
| 299 | x | | | | | x | | | x | | | x | | | x | | |
| 300 | x | | | | | x | | | x | | | x | | | | x | |
| 301 | x | | | | | x | | | x | | | x | | | | | x |
| 302 | x | | | | | x | | | x | | x | | | x | | | |
| 303 | x | | | | | x | | | x | | x | | | | x | | |
| 304 | x | | | | | x | | | x | | x | | | | | x | |
| 305 | x | | | | | x | | | x | | x | | | | | | x |
| 306 | x | | | | | x | | | x | | | | x | x | | | |
| 307 | x | | | | | x | | | x | | | | x | | x | | |
| 308 | x | | | | | x | | | x | | | | x | | | x | |
| 309 | x | | | | | x | | | x | | | | x | | | | x |
| 310 | x | | | | | x | x | | | | | x | | x | | | |
| 311 | x | | | | | x | x | | | | | x | | | x | | |
| 312 | x | | | | | x | x | | | | | x | | | | x | |
| 313 | x | | | | | x | x | | | | | x | | | | | x |
| 314 | x | | | | | x | x | | | | x | | | x | | | |
| 315 | x | | | | | x | x | | | | x | | | | x | | |
| 316 | x | | | | | x | x | | | | x | | | | | x | |
| 317 | x | | | | | x | x | | | | x | | | | | | x |
| 318 | x | | | | | x | x | | | | | x | | x | | | |
| 319 | x | | | | | x | x | | | | | x | | | x | | |
| 320 | x | | | | | x | x | | | | | x | | | | x | |
| 321 | x | | | | | x | x | | | | | x | | | | | x |
| 322 | x | | | | | | x | | | x | | | x | x | | | |
| 323 | x | | | | | | x | | | x | | | x | | x | | |
| 324 | x | | | | | | x | | | x | | | x | | | x | |
| 325 | x | | | | | | x | | | x | | | x | | | | x |
| 326 | x | | | | | | x | | | x | | x | | x | | | |
| 327 | x | | | | | | x | | | x | | x | | | x | | |
| 328 | x | | | | | | x | | | x | | x | | | | x | |
| 329 | x | | | | | | x | | | x | | x | | | | | x |
| 330 | x | | | | | | x | | | x | x | | | x | | | |
| 331 | x | | | | | | x | | | x | x | | | | x | | |
| 332 | x | | | | | | x | | | x | x | | | | | x | |
| 333 | x | | | | | | x | | | x | x | | | | | | x |
| 334 | x | | | | | | x | | x | | | x | | x | | | |
| 335 | x | | | | | | x | | x | | | x | | | x | | |
| 336 | x | | | | | | x | | x | | | x | | | | x | |
| 337 | x | | | | | | x | | x | | | x | | | | | x |
| 338 | x | | | | | | x | | x | | x | | | x | | | |
| 339 | x | | | | | | x | | x | | x | | | | x | | |
| 340 | x | | | | | | x | | x | | x | | | | | x | |
| 341 | x | | | | | | x | | x | | x | | | | | | x |
| 342 | x | | | | | | x | | x | | | | x | x | | | |
| 343 | x | | | | | | x | | x | | | | x | | x | | |
| 344 | x | | | | | | x | | x | | | | x | | | x | |
| 345 | x | | | | | | x | | x | | | | x | | | | x |
| 346 | x | | | | | | x | x | | | | x | | x | | | |
| 347 | x | | | | | | x | x | | | | x | | | x | | |
| 348 | x | | | | | | x | x | | | | x | | | | x | |
| 349 | x | | | | | | x | x | | | | x | | | | | x |
| 350 | x | | | | | | x | x | | | x | | | x | | | |
| 351 | x | | | | | | x | x | | | x | | | | x | | |
| 352 | x | | | | | | x | x | | | x | | | | | x | |
| 353 | x | | | | | | x | x | | | x | | | | | | x |
| 354 | x | | | | | | x | x | | | | | x | x | | | |
| 355 | x | | | | | | x | x | | | | | x | | x | | |
| 356 | x | | | | | | x | x | | | | | x | | | x | |
| 357 | x | | | | | | x | x | | | | | x | | | | x |
| 358 | x | | | | x | | | | | | x | | | x | | | |
| 359 | x | | | | x | | | | | | x | | | | x | | |
| 360 | x | | | | x | | | | | | x | | | | | x | |
| 361 | x | | | | x | | | | | | x | | | | | | x |
| 362 | x | | | | x | | | | | | x | x | | x | | | |
| 363 | x | | | | x | | | | | | x | x | | | x | | |

TABLE 4a-continued

Exemplary R¹, W¹, W², W⁴ and W⁵ for Compounds of Formula IV in combination with R² and R⁵ as illustrated in Tables 4b and 4c.

| Sub class # | R¹ | | | W¹ | | | | W² | | | W⁴ | | | W⁵ | | | |
|---|---|---|---|---|---|---|---|---|---|---|---|---|---|---|---|---|---|
| 1 | NH₂ | CMe | CF₃ | NEt | N | CMe | CH | CMe | CH | N | CMe | CH | N | N | CH | C(O) | CMe |
| 364 | x | | | | x | | | x | | | x | | | | x | | |
| 365 | x | | | | x | | | x | | | x | | | | | | x |
| 366 | x | | | | x | | | x | | | | x | | | x | | |
| 367 | x | | | | x | | | x | | | | x | | | | x | |
| 368 | x | | | | x | | | x | | | | x | | | | | x |
| 369 | x | | | | x | | | x | | | | x | | | | | x |
| 370 | x | | | | x | | | | x | | | | x | | x | | |
| 371 | x | | | | x | | | | x | | | | x | | | x | |
| 372 | x | | | | x | | | | x | | | | x | | | | x |
| 373 | x | | | | x | | | | x | | | | x | | | | x |
| 374 | x | | | | x | | | | x | | x | | | | x | | |
| 375 | x | | | | x | | | | x | | x | | | | | x | |
| 376 | x | | | | x | | | | x | | x | | | | | | x |
| 377 | x | | | | x | | | | x | | x | | | | | | x |
| 378 | x | | | | x | | | | x | | | x | | | x | | |
| 379 | x | | | | x | | | | x | | | x | | | | x | |
| 380 | x | | | | x | | | | x | | | x | | | | | x |
| 381 | x | | | | x | | | | x | | | x | | | | | x |
| 382 | x | | | | x | | | x | | | | x | | | x | | |
| 383 | x | | | | x | | | x | | | | x | | | | x | |
| 384 | x | | | | x | | | x | | | | x | | | | | x |
| 385 | x | | | | x | | | x | | | | x | | | | | x |
| 386 | x | | | | x | | | x | | | x | | | | x | | |
| 387 | x | | | | x | | | x | | | x | | | | | x | |
| 388 | x | | | | x | | | x | | | x | | | | | | x |
| 389 | x | | | | x | | | x | | | x | | | | | | x |
| 390 | x | | | | x | | | x | | | x | | | | x | | |
| 391 | x | | | | x | | | x | | | x | | | | | x | |
| 392 | x | | | | x | | | x | | | x | | | | | | x |
| 393 | x | | | | x | | | x | | | x | | | | | | x |
| 394 | x | | | x | | | | | | x | x | | | x | | | |
| 395 | x | | | x | | | | | | x | x | | | | x | | |
| 396 | x | | | x | | | | | | x | x | | | | | | x |
| 397 | x | | | x | | | | | | x | x | | | | | | x |
| 398 | x | | | x | | | | | | x | | x | | | x | | |
| 399 | x | | | x | | | | | | x | | x | | | | x | |
| 400 | x | | | x | | | | | | x | | x | | | | | x |
| 401 | x | | | x | | | | | | x | | x | | | | | x |
| 402 | x | | | x | | | | | | x | x | | | | x | | |
| 403 | x | | | x | | | | | | x | x | | | | | x | |
| 404 | x | | | x | | | | | | x | x | | | | | | x |
| 405 | x | | | x | | | | | | x | x | | | | | | x |
| 406 | x | | | x | | | | | x | | | x | | | x | | |
| 407 | x | | | x | | | | | x | | | x | | | | x | |
| 408 | x | | | x | | | | | x | | | x | | | | | x |
| 409 | x | | | x | | | | | x | | | x | | | | | x |
| 410 | x | | | x | | | | | x | | x | | | | x | | |
| 411 | x | | | x | | | | | x | | x | | | | | x | |
| 412 | x | | | x | | | | | x | | x | | | | | | x |
| 413 | x | | | x | | | | | x | | x | | | | | | x |
| 414 | x | | | x | | | | | x | | x | | | | x | | |
| 415 | x | | | x | | | | | x | | x | | | | | x | |
| 416 | x | | | x | | | | | x | | x | | | | | | x |
| 417 | x | | | x | | | | | x | | x | | | | | | x |
| 418 | x | | | x | | | | x | | | | x | | | x | | |
| 419 | x | | | x | | | | x | | | | x | | | | x | |
| 420 | x | | | x | | | | x | | | | x | | | | | x |
| 421 | x | | | x | | | | x | | | | x | | | | | x |
| 422 | x | | | x | | | | x | | | x | | | | x | | |
| 423 | x | | | x | | | | x | | | x | | | | | x | |
| 424 | x | | | x | | | | x | | | x | | | | | | x |
| 425 | x | | | x | | | | x | | | x | | | | | | x |
| 426 | x | | | x | | | | x | | | x | | | | x | | |
| 427 | x | | | x | | | | x | | | x | | | | | x | |
| 428 | x | | | x | | | | x | | | x | | | | | | x |
| 429 | x | | | x | | | | x | | | x | | | | | | x |

TABLE 4b
Exemplary R² for compounds of Formula IV, in combination with the exemplary R¹, W¹, W², W⁴ and W⁵ of Table 4a and exemplary R⁵ of Table 4c.
| Sub-class # | R² |
|---|---|
| 1 | —CH₃ |
| 2 | —CH₂CH₃ |
| 3 | —CH(CH₃)2 |
| 4 | 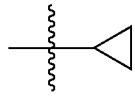 [SMILES: *C1CC1] |
| 5 | 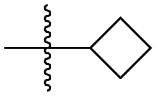 [SMILES: *C1CCC1] |
| 6 | 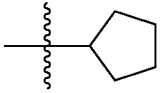 [SMILES: *C1CCCC1] |
| 7 | 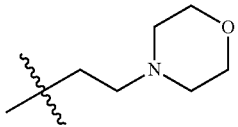 [SMILES: *CCN1CCOCC1] |
| 8 | 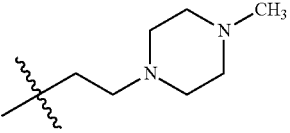 [SMILES: *CCN1CCN(C)CC1] |
| 9 | 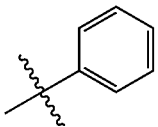 |
| 10 | 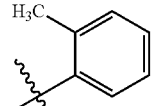 |
| 11 | 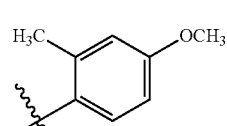 |
| 12 | 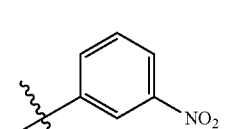 |
| 13 | 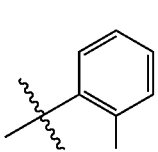 |
TABLE 4b-continued
Exemplary R² for compounds of Formula IV, in combination with the exemplary R¹, W¹, W², W⁴ and W⁵ of Table 4a and exemplary R⁵ of Table 4c.
| Sub-class # | R² |
|---|---|
| 14 | 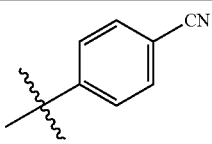 |
| 15 | 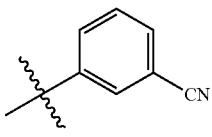 [SMILES: *c1cccc(C#N)c1] |
| 16 | 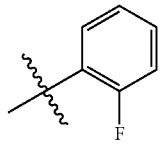 [SMILES: *c1ccccc1F] |
| 17 | 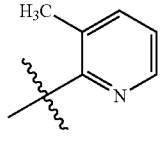 [SMILES: *c1ncccc1C] |
| 18 | 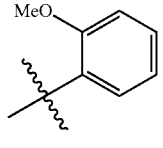 [SMILES: *c1ccccc1OC] |
| 19 | 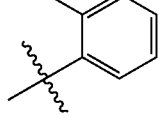 |
| 20 | 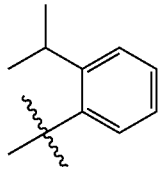 [SMILES: *c1ccccc1C(C)C] |
| 21 | 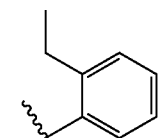 |
| 22 | 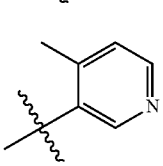 |

TABLE 4b-continued

Exemplary R² for compounds of Formula IV, in combination with the exemplary R¹, W¹, W², W⁴ and W⁵ of Table 4a and exemplary R⁵ of Table 4c.

| Sub-class # | R² |
|---|---|
| 23 | cyclohexyl |
| 24 | 2-(2-morpholinoethoxy)phenyl |
| 25 | tetrahydropyran-4-yl |
| 26 | 2-(trifluoromethyl)phenyl |
| 27 | pyridin-2-yl |
| 28 | 6-chloropyridin-2-yl |
| 29 | 6-methylpyridin-2-yl |
| 30 | 5-methylpyridin-2-yl |
| 31 | 4-methylpyridin-2-yl |
| 32 | 6-methoxypyridin-2-yl |
| 33 | methyl pyridine-2-carboxylate-6-yl |
| 34 | 1H-indazol-5-yl |
| 35 | 1H-indazol-6-yl |
| 36 | 5-aminopyridin-2-yl |
| 37 | 6-aminopyridin-2-yl |
| 38 | 6-cyanopyridin-2-yl |
| 39 | methyl nicotinate-6-yl |
| 40 | 2-aminopyridin-4-yl |

TABLE 4b-continued

Exemplary R² for compounds of Formula IV, in combination with the exemplary R¹, W¹, W², W⁴ and W⁵ of Table 4a and exemplary R⁵ of Table 4c.

| Sub-class # | R² |
|---|---|
| 41 | 4-pyridyl with 2-CF₃ |
| 42 | 4-pyridyl with 2-C(O)OCH₃ |
| 43 | 4-pyridyl with 2-CN |
| 44 | 4-pyridyl with 2-CH₃ |
| 45 | 6-(2-oxo-1H-pyridyl) |
| 46 | 2-pyridyl with 5-OH |
| 47 | 2-pyridyl with 5-F |
| 48 | 5-(2-chloropyrazinyl) |
| 49 | 5-(2-methoxypyrazinyl) |
| 50 | 5-(2-aminopyrazinyl) |
| 51 | 5-(2-methylpyrazinyl) |
| 52 | 5-(2-dimethylaminopyrazinyl) |
| 53 | 5-(2-(N-methyl-N-ethylamino)pyrazinyl) |
| 54 | 5-(2-diethylaminopyrazinyl) |
| 55 | 5-(2-(4-methylpiperazin-1-yl)pyrazinyl) |
| 56 | 5-(2-(pyrrolidin-1-yl)pyrazinyl) |
| 57 | 5-(2-(piperidin-1-yl)pyrazinyl) |

TABLE 4b-continued
Exemplary R² for compounds of Formula IV, in combination with the exemplary R¹, W¹, W², W⁴ and W⁵ of Table 4a and exemplary R⁵ of Table 4c.
| Sub-class # | R² |
|---|---|
| 58 | 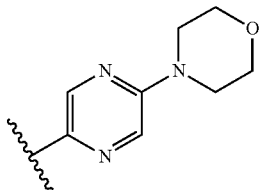 [SMILES: *c1cnc(N2CCOCC2)cn1] |
| 59 | 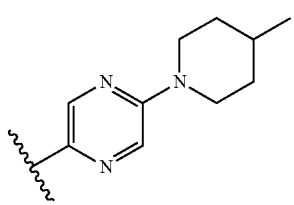 [SMILES: *c1cnc(N2CCC(C)CC2)cn1] |
| 60 | 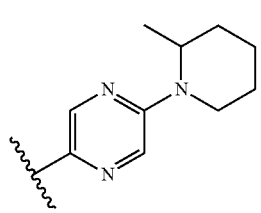 [SMILES: *c1cnc(N2CCCCC2C)cn1] |
| 61 | 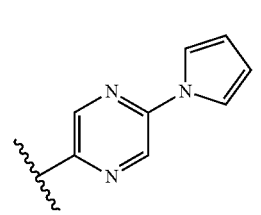 |
| 62 | 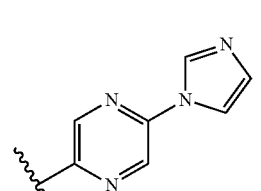 |
| 63 | 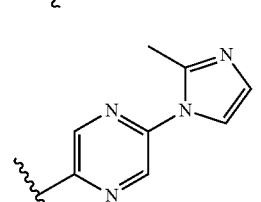 |
| 64 | 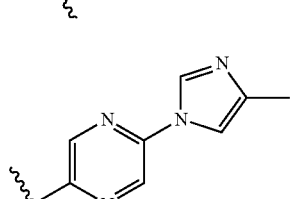 |
| 65 | 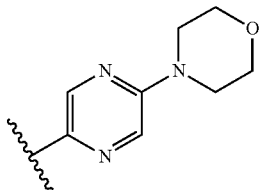 [SMILES: *c1cnc(N2CCOCC2)cn1] |
| 66 | 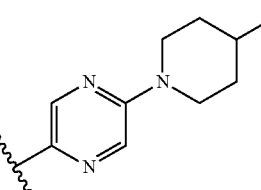 |
| 67 | 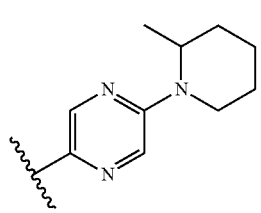 [SMILES: *c1cnc(N2CCCCC2C)cn1] |
| 68 | 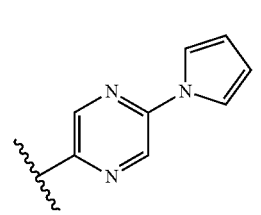 |
| 69 | 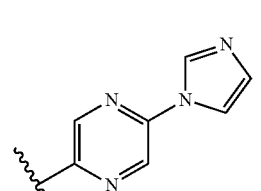 |
| 70 | 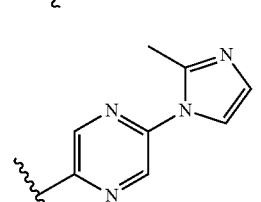 |
| 71 | 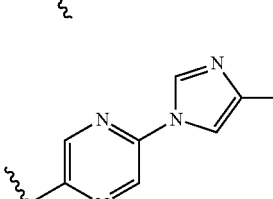 |
| 72 | 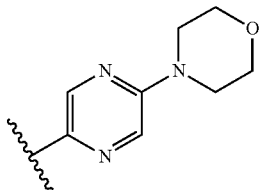 [SMILES: *c1cnc(N2CCOCC2)cn1] |

TABLE 4b-continued
Exemplary R² for compounds of Formula IV, in combination with the exemplary R¹, W¹, W², W⁴ and W⁵ of Table 4a and exemplary R⁵ of Table 4c.
| Sub-class # | R² |
|---|---|
| 73 | 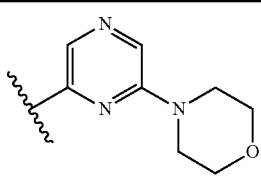 |
| 74 | 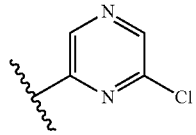 |
| 75 | 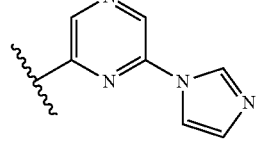 |
| 76 | 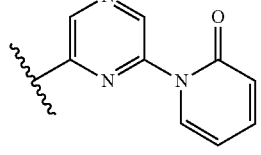 |
| 77 | 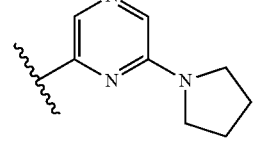 |
| 78 | 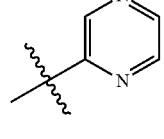 |
| 79 | 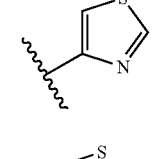 |
| 80 | 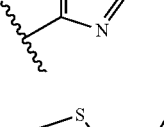 |
| 81 | 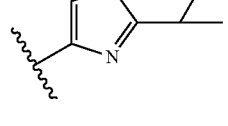 |
| 82 | 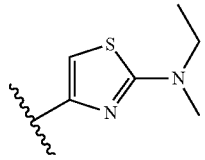 [SMILES: *c1csc(N(C)CC)n1] |
| 83 | 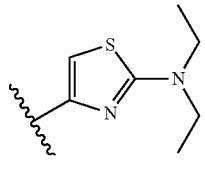 [SMILES: *c1csc(N(CC)CC)n1] |
| 84 | 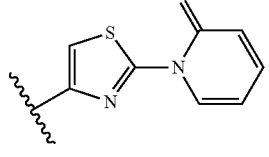 |
| 85 | 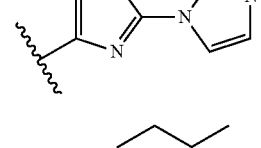 |
| 86 | 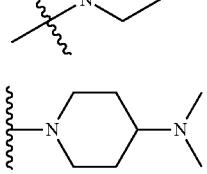 |
| 87 | 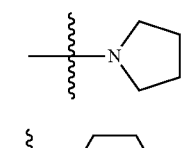 |
| 88 | 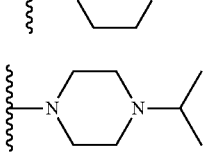 |
| 89 | 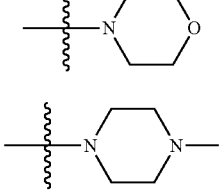 |
| 90 |  |
| 91 |  |
| 92 |  |

TABLE 4b-continued
Exemplary R² for compounds of Formula IV, in combination with the exemplary R¹, W¹, W², W⁴ and W⁵ of Table 4a and exemplary R⁵ of Table 4c.
| Sub-class # | R² |
|---|---|
| 92 | 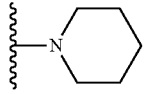 |
| 94 | 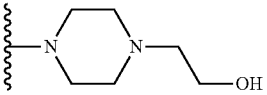 |
| 95 | 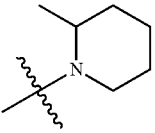 [SMILES: *N1CCCCC1C] |
| 96 | 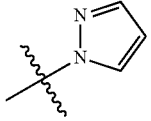 [SMILES: *n1cccn1] |
| 97 | 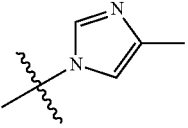 [SMILES: *n1cnc(C)c1] |
| 98 | 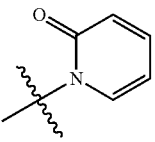 [SMILES: *n1ccccc1=O] |
| 99 | 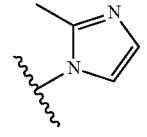 [SMILES: *n1ccnc1C] |
| 100 | 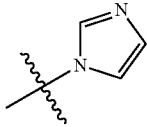 [SMILES: *n1ccnc1] |
| 101 | —Br |
| 102 | 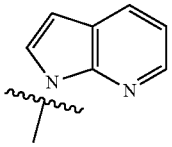 |
| 103 | 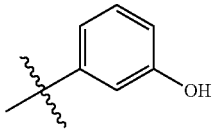 [SMILES: *c1cccc(O)c1] |
| 104 | 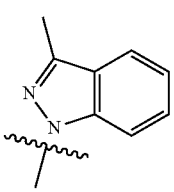 |
| 105 | 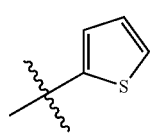 [SMILES: *c1cccs1] |
| 106 | 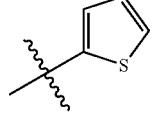 |
| 107 | 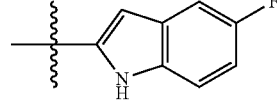 |
| 108 | 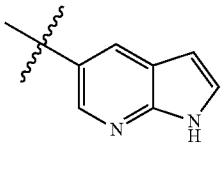 [SMILES: *c1cnc2[nH]ccc2c1] |
| 109 | 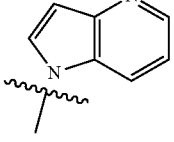 |
| 110 | 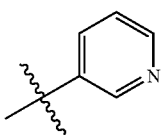 [SMILES: *c1cccnc1] |
| 111 | 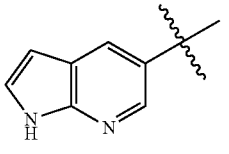 [SMILES: *c1cnc2[nH]ccc2c1] |
| 112 | 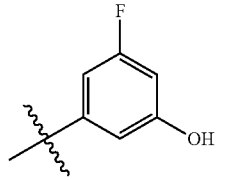 [SMILES: *c1cc(O)cc(F)c1] |

TABLE 4b-continued
Exemplary R² for compounds of Formula IV, in combination with the exemplary R¹, W¹, W², W⁴ and W⁵ of Table 4a and exemplary R⁵ of Table 4c.
| Sub-class # | R² |
|---|---|
| 113 | 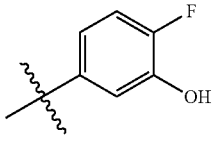 |
| 114 | 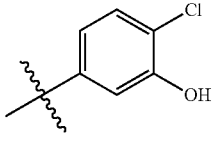 [SMILES: *c1ccc(Cl)c(O)c1] |
| 115 | 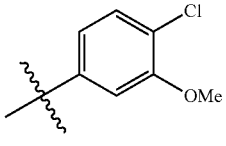 [SMILES: *c1ccc(Cl)c(OC)c1] |
| 116 | 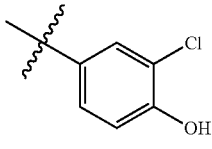 |
| 117 | 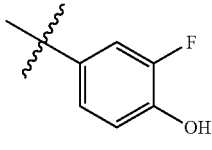 [SMILES: *c1ccc(O)c(F)c1] |
| 118 | 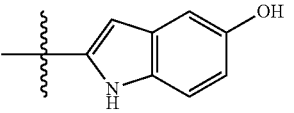 [SMILES: *c1cc2cc(O)ccc2[nH]1] |
| 119 | 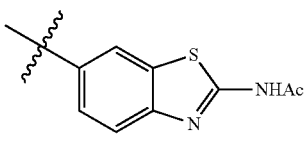 [SMILES: *c1ccc2nc(NC(C)=O)sc2c1] |
| 120 | 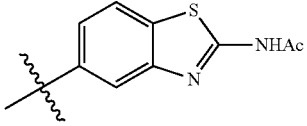 [SMILES: *c1ccc2sc(NC(C)=O)nc2c1] |
| 121 | 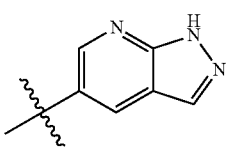 [SMILES: *c1cnc2[nH]ncc2c1] |
| 122 | 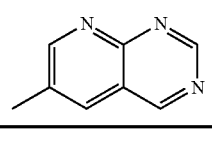 |
TABLE 4c
Exemplary embodiments of R⁵ of Formula IV in combination with the exemplary R¹, W¹, W², W⁴ and W⁵ of Table 4a and in combination with the exemplary R² of Table 4b.
| Sub-class # | R⁵ |
|---|---|
| 1 | —CH₃ |
| 2 | —CH₂CH₃ |
| 3 | —CH(CH₃)₂ |
| 4 | 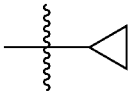 |
| 5 | 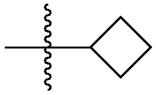 |
| 6 | 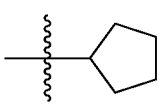 |
| 7 | 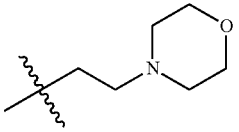 [SMILES: *CCN1CCOCC1] |
| 8 | 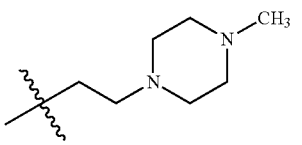 [SMILES: *CCN1CCN(C)CC1] |
| 9 | 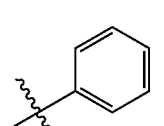 |
| 10 | 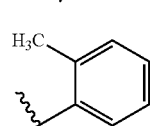 |
| 11 | 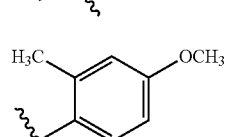 |
| 12 | 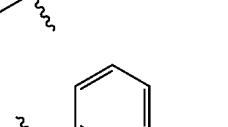 |
| 13 | 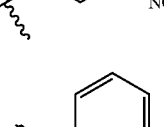 |

TABLE 4c-continued
Exemplary embodiments of R⁵ of Formula IV in combination with the exemplary R¹, W¹, W², W⁴ and W⁵ of Table 4a and in combination with the exemplary R² of Table 4b.
| Sub-class # | R⁵ |
|---|---|
| 14 | 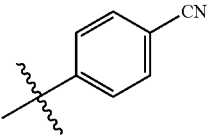 [SMILES: *c1ccc(C#N)cc1] |
| 15 | 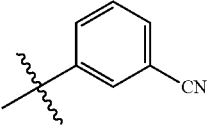 [SMILES: *c1cccc(C#N)c1] |
| 16 | 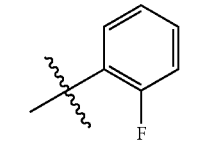 |
| 17 | 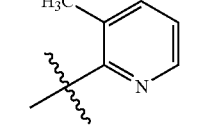 |
| 18 | 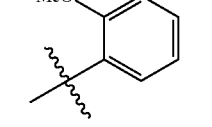 |
| 19 | 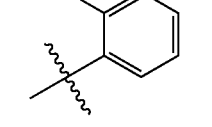 |
| 20 | 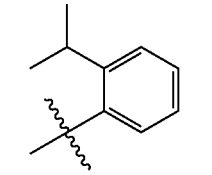 [SMILES: *c1ccccc1C(C)C] |
| 21 | 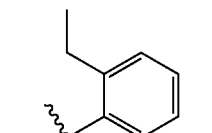 |
| 22 | 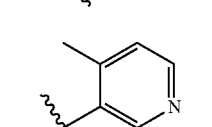 |
| 23 | 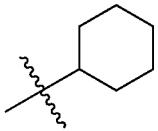 [SMILES: *C1CCCCC1] |
| 24 | 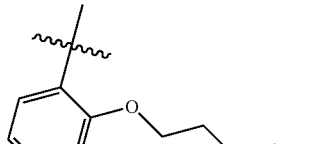 |
| 25 | 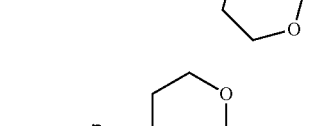 |
| 26 | 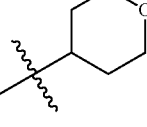 |
| 27 | 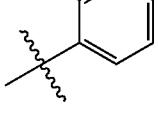 |
| 28 | 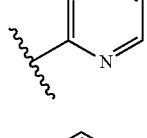 |
| 29 | 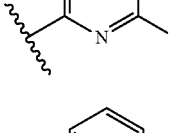 |
| 30 | 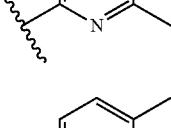 |
| 31 | 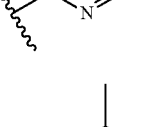 |

TABLE 4c-continued

Exemplary embodiments of $R^5$ of Formula IV in combination with the exemplary $R^1$, $W^1$, $W^2$, $W^4$ and $W^5$ of Table 4a and in combination with the exemplary $R^2$ of Table 4b.

| Sub-class # | $R^5$ |
|---|---|
| 32 | 6-methoxypyridin-2-yl |
| 33 | 6-(methoxycarbonyl)pyridin-2-yl |
| 34 | 1H-indazol-5-yl |
| 35 | 1H-indazol-6-yl |
| 36 | 5-aminopyridin-2-yl |
| 37 | 6-aminopyridin-2-yl |
| 38 | 6-cyanopyridin-2-yl |
| 39 | 5-(methoxycarbonyl)pyridin-2-yl |
| 40 | 2-aminopyridin-4-yl |
| 41 | 2-(trifluoromethyl)pyridin-4-yl |
| 42 | 2-(methoxycarbonyl)pyridin-4-yl |
| 43 | 2-cyanopyridin-4-yl |
| 44 | 2-methylpyridin-4-yl |
| 45 | 6-oxo-1,6-dihydropyridin-2-yl |
| 46 | 5-hydroxypyridin-2-yl |
| 47 | 5-fluoropyridin-2-yl |
| 48 | 5-chloropyrazin-2-yl |
| 49 | 5-methoxypyrazin-2-yl |

TABLE 4c-continued
Exemplary embodiments of $R^5$ of Formula IV in combination with the exemplary $R^1$, $W^1$, $W^2$, $W^4$ and $W^5$ of Table 4a and in combination with the exemplary $R^2$ of Table 4b.
| Sub-class # | $R^5$ |
|---|---|
| 50 | 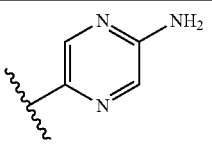 |
| 51 | 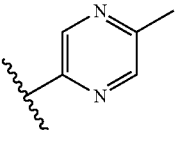 [SMILES: *c1cnc(C)cn1] |
| 52 | 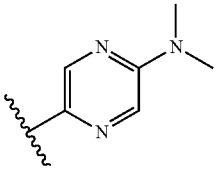 [SMILES: *c1cnc(N(C)C)cn1] |
| 53 | 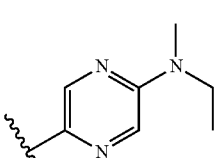 |
| 54 | 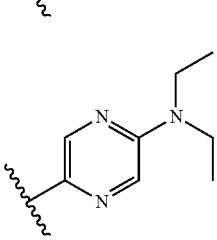 |
| 55 | 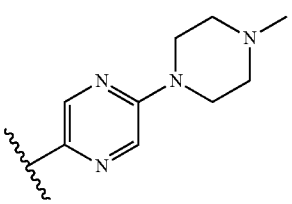 |
| 56 | 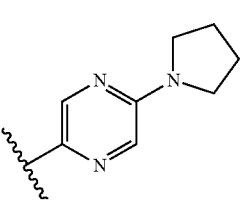 |
| 57 | 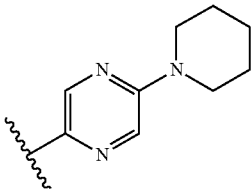 [SMILES: *c1cnc(N2CCCCC2)cn1] |
| 58 | 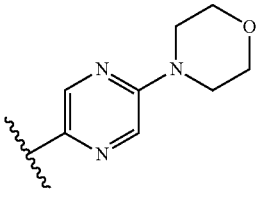 [SMILES: *c1cnc(N2CCOCC2)cn1] |
| 59 | 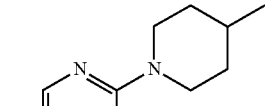 |
| 60 | 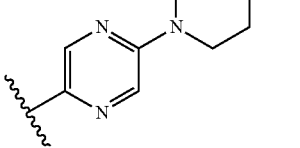 |
| 61 | 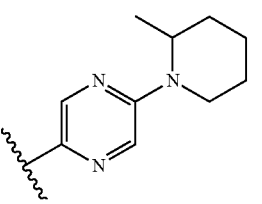 [SMILES: *c1cnc(N2CCCCC2C)cn1] |
| 62 | 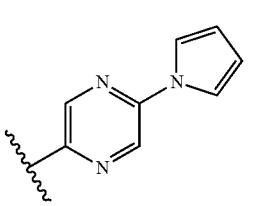 |
| 63 | 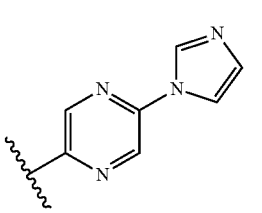 [SMILES: *c1cnc(-n2ccnc2)cn1] |
| 64 | 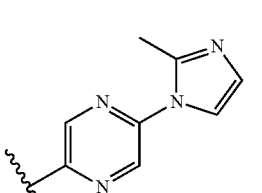 |

TABLE 4c-continued

Exemplary embodiments of R⁵ of Formula IV in combination with the exemplary R¹, W¹, W², W⁴ and W⁵ of Table 4a and in combination with the exemplary R² of Table 4b.

| Sub-class # | R⁵ |
|---|---|
| 65 | (pyrazin-2-yl with pyrazol-1-yl) |
| 66 | (pyrazin-2-yl with 4-methylpyrazol-1-yl) |
| 67 | (pyrazin-2-yl with 3-methylpyrazol-1-yl) |
| 68 | (pyrazin-2-yl with 2-oxopyridin-1-yl) |
| 69 | (6-cyanopyrazin-2-yl) |
| 70 | (6-methoxypyrazin-2-yl) |
| 71 | (6-dimethylaminopyrazin-2-yl) |
| 72 | (6-diethylaminopyrazin-2-yl) |
| 73 | (6-morpholinopyrazin-2-yl) |
| 74 | (6-chloropyrazin-2-yl) |
| 75 | (6-imidazol-1-yl-pyrazin-2-yl) |
| 76 | (6-(2-oxopyridin-1-yl)pyrazin-2-yl) |
| 77 | (6-pyrrolidin-1-yl-pyrazin-2-yl) |
| 78 | (pyrazin-2-yl) |
| 79 | (thiazol-4-yl) |
| 80 | (2-methylthiazol-4-yl) |

TABLE 4c-continued

Exemplary embodiments of R⁵ of Formula IV in combination with the exemplary R¹, W¹, W², W⁴ and W⁵ of Table 4a and in combination with the exemplary R² of Table 4b.

| Subclass # | R⁵ |
|---|---|
| 81 | 2-isopropyl-thiazol-4-yl |
| 82 | 2-(N-methyl-N-methylamino)-thiazol-4-yl |
| 83 | 2-(N,N-diethylamino)-thiazol-4-yl |
| 84 | 2-(2-oxopyridin-1-yl)-thiazol-4-yl |
| 85 | 2-(imidazol-1-yl)-thiazol-4-yl |
| 86 | 3-hydroxyphenyl |
| 87 | 1H-pyrazol-4-yl |
| 88 | thiophen-2-yl |
| 89 | 5-fluoro-1H-indol-2-yl |
| 90 | 1H-pyrrolo[2,3-b]pyridin-5-yl |
| 91 | 2-(NHAc)-benzothiazol-5-yl |
| 92 | pyridin-3-yl |
| 93 | 1H-pyrrolo[2,3-b]pyridin-5-yl |
| 94 | 3-fluoro-5-hydroxyphenyl |
| 95 | 4-fluoro-3-hydroxyphenyl |
| 96 | 4-chloro-3-hydroxyphenyl |
| 97 | 4-chloro-3-methoxyphenyl |
| 98 | 3-chloro-4-hydroxyphenyl |

TABLE 4c-continued

Exemplary embodiments of R⁵ of Formula IV in combination with the exemplary R¹, W¹, W², W⁴ and W⁵ of Table 4a and in combination with the exemplary R² of Table 4b.

| Subclass # | R⁵ |
|---|---|
| 99 |  |
| 100 |  |
| 101 |  |
| 102 |  |
| |  |
| |  |
| |  |
| |  |
| |  |
| |  |

TABLE 4c-continued

Exemplary embodiments of R⁵ of Formula IV in combination with the exemplary R¹, W¹, W², W⁴ and W⁵ of Table 4a and in combination with the exemplary R² of Table 4b.

| Subclass # | R⁵ |
|---|---|
| |  |
| |  |
| |  |
| |  |

The chemical entities described herein can be synthesized utilizing techniques well known in the art, e.g., as illustrated below with reference to the Reaction Schemes.

Unless specified to the contrary, the reactions described herein take place at atmospheric pressure, generally within a temperature range from −10° C. to 200° C. Further, except as otherwise specified, reaction times and conditions are intended to be approximate, e.g., taking place at about atmospheric pressure within a temperature range of about −10° C. to about 110° C. over a period of about 1 to about 24 hours; reactions left to run overnight average a period of about 16 hours.

The terms "solvent," "organic solvent," and "inert solvent" each mean a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane), diethyl ether, methanol, N-methylpyrrolidone ("NMP"), pyridine and the like]. Unless specified to the contrary, the solvents used in the reactions described herein are inert organic solvents. Unless specified to the contrary, for each gram of the limiting reagent, one cc (or mL) of solvent constitutes a volume equivalent.

Isolation and purification of the chemical entities and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. However, other equivalent separation or isolation procedures can also be used.

When desired, the (R)- and (S)-isomers may be resolved by methods known to those skilled in the art, for example by formation of diastereoisomeric salts or complexes which may be separated, for example, by crystallization; via formation of diastereoisomeric derivatives which may be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. Alternatively, a specific enantiomer may be synthesized by asymmetric synthesis using optically active reagents, substrates, catalysts or solvents, or by converting one enantiomer to the other by asymmetric transformation.

Many of the optionally substituted starting compounds and other reactants are commercially available, e.g., from Aldrich Chemical Company (Milwaukee, Wis.) or can be readily prepared by those skilled in the art using commonly employed synthetic methodology.

The chemical entities are synthesized by an appropriate combination of generally well known synthetic methods. Techniques useful in synthesizing these chemical entities are both readily apparent and accessible to those of skill in the relevant art.

I. Reaction Scheme 1:

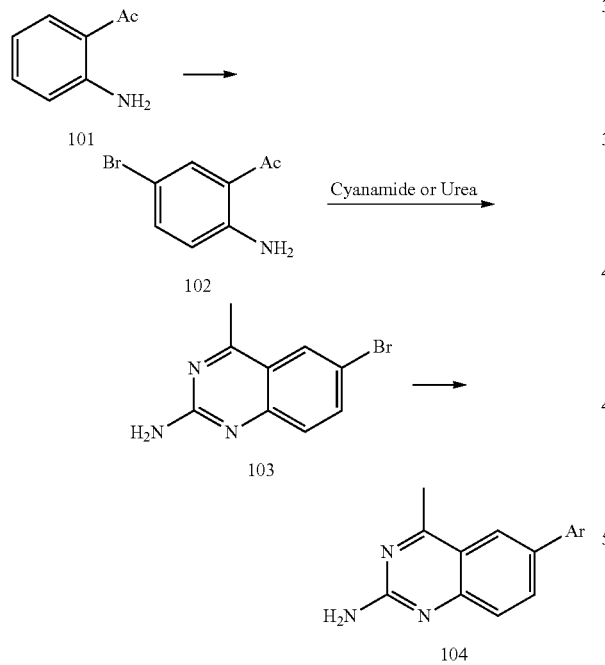

Referring to Reaction Scheme 1, Step 1, a compound of Formula 101 is brominated using commonly employed synthetic methodology such as acylation, bromination, and de-acylation. In particular, the compound of Formula 101 is treated with acetyl chloride in methylene chloride in the presence of triethylamine to produce an N-acetyl protected compound, which is treated with bromine, in acetic acid to yield a brominated aniline analog. The acetyl protection of the amino group is removed in refluxing 6N hydrochloric acid to provide a compound of Formula 102, which is isolated and optionally purified.

Referring to Reaction Scheme 1, Step 2, a compound of Formula 102 undergoes a condensation reaction, for example with cyanamide or urea. The product, a compound of Formula 103, is isolated and optionally purified.

Referring to Reaction Scheme 1, Step 3, a compound of Formula 103 is arylated. The product, a compound of Formula 104, is isolated and optionally purified.

II. Reaction Scheme 2:

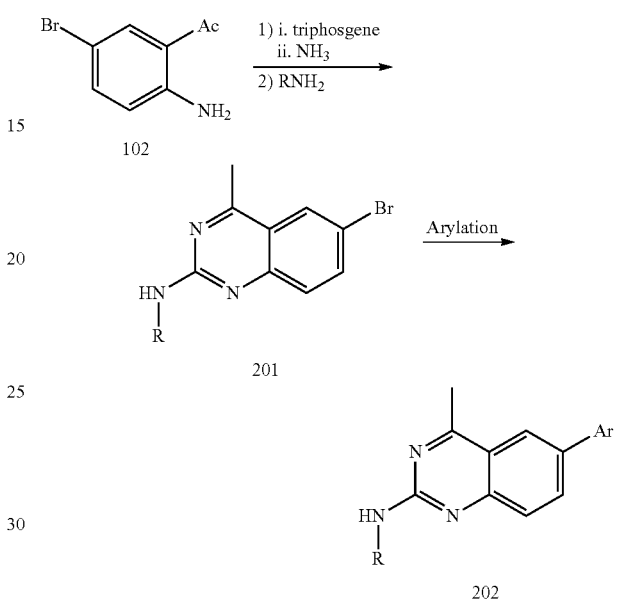

Referring to Reaction Scheme 2, Step 1, a compound of Formula 102 is combined with triphosgene and ammonia, followed by addition of an optionally substituted amine. The product, a compound of Formula 201, is isolated and optionally purified.

Referring to Reaction Scheme 2, Step 2, a compound of Formula 201 is arylated. The product, a compound of Formula 202, is isolated and optionally purified.

III. Reaction Scheme 3:

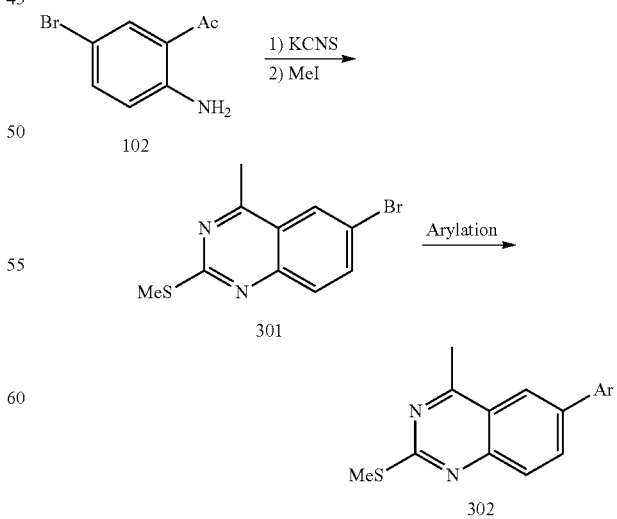

Referring to Reaction Scheme 3, Step 1, a compound of Formula 102 undergoes a condensation reaction with potassium isothiocyanate, followed by alkylation with methyl iodide. The product, a compound of Formula 301, is isolated and optionally purified.

Referring to Reaction Scheme 3, Step 2, a compound of Formula 301 is arylated. The product, a compound of Formula 302, is isolated and optionally purified.

IV. A. Reaction Scheme 4a:

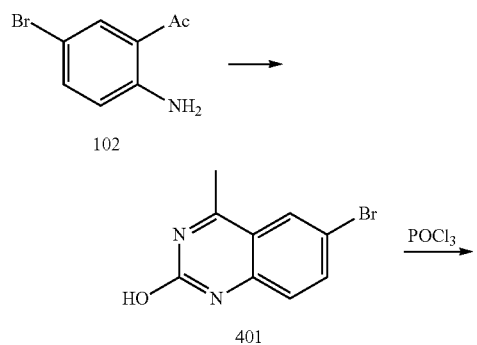

Referring to Reaction Scheme 4, Step 1, a compound of Formula 102 undergoes a condensation, for example with potassium isocyanate. The product, a compound of Formula 401, is isolated and optionally purified.

Referring to Reaction Scheme 4, Step 2, a compound of Formula 401 is chlorinated, for example with phosphorous oxychloride or thionyl chloride. The product, a compound of Formula 402, is isolated and optionally purified.

B. Reaction Scheme 4b:

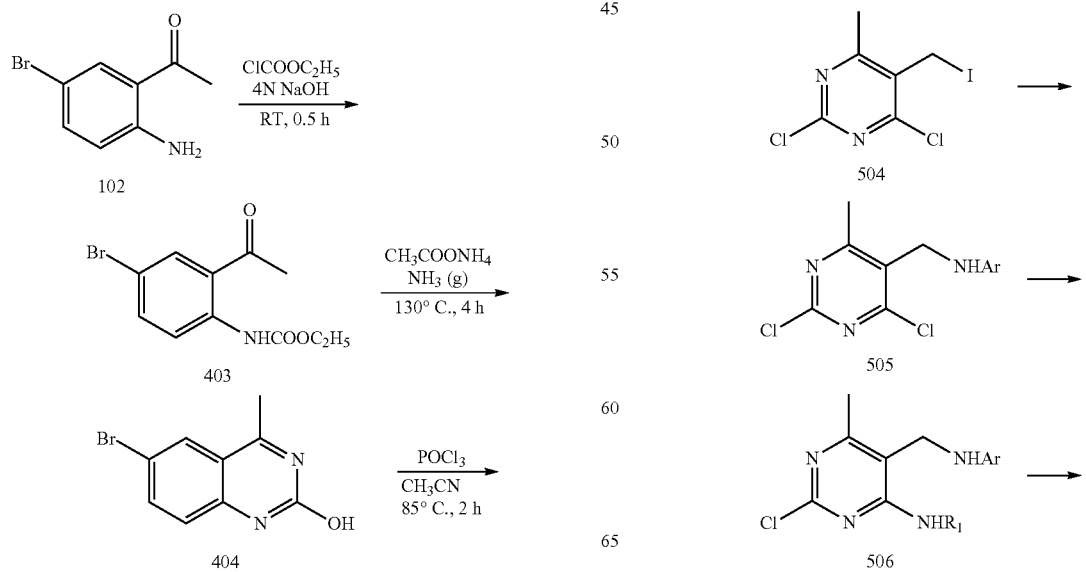

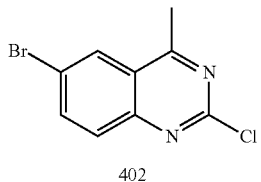

In Reaction Scheme 4b, Step 1, a compound of Formula 102 is treated with ethylchloroformate and 4N sodium hydroxide to produce the compound of Formula 403. This carbamate is treated with ammonium acetate and ammonia at 130° C. and cyclizes to form the quinazoline of Formula 404, which is treated with phosphorus oxychloride at 85° C., in acetonitrile to yield the compound of Formula 402, which is isolated and optionally purified.

V. Reaction Scheme 5:

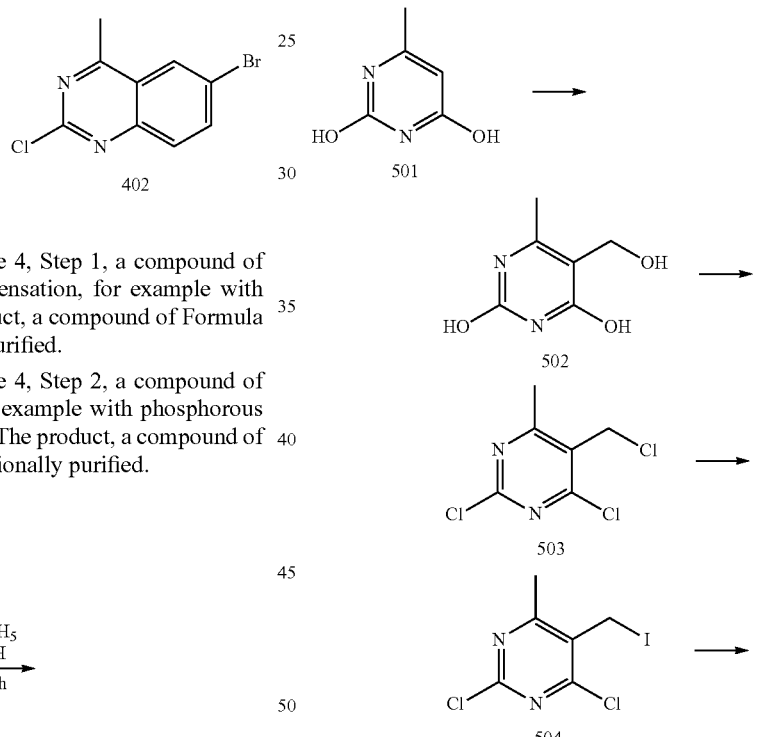

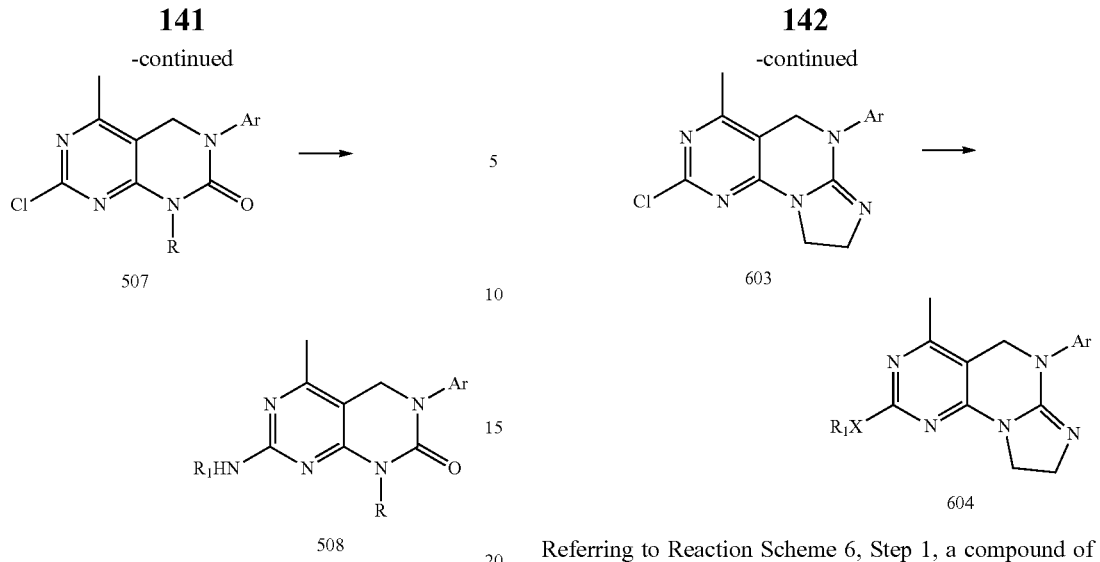

Referring to Reaction Scheme 5, Step 1, a compound of Formula 501 is alkylated with a formyl equivalent. The product, a compound of Formula 502, is isolated and optionally purified.

Referring to Reaction Scheme 5, Step 2, a compound of Formula 502 is chlorinated, for example with phosphorous oxychloride or thionyl chloride. The product, a compound of Formula 503, is isolated and optionally purified.

Referring to Reaction Scheme 5, Step 3, a compound of Formula 503 is converted to an iodide, for example with sodium iodide in acetone. The product, a compound of Formula 504, is isolated and optionally purified.

Referring to Reaction Scheme 5, Step 4, a compound of Formula 504 is aminated with an optionally substituted amine. The product, a compound of Formula 505, is isolated and optionally purified.

Referring to Reaction Scheme 5, Step 5, a compound of Formula 505 is aminated with an optionally substituted amine. The product, a compound of Formula 506, is isolated and optionally purified.

Referring to Reaction Scheme 5, Step 6, a compound of Formula 506 is acylated, for example with a compound triphosgene or carbonyl diimidazole. The product, a compound of Formula 507, is isolated and optionally purified.

Referring to Reaction Scheme 5, Step 7, a compound of Formula 507 is aminated with an optionally substituted amine. The product, a compound of Formula 508, is isolated and optionally purified.

VI. Reaction Scheme 6:

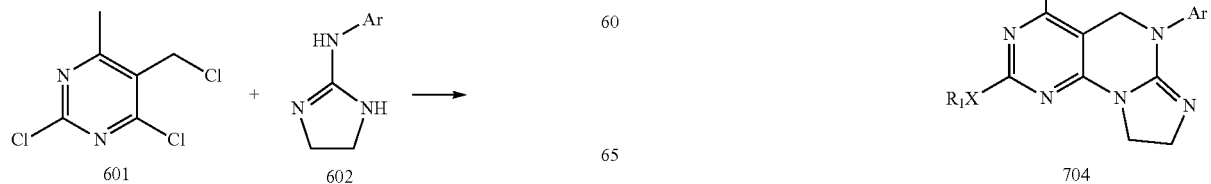

Referring to Reaction Scheme 6, Step 1, a compound of Formula 601 is cyclized, for example with a compound of Formula 602. The product, a compound of Formula 603, is isolated and optionally purified.

Referring to Reaction Scheme 6, Step 2, a compound of Formula 603 reacts with a nucleophile, for example an optionally substituted amine, an optionally substituted amine alcohol, an optionally substituted thiol, an optionally substituted aniline, an optionally substituted phenol, or an optionally substituted thiophenol. The product, a compound of Formula 604, is isolated and optionally purified.

VII. Reaction Scheme 7:

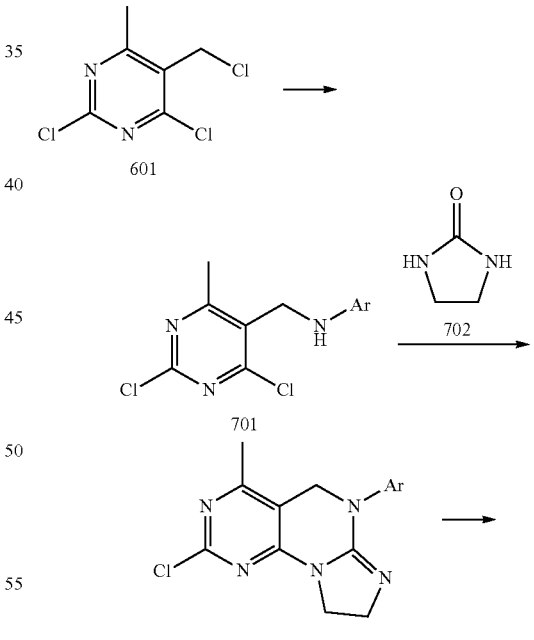

Referring to Reaction Scheme 7, Step 1, a compound of Formula 601 is aminated with an optionally substituted amine. The product, a compound of Formula 701, is isolated and optionally purified.

Referring to Reaction Scheme 7, Step 2, a compound of Formula 701 is cyclized, for example with a compound of Formula 702. The product, a compound of Formula 703, is then isolated and optionally purified.

Referring to Reaction Scheme 7, Step 3, a compound of Formula 703 is aminated with an optionally substituted amine. The product, a compound of Formula 704, is isolated and optionally purified.

VIII. Reaction Scheme 8:

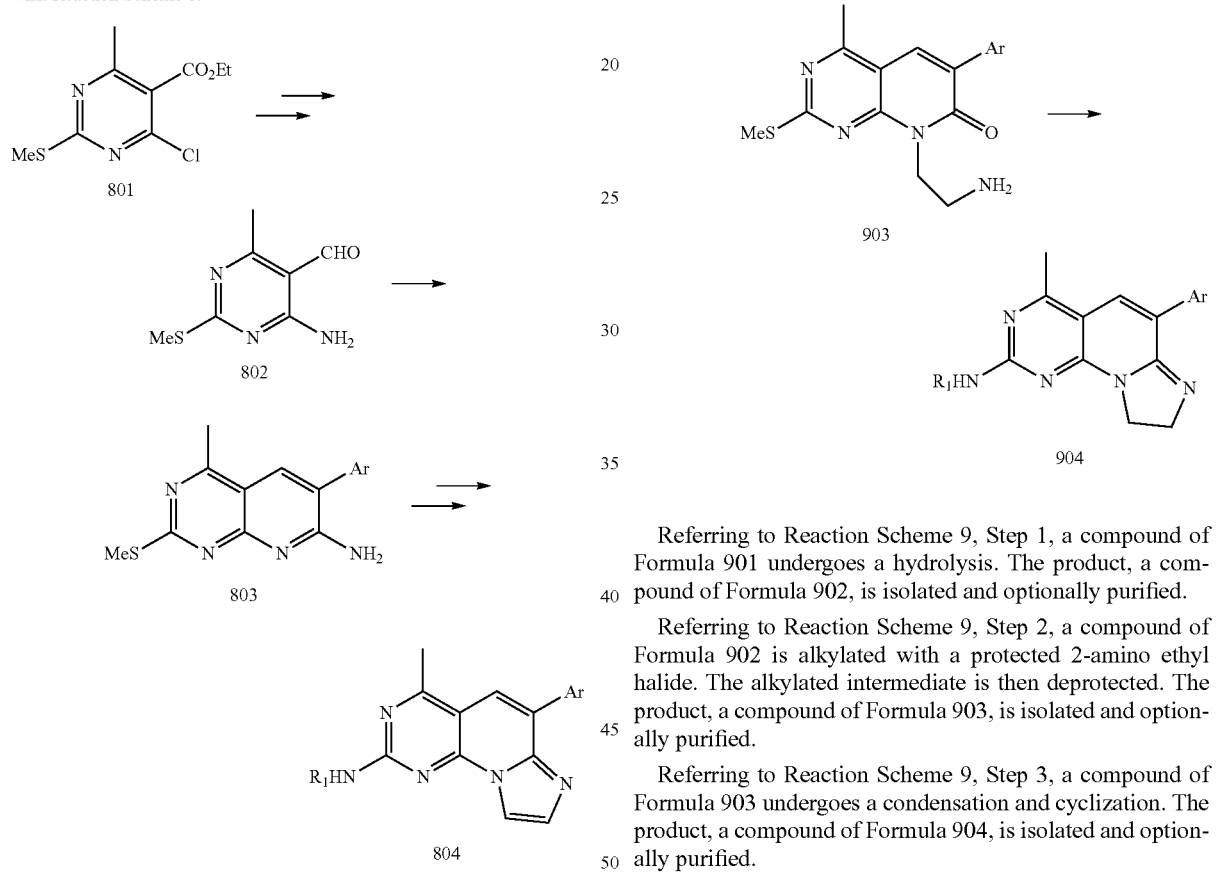

Referring to Reaction Scheme 8, Step 1, a compound of Formula 801 is aminated and converted to an aldehyde using commonly employed synthetic techniques. The product, a compound of Formula 802, is isolated and optionally purified.

Referring to Reaction Scheme 8, Step 2, a compound of Formula 802 is cyclized with 2-(optionally substituted)phenylacetonitriles. The product, a compound of Formula 803, is isolated and optionally purified.

Referring to Reaction Scheme 8, Step 3, a compound of Formula 803 is cyclized using commonly employed synthetic methodology. The product, a compound of Formula 804, is isolated and optionally purified.

IX. Reaction Scheme 9:

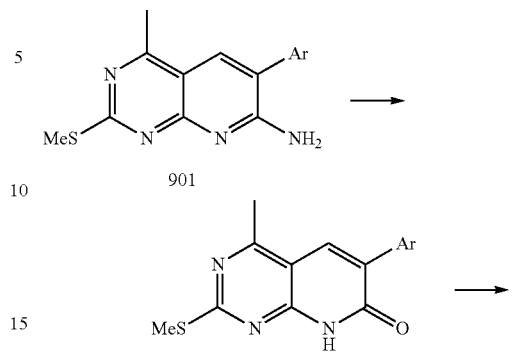

Referring to Reaction Scheme 9, Step 1, a compound of Formula 901 undergoes a hydrolysis. The product, a compound of Formula 902, is isolated and optionally purified.

Referring to Reaction Scheme 9, Step 2, a compound of Formula 902 is alkylated with a protected 2-amino ethyl halide. The alkylated intermediate is then deprotected. The product, a compound of Formula 903, is isolated and optionally purified.

Referring to Reaction Scheme 9, Step 3, a compound of Formula 903 undergoes a condensation and cyclization. The product, a compound of Formula 904, is isolated and optionally purified.

X. Reaction Scheme 10:

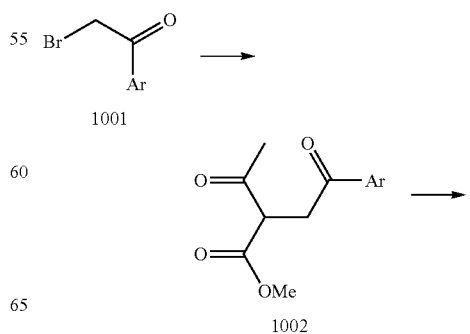

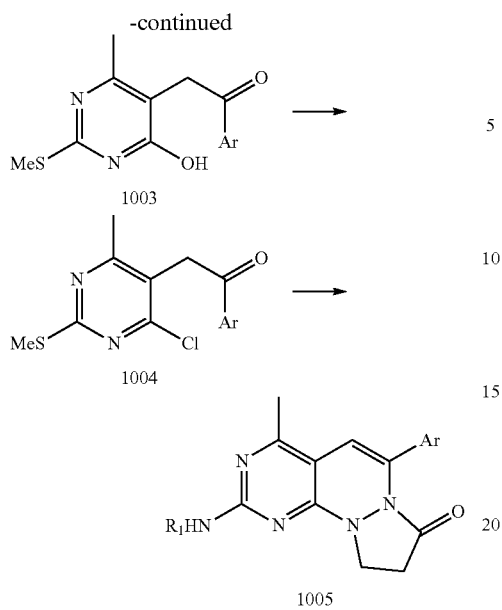

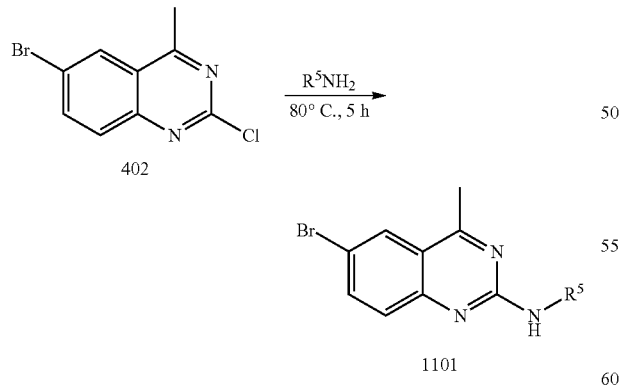

Referring to Reaction Scheme 10, Step 1, a compound of Formula 1001 is alkylated with an optionally substituted β-keto ester. The product, a compound of Formula 1002, is isolated and optionally purified.

Referring to Reaction Scheme 10, Step 2, a compound of Formula 1002 undergoes a condensation and cyclization with a reagent such as thiourea. The product, a compound of Formula 1003, is isolated and optionally purified.

Referring to Reaction Scheme 10, Step 3, a compound of Formula 1003 is chlorinated with a reagent such as thionyl chloride or phosphorous oxychloride. The product, a compound of Formula 1004, is isolated and optionally purified.

Referring to Reaction Scheme 10, Step 4, a compound of Formula 1004 undergoes a cyclization reaction with an optionally substituted pyrazolidin-3-one. The product, a compound of Formula 1005, is isolated and optionally purified.

XI. Reaction Scheme XI:

In Reaction Scheme XI, the chloro quinazoline compound of Formula 402 is treated with a primary amine at elevated temperature, and is converted to the amine, a compound of Formula 1101.

The chemical entities can be synthesized by an appropriate combination of generally well known synthetic methods. Techniques useful in synthesizing the chemical entities are both readily apparent and accessible to those of skill in the relevant art.

A racemic mixture can be optionally placed on a chromatography column and separated into (R)- and (S)-enantiomers.

The compounds described herein can be optionally contacted with a pharmaceutically acceptable acid to form the corresponding acid addition salts.

Additional Illustrative Compounds of the Invention include the following embodiments:

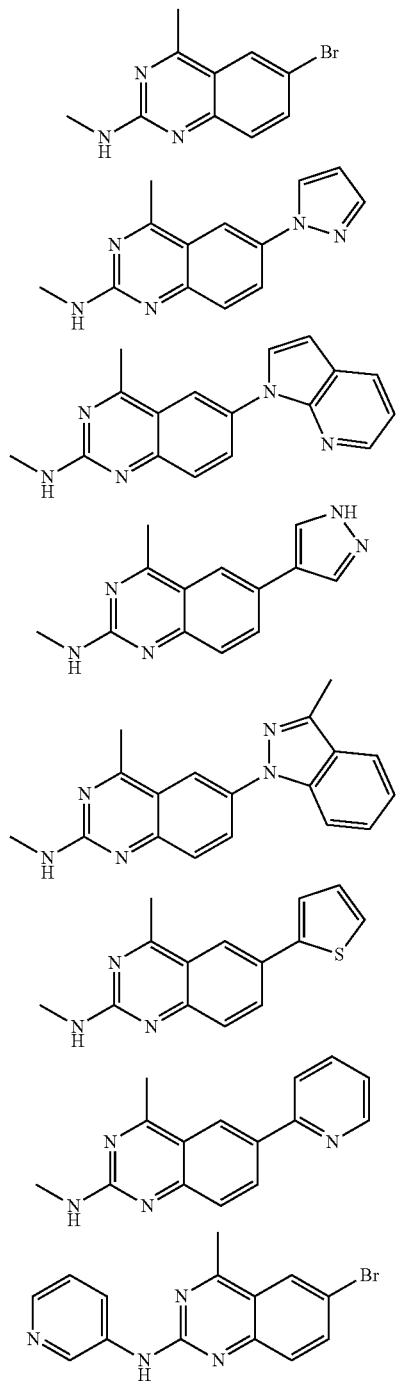

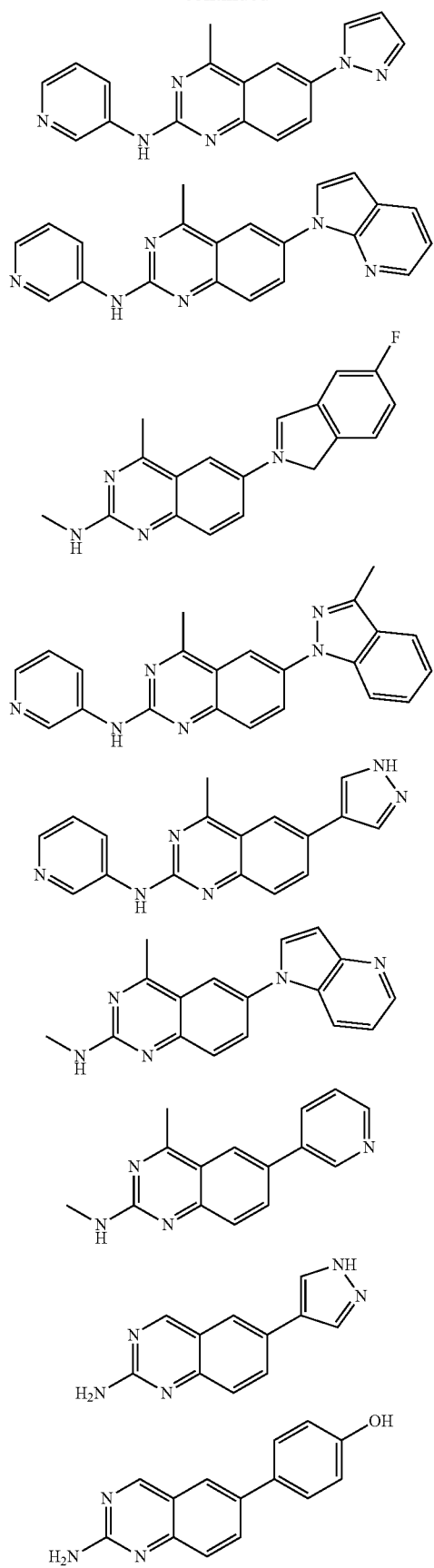
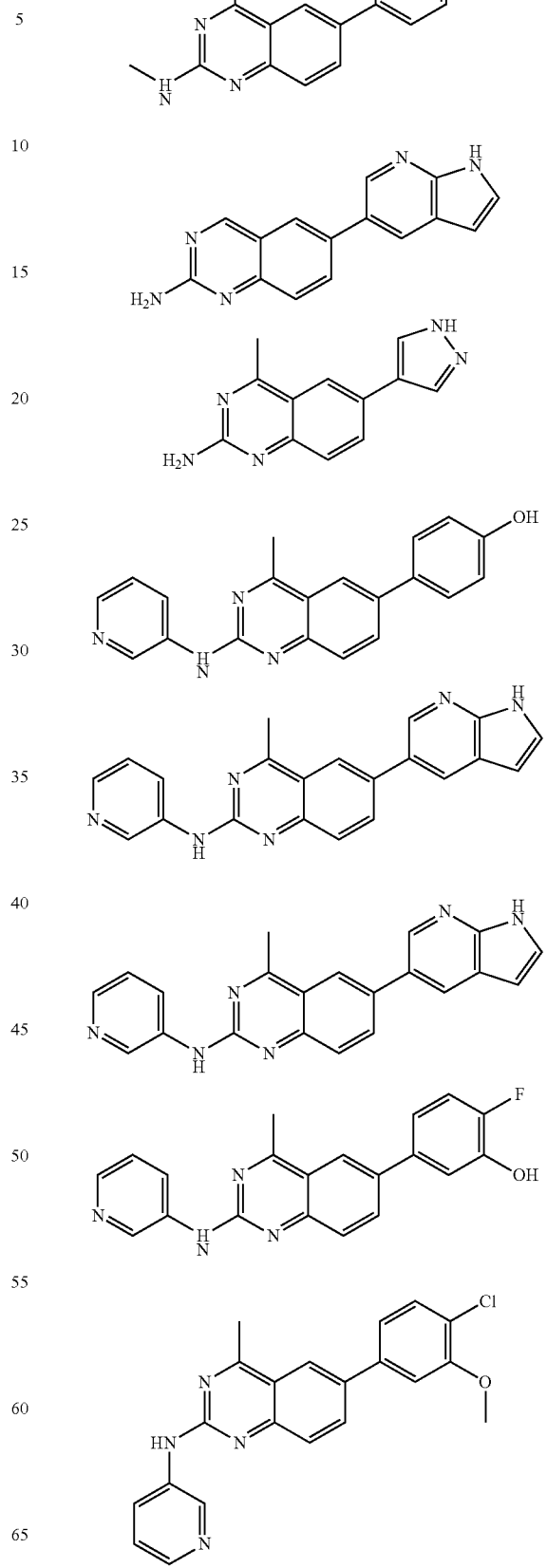

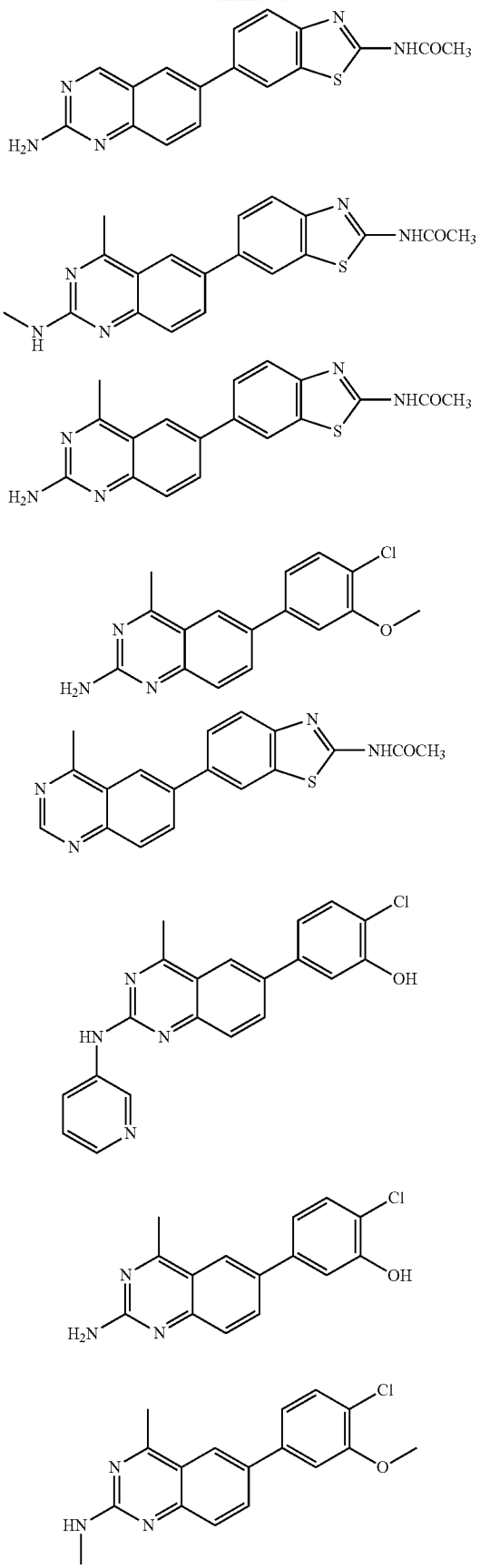
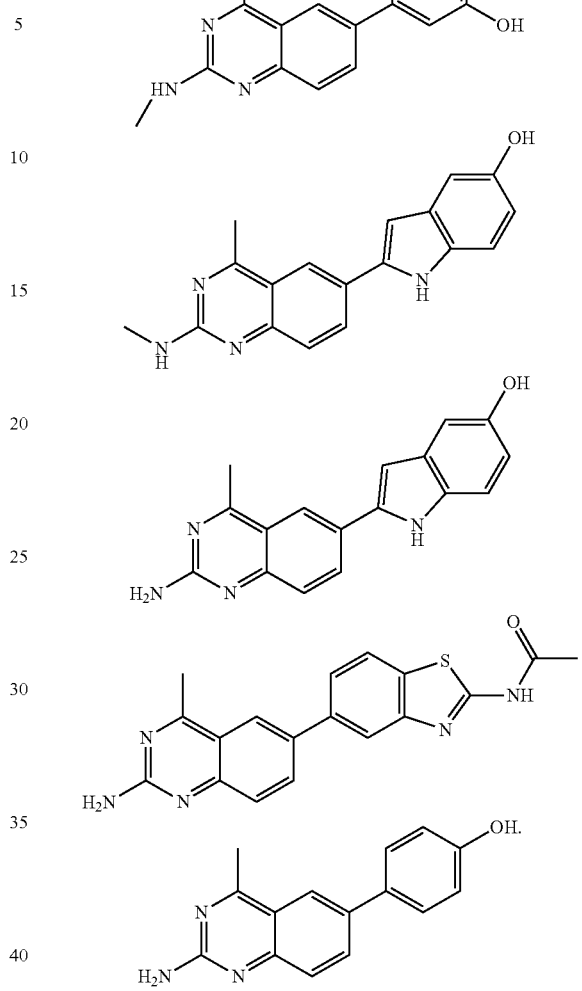

In some embodiments, one or more subject compounds bind specifically to a PI3 kinase or a protein kinase selected from the group consisting of mTor, DNA-dependent protein kinase DNA-dependent protein kinase (Pubmed protein accession number (PPAN) AAA79184), Abl tyrosine kinase (CAA52387), Bcr-Abl, hemopoietic cell kinase (PPAN CAI19695), Src (PPAN CAA24495), vascular endothelial growth factor receptor 2 (PPAN ABB82619), vascular endothelial growth factor receptor-2 (PPAN ABB82619), epidermal growth factor receptor (PPAN AG43241), EPH receptor B4 (PPAN EAL23820), stem cell factor receptor (PPAN AAF22141), Tyrosine-protein kinase receptor TIE-2 (PPAN Q02858), fins-related tyrosine kinase 3 (PPAN NP_004110), platelet-derived growth factor receptor alpha (PPAN NP_990080), RET (PPAN CAA73131), and any other protein kinases listed in the appended tables and figures, as well as any functional mutants thereof. In some embodiments, the IC50 of a subject compound for p110α, p110β, p110γ, or p110δ is less than about 1 μM, less than about 100 nM, less than about 50 nM, less than about 10 nM, less than 1 nM or even less than about 0.5 nM. In some embodiments, the IC50 of a subject compound for mTor is less than about 1 μM, less than about 100 nM, less than about 50 nM, less than about 10 nM, less than 1 nM or even less than about 0.5 nM. In some other embodiments, one or more subject compounds exhibit dual binding specificity and are capable of inhibiting a PI3 kinase (e.g., a class I PI3 kinase) as well as a protein kinase (e.g., mTor) with an IC50 value less than about 1 µM, less than about 100 nM, less than about 50 nM, less than about 10 nM, less than 1 nM or even less than about 0.5 nM. One or more subject compounds are capable of inhibiting tyrosine kinases including, for example, DNA-dependent protein kinase DNA-dependent protein kinase (Pubmed protein accession number (PPAN) AAA79184), Abl tyrosine kinase (CAA52387), Bcr-Abl, hemopoietic cell kinase (PPAN CAI19695), Src (PPAN CAA24495), vascular endothelial growth factor receptor 2 (PPAN ABB82619), vascular endothelial growth factor receptor-2 (PPAN ABB82619), epidermal growth factor receptor (PPAN AG43241), EPH receptor B4 (PPAN EAL23820), stem cell factor receptor (PPAN AAF22141), Tyrosine-protein kinase receptor TIE-2 (PPAN Q02858), fms-related tyrosine kinase 3 (PPAN NP_004110), platelet-derived growth factor receptor alpha (PPAN NP_990080), RET (PPAN CAA73131), and functional mutants thereof. In some embodiments, the tyrosine kinase is Abl, Bcr-Abl, EGFR, or Flt-3, and any other kinases listed in the Tables herein.

In some embodiments, one or more of the subject compound may selectively inhibit one or more members of type I or class I phosphatidylinositol 3-kinases (PI3-kinase) with an IC50 value of about 100 nM, 50 nM, 10 nM, 5 nM, 100 pM, 10 pM or even 1 pM, or less as ascertained in an in vitro kinase assay.

In some embodiments, one or more of the subject compound may selectively inhibit one or two members of type I or class I phosphatidylinositol 3-kinases (PI3-kinase) consisting of PI3-kinase α, PI3-kinase β, PI3-kinase γ, and PI3-kinase δ. In some aspects, some of the subject compounds selectively inhibit PI3-kinase δ as compared to all other type I PI3-kinases. In other aspects, some of the subject compounds selectively inhibit PI3-kinase δ and PI3-kinase γ as compared to the rest of the type I PI3-kinases. In yet other aspects, some of the subject compounds selectively inhibit PI3-kinase α and PI3-kinase β or α as compared to the rest of the type I PI3-kinases. In still yet some other aspects, some of the subject compounds selectively inhibit PI3-kinase δ and PI3-kinase β as compared to the rest of the type I PI3-kinases.

In yet another aspect, an inhibitor selectively inhibits one or more members of type I PI3-kinase inhibitor, or an inhibitor that selectively inhibits one or more members of the type I PI3-kinases mediated signaling, alternatively can be understood to refer to a compound that exhibits a 50% inhibitory concentration ($IC_{50}$) with respect to a given type I PI3-kinase, that is at least at least 10-fold, at least 20-fold, at least 50-fold, at least 100-fold, at least 1000-fold, at least 10.100-fold, or lower, than the inhibitor's $IC_{50}$ with respect to the rest of the other type I PI3-kinases.

The invention provides a pharmaceutical composition comprising one or more compounds disclosed herein. In some embodiments the invention provides pharmaceutical compositions for the treatment of disorders such as hyperproliferative disorder in a mammal. In some embodiment, the treatment of said disorders comprises a therapeutically effective amount of a compound of the present invention, or a pharmaceutically acceptable salt, ester, prodrug, solvate, hydrate or derivative thereof, and a pharmaceutically acceptable carrier.

In some embodiments, the invention also relates to compositions for the treatment of cancer such as acute myeloid leukemia, thymus, brain, lung, squamous cell, skin, eye, retinoblastoma, intraocular melanoma, oral cavity and oropharyngeal, bladder, gastric, stomach, pancreatic, bladder, breast, cervical, head, neck, renal, kidney, liver, ovarian, prostate, colorectal, esophageal, testicular, gynecological, thyroid, CNS, PNS, AIDS related AIDS-Related (e.g. Lymphoma and Kaposi's Sarcoma) or Viral-Induced cancer. In some embodiments, said pharmaceutical composition is for the treatment of a non-cancerous hyperproliferative disorder such as benign hyperplasia of the skin (e.g., psoriasis), restenosis, or prostate (e.g., benign prostatic hypertrophy (BPH)).

The invention also relates to compositions for the treatment of diabetes in a mammal which comprises a therapeutically effective amount of a compound of the present invention, or a pharmaceutically acceptable salt, ester, prodrug, solvate, hydrate or derivative thereof, and a pharmaceutically acceptable carrier.

The invention also relates to compositions for the treatment of pancreatitis or kidney disease (including proliferative glomerulonephritis and diabetes—induced renal disease) or pain in a mammal which comprises a therapeutically effective amount of a compound of the present invention, or a pharmaceutically acceptable salt, ester, prodrug, solvate, hydrate or derivative thereof, and a pharmaceutically acceptable carrier.

The invention also relates to a composition for the prevention of blastocyte implantation in a mammal. In some embodiments, the invention relates to pharmaceutical compositions for the prevention of blastocyte implantation in a mammal which comprises a therapeutically effective amount of a compound of the present invention, or a pharmaceutically acceptable salt, ester, prodrug, solvate, hydrate or derivative thereof, and a pharmaceutically acceptable carrier.

The invention also relates to a composition for treating a disease related to vasculogenesis or angiogenesis in a mammal. In some embodiments, the invention relates to pharmaceutical compositions for treating a disease related to vasculogenesis or angiogenesis in a mammal which comprises a therapeutically effective amount of a compound of the present invention, or a pharmaceutically acceptable salt, ester, prodrug, solvate, hydrate or derivative thereof, and a pharmaceutically acceptable carrier. In some embodiments, said pharmaceutical composition is for treating a disease selected from the group consisting of tumor angiogenesis, chronic inflammatory disease such as rheumatoid arthritis, inflammatory bowel disease, atherosclerosis, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

In some embodiments, the invention provides a composition that contains a compound of the present invention. In some embodiments, the concentration of one or more of the compounds is less than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v or v/v.

In some embodiments, the concentration of one or more of the compounds of the present invention is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25%

14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v.

In some embodiments, the concentration of one or more of the compounds of the present invention is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v. v/v.

In some embodiments, the concentration of one or more of the compounds of the present invention is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In some embodiments, the amount of one or more of the compounds of the present invention is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of one or more of the compounds of the present invention is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

In some embodiments, the amount of one or more of the compounds of the present invention is in the range of 0.0001-10 g, 0.0005-9 g, 0.001-8 g, 0.005-7 g, 0.01-6 g, 0.05-5 g, 0.1-4 g, 0.5-4 g, or 1-3 g.

The compounds according to the invention are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. A most preferable dosage is 10 to 30 mg per day. The exact dosage will depend upon the route of administration, the form in which the compound is administered, the subject to be treated, the body weight of the subject to be treated, and the preference and experience of the attending physician.

The compounds of the present invention are usually administered in the form of pharmaceutical compositions. The other agents described herein are also administered in the form of pharmaceutical compositions. When the compounds of the present invention are used in combination with other agents, both components may be mixed into a preparation or both components may be formulated into separate preparations to use them in combination separately or at the same time.

This invention therefore provides pharmaceutical compositions that contain, as the active ingredient, a compound of the present invention or a pharmaceutically acceptable salt and/or coordination complex thereof, and one or more pharmaceutically acceptable excipients, carriers, including inert solid diluents and fillers, diluents, including sterile aqueous solution and various organic solvents, permeation enhancers, solubilizers and adjuvants.

This invention further provides pharmaceutical compositions that contain, as the active ingredient, a compound of the present invention or a pharmaceutically acceptable salt and/or coordination complex thereof, a second agent or a pharmaceutically acceptable salt and/or coordination complex thereof, and one or more pharmaceutically acceptable excipients, carriers, including inert solid diluents and fillers, diluents, including sterile aqueous solution and various organic solvents, permeation enhancers, solubilizers and adjuvants.

The compound of the present invention may be prepared into pharmaceutical compositions in dosages as described herein (see, e.g., Compositions). Such compositions are prepared in a manner well known in the pharmaceutical art.

Pharmaceutical compositions for oral administration In some embodiments, the invention provides a pharmaceutical composition for oral administration containing a compound of the present invention, and a pharmaceutical excipient suitable for oral administration.

In some embodiments, the invention provides a solid pharmaceutical composition for oral administration containing: (i) an effective amount of a compound of the present invention; (ii) an effective amount of a second agent; and (iii) a pharmaceutical excipient suitable for oral administration. In some embodiments, the composition further contains: (iv) an effective amount of a third agent.

In some embodiments, the pharmaceutical composition may be a liquid pharmaceutical composition suitable for oral consumption. Pharmaceutical compositions of the invention suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion. Such dosage forms can be prepared by any of the methods of pharmacy, but all methods include the step of bringing the active ingredient into association with the carrier, which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

This invention further encompasses anhydrous pharmaceutical compositions and dosage forms comprising an active ingredient, since water can facilitate the degradation of some compounds. For example, water may be added (e.g., 5%) in the pharmaceutical arts as a means of simulating long-term storage in order to determine characteristics such as shelf-life or the stability of formulations over time. Anhydrous pharmaceutical compositions and dosage forms of the invention can be prepared using anhydrous or low moisture containing ingredients and low moisture or low humidity conditions. Pharmaceutical compositions and dosage forms of the invention which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

An active ingredient can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, microcrystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the compositions of the invention to provide tablets that disintegrate when exposed to an aqueous environment. Too much of a disintegrant may produce tablets which may disintegrate in the bottle. Too little may be insufficient for disintegration to occur and may thus alter the rate and extent of release of the active ingredient(s) from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

When aqueous suspensions and/or elixirs are desired for oral administration, the essential active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactant which can be used to form pharmaceutical compositions and dosage forms of the invention include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Within the aforementioned group, preferred ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In one embodiment, the composition may include a solubilizer to ensure good solubilization and/or dissolution of the compound of the present invention and to minimize precipitation of the compound of the present invention. This can be especially important for compositions for non-oral use, e.g., compositions for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, .epsilon.-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, s-caprolactone and isomers thereof, δ-valerolactone and isomers thereof, β-butyrolactone and isomers thereof; and other solubilizers known in the art, such as dimethyl acetamide, dimethyl isosorbide, N-methylpyrrolidones, monooctanoin, diethylene glycol monoethyl ether, and water.

Mixtures of solubilizers may also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a patient using conventional techniques, such as distillation or evaporation. Thus, if present, the solubilizer can be in a weight ratio of 10%, 25%, 50%, 100%, or up to about 200% by weight, based on the combined weight of the drug, and other excipients. If desired, very small amounts of solubilizer may also be used, such as 5%, 2%, 1% or even less. Typically, the solubilizer may be present in an amount of about 1% to about 100%, more typically about 5% to about 25% by weight.

The composition can further include one or more pharmaceutically acceptable additives and excipients. Such additives and excipients include, without limitation, detackifiers, antifoaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl) aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Example may include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

Pharmaceutical compositions for injection. In some embodiments, the invention provides a pharmaceutical composition for injection containing a compound of the present invention and a pharmaceutical excipient suitable for injection. Components and amounts of agents in the compositions are as described herein.

The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of the present invention in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Pharmaceutical compositions for topical (e.g., transdermal) delivery. In some embodiments, the invention provides a pharmaceutical composition for transdermal delivery containing a compound of the present invention and a pharmaceutical excipient suitable for transdermal delivery.

Compositions of the present invention can be formulated into preparations in solid, semi-solid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation may provide more immediate exposure of the active ingredient to the chosen area.

The pharmaceutical compositions also may comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation. Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Another preferred formulation for use in the methods of the present invention employs transdermal delivery devices ("patches"). Such transdermal patches may be used to provide continuous or discontinuous infusion of a compound of the present invention in controlled amounts, either with or without another agent.

The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

Pharmaceutical compositions for inhalation. Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

Other pharmaceutical compositions. Pharmaceutical compositions may also be prepared from compositions described herein and one or more pharmaceutically acceptable excipients suitable for sublingual, buccal, rectal, intraosseous, intraocular, intranasal, epidural, or intraspinal administration. Preparations for such pharmaceutical compositions are well-known in the art. See, e.g., See, e.g., Anderson, Philip O.; Knoben, James E.; Troutman, William G, eds., Handbook of Clinical Drug Data, Tenth Edition, McGraw-Hill, 2002; Pratt and Taylor, eds., *Principles of Drug Action*, Third Edition, Churchill Livingston, New York, 1990; Katzung, ed., *Basic and Clinical Pharmacology*, Ninth Edition, McGraw Hill, 20037ybg; Goodman and Gilman, eds., *The Pharmacological Basis of Therapeutics*, Tenth Edition, McGraw Hill, 2001; Remingtons Pharmaceutical Sciences, 20th Ed., Lippincott Williams & Wilkins., 2000; Martindale, *The Extra Pharmacopoeia*, Thirty-Second Edition (The Pharmaceutical Press, London, 1999); all of which are incorporated by reference herein in their entirety.

The invention also provides kits. The kits include a compound or compounds of the present invention as described herein, in suitable packaging, and written material that can include instructions for use, discussion of clinical studies, listing of side effects, and the like. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. The kit may further contain another agent. In some embodiments, the compound of the present invention and the agent are provided as separate compositions in separate containers within the kit. In some embodiments, the compound of the present invention and the agent are provided as a single composition within a container in the kit. Suitable packaging and additional articles for use (e.g., measuring cup for liquid preparations, foil wrapping to minimize exposure to air, and the like) are known in the art and may be included in the kit. Kits described herein can be provided, marketed and/or promoted to health providers, including physicians, nurses, pharmacists, formulary officials, and the like. Kits may also, in some embodiments, be marketed directly to the consumer.

Methods

The invention also relates to a method of treating a hyperproliferative disorder in a mammal that comprises administering to said mammal a therapeutically effective amount of a compound of the present invention, or a pharmaceutically acceptable salt, ester, prodrug, solvate, hydrate or derivative thereof. In some embodiments, said method relates to the treatment of cancer such as acute myeloid leukemia, thymus, brain, lung, squamous cell, skin, eye, retinoblastoma, intraocular melanoma, oral cavity and oropharyngeal, bladder, gastric, stomach, pancreatic, bladder, breast, cervical, head, neck, renal, kidney, liver, ovarian, prostate, colorectal, esophageal, testicular, gynecological, thyroid, CNS, PNS, AIDS-related (e.g. Lymphoma and Kaposi's Sarcoma) or viral-induced cancer. In some embodiments, said method relates to the treatment of a non-cancerous hyperproliferative disorder such as benign hyperplasia of the skin (e.g., psoriasis), restenosis, or prostate (e.g., benign prostatic hypertrophy (BPH)).

The invention also relates to a method for the treatment of a hyperproliferative disorder in a mammal that comprises administering to said mammal a therapeutically effective amount of a compound of the present invention, or a pharmaceutically acceptable salt, ester, prodrug, solvate, hydrate or derivative thereof, in combination with an anti-tumor agent. In some embodiments, the anti-tumor agent is selected from the group consisting of mitotic inhibitors, alkylating agents, anti-metabolites, intercalating antibiotics, growth factor inhibitors, cell cycle inhibitors, enzyme inhibitors, topoisomerase inhibitors, biological response modifiers, anti-hormones, angiogenesis inhibitors, and anti-androgens.

The invention also relates to a method of treating diseases related to vasculogenesis or angiogenesis in a mammal that comprises administering to said mammal a therapeutically effective amount of a compound of the present invention, or a pharmaceutically acceptable salt, ester, prodrug, solvate, hydrate or derivative thereof. In some embodiments, said method is for treating a disease selected from the group consisting of tumor angiogenesis, chronic inflammatory disease such as rheumatoid arthritis, atherosclerosis, inflammatory bowel disease, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

Patients that can be treated with compounds of the present invention, or pharmaceutically acceptable salt, ester, prodrug, solvate, hydrate or derivative of said compounds, according to the methods of this invention include, for example, patients that have been diagnosed as having psoriasis; restenosis; atherosclerosis; BPH; breast cancer such as a ductal carcinoma in duct tissue in a mammary gland, medullary carcinomas, colloid carcinomas, tubular carcinomas, and inflammatory breast cancer; ovarian cancer, including epithelial ovarian tumors such as adenocarcinoma in the ovary and an adenocarcinoma that has migrated from the ovary into the abdominal cavity; uterine cancer; cervical cancer such as adenocarcinoma in the cervix epithelial including squamous cell carcinoma and adenocarinomas; prostate cancer, such as a prostate cancer selected from the following: an adenocarcinoma or an adenocarinoma that has migrated to the bone; pancreatic cancer such as epitheliod carcinoma in the pancreatic duct tissue and an adenocarcinoma in a pancreatic duct; bladder cancer such as a transitional cell carcinoma in urinary bladder, urothelial carcinomas (transitional cell carcinomas), tumors in the urothelial cells that line the bladder, squamous cell carcinomas, adenocarcinomas, and small cell cancers; leukemia such as acute myeloid leukemia (AML), acute lymphocytic leukemia, chronic lymphocytic leukemia, chronic myeloid leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MM), and myelodysplastic syndrome (MDS); bone cancer; lung cancer such as non-small cell lung cancer (NSCLC), which is divided into squamous cell carcinomas, adenocarcinomas, and large cell undifferentiated carcinomas, and small cell lung cancer; skin cancer such as basal cell carcinoma, melanoma, squamous cell carcinoma and actinic keratosis, which is a skin condition that sometimes develops into squamous cell carcinoma; eye retinoblastoma; cutaneous or intraocular (eye) melanoma; primary liver cancer (cancer that begins in the liver); kidney cancer; thyroid cancer such as papillary, follicular, medullary and anaplastic; AIDS-related lymphoma such as diffuse large B-cell lymphoma, B-cell immunoblastic lymphoma and small non-cleaved cell lymphoma; Kaposi's Sarcoma; viral-induced cancers including hepatitis B virus (HBV), hepatitis C virus (HCV), and hepatocellular carcinoma; human lymphotropic virus-type 1 (HTLV-1) and adult T-cell leukemia/lymphoma; and human papilloma virus (HPV) and cervical cancer; central nervous system cancers (CNS) such as primary brain tumor, which includes gliomas (astrocytoma, anaplastic astrocytoma, or glioblastoma multiforme), Oligodendroglioma, Ependymoma, Meningioma, Lymphoma, Schwannoma, and Medulloblastoma; peripheral nervous system (PNS) cancers such as acoustic neuromas and malignant peripheral nerve sheath tumor (MPNST) including neurofibromas and schwannomas, malignant fibrous cytoma, malignant fibrous histiocytoma, malignant meningioma, malignant mesothelioma, and malignant mixed Müllerian tumor; oral cavity and oropharyngeal cancer such as, hypopharyngeal cancer, laryngeal cancer, nasopharyngeal cancer, and oropharyngeal cancer; stomach cancer such as lymphomas, gastric stromal tumors, and carcinoid tumors; testicular cancer such as germ cell tumors (GCTs), which include seminomas and nonseminomas, and gonadal stromal tumors, which include Leydig cell tumors and Sertoli cell tumors; thymus cancer such as to thymomas, thymic carcinomas, Hodgkin disease, non-Hodgkin lymphomas carcinoids or carcinoid tumors; rectal cancer; and colon cancer The invention also relates to a method of treating diabetes in a mammal that comprises administering to said mammal a therapeutically effective amount of a compound of the present invention, or a pharmaceutically acceptable salt, ester, prodrug, solvate, hydrate or derivative thereof.

The invention also relates to a method of treating an inflammation disorder, including autoimmune diseases, in a mammal that comprises administering to said mammal a therapeutically effective amount of a compound of the present invention, or a pharmaceutically acceptable salt, ester, prodrug, solvate, hydrate or derivative thereof. Examples of autoimmune diseases includes but is not limited to acute disseminated encephalomyelitis (ADEM), Addison's disease, antiphospholipid antibody syndrome (APS), aplastic anemia, autoimmune hepatitis, coeliac disease, Crohn's disease, Diabetes mellitus (type 1), Goodpasture's syndrome, Graves' disease, Guillain-Barré syndrome (GBS), Hashimoto's disease, lupus erythematosus, multiple sclerosis, myasthenia gravis, opsoclonus myoclonus syndrome (OMS), optic neuritis, Ord's thyroiditis, oemphigus, polyarthritis, primary biliary cirrhosis, psoriasis, rheumatoid arthritis, Reiter's syndrome, Takayasu's arteritis, temporal arteritis (also known as "giant cell arteritis"), warm autoimmune hemolytic anemia, Wegener's granulomatosis, alopecia universalis, Chagas' disease, chronic fatigue syndrome, dysautonomia, endometriosis, hidradenitis suppurativa, interstitial cystitis, neuromyotonia, sarcoidosis, scleroderma, ulcerative colitis, vitiligo, and vulvodynia. Other disorders include bone-resorption disorders and thromobsis.

For instance, the compounds described herein can be used to treat encephalomyelitis. In other embodiments the compounds described herein are used for the treatment of obstructive pulmonary disease. Chronic obstructive pulmonary disease (COPD) is an umbrella term for a group of respiratory tract diseases that are characterized by airflow obstruction or limitation. Conditions included in this umbrella term are: chronic bronchitis, emphysema, and bronchiectasis.

In another embodiment, the compounds described herein are used for the treatment of asthma. Also, the compounds described herein may be used for the treatment of endotoxemia and sepsis. In one embodiment, the compounds described herein are used to for the treatment of rheumatoid arthritis (RA). In yet another embodiment, the compounds described herein is used for the treatment of contact or atopic dermatitis. Contact dermatitis includes irritant dermatitis, phototoxic dermatitis, allergic dermatitis, photoallergic dermatitis, contact urticaria, systemic contact-type dermatitis and the like. Irritant dermatitis can occur when too much of a substance is used on the skin of when the skin is sensitive to certain substance. Atopic dermatitis, sometimes called eczema, is a kind of dermatitis, an atopic skin disease.

In addition, the compounds described herein may be used to treat acne.

In addition, the compounds described herein may be used for the treatment of arteriosclerosis, including atherosclerosis. Arteriosclerosis is a general term describing any hardening of medium or large arteries. Atherosclerosis is a hardening of an artery specifically due to an atheromatous plaque.

Further the compounds described herein may be used for the treatment of glomerulonephritis. Glomerulonephritis is a primary or secondary autoimmune renal disease characterized by inflammation of the glomeruli. It may be asymptomatic, or present with hematuria and/or proteinuria. There are many recognized types, divided in acute, subacute or chronic glomerulonephritis. Causes are infectious (bacterial, viral or parasitic pathogens), autoimmune or paraneoplastic.

Additionally, the compounds described herein may be used for the treatment of bursitis, lupus, acute disseminated encephalomyelitis (ADEM), Addison's disease, antiphospholipid antibody syndrome (APS), aplastic anemia, autoimmune hepatitis, coeliac disease, crohn's disease, diabetes mellitus (type 1), goodpasture's syndrome, graves' disease, guillain-barré syndrome (GBS), hashimoto's disease, inflammatory bowel disease, lupus erythematosus, myasthenia gravis, opsoclonus myoclonus syndrome (OMS), optic neuritis, ord's thyroiditis,ostheoarthritis, uveoretinitis, pemphigus, polyarthritis, primary biliary cirrhosis, reiter's syndrome, takayasu's arteritis, temporal arteritis, warm autoimmune hemolytic anemia, wegener's granulomatosis, alopecia universalis, chagas' disease, chronic fatigue syndrome, dysautonomia, endometriosis, hidradenitis suppurativa, interstitial cystitis, neuromyotonia, sarcoidosis, scleroderma, ulcerative colitis, vitiligo, vulvodynia, appendicitis, arteritis, arthritis, blepharitis, bronchiolitis, bronchitis, cervicitis, cholangitis, cholecystitis, chorioamnionitis, colitis, conjunctivitis, cystitis, dacryoadenitis, dermatomyositis, endocarditis, endometritis, enteritis, enterocolitis, epicondylitis, epididymitis, fasciitis, fibrositis, gastritis, gastroenteritis, gingivitis, hepatitis, hidradenitis, ileitis, iritis, laryngitis, mastitis, meningitis, myelitis, myocarditis, myositis, nephritis, omphalitis, oophoritis, orchitis, osteitis, otitis, pancreatitis, parotitis, pericarditis, peritonitis, pharyngitis, pleuritis, phlebitis, pneumonitis, proctitis, prostatitis, pyelonephritis, rhinitis, salpingitis, sinusitis, stomatitis, synovitis, tendonitis, tonsillitis, uveitis, vaginitis, vasculitis, or vulvitis.

The invention also relates to a method of treating a cardiovascular disease in a mammal that comprises administering to said mammal a therapeutically effective amount of a compound of the present invention, or a pharmaceutically acceptable salt, ester, prodrug, solvate, hydrate or derivative thereof. Examples of cardiovascular conditions include, but are not limited to, atherosclerosis, restenosis, vascular occlusion and carotid obstructive disease.

In another aspect, the present invention provides methods of disrupting the function of a leukocyte or disrupting a function of an osteoclast. The method includes contacting the leukocyte or the osteoclast with a function disrupting amount of a compound of the invention.

The invention further provides methods of modulating kinase activity by contacting a kinase with an amount of a compound of the invention sufficient to modulate the activity of the kinase. Modulate can be inhibiting or activating kinase activity. In some embodiments, the invention provides methods of inhibiting kinase activity by contacting a kinase with an amount of a compound of the invention sufficient to inhibit the activity of the kinase. In some embodiments, the invention provides methods of inhibiting kinase activity in a solution by contacting said solution with an amount of a compound of the invention sufficient to inhibit the activity of the kinase in said solution. In some embodiments, the invention provides methods of inhibiting kinase activity in a cell by contacting said cell with an amount of a compound of the invention sufficient to inhibit the activity of the kinase in said cell. In some embodiments, the invention provides methods of inhibiting kinase activity in a tissue by contacting said tissue with an amount of a compound of the invention sufficient to inhibit the activity of the kinase in said tissue. In some embodiments, the invention provides methods of inhibiting kinase activity in an organism by contacting said organism with an amount of a compound of the invention sufficient to inhibit the activity of the kinase in said organism. In some embodiments, the invention provides methods of inhibiting kinase activity in an animal by contacting said animal with an amount of a compound of the invention sufficient to inhibit the activity of the kinase in said animal. In some embodiments, the invention provides methods of inhibiting kinase activity in a mammal by contacting said mammal with an amount of a compound of the invention sufficient to inhibit the activity of the kinase in said mammal. In some embodiments, the invention provides methods of inhibiting kinase activity in a human by contacting said human with an amount of a compound of the invention sufficient to inhibit the activity of the kinase in said human. In some embodiments, the % of kinase activity after contacting a kinase with a compound of the invention is less than 10, 20, 30, 40, 50, 60, 70, 80 or 90% of the kinase activity in the absence of said contacting step.

In some embodiments, the kinase is a lipid kinase or a protein kinase. In some embodiments, the kinase is selected from the group consisting of PI3 kinase including different isoforms such as PI3 kinase a, PI3 kinase β, PI3 kinase γ, PI3 kinase δ; DNA-PK; mTor; Abl, VEGFR, Ephrin receptor B4 (EphB4); TEK receptor tyrosine kinase (TIE2); FMS-related tyrosine kinase 3 (FLT-3); Platelet derived growth factor receptor (PDGFR); RET; ATM; ATR; hSmg-1; Hck; Src; Epidermal growth factor receptor (EGFR); KIT; Insulin Receptor (IR) and IGFR.

The invention further provides methods of modulating PI3 kinase activity by contacting a PI3 kinase with an amount of a compound of the invention sufficient to modulate the activity of the PI3 kinase. Modulate can be inhibiting or activating PI3 kinase activity. In some embodiments, the invention provides methods of inhibiting PI3 kinase activity by contacting a PI3 kinase with an amount of a compound of the invention sufficient to inhibit the activity of the PI3 kinase. In some embodiments, the invention provides methods of inhibiting PI3 kinase activity in a solution by contacting said solution with an amount of a compound of the invention sufficient to inhibit the activity of the PI3 kinase in said solution. In some embodiments, the invention provides methods of inhibiting PI3 kinase activity in a cell by contacting said cell with an amount of a compound of the invention sufficient to inhibit the activity of the PI3 kinase in said cell. In some embodiments, the invention provides methods of inhibiting PI3 kinase activity in a tissue by contacting said tissue with an amount of a compound of the invention sufficient to inhibit the activity of the PI3 kinase in said tissue. In some embodiments, the invention provides methods of inhibiting PI3 kinase activity in an organism by contacting said organism with an amount of a compound of the invention sufficient to inhibit the activity of the PI3 kinase in said organism. In some embodiments, the invention provides methods of inhibiting PI3 kinase activity in an animal by contacting said animal with an amount of a compound of the invention sufficient to inhibit the activity of the PI3 kinase in said animal. In some embodiments, the invention provides methods of inhibiting PI3 kinase activity in a mammal by contacting said mammal with an amount of a compound of the invention sufficient to inhibit the activity of the PI3 kinase in said mammal. In some embodiments, the invention provides methods of inhibiting PI3 kinase activity in a human by contacting said human with an amount of a compound of the invention sufficient to inhibit the activity of the PI3 kinase in said human.

The present invention provides methods of treating a disease mediated by PI3-Kinase activity (e.g. p110δ kinase activity or p110γ kinase activity) in a subject in need of such treatment. The method includes administering to the subject a therapeutically effective amount of a compound of the invention. A detailed description of conditions and disorders mediated by p110δ kinase activity is set forth in Sadu et al., WO 01/81346, which is incorporated herein by reference in its entirety for all purposes.

The present chemical entities, pharmaceutical compositions and methods provide manners of modulating the catalytic activity of a PI3 kinase, such as a p110α kinase. The method includes the step of contacting the PI3 kinase (e.g. p110α kinase) with an activity modulating amount of a p110α-affinity pocket binding chemical entity antagonist (described above). In some embodiments, the p110α-affinity pocket binding chemical entity antagonist could be specific to p110α relative to the antagonist action against p110β, p100δ, and/or p110γ. In some embodiments, the IC50 against the p110α kinase could be at least 1.5, 2.0, 3.0, 4.0, 5.0, 10, 20, 30, 40, 50, 60, 70, 80, 90, or 100 fold lower than the IC50 against p110β, p100δ, and/or p110γ. In other embodiments, the IC50 of the p110α-affinity pocket binding chemical entity antagonist against p110α kinase is less than 100 µM, 50 µM, 40 µM, 30 µM, 20 µM, 10 µM, 5 µM, 1 µM, 0.5 µM, 0.1 µM, 50 nM, 10 nM, or 1 nM.

Also provided are methods of treating a condition or disorder mediated by PI3 kinase activity (e.g. p110α kinase activity) in a subject in need of such treatment. The method includes administering to the subject a therapeutically effective amount of a p110α-affinity pocket binding chemical entity antagonist.

Combination Treatment

The present invention also provides methods for combination therapies in which an agent known to modulate other pathways, or other components of the same pathway, or even overlapping sets of target enzymes are used in combination with a compound of the present invention, or a pharmaceutically acceptable salt, ester, prodrug, solvate, hydrate or derivative thereof. In one aspect, such therapy includes but is not limited to the combination of the subject compound with chemotherapeutic agents, therapeutic antibodies, and radiation treatment, to provide a synergistic therapeutic effect.

Specifically, in one aspect, this invention also relates to a pharmaceutical composition for inhibiting abnormal cell growth in a mammal which comprises an amount of a compound of the present invention, or a pharmaceutically acceptable salt, ester, prodrug, solvate, hydrate or derivative thereof, in combination with an amount of an anti-cancer agent (e.g. a chemotherapeutic agent), wherein the amounts of the compound, salt, ester, prodrug, solvate, hydrate or derivative, and of the chemotherapeutic are together effective in inhibiting abnormal cell growth. Many chemotherapeutics are presently known in the art and can be used in combination with the compounds of the invention.

In some embodiments, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens.

A wide variety of anti-cancer agents can be employed in combination. Non-limiting examples are chemotherapeutic agents, cytotoxic agents, and non-peptide small molecules such as Gleevec (Imatinib Mesylate), Velcade (bortezomib), Casodex (bicalutamide), Iressa (gefitinib), and Adriamycin as well as a host of chemotherapeutic agents. Non-limiting examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK.R™; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL™, Bristol-Myers Squibb Oncology, Princeton, N.J.) and docetaxel (TAXOTERE™, Rhone-Poulenc Rorer, Antony, France); retinoic acid; esperamicins; capecitabine; and pharmaceutically acceptable salts, acids or derivatives of any of the above. Also included as suitable chemotherapeutic cell conditioners are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide;

daunomycin; aminopterin; xeloda; ibandronate; camptothecin-11 (CPT-11); topoisomerase inhibitor RFS 2000; difluoromethylornithine (DMFO).

This invention further relates to a method for inhibiting abnormal cell growth in a mammal or treating a hyperproliferative disorder which method comprises administering to the mammal an amount of a compound of the present invention, or a pharmaceutically acceptable salt, ester, prodrug, solvate, hydrate or derivative thereof, in combination with radiation therapy, wherein the amounts of the compound, salt, ester, prodrug, solvate, hydrate or derivative, is in combination with the radiation therapy effective in inhibiting abnormal cell growth or treating the hyperproliferative disorder in the mammal. Techniques for administering radiation therapy are known in the art, and these techniques can be used in the combination therapy described herein. The administration of the compound of the invention in this combination therapy can be determined as described herein.

Radiation therapy can be administered through one of several methods, or a combination of methods, including without limitation external-beam therapy, internal radiation therapy, implant radiation, stereotactic radiosurgery, systemic radiation therapy, radiotherapy and permanent or temporary interstitial brachytherapy. The term "brachytherapy," as used herein, refers to radiation therapy delivered by a spatially confined radioactive material inserted into the body at or near a tumor or other proliferative tissue disease site. The term is intended without limitation to include exposure to radioactive isotopes (e.g. At-211, I-131, I-125, Y-90, Re-186, Re-188, Sm-153, Bi-212, P-32, and radioactive isotopes of Lu), Suitable radiation sources for use as a cell conditioner of the present invention include both solids and liquids. By way of non-limiting example, the radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, Y-90. Moreover, the radionuclide(s) can be embodied in a gel or radioactive micro spheres.

Without being limited by any theory, the compounds of the present invention can render abnormal cells more sensitive to treatment with radiation for purposes of killing and/or inhibiting the growth of such cells. Accordingly, this invention further relates to a method for sensitizing abnormal cells in a mammal to treatment with radiation which comprises administering to the mammal an amount of a compound of the present invention or pharmaceutically acceptable salt, ester, prodrug, solvate, hydrate or derivative thereof, which amount is effective is sensitizing abnormal cells to treatment with radiation. The amount of the compound, salt, or solvate in this method can be determined according to the means for ascertaining effective amounts of such compounds described herein.

The invention also relates to a method of and to a pharmaceutical composition of inhibiting abnormal cell growth in a mammal which comprises an amount of a compound of the present invention, or a pharmaceutically acceptable salt, ester, prodrug, solvate, hydrate or derivative thereof, or an isotopically-labeled derivative thereof, and an amount of one or more substances selected from anti-angiogenesis agents, signal transduction inhibitors, and antiproliferative agents.

Anti-angiogenesis agents, such as MMP-2 (matrix-metalloprotienase 2) inhibitors, MMP-9 (matrix-metalloprotienase 9) inhibitors, and COX-11 (cyclooxygenase 11) inhibitors, can be used in conjunction with a compound of the present invention and pharmaceutical compositions described herein. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931, 788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain Patent Application No. 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780, 386 (published Jun. 25, 1997), all of which are incorporated herein in their entireties by reference. Preferred MMP-2 and MMP-9 inhibitors are those that have little or no activity inhibiting MMP-1. More preferred, are those that selectively inhibit MMP-2 and/or AMP-9 relative to the other matrix-metalloproteinases (i.e., MAP-1, MMP-3, MMP-4, MMP-5, MMP-6, MMP-7, MMP-8, MMP-10, MMP-11, MMP-12, and MMP-13). Some specific examples of MMP inhibitors useful in the present invention are AG-3340, RO 32-3555, and RS 13-0830.

The invention also relates to a method of and to a pharmaceutical composition of treating a cardiovascular disease in a mammal which comprises an amount of a compound of the present invention, or a pharmaceutically acceptable salt, ester, prodrug, solvate, hydrate or derivative thereof, or an isotopically-labeled derivative thereof, and an amount of one or more therapeutic agents use for the treatment of cardiovascular diseases.

Examples for use in cardiovascular disease applications are anti-thrombotic agents, e.g., prostacyclin and salicylates, thrombolytic agents, e.g., streptokinase, urokinase, tissue plasminogen activator (TPA) and anisoylated plasminogen-streptokinase activator complex (APSAC), anti-platelets agents, e.g., acetyl-salicylic acid (ASA) and clopidrogel, vasodilating agents, e.g., nitrates, calcium channel blocking drugs, anti-proliferative agents, e.g., colchicine and alkylating agents, intercalating agents, growth modulating factors such as interleukins, transformation growth factor-beta and congeners of platelet derived growth factor, monoclonal antibodies directed against growth factors, anti-inflammatory agents, both steroidal and non-steroidal, and other agents that can modulate vessel tone, function, arteriosclerosis, and the healing response to vessel or organ injury post intervention. Antibiotics can also be included in combinations or coatings comprised by the invention. Moreover, a coating can be used to effect therapeutic delivery focally within the vessel wall. By incorporation of the active agent in a swellable polymer, the active agent will be released upon swelling of the polymer.

The compounds of the invention may be formulated or administered in conjunction with other agents that act to relieve the symptoms of inflammatory conditions such as encephalomyelitis, asthma, and the other diseases described herein. These agents include non-steroidal anti-inflammatory drugs (NSAIDs), e.g. acetylsalicylic acid; ibuprofen; naproxen; indomethacin; nabumetone; tolmetin; etc. Corticosteroids are used to reduce inflammation and suppress activity of the immune system. The most commonly prescribed drug of this type is Prednisone. Chloroquine (Aralen) or hydroxychloroquine (Plaquenil) may also be very useful in some individuals with lupus. They are most often prescribed for skin and joint symptoms of lupus. Azathioprine (Imuran) and cyclophosphamide (Cytoxan) suppress inflammation and tend to suppress the immune system. Other agents, e.g. methotrexate and cyclosporin are used to control the symptoms of lupus. Anticoagulants are employed to prevent blood from clotting rapidly. They range from aspirin at very low dose which prevents platelets from sticking, to heparin/coumadin.

The compounds describe herein may be formulated or administered in conjunction with liquid or solid tissue barriers also known as lubricants. Examples of tissue barriers include, but are not limited to, polysaccharides, polyglycans, seprafilm, interceed and hyaluronic acid.

Medicaments which may be administered in conjunction with the compounds described herein include any suitable drugs usefully delivered by inhalation for example, analgesics, e.g. codeine, dihydromorphine, ergotamine, fentanyl or morphine; anginal preparations, e.g. diltiazem; antiallergics, e.g. cromoglycate, ketotifen or nedocromil; anti-infectives, e.g. cephalosporins, penicillins, streptomycin, sulphonamides, tetracyclines or pentamidine; antihistamines, e.g. methapyrilene; anti-inflammatories, e.g. beclomethasone, flunisolide, budesonide, tipredane, triamcinolone acetonide or fluticasone; antitussives, e.g. noscapine; bronchodilators, e.g. ephedrine, adrenaline, fenoterol, formoterol, isoprenaline, metaproterenol, phenylephrine, phenylpropanolamine, pirbuterol, reproterol, rimiterol, salbutamol, salmeterol, terbutalin, isoetharine, tulobuterol, orciprenaline or (−)-4-amino-3,5-dichloro-α[[[6-[6-(2-(2-pyridinyl)ethoxy]hexyl]-amino]methyl]benzenemethanol; diuretics, e.g. amiloride; anticholinergics e.g. ipratropium, atropine or oxitropium; hormones, e.g. cortisone, hydrocortisone or prednisolone; xanthines e.g. aminophylline, choline theophyllinate, lysine theophyllinate or theophylline; and therapeutic proteins and peptides, e.g. insulin or glucagon. It will be clear to a person skilled in the art that, where appropriate, the medicaments may be used in the form of salts (e.g. as alkali metal or amine salts or as acid addition salts) or as esters (e.g. lower alkyl esters) or as solvates (e.g. hydrates) to optimize the activity and/or stability of the medicament.

Other exemplary therapeutic agents useful for a combination therapy include but are not limited to agents as described above, radiation therapy, hormone antagonists, hormones and their releasing factors, thyroid and antithyroid drugs, estrogens and progestins, androgens, adrenocorticotropic hormone; adrenocortical steroids and their synthetic analogs; inhibitors of the synthesis and actions of adrenocortical hormones, insulin, oral hypoglycemic agents, and the pharmacology of the endocrine pancreas, agents affecting calcification and bone turnover: calcium, phosphate, parathyroid hormone, vitamin D, calcitonin, vitamins such as water-soluble vitamins, vitamin B complex, ascorbic acid, fat-soluble vitamins, vitamins A, K, and E, growth factors, cytokines, chemokines, muscarinic receptor agonists and antagonists; anticholinesterase agents; agents acting at the neuromuscular junction and/or autonomic ganglia; catecholamines, sympathomimetic drugs, and adrenergic receptor agonists or antagonists; and 5-hydroxytryptamine (5-HT, serotonin) receptor agonists and antagonists.

Therapeutic agents can also include agents for pain and inflammation such as histamine and histamine antagonists, bradykinin and bradykinin antagonists, 5-hydroxytryptamine (serotonin), lipid substances that are generated by biotransformation of the products of the selective hydrolysis of membrane phospholipids, eicosanoids, prostaglandins, thromboxanes, leukotrienes, aspirin, nonsteroidal anti-inflammatory agents, analgesic-antipyretic agents, agents that inhibit the synthesis of prostaglandins and thromboxanes, selective inhibitors of the inducible cyclooxygenase, selective inhibitors of the inducible cyclooxygenase-2, autacoids, paracrine hormones, somatostatin, gastrin, cytokines that mediate interactions involved in humoral and cellular immune responses, lipid-derived autacoids, eicosanoids, β-adrenergic agonists, ipratropium, glucocorticoids, methylxanthines, sodium channel blockers, opioid receptor agonists, calcium channel blockers, membrane stabilizers and leukotriene inhibitors.

Additional therapeutic agents contemplated herein include diuretics, vasopressin, agents affecting the renal conservation of water, rennin, angiotensin, agents useful in the treatment of myocardial ischemia, anti-hypertensive agents, angiotensin converting enzyme inhibitors, fradrenergic receptor antagonists, agents for the treatment of hypercholesterolemia, and agents for the treatment of dyslipidemia.

Other therapeutic agents contemplated include drugs used for control of gastric acidity, agents for the treatment of peptic ulcers, agents for the treatment of gastroesophageal reflux disease, prokinetic agents, antiemetics, agents used in irritable bowel syndrome, agents used for diarrhea, agents used for constipation, agents used for inflammatory bowel disease, agents used for biliary disease, agents used for pancreatic disease. Therapeutic agents used to treat protozoan infections, drugs used to treat Malaria, Amebiasis, Giardiasis, Trichomoniasis, Trypanosomiasis, and/or Leishmaniasis, and/or drugs used in the chemotherapy of helminthiasis. Other therapeutic agents include antimicrobial agents, sulfonamides, trimethoprim-sulfamethoxazole quinolones, and agents for urinary tract infections, penicillins, cephalosporins, and other, β-Lactam antibiotics, an agent comprising an aminoglycoside, protein synthesis inhibitors, drugs used in the chemotherapy of tuberculosis, *mycobacterium avium* complex disease, and leprosy, antifungal agents, antiviral agents including nonretroviral agents and antiretroviral agents.

Examples of therapeutic antibodies that can be combined with a subject compound include but are not limited to anti-receptor tyrosine kinase antibodies (cetuximab, panitumumab, trastuzumab), anti CD20 antibodies (rituximab, tositumomab), and other antibodies such as alemtuzumab, bevacizumab, and gemtuzumab.

Moreover, therapeutic agents used for immunomodulation, such as immunomodulators, immunosuppressive agents, tolerogens, and immunostimulants are contemplated by the methods herein. In addition, therapeutic agents acting on the blood and the blood-forming organs, hematopoietic agents, growth factors, minerals, and vitamins, anticoagulant, thrombolytic, and antiplatelet drugs.

Further therapeutic agents that can be combined with a subject compound may be found in Goodman and Gilman's "The Pharmacological Basis of Therapeutics" Tenth Edition edited by Hardman, Limbird and Gilman or the Physician's Desk Reference, both of which are incorporated herein by reference in their entirety.

The compounds described herein can be used in combination with the agents disclosed herein or other suitable agents, depending on the condition being treated. Hence, in some embodiments the compounds of the invention will be coadminister with other agents as described above. When used in combination therapy, the compounds described herein may be administered with the second agent simultaneously or separately. This administration in combination can include simultaneous administration of the two agents in the same dosage form, simultaneous administration in separate dosage forms, and separate administration. That is, a compound described herein and any of the agents described above can be formulated together in the same dosage form and administered simultaneously. Alternatively, a compound of the present invention and any of the agents described above can be simultaneously administered, wherein both the agents are present in separate formulations. In another alternative, a compound of the present invention can be administered just followed by and any of the agents described above, or vice versa. In the separate administration protocol, a compound of the present invention and any of the agents described above may be administered a few minutes apart, or a few hours apart, or a few days apart.

I. Administration

Administration of the compounds of the present invention can be effected by any method that enables delivery of the compounds to the site of action. These methods include oral routes, intraduodenal routes, parenteral injection (including intravenous, intraarterial, subcutaneous, intramuscular, intravascular, intraperitoneal or infusion), topical (e.g. transdermal application), rectal administration, via local delivery by catheter or stent. Compounds can also abe administered intraadiposally or intrathecally.

The amount of the compound administered will be dependent on the mammal being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to 7 g/day, preferably about 0.05 to about 2.5 g/day. In some instances, dosage levels below the lower limit of the aforesaid range may be more than adequate, while in other cases still larger doses may be employed without causing any harmful side effect, e.g. bydividing such larger doses into several small doses for administration throughout the day.

The compound may be applied as a sole therapy or may involve one or more other anti-tumor substances, for example those selected from, mitotic inhibitors, for example vinblastine; alkylating agents, for example cis-platin, carboplatin and cyclophosphamide; anti-metabolites, for example 5-fluorouracil, cytosine arabinside and hydroxyurea, or, for example, one of the preferred anti-metabolites disclosed in European Patent Application No. 239362 such as N-(5-[N-(3,4-dihydro-2-methyl-4-oxoquinazolin-6-yhmethyl)-N-methylamino]-2-thenoyl)-L-glutamic acid; growth factor inhibitors; cell cycle inhibitors; intercalating antibiotics, for example adriamycin and bleomycin; enzymes, for example, interferon; and anti-hormones, for example anti-estrogens such as Nolvadex™ (tamoxifen) or, for example anti-androgens such as Casodex™ (4'-cyano-3-(4-fluorophenylsulphonyl)-2-hydroxy-2-methyl-3'-(trifluoromethyl) propionanilide). Such conjoint treatment may be achieved by way of the simultaneous, sequential or separate dosing of the individual components of treatment.

In some embodiments, a compound of the invention is administered in a single dose. Typically, such administration will be by injection, e.g., intravenous injection, in order to introduce the agent quickly. However, other routes may be used as appropriate. A single dose of a compound of the invention may also be used for treatment of an acute condition.

In some embodiments, a compound of the invention is administered in multiple doses. Dosing may be about once, twice, three times, four times, five times, six times, or more than six times per day. Dosing may be about once a month, once every two weeks, once a week, or once every other day. In another embodiment a compound of the invention and another agent are administered together about once per day to about 6 times per day. In another embodiment the administration of a compound of the invention and an agent continues for less than about 7 days. In yet another embodiment the administration continues for more than about 6, 10, 14, 28 days, two months, six months, or one year. In some cases, continuous dosing is achieved and maintained as long as necessary.

Administration of the agents of the invention may continue as long as necessary. In some embodiments, an agent of the invention is administered for more than 1, 2, 3, 4, 5, 6, 7, 14, or 28 days. In some embodiments, an agent of the invention is administered for less than 28, 14, 7, 6, 5, 4, 3, 2, or 1 day. In some embodiments, an agent of the invention is administered chronically on an ongoing basis, e.g., for the treatment of chronic effects.

An effective amount of a compound of the invention may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, or as an inhalant.

The compositions of the invention may also be delivered via an impregnated or coated device such as a stent, for example, or an artery-inserted cylindrical polymer. Such a method of administration may, for example, aid in the prevention or amelioration of restenosis following procedures such as balloon angioplasty. Without being bound by theory, compounds of the invention may slow or inhibit the migration and proliferation of smooth muscle cells in the arterial wall which contribute to restenosis. A compound of the invention may be administered, for example, by local delivery from the struts of a stent, from a stent graft, from grafts, or from the cover or sheath of a stent. In some embodiments, a compound of the invention is admixed with a matrix. Such a matrix may be a polymeric matrix, and may serve to bond the compound to the stent. Polymeric matrices suitable for such use, include, for example, lactone-based polyesters or copolyesters such as polylactide, polycaprolactonglycolide, polyorthoesters, polyanhydrides, polyaminoacids, polysaccharides, polyphosphazenes, poly (ether-ester) copolymers (e.g. PEO-PLLA); polydimethylsiloxane, poly(ethylene-vinylacetate), acrylate-based polymers or copolymers (e.g. polyhydroxyethyl methylmethacrylate, polyvinyl pyrrolidinone), fluorinated polymers such as polytetrafluoroethylene and cellulose esters. Suitable matrices may be nondegrading or may degrade with time, releasing the compound or compounds. Compounds of the invention may be applied to the surface of the stent by various methods such as dip/spin coating, spray coating, dip-coating, and/or brush-coating. The compounds may be applied in a solvent and the solvent may be allowed to evaporate, thus forming a layer of compound onto the stent. Alternatively, the compound may be located in the body of the stent or graft, for example in microchannels or micropores. When implanted, the compound diffuses out of the body of the stent to contact the arterial wall. Such stents may be prepared by dipping a stent manufactured to contain such micropores or microchannels into a solution of the compound of the invention in a suitable solvent, followed by evaporation of the solvent. Excess drug on the surface of the stent may be removed via an additional brief solvent wash. In yet other embodiments, compounds of the invention may be covalently linked to a stent or graft. A covalent linker may be used which degrades in vivo, leading to the release of the compound of the invention. Any bio-labile linkage may be used for such a purpose, such as ester, amide or anhydride linkages. Compounds of the invention may additionally be administered intravascularly from a balloon used during angioplasty. Extravascular administration of the compounds via the pericard or via advential application of formulations of the invention may also be performed to decrease restenosis.

A variety of stent devices which may be used as described are disclosed, for example, in the following references, all of which are hereby incorporated by reference: U.S. Pat. Nos. 5,451,233; 5,040,548; 5,061,273; 5,496,346; 5,292,331; 5,674,278; 3,657,744; 4,739,762; 5,195,984; 5,292,331; 5,674,278; 5,879,382; 6,344,053; 4,762,129; 6,152,946; 6,663,652; 6,027,520; 6,676,682; 6,663,652; 6,872,216; 6,027,520; 6,114,653; 5,852,277; 5,843,120; 5,643,312; 5,733,303; 5,597,378; 5,653,727; 4,762,129; 5,922,021; 3,657,744; 4,739,762; 5,195,984; 5,451,233; 3,657,744; 4,739,762; 5,195,984; 4,739,762; 3,657,744; 4,739,762; 5,195,984; 5,292,331; 5,674,278; 5,643,312; 5,879,370; 5,421,955; 5,514,154; 5,603,721; 5,421,955; 5,514,154; 5,603,721; 5,292,331; 5,674,278; 5,879,382; 6,344,053; 5,728,067; 5,980,486; 6,129,708; 5,733,303; 5,843,120; 5,972,018; 5,972,018; 5,733,303; 5,843,120; 4,739,762; 5,195,984; 5,902,332; 5,156,594; 5,395,334; 6,090,083; 5,639,278; 6,051,020; 6,117,167; 5,632,772; 6,165,213; 4,762,129; 5,156,594; 5,217,482; 5,395,334; 4,641,653; 4,739,762; 5,922,021; 5,895,406; 6,251,920; 6,120,536; 5,292,331; 5,674,278; 5,879,382; 6,344,053; 5,609,627; 6,251,920; 5,733,303; 5,843,120; 5,972,018; 6,344,053; 5,292,331; 5,674,278; 5,879,382; 5,653,760; 6,190,358; 6,210,364; 6,283,939; 6,605,057; 5,292,331; 5,674,278; 5,879,382; 6,344,053; 5,423,851; 6,007,575; 5,501,759; 5,674,208; 5,843,032; 5,961,765; 6,027,477; 6,319,228; 6,471,673; 6,190,358; 6,605,057; 6,858,037; 7,001,358; 5,156,594; 5,217,482; 5,395,334; 5,702,439; 5,501,759; 5,674,208; 5,843,032; 5,961,765; 6,027,477; 6,319,228; 6,471,673; 5,759,192; 6,527,789; 5,147,302; 5,342,307; 6,290,485; 6,352,551; 6,402,778; 6,488,694; 6,511,505; 6,613,073; 6,582,458; 5,820,594; 5,824,173; 5,538,510; 4,323,071; 4,762,129; 4,846,186; 5,156,594; 5,217,482; 5,395,334; 5,156,594; 4,323,071; 5,040,548; 5,061,273; 5,451,233; 5,496,346; 5,496,275; 5,496,346; 5,040,548; 5,061,273; 5,451,233; 5,496,346; 4,596,563; 5,040,548; 5,061,273; 5,350,395; 5,451,233; 5,445,625; 6,083,213; 6,475,195; 5,421,955; 5,514,154; 5,603,721; 5,292,331; 5,674,278; 5,879,382; 6,344,053; 6,238,415; 5,421,955; 5,514,154; 5,603,721.

The compounds of the invention may be administered in dosages as described herein (see, e.g., Compositions). It is known in the art that due to intersubject variability in compound pharmacokinetics, individualization of dosing regimen is necessary for optimal therapy. Dosing for a compound of the invention may be found by routine experimentation.

When a compound of the invention, is administered in a composition that comprises one or more agents, and the agent has a shorter half-life than the compound of the invention unit dose forms of the agent and the compound of the invention may be adjusted accordingly. See e.g., Compositions.

The subject pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compound in sterile aqueous solutions, for example, aqueous propylene glycol or dextrose solutions. Such dosage forms can be suitably buffered, if desired.

The activity of the compounds of the present invention may be determined by the following procedure, as well as the procedure described in the examples below. N-terminal 6 His-tagged, constitutively active kinase is expressed in $E.\ coli$ and protein is purified by conventional methods (Ahn et al. Science 1994, 265, 966-970). The activity of the kinase is assessed by measuring the incorporation of γ-33P-phosphate from γ-33P-ATP onto N-terminal His tagged substrate, which is expressed in $E.\ coli$ and is purified by conventional methods, in the presence of the kinase. The assay is carried out in 96-well polypropylene plate. The incubation mixture (100, μL) comprises of 25 mM Hepes, pH 7.4, 10 mM MgCl2, 5 mM β-glycerolphosphate, 100 μM Na-orthovanadate, 5 mM DTT, 5 nM kinase, and 1 μM substrate. Inhibitors are suspended in DMSO, and all reactions, including controls are performed at a final concentration of 1% DMSO. Reactions are initiated by the addition of 10 KM ATP (with 0.5 μCi γ-$^{33}$P—ATP/well) and incubated at ambient temperature for 45 minutes. Equal volume of 25% TCA is added to stop the reaction and precipitate the proteins. Precipitated proteins are trapped onto glass fiber B filterplates, and excess labeled ATP washed off using a Tomtec MACH III harvestor. Plates are allowed to air-dry prior to adding 30 μL/well of Packard Microscint 20, and plates are counted using a Packard Top-Count.

The examples and preparations provided below further illustrate and exemplify the compounds of the present invention and methods of preparing such compounds. It is to be understood that the scope of the present invention is not limited in any way by the scope of the following examples and preparations. In the following examples molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

EXAMPLES

Example 1

Expression and Inhibition Assays of p110α/p850α, p110β/p85α, p110δ/p85α, and p110γ

Class I PI3-Ks can be either purchased (p110α/p85α, p110β/p85α, p110δ/p85α from Upstate, and p110γ from Sigma) or expressed as previously described (Knight at al., 2004). IC50 values are measured using either a standard TLC assay for lipid kinase activity (described below) or a high-throughput membrane capture assay. Kinase reactions are performed by preparing a reaction mixture containing kinase, inhibitor (2% DMSO final concentration), buffer (25 mM HEPES, pH 7.4, 10 mM MgCl2), and freshly sonicated phosphatidylinositol (100 µg/ml). Reactions are initiated by the addition of ATP containing 10 µCi of γ-32P-ATP to a final concentration 10 or 100 µM and allowed to proceed for 5 minutes at room temperature. For TLC analysis, reactions are then terminated by the addition of 105 µl 1N HCl followed by 160 µl CHCl$_3$:MeOH (1:1). The biphasic mixture is vortexed, briefly centrifuged, and the organic phase is transferred to a new tube using a gel loading pipette tip precoated with CHCl$_3$. This extract is spotted on TLC plates and developed for 3-4 hours in a 65:35 solution of n-propanol: 1M acetic acid. The TLC plates are then dried, exposed to a phosphorimager screen (Storm, Amersham), and quantitated. For each compound, kinase activity is measured at 10-12 inhibitor concentrations representing two-fold dilutions from the highest concentration tested (typically, 200 µM). For compounds showing significant activity, IC50 determinations are repeated two to four times, and the reported value is the average of these independent measurements.

Other commercial kits or systems for assaying PI3-K activities are avaiable. The commercially available kits or systems can be used to screen for inhibitors and/or agonists of PI3-Ks including but not limited to PI 3-Kinase α, β, δ, and γ. Anr exemplary system is PI 3-Kinase (human) HTRF™ Assay from Upstate. The assay can be carried out according to the procedures suggested by the manufacturer. Briefly, the assay is a time resolved FRET assay that indirectly measures PIP3 product formed by the activity of a PI3-K. The kinase reaction is performed in a microtitre plate (e.g., a 384 well microtitre plate). The total reaction volume is approximately 20 ul per well. In the first step, each well receives 2 ul of test compound in 20% dimethylsulphoxide resulting in a 2% DMSO final concentration. Next, approximately 14.5 ul of a kinase/PIP2 mixture (diluted in 1× reaction buffer) is added per well for a final concentration of 0.25-0.3 ug/ml kinase and 10 uM PIP2. The plate is sealed and incubated for 15 minutes at room temperature. To start the reaction, 3.5 ul of ATP (diluted in 1× reaction buffer) is added per well for a final concentration of 10 uM ATP. The plate is sealed and incubated for 1 hour at room temperature. The reaction is stopped by adding 5 ul of Stop Solution per well and then 5 ul of Detection Mix is added per well. The plate is sealed, incubated for 1 hour at room temperature, and then read on an appropriate plate reader. Data is analyzed and IC50s are generated using GraphPad Prism 5.

Example 2

Expression and Inhibition Assays of Abl

The compounds described herein can be assayed in triplicate against recombinant full-length Abl or Abl (T315I) (Upstate) in an assay containing 25 mM HEPES, pH 7.4, 10 mM MgCl2, 200 µM ATP (2.5 µCi of γ-32P-ATP), and 0.5 mg/mL BSA. The optimized Abl peptide substrate EAIYAAP-FAKKK is used as phosphoacceptor (200 µM). Reactions are terminated by spotting onto phosphocellulose sheets, which are washed with 0.5% phosphoric acid (approximately 6 times, 5-10 minutes each). Sheets are dried and the transferred radioactivity quantitated by phosphorimaging.

Example 3

Expression and Inhibition Assays of Hck

The compounds described herein can be assayed in triplicate against recombinant full-length Hck in an assay containing 25 mM HEPES, pH 7.4, 10 mM MgCl2, 200 µM ATP (2.5 µCi of 7-32P-ATP), and 0.5 mg/mL BSA. The optimized Src family kinase peptide substrate EIYGEFKKK is used as phosphoacceptor (200 µM). Reactions are terminated by spotting onto phosphocellulose sheets, which are washed with 0.5% phosphoric acid (approximately 6 times, 5-10 minutes each). Sheets are dried and the transferred radioactivity quantitated by phosphorimaging.

Example 4

Expression and Inhibition Assays of Inulsin Receptor (IR)

The compounds described herein can be assayed in triplicate against recombinant insulin receptor kinase domain (Upstate) in an assay containing 25 mM HEPES, pH 7.4, 10 mM MgCl2, 10 mM MnCl$_2$, 200 µM ATP (2.5 µCi of γ-32P-ATP), and 0.5 mg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Example 5

Expression and Inhibition Assays of Src

The compounds described herein can be assayed in triplicate against recombinant full-length Src or Src (T338I) in an assay containing 25 mM HEPES, pH 7.4, 10 mM MgCl2, 200 µM ATP (2.5 µCi of γ-32P-ATP), and 0.5 mg/mL BSA. The optimized Src family kinase peptide substrate EIYGEFKKK is used as phosphoacceptor (200 µM). Reactions are terminated by spotting onto phosphocellulose sheets, which are washed with 0.5% phosphoric acid (approximately 6 times, 5-10 minutes each). Sheets were dried and the transferred radioactivity quantitated by phosphorimaging.

Example 6

Expression and Inhibition Assays of DNA-PK (DNAK)

DNA-PK can be purchased from Promega and assayed using the DNA-PK Assay System (Promega) according to the manufacturer's instructions.

Example 7

Expression and Inhibition Assays mTOR

The compounds described herein can be tested against recombinant mTOR (Invitrogen) in an assay containing 50 mM HEPES, pH 7.5, 1 mM EGTA, 10 mM MgCl2, 2.5 mM, 0.01% Tween, 10 µM ATP (2.5 µCi of µ-32P-ATP), and 3 µg/mL BSA. Rat recombinant PHAS-1/4EBP1 (Calbiochem; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Other kits or systems for assaying mTOR activity are commercially avaiable. For instance, one can use Invitrogen's LanthaScreen™ Kinase assay to test the inhibitors of mTOR disclosed herein. This assay is a time resolved FRET platform that measures the phosphorylation of GFP labeled 4EBP1 by mTOR kinase. The kinase reaction is performed in a white 384 well microtitre plate. The total reaction volume is 20 ul per well and the reaction buffer composition is 50 mM HEPES pH7.5, 0.01% Polysorbate 20, 1 mM EGTA, 10 mM MnCl2, and 2 mM DTT. In the first step, each well receives 2 ul of test compound in 20% dimethylsulphoxide resulting in a 2% DMSO final concentration. Next, 8 ul of mTOR diluted in reaction buffer is added per well for a 60 ng/ml final concentration. To start the reaction, 10 ul of an ATP/GFP-4EBP1 mixture (diluted in reaction buffer) is added per well for a final concentration of 10 uM ATP and 0.5 uM GFP-4EBP1. The plate is sealed and incubated for 1 hour at room temperature. The reaction is stopped by adding 10 ul per well of a Tb-anti-pT46 4EBP1 antibody/EDTA mixture (diluted in TR-FRET buffer) for a final concentration of 1.3 nM antibody and 6.7 mM EDTA. The plate is sealed, incubated for 1 hour at room temperature, and then read on a plate reader set up for LanthaScreen™ TR-FRET. Data is analyzed and IC50s are generated using GraphPad Prism 5.

Example 8

Expression and Inhibition Assays of Vascular Endothelial Growth Receptor

The compounds described herein can be tested against recombinant KDR receptor kinase domain (Invitrogen) in an assay containing 25 mM HEPES, pH 7.4, 10 mM MgCl2, 0.1% BME, 10 µM ATP (2.5 µCi of µ-32P-ATP), and 3 µg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Example 9

Expression and Inhibition Assays of Ephrin receptor B4 (EphB4)

The compounds described herein can be tested against recombinant Ephrin receptor B4 kinase domain (Invitrogen) in an assay containing 25 mM HEPES, pH 7.4, 10 mM MgCl2, 0.1% BME, 10 µM ATP (2.5 µCi of µ-32P-ATP), and 3 µg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Example 10

Expression and Inhibition Assays of Epidermal Growth Factor Receptor (EGFR)

The compounds described herein can be tested against recombinant EGF receptor kinase domain (Invitrogen) in an assay containing 25 mM HEPES, pH 7.4, 10 mM MgCl2, 0.1% BME, 10 µM ATP (2.5 µCi of µ-32P-ATP), and 3 µg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Example 11

Expression and Inhibition Assays of KIT Assay

The compounds described herein can be tested against recombinant KIT kinase domain (Invitrogen) in an assay containing 25 mM HEPES, pH 7.4, 10 mM MgCl2, 1 mM DTT, 10 mM MnCl$_2$, 10 µM ATP (2.5 of µ-32P-ATP), and 3 µg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Example 12

Expression and Inhibition Assays of RET

The compounds described herein can be tested against recombinant RET kinase domain (Invitrogen) in an assay containing 25 mM HEPES, pH 7.4, 10 mM MgCl2, 2.5 mM DTT, 10 µM ATP (2.5 µCi of µ-32P-ATP), and 3 µg/mL BSA. The optimized Abl peptide substrate EAIYAAPFAKKK is used as phosphoacceptor (200 µM). Reactions are terminated by spotting onto phosphocellulose sheets, which are washed with 0.5% phosphoric acid (approximately 6 times, 5-10 minutes each). Sheets are dried and the transferred radioactivity quantitated by phosphorimaging.

Example 13

Expression and Inhibition Assays of Platelet Derived Growth Factor Receptor (PDGFR)

The compounds described herein can be tested against recombinant PDG receptor kinase domain (Invitrogen) in an assay containing 25 mM HEPES, pH 7.4, 10 mM MgCl2, 2.5 mM DTT, 10 µM ATP (2.5 µCi of µ-32P-ATP), and 3 µg/mL BSA. The optimized Abl peptide substrate EAIYAAP-FAKKK is used as phosphoacceptor (200 µM). Reactions are terminated by spotting onto phosphocellulose sheets, which are washed with 0.5% phosphoric acid (approximately 6 times, 5-10 minutes each). Sheets are dried and the transferred radioactivity quantitated by phosphorimaging.

Example 14

Expression and Inhibition Assays of FMS-related Tyrosine Kinase 3 (FLT-3)

The compounds described herein can be tested against recombinant FLT-3 kinase domain (Invitrogen) in an assay containing 25 mM HEPES, pH 7.4, 10 mM MgCl2, 2.5 mM DTT, 10 µM ATP (2.5 µCi of µ-32P-ATP), and 3 µg/mL BSA. The optimized Abl peptide substrate EAIYAAPFAKKK is used as phosphoacceptor (200 µM). Reactions are terminated by spotting onto phosphocellulose sheets, which are washed with 0.5% phosphoric acid (approximately 6 times, 5-10 minutes each). Sheets are dried and the transferred radioactivity quantitated by phosphorimaging.

Example 15

Expression and Inhibition Assays of TEK Receptor Tyrosine Kinase (TIE2)

The compounds described herein can be tested against recombinant TIE2 kinase domain (Invitrogen) in an assay containing 25 mM HEPES, pH 7.4, 10 mM MgCl2, 2 mM DTT, 10 mM $MnCl_2$, 10 µM ATP (2.5 of µ-32P-ATP), and 3 µg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Example 16

B Cell Activation and Proliferation Assay

The ability of one or more subject compounds to inhibit B cell activitation and proliferation is determined according to standard procedures known in the art. For example, an in vitro cellular proliferation assay is established that measures the metabolic activity of live cells. The assay is performed in a 96 well microtiter plate using Alamar Blue reduction. Balb/c splenic B cells are purified over a Ficoll-Paque™ PLUS gradient followed by magnetic cell separation using a MACS B cell Isolation Kit (Miletenyi). Cells are plated in 90 ul at 50,000 cells/well in B Cell Media (RPMI+10% FBS+Penn/Strep +50 uM bME+5 mM HEPES). A compound disclosed herein is diluted in B Cell Media and added in a 10 ul volume. Plates are incubated for 30 min at 37 C and 5% $CO_2$ (0.2% DMSO final concentration). A 50 ul B cell stimulation cocktail is then added containing either 10 ug/ml LPS or 5 ug/ml F(ab')2 Donkey anti-mouse IgM plus 2 ng/ml recombinant mouse IL4 in B Cell Media. Plates are incubated for 72 hours at 37° C. and 5% $CO_2$. A volume of 15 uL of Alamar Blue reagent is added to each well and plates are incubated for 5 hours at 37 C and 5% $CO_2$. Alamar Blue fluoresce is read at 560ExJ590Em, and IC50 or EC50 values are calculated using GraphPad Prism 5.

Example 17

Tumor Cell Line Proliferation Assay

The ability of one or more subject compounds to inhibit tumor cell line proliferation is determined according to standard procedures known in the art. For instance, an in vitro cellular proliferation assay can be performed to measure the metabolic activity of live cells. The assay is performed in a 96 well microtiter plate using Alamar Blue reduction. Human tumor cell lines are obtained from ATCC (e.g., MCF7, U-87 MG, MDA-MB-468, PC-3), grown to confluency in T75 flasks, trypsinized with 0.25% trypsin, washed one time with Tumor Cell Media (DMEM+10% FBS), and plated in 90 ul at 5,000 cells/well in Tumor Cell Media. A compound disclosed herein is diluted in Tumor Cell Media and added in a 10 ul volume. Plates are incubated for 72 hours at 37 C and 5% $CO_2$. A volume of 10 uL of Alamar Blue reagent is added to each well and plates are incubated for 3 hours at 37 C and 5% $CO_2$. Alamar Blue fluoresce is read at 560Ex/590Em, and IC50 values are calculated using GraphPad Prism 5.

Example 18

Antitumor Activity in Vivo

The compounds described herein can be evaluated in a panel of human and murine tumor models.
Paclitaxel-refractory Tumor Models
I. Clinically-derived Ovarian Carcinoma Model.
This tumor model is established from a tumor biopsy of an ovarian cancer patient. Tumor biopsy is taken from the patient.
The compounds described herein are administered to nude mice bearing staged tumors using an every 2 days×5 schedule.
2. A2780Tax Human Ovarian Carcinoma Xenograft (Mutated Tubulin).
A2780Tax is a paclitaxel-resistant human ovarian carcinoma model. It is derived from the sensitive parent A2780 line by co-incubation of cells with paclitaxel and verapamil, an MDR-reversal agent. Its resistance mechanism has been shown to be non-MDR related and is attributed to a mutation in the gene encoding the beta-tubulin protein.
The compounds described herein can be administered to mice bearing staged tumors on an every 2 days×5 schedule.
3. HCT116/VM46 Human Colon Carcinoma Xenograft (Multi-Drug Resistant).
HCT116/VM46 is an MDR-resistant colon carcinoma developed from the sensitive HCT 116 parent line. In vivo, grown in nude mice, HCT116/VM46 has consistently demonstrated high resistance to paclitaxel.
The compounds described herein can be administered to mice bearing staged tumors on an every 2 days×5 schedule.
5. M5076 Murine Sarcoma Model
M5076 is a mouse fibrosarcoma that is inherently refractory to paclitaxel in vivo.
The compounds described herein can be administered to mice bearing staged tumors on an every 2 days×5 schedule.
One or more compounds of the invention can be used in combination other therapeutic agents in vivo in the multidrug resistant human colon carcinoma xenografts HCT/VM46 or any other model known in the art including those described herein.

Example 19

Microsome Stability Assay

The stability of one or more subject compounds is determined according to standard procedures known in the art. For example, stability of one or more subject compounds is established by an in vitro assay. In particular, an in vitro microsome stability assay is established that measures stability of one or more subject compounds when reacting with mouse, rat or human microsomes from liver. The microsome reaction with compounds is performed in 1.5 mL Eppendorf tube. Each tube contains 0.1 µL of 10.0 mg/ml NADPH; 75 µL of 20.0 mg/ml mouse, rat or human liver microsome; 0.4 µL of 0.2 M phosphate buffer, and 425 µL of $ddH_2O$, Negative control (without NADPH) tube contains 75 µL of 20.0 mg/ml mouse, rat or human liver microsome; 0.4 µL of 0.2 M phosphate buffer, and 525 µL of $ddH_2O$. The reaction is started by adding 1.0 µL of 10.0 mM tested compound. The reaction tubes are incubated at 37° C. 100 µL sample is collected into new Eppendorf tube containing 300 µL cold Methanol at 0, 5, 10, 15, 30 and 60 minutes of reaction. Samples are centrifuged at 15,000 rpm to remove protein. Supernatant of centrifuged sample is transferred to new tube. Concentration of stable compound after reaction with microsome in the supernatant is measured by Liquid Chromatography/Mass Spectrometry (LC-MS).

Example 20

Plasma Stability Assay

The stability of one or more subject compounds in plasma is determined according to standard procedures known in the art. See, e.g., *Rapid Commun. Mass Spectrom.*, 10: 1019-1026. The following procedure is an HPLC-MS/MS assay using human plasma; other species including monkey, dog, rat, and mouse are also available. Frozen, heparinized human plasma is thawed in a cold water bath and spun for 10 minutes at 2000 rpm at 4° C. prior to use. A subject compound is added from a 400 µM stock solution to an aliquot of pre-warmed plasma to give a final assay volume of 400 µL (or 800 µL for half-life determination), containing 5 µM test compound and 0.5% DMSO. Reactions are incubated, with shaking, for 0 minutes and 60 minutes at 37° C., or for 0, 15, 30, 45 and 60 minutes at 37 C for half life determination. Reactions are stopped by transferring 50 µL of the incubation mixture to 200 µL of ice-cold acetonitrile and mixed by shaking for 5 minutes. The samples are centrifuged at 6000×g for 15 minutes at 4° C. and 120 µL of supernatant removed into clean tubes. The samples are then evaporated to dryness and submitted for analysis by HPLC-MS/MS.

Where desired, one or more control or reference compounds (5 µM) are tested simultaneously with the test compounds: one compound, propoxycaine, with low plasma stability and another compound, propantheline, with intermediate plasma stability.

Samples are reconstituted in acetonitrile/methanol/water (1/1/2, v/v/v) and analyzed via (RP)HPLC-MS/MS using selected reaction monitoring (SRM). The HPLC conditions consist of a binary LC pump with autosampler, a mixed-mode, C12, 2×20 mm column, and a gradient program. Peak areas corresponding to the analytes are recorded by HPLC-MS/MS. The ratio of the parent compound remaining after 60 minutes relative to the amount remaining at time zero, expressed as percent, is reported as plasma stability. In case of half-life determination, the half-life is estimated from the slope of the initial linear range of the logarithmic curve of compound remaining (%) vs. time, assuming first order kinetics.

Example 21

Chemical Stability

The chemical stability of one or more subject compounds is determined according to standard procedures known in the art. The following details an exemplary procedure for ascertaining chemical stability of a subject compound. The default buffer used for the chemical stability assay is phosphate-buffered saline (PBS) at pH 7.4; other suitable buffers can be used. A subject compound is added from a 100 µM stock solution to an aliquot of PBS (in duplicate) to give a final assay volume of 400 µL, containing 5 µM test compound and 1% DMSO (for half-life determination a total sample volume of 700 µL is prepared). Reactions are incubated, with shaking, for 0 minutes and 24 hours at 37° C.; for half-life determination samples are incubated for 0, 2, 4, 6, and 24 hours. Reactions are stopped by adding immediately 100 µL of the incubation mixture to 100 µL of acetonitrile and vortexing for 5 minutes. The samples are then stored at −20° C. until analysis by HPLC-MS/MS. Where desired, a control compound or a reference compound such as chlorambucil (5 µM) is tested simultaneously with a subject compound of interest, as this compound is largely hydrolyzed over the course of 24 hours. Samples are analyzed via (RP)HPLC-MS/MS using selected reaction monitoring (SRM). The HPLC conditions consist of a binary LC pump with autosampler, a mixed-mode, C12, 2×20 mm column, and a gradient program. Peak areas corresponding to the analytes are recorded by HPLC-MS/MS. The ratio of the parent compound remaining after 24 hours relative to the amount remaining at time zero, expressed as percent, is reported as chemical stability. In case of half-life determination, the half-life is estimated from the slope of the initial linear range of the logarithmic curve of compound remaining (%) vs. time, assuming first order kinetics.

Example 22

Akt Kinase Assay

Cells comprising components of the Akt/mTOR pathway, including but not limited to L6 myoblasts, B-ALL cells, B-cells, T-cells, leukemia cells, bone marrow cells, p190 transduced cells, philladelphia chromosome positive cells (Ph+), and mouse embryonic fibroblasts, are typically grown in cell growth media such as DMEM supplemented with fetal bovine serum and/or antibiotics, and grown to confluency.

In order to compare the effect of one or more compounds disclosed herein on Akt activation, said cells are serum starved overnight and incubated with one or more compounds disclosed herein or about 0.1% DMSO for approximately 1 minute to about 1 hour prior to stimulation with insulin (e.g. 100 nM) for about 1 minutes to about 1 hour. Cells are lysed by scraping into ice cold lysis buffer containing detergents such as sodium dodecyl sulfate and protease inhibitors (e.g., PMSF). After contacting cells with lysis buffer, the solution is briefly sonicated, cleared by centrifugation, resolved by SDS-PAGE, transferred to nitrocellulose or PVDF and immunoblotted using antibodies to phospho-Akt S473, phospho-Akt T308, Akt, and β-actin (Cell Signaling Technologies).

The results demonstrate that one or more compounds of the present disclosure inhibit insulin stimulated phosphorylation of Akt at S473. Alternatively, some compounds disclosed herein additionally inhibit insulin stimulated phosphorylation of Akt at T308. Such class of compounds can inhibit Akt more effectively than rapamycin and may be indicative of mTORC2 inhibitors or inhibitors of upstream kinases such as PI3K or Akt.

Example 23

Kinase Signaling in Blood

PI3K/Akt/mTor signaling is measured in blood cells using the phosflow method (Methods Enzymol. 2007; 434:131-54). The advantage of this method is that it is by nature a single cell assay so that cellular heterogeneity can be detected rather than population averages. This allows concurrent dinstinction of signaling states in different populations defined by other markers. Phosflow is also highly quantitative. To test the effects of one or more compounds disclosed herein, unfractionated splenocytes, or peripheral blood mononuclear cells are stimulated with anti-CD3 to initiate T-cell receptor signaling. The cells are then fixed and stained for surface markers and intracellular phosphoproteins.

Similarly, aliquots of whole blood are incubated for 15 minutes with vehicle (e.g. 0.1% DMSO) or kinase inhibitors at various concentrations, before addition of stimuli to crosslink the T cell receptor (TCR) (anti-CD3 with secondary antibody) or the B cell receptor (BCR) using anti-kappa light chain antibody (Fab'2 fragments). After approximately 5 and 15 minutes, samples are fixed (e.g. with cold 4% paraformaldehyde) and used for phosflow. Surface staining is used to distinguish T and B cells using antibodies directed to cell surface markers that are known to the art. The level of phosphrylation of kinase substrates such as Akt and S6 are then measured by incubating the fixed cells with labeled antibodies specific to the phosphorylated isoforms of these proteins. The population of cells are then analyzed by flow cytometry.

Example 24

Colony Formation Assay

Murine bone marrow cells freshly transformed with a p190 BCR-Abl retrovirus (herein referred to as p190 transduced cells) are plated in the presence of various drug combinations in M3630 methylcellulose media for about 7 days with recombinant human IL-7 in about 30% serum, and the number of colonies formed is counted by visual examination under a microscope.

Alternatively, human peripheral blood mononuclear cells are obtained from Philadelphia chromosome positive (Ph+) and negative (Ph-) patients upon initial diagnosis or relapse. Live cells are isolated and enriched for CD19+CD34+ B cell progenitors. After overnight liquid culture, cells are plated in methocult GF+H4435, Stem Cell Tehcnologies) suplemented with cytokines (IL-3, IL-6, IL-7, G-CSF, GM-CSF, CF, Flt3 ligand, and erythropoietin) and various concentrations of known chemotherapeutic agents in combination with either compounds of the present disclosure. Colonies are counted by microscopy 12-14 days later. This method can be used to test for evidence of additive or synergistic activity.

Example 25

In Vivo Effect of Kinase Inhibitors on Leukemic Cells

Female recipient mice are lethally irradiated from a γ source in two doses about 4 hr apart, with approximately 5Gy each. About 1 hr after the second radiation dose, mice are injected i.v. with about $1\times10^6$ leukemic cells (e.g. Ph+ human or murine cells, or p190 transduced bone marrow cells). These cells are administered together with a radioprotective dose of about $5\times10^6$ normal bone marrow cells from 3-5 week old donor mice. Recipients are given antibiotics in the water and monitored daily. Mice who become sick after about 14 days are euthanized and lymphoid organs are harvested for analysis. Kinase inhibitor treatment begins about 10 days after leukemic cell injection and continues daily until the mice become sick or a maximum of approximately 35 days post-transplant. Inhibitors are given by oral lavage.

Peripheral blood cells are collected approximately on day 10 (pre-treatment) and upon euthanization (post treatment), contacted with tabled anti-hCD4 antibodies and counted by flow cytometry. This method can be used to demonstrate that the synergistic effect of one or more compounds disclosed herein in combination with known chemotherapeutic agents significantly reduce leukemic blood cell counts as compared to treatment with known chemotherapeutic agents (e.g. Gleevac) alone under the conditions tested.

Example 26

Treatment of Lupus Disease Model Mice

Mice lacking the inhibitory receptor FcγRIIb that opposes PI3K signaling in B cells develop lupus with high penetrance. FcγRIIb knockout mice (R2KO, Jackson Labs) are considered a valid model of the human disease as some lupus patients show decreased expression or function of FcγRIIb (S. Bolland and J. V. Ravtech 2000. *Immunity* 12:277-285).

The R2KO mice develop lupus-like disease with antinuclear antibodies, glomerulonephritis and proteinurea within about 4-6 months of age. For these experiments, the rapamycin analogue RAD001 (available from LC Laboratories) is used as a benchmark compound, and administered orally. This compound has been shown to ameliorate lupus symptoms in the B6.Sle1z.S1e3z model (T. Wu et al. *J. Clin Invest.* 117:2186-2196).

Lupus disease model mice such as R2KO, BXSB or MLR/lpr are treated at about 2 months old, approximately for about two months. Mice are given doses of: vehicle, RAD001 at about 10 mg/kg, or compounds disclosed herein at approximately 1 mg/kg to about 500 mg/kg. Blood and urine samples are obtained at approximately throughout the testing period, and tested for antinuclear antibodies (in dilutions of serum) or protein concentration (in urine). Serum is also tested for anti-ssDNA and anti-dsDNA antibodies by ELISA. Animals are euthanized at day 60 and tissues harvested for measuring spleen weight and kidney disease. Glomerulonephritis is assessed in kidney sections stained with H&E. Other animals are studied for about two months after cessation of treatment, using the same endpoints.

This model established in the art can be employed to demonstrate that the kinase inhibitors disclosed herein can suppress or delay the onset of lupus symptoms in lupus disease model mice.

Example 27

Murine Bone Marrow Transplant Assay

Female recipient mice are lethally irradiated from a γ ray source. About 1 hr after the radiation dose, mice are injected with about $1\times106$ leukemic cells from early passage p190 transduced cultures (e.g. as described in *Cancer Genet Cytogenet.* 2005 August; 161(1):51-6). These cells are administered together with a radioprotective dose of approximately $5\times106$ normal bone marrow cells from 3-5 wk old donor mice. Recipients are given antibiotics in the water and monitored daily. Mice who become sick after about 14 days are euthanized and lymphoid organs harvested for flow cytometry and/or magnetic enrichment. Treatment begins on approximately day 10 and continues daily until mice become sick, or after a maximum of about 35 days post-transplant. Drugs are given by oral gavage (p.o.). In a pilot experiment a dose of chemotherapeutic that is not curative but delays leukemia onset by about one week or less is identified; controls are vehicle-treated or treated with chemotherapeutic agent, previously shown to delay but not cure leukemogenesis in this model (e.g. imatinib at about 70 mg/kg twice daily). For the first phase p190 cells that express eGFP are used, and post-mortem analysis is limited to enumeration of the percentage of leukemic cells in bone marrow, spleen and lymph node (LN) by flow cytometry. In the second phase, p190 cells that express a tailless form of human CD4 are used and the post-mortem analysis includes magnetic sorting of hCD4+ cells from spleen followed by immunoblot analysis of key signaling endpoints: p Akt-T308 and S473; pS6 and p4EBP-1. As controls for immunoblot detection, sorted cells are incubated in the presence or absence of kinase inhibitors of the present disclosure inhibitors before lysis. Optionally, "phosflow" is used to detect p Akt-S473 and pS6-S235/236 in hCD4-gated cells without prior sorting. These signaling studies are particularly useful if, for example, drug-treated mice have not developed clinical leukemia at the 35 day time point. Kaplan-Meier plots of survival are generated and statistical analysis done according to methods known in the art. Results from p190 cells are analyzed separated as well as cumulatively.

Samples of peripheral blood (100-200 µl) are obtained weekly from all mice, starting on day 10 immediately prior to commencing treatment. Plasma is used for measuring drug concentrations, and cells are analyzed for leukemia markers (eGFP or hCD4) and signaling biomarkers as described herein.

This general assay known in the art may be used to demonstrate that effective therapeutic doses of the compounds disclosed herein can be used for inhibiting the proliferation of leukemic cells.

Example 28

The synthesis of Compound 2801

Compound 2801

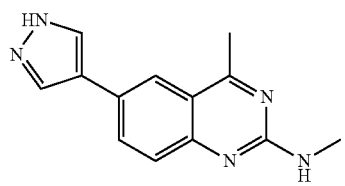

Compound 2801 is synthesized as shown in Scheme 12. The compound of Formula 402 is synthesized as described in Scheme 4b, and is then treated with methylamine at 80° C., for 5 hours to produce compound 1201 in 80% yield. The compound of Formula 1201 is coupled with borolan 1202 using palladium catalysis at 90° C. and compound 2801 is isolated in 43% yield.

Scheme 12. Synthesis of Compound 2801.

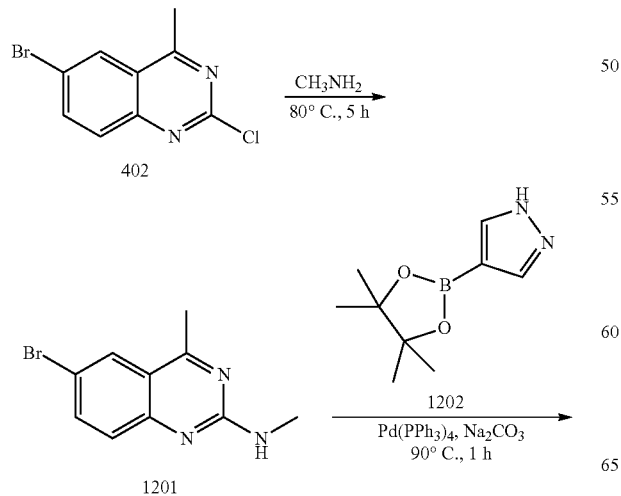

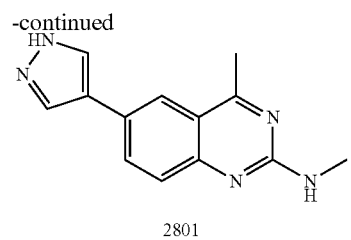

2801

Example 29

Synthesis of Compound 2901

Compound 2901

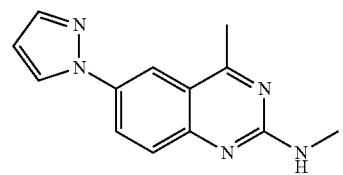

Compound 2901 is synthesized as shown in Scheme 13. Compound 1201 is synthesized as described in Scheme 12, and is then subjected to copper catalyzed coupling with the compound of Formula 1301 in the presence of potassium phosphate in dioxane to provide compound 2901 in 29% yield, as an isolated product.

Scheme 13. Synthesis of Compound 2901.

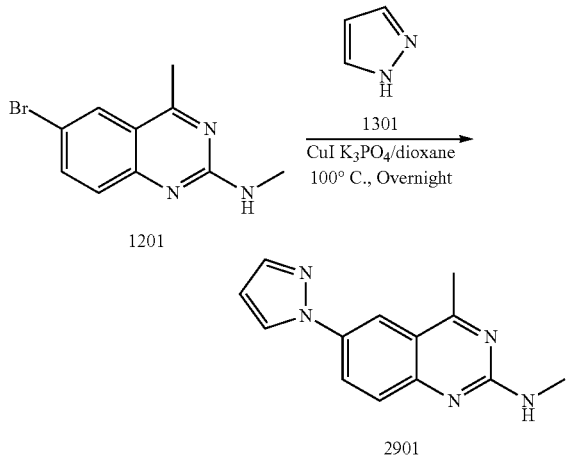

Example 30

The Synthesis of Compound 3001

Compound 3001

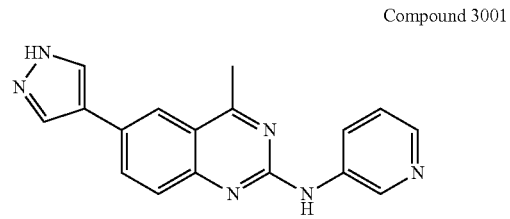 [SMILES: Cc1nc(Nc2cccnc2)nc2ccc(-c3cn[nH]c3)cc12]

Compound 3001 is synthesized as shown in Scheme 14. The compound of Formula 402 is synthesized as described in Scheme 4b, and is then treated with 3-aminopyridine in dimethylsulfoxide at 80° C., in the presence of sodium hydride for 2 hours to produce compound 1401 in 80% yield. The compound of Formula 1401 is coupled with borolan 1202 using palladium catalysis at 90° C. and compound 3001 is isolated in 41% yield.

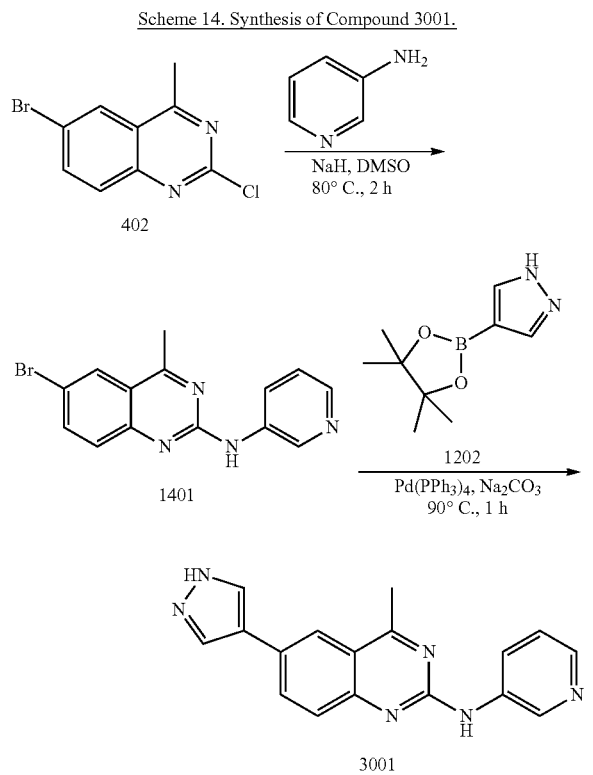

Example 31

Synthesis of Compound 3101

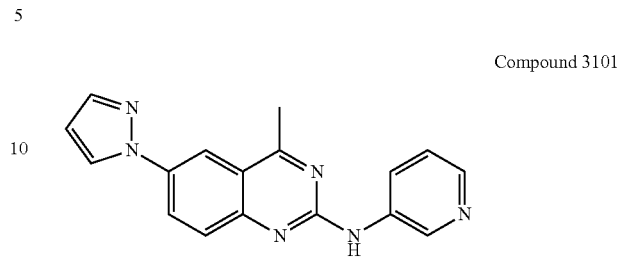

Compound 3101 is synthesized as shown in Scheme 15. Compound 1401 is synthesized as described in Scheme 14, and is then subjected to copper catalyzed coupling with the compound of Formula 1301 in the presence of potassium phosphate in dioxane to provide compound 3101 in 28% yield, as an isolated product.

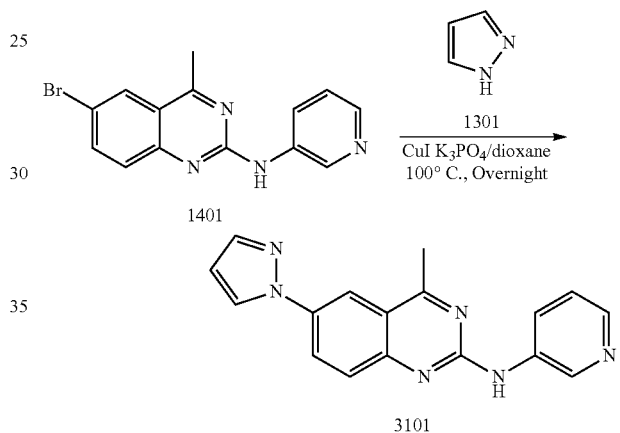

Example 32

TABLE 4

| | In-Vitro Assay Values for Selected Compounds of the Invention. | | | | | | |
|---|---|---|---|---|---|---|---|
| | Structure | PI3K α IC$_{50}$ (nM) | mTOR IC$_{50}$ (nM) | PI3K β IC$_{50}$ (nM) | PI3K γ IC$_{50}$ (nM) | PI3K δ IC$_{50}$ (nM) | PC-3 Proliferation EC$_{50}$ (μM) |
| 1 | [structure] | +++ | + | + | ++++ | +++ | * |
| 2 | [structure] | ++ | + | + | +++ | + | * |

TABLE 4-continued
In-Vitro Assay Values for Selected Compounds of the Invention.
| Structure | PI3K α IC$_{50}$ (nM) | mTOR IC$_{50}$ (nM) | PI3K β IC$_{50}$ (nM) | PI3K γ IC$_{50}$ (nM) | PI3K δ IC$_{50}$ (nM) | PC-3 Proliferation EC$_{50}$ (μM) |
|---|---|---|---|---|---|---|
| 3 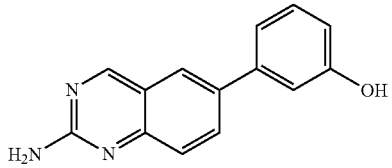 [SMILES: Nc1ncc2cc(-c3cccc(O)c3)ccc2n1] | +++ | + | NA | NA | NA | * |
| 4 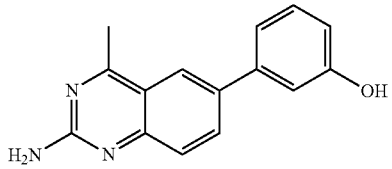 [SMILES: Cc1nc(N)nc2ccc(-c3cccc(O)c3)cc12] | +++ | + | +++ | ++++ | ++++ | ** |
| 5 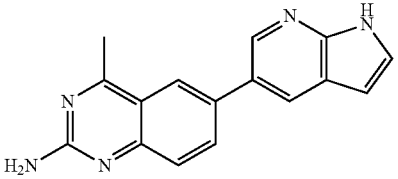 | ++ | + | NA | NA | NA | * |
| 6 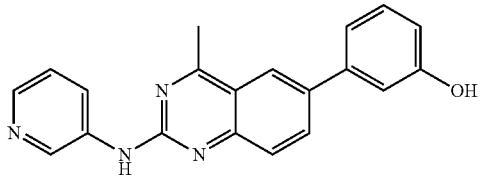 [SMILES: Cc1nc(Nc2cccnc2)nc2ccc(-c3cccc(O)c3)cc12] | ++++ | + | + | ++++ | ++++ | * |
| 7 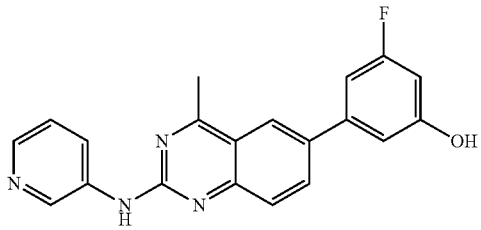 [SMILES: Cc1nc(Nc2cccnc2)nc2ccc(-c3cc(O)cc(F)c3)cc12] | ++++ | + | + | ++++ | ++++ | ** |
| 8 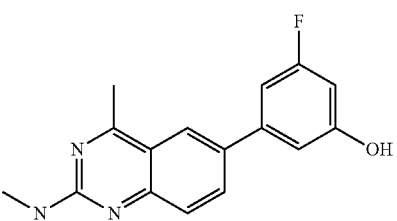 | +++ | + | ++ | ++++ | ++++ | ** |
| 9 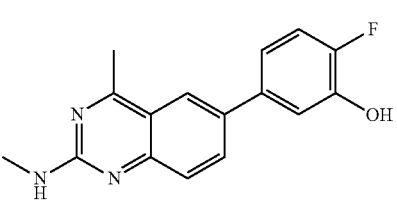 [SMILES: CNc1nc(C)c2cc(-c3ccc(F)c(O)c3)ccc2n1] | ++ | + | NA | NA | NA | ** |

TABLE 4-continued

In-Vitro Assay Values for Selected Compounds of the Invention.

| | Structure | PI3K α IC$_{50}$ (nM) | mTOR IC$_{50}$ (nM) | PI3K β IC$_{50}$ (nM) | PI3K γ IC$_{50}$ (nM) | PI3K δ IC$_{50}$ (nM) | PC-3 Proliferation EC$_{50}$ (μM) |
|---|---|---|---|---|---|---|---|
| 10 | 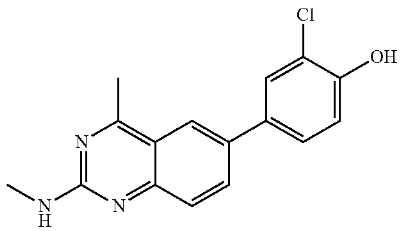 [SMILES: CNc1nc(C)c2cc(-c3ccc(O)c(Cl)c3)ccc2n1] | ++ | + | NA | NA | NA | ** |
| 11 | 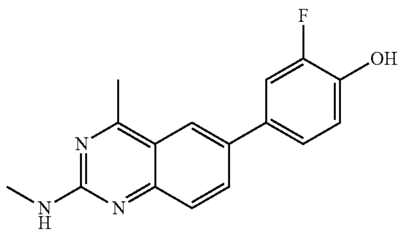 [SMILES: CNc1nc(C)c2cc(-c3ccc(O)c(F)c3)ccc2n1] | ++ | + | NA | NA | NA | * |

The scales represent the following:
+ represents greater than 1 μm,
++ represents 1 μm or less,
+++ represents 500 nM or less,
++++ represents 100 nM or less;
* represents 50 μm or less, and
** represents 20 μm or less.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. All patents, patent publications, and references cited herein are hereby incorporated by reference. While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A compound of Formula II:

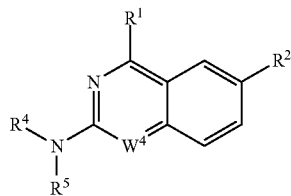

Formula II or a pharmaceutically acceptable salt thereof, wherein
W$^4$ is N;
R$^1$ is unsubstituted methyl or methyl substituted with one or more fluoro;
R$^2$ is aryl, or heteroaryl, each independently substituted with OH or halo;
R$^4$ is hydrogen; and
R$^5$ is hydrogen, alkyl, aryl or heteroaryl, wherein the alkyl, aryl or heteroaryl is optionally substituted;
or R$^4$ and R$^5$, taken together with the nitrogen atom to which they are attached form an optionally substituted heteroaryl ring;
wherein, when a moiety is optionally substituted, substituents are each independently selected from R$^a$, —OR$^b$, amino, halo, cyano, nitro, oxo, acyl, alkoxycarbonyl, aminocarbonyl, —OCOR$^b$, —OCO$_2$R$^a$, —OCONR$^b$R$^c$, sulfanyl, sulfinyl, and sulfonyl;
each R$^a$ is independently C$_1$-C$_6$ alkyl, cycloalkyl, heterocycloalkyl, alkenyl, alkynyl, aryl, or heteroaryl;
each R$^b$ is independently hydrogen or C$_1$-C$_6$ alkyl, cycloalkyl, heterocycloalkyl, aryl, or heteroaryl; and
each R$^c$ is independently hydrogen or C$_1$-C$_4$ alkyl; or
R$^b$ and R$^c$ together with the nitrogen to which they are attached form a heterocycloalkyl group.

2. The compound of claim 1, or a pharmaceutically acceptable salt thereof, wherein R$^1$ is unsubstituted methyl.

3. The compound of claim 1, or a pharmaceutically acceptable salt thereof, wherein R$^1$ is methyl substituted with one or more fluoro.

4. The compound of claim 1, or a pharmaceutically acceptable salt thereof, wherein R$^2$ is aryl, substituted at one or both meta positions.

5. The compound of claim 1, or a pharmaceutically acceptable salt thereof, wherein R$^2$ is a bicyclic aryl or bicyclic heteroaryl.

6. The compound of claim 1, or a pharmaceutically acceptable salt thereof, wherein $R^5$ is alkyl, aryl, or heteroaryl, each of which is optionally substituted.

7. A pharmaceutical composition comprising a pharmaceutically acceptable carrier and a compound of claim 1, or a pharmaceutically acceptable salt thereof.

8. The pharmaceutical composition of claim 7 wherein the composition is formulated as a solid, semi-solid, liquid, or aerosol dosage form.

9. A compound selected from the group consisting of:

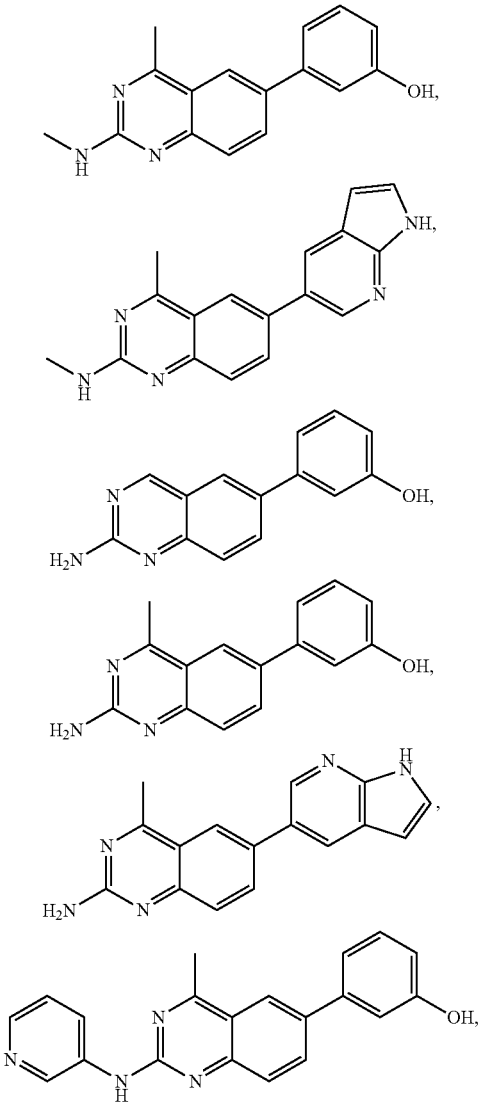

-continued

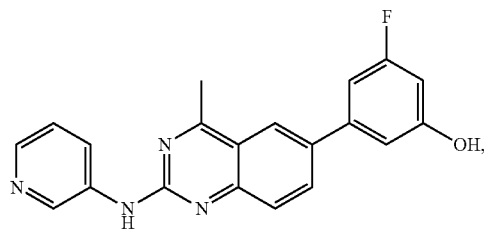

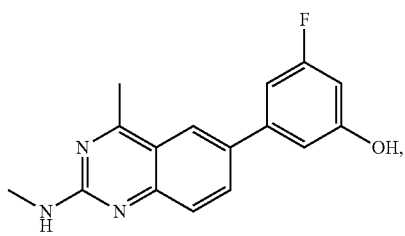

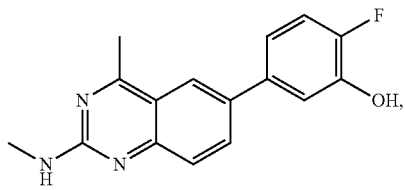

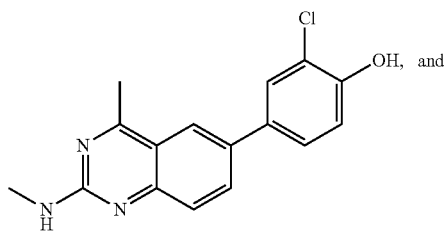

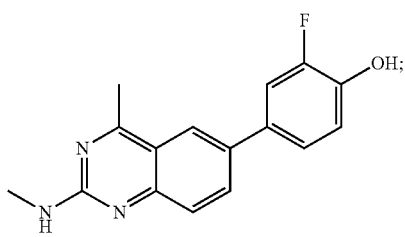

or a pharmaceutically acceptable salt thereof.

* * * * *